(12) United States Patent
Davidson et al.

(10) Patent No.: US 10,072,264 B2
(45) Date of Patent: Sep. 11, 2018

(54) RNA INTERFERENCE SUPPRESSION OF NEURODEGENERATIVE DISEASES AND METHODS OF USE

(71) Applicant: UNIVERSITY OF IOWA RESEARCH FOUNDATION, Iowa City, IA (US)

(72) Inventors: Beverly L. Davidson, Iowa City, IA (US); Haibin Xia, Iowa City, IA (US); Qinwen Mao, Iowa City, IA (US); Henry Paulson, Iowa City, IA (US); Ryan Boudreau, Iowa City, IA (US); Scott Harper, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/395,993

(22) Filed: Dec. 30, 2016

(65) Prior Publication Data
US 2017/0335318 A1    Nov. 23, 2017

Related U.S. Application Data

(63) Continuation of application No. 14/931,667, filed on Nov. 3, 2015, now abandoned, which is a continuation of application No. 13/920,969, filed on Jun. 18, 2013, now Pat. No. 9,260,716, which is a continuation of application No. 12/963,793, filed on Dec. 9, 2010, now Pat. No. 8,481,710, which is a continuation of application No. 11/597,225, filed as application No. PCT/US2005/019749 on Jun. 2, 2005, now abandoned, which is a continuation-in-part of application No. 11/048,627, filed on Jan. 31, 2005, now abandoned, which is a continuation-in-part of application No. 10/859,751, filed on Jun. 2, 2004, now abandoned, and a continuation-in-part of application No. 10/738,642, filed on Dec. 16, 2003, now abandoned, said application No. 10/859,751 is a continuation-in-part of application No. PCT/US03/16887, filed on May 26, 2003, which is a continuation-in-part of application No. 10/430,351, filed on May 5, 2003, now abandoned, which is a continuation-in-part of application No. 10/322,086, filed on Dec. 17, 2002, now abandoned, which is a continuation-in-part of application No. 10/212,322, filed on Aug. 5, 2002, now abandoned, said application No. 10/738,642 is a continuation-in-part of application No. PCT/US03/16887, filed on May 26, 2003.

(51) Int. Cl.
| | |
|---|---|
| *C07H 21/04* | (2006.01) |
| *C12N 15/113* | (2010.01) |
| *C12N 15/86* | (2006.01) |
| *A61K 48/00* | (2006.01) |
| *A61K 38/00* | (2006.01) |

(52) U.S. Cl.
CPC ............ *C12N 15/113* (2013.01); *C12N 15/86* (2013.01); *A01K 2217/05* (2013.01); *A61K 38/00* (2013.01); *A61K 48/00* (2013.01); *C12N 2310/111* (2013.01); *C12N 2310/14* (2013.01); *C12N 2310/53* (2013.01); *C12N 2310/531* (2013.01); *C12N 2750/14143* (2013.01); *C12N 2799/021* (2013.01); *C12N 2799/022* (2013.01); *C12N 2799/025* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 4,873,192 | A | 10/1989 | Kunkel |
| 4,962,091 | A | 10/1990 | Eppstein et al. |
| 5,350,674 | A | 9/1994 | Boenisch et al. |
| 5,580,859 | A | 12/1996 | Felgner et al. |
| 5,585,362 | A | 12/1996 | Wilson et al. |
| 5,686,288 | A | 11/1997 | MacDonald et al. |
| 5,814,500 | A | 9/1998 | Dietz |
| 5,837,449 | A | 11/1998 | Monia et al. |
| 5,849,995 | A | 12/1998 | Hayden et al. |
| 5,902,880 | A | 5/1999 | Thompson |
| 5,922,602 | A | 7/1999 | Kumagai et al. |
| 5,928,906 | A | 7/1999 | Koster et al. |
| 5,972,704 | A | 10/1999 | Draper et al. |
| 6,001,990 | A | 12/1999 | Wands et al. |
| 6,177,246 | B1 | 1/2001 | Monia et al. |
| 6,387,616 | B1 | 5/2002 | Ozelius et al. |
| 6,420,345 | B1 | 7/2002 | Patel et al. |
| 6,468,524 | B1 | 10/2002 | Chiorini et al. |
| 6,479,291 | B2 | 11/2002 | Kumagai et al. |
| 6,506,559 | B1 | 1/2003 | Fire et al. |

(Continued)

FOREIGN PATENT DOCUMENTS

| | | |
|---|---|---|
| DE | 10100586 | 4/2002 |
| DE | 10100588 | 7/2002 |

(Continued)

OTHER PUBLICATIONS

Abdallah, et al., Biology of the Cell, 1995, 85(1):1-7.

(Continued)

*Primary Examiner* — Kimberly Chong
(74) *Attorney, Agent, or Firm* — Viksnins Harris Padys Malen LLP

(57) ABSTRACT

The present invention is directed to small interfering RNA molecules (siRNA) targeted against nucleic acid sequence that encodes huntingtin or ataxin-1, and methods of using these siRNA molecules.

38 Claims, 64 Drawing Sheets
Specification includes a Sequence Listing.

(56) References Cited

U.S. PATENT DOCUMENTS

| | | |
|---|---|---|
| 6,531,647 B1 | 3/2003 | Baulcombe et al. |
| 6,573,099 B2 | 6/2003 | Graham |
| 6,596,535 B1 | 7/2003 | Carter |
| 6,794,414 B1 | 9/2004 | Steinman |
| 6,852,535 B1 | 2/2005 | Thompson |
| 7,186,552 B2 | 3/2007 | Wilson et al. |
| 7,404,969 B2 | 7/2008 | Chen et al. |
| 7,691,997 B2 | 4/2010 | Khvorova et al. |
| 7,820,809 B2 | 10/2010 | Khvorova et al. |
| 7,829,694 B2 | 11/2010 | Kaemmerer |
| 7,902,352 B2 | 3/2011 | Kaemmerer et al. |
| 8,090,542 B2 | 1/2012 | Khvorova et al. |
| 8,227,592 B2 | 7/2012 | Harper et al. |
| 8,258,286 B2 | 9/2012 | Davidson et al. |
| 8,329,890 B2 | 12/2012 | Davidson et al. |
| 8,481,710 B2 | 7/2013 | Davidson et al. |
| 8,487,088 B2 | 7/2013 | Davidson et al. |
| 8,524,879 B2 | 9/2013 | Davidson et al. |
| 8,524,881 B2 | 9/2013 | Davidson et al. |
| 8,691,567 B2 | 4/2014 | Harper et al. |
| 8,779,116 B2 | 7/2014 | Davidson |
| 9,169,483 B2 | 10/2015 | Davidson et al. |
| 9,260,716 B2 | 2/2016 | Davidson et al. |
| 9,388,410 B2 | 7/2016 | Harper et al. |
| 9,487,779 B2 | 11/2016 | Davidson et al. |
| 2002/0086356 A1 | 7/2002 | Tuschl et al. |
| 2002/0132788 A1 | 9/2002 | Lewis et al. |
| 2002/0173478 A1 | 11/2002 | Gewirtz |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0108923 A1 | 6/2003 | Tuschl et al. |
| 2003/0143732 A1 | 7/2003 | Fosnaugh et al. |
| 2003/0148519 A1 | 8/2003 | Engelke et al. |
| 2003/0165853 A1 | 9/2003 | Partridge et al. |
| 2004/0023390 A1 | 2/2004 | Davidson et al. |
| 2004/0053875 A1 | 3/2004 | Kreutzer et al. |
| 2004/0096843 A1 | 5/2004 | Rossi et al. |
| 2004/0192629 A1 | 9/2004 | Xu et al. |
| 2004/0241854 A1 | 12/2004 | Davidson et al. |
| 2005/0042646 A1 | 2/2005 | Davidson et al. |
| 2005/0074887 A1 | 4/2005 | Rossi et al. |
| 2005/0096284 A1 | 5/2005 | McSwiggen |
| 2005/0106731 A1 | 5/2005 | Davidson et al. |
| 2005/0186586 A1 | 8/2005 | Zamore et al. |
| 2005/0191638 A1 | 9/2005 | McSwiggen |
| 2005/0196862 A1 | 9/2005 | Wooddell et al. |
| 2005/0197315 A1 | 9/2005 | Taira et al. |
| 2005/0255086 A1 | 11/2005 | Davidson et al. |
| 2005/0255487 A1 | 11/2005 | Khvorova et al. |
| 2005/0277133 A1 | 12/2005 | McSwiggen |
| 2006/0009408 A1 | 1/2006 | Davidson et al. |
| 2006/0257912 A1 | 11/2006 | Kaemmerer et al. |
| 2006/0270623 A1 | 11/2006 | McSwiggen |
| 2007/0207974 A1 | 9/2007 | Khvorova |
| 2008/0113351 A1 | 5/2008 | Naito et al. |
| 2008/0176812 A1 | 7/2008 | Davidson et al. |
| 2008/0274989 A1 | 11/2008 | Davidson et al. |
| 2009/0036395 A1 | 2/2009 | Davidson et al. |
| 2009/0105169 A1 | 4/2009 | Davidson et al. |
| 2010/0008981 A1 | 1/2010 | Kaemmerer et al. |
| 2010/0144026 A1 | 6/2010 | Davidson et al. |
| 2010/0190243 A1 | 7/2010 | Davidson et al. |
| 2010/0325746 A9 | 12/2010 | Kaemmerer et al. |
| 2012/0052487 A9 | 3/2012 | Khvorova et al. |
| 2012/0270317 A1 | 10/2012 | Harper et al. |
| 2013/0065298 A1 | 3/2013 | Davidson et al. |
| 2014/0303362 A1 | 10/2014 | Davidson et al. |
| 2016/0230169 A1 | 8/2016 | Davidson et al. |
| 2016/0281084 A1 | 9/2016 | Davidson et al. |
| 2016/0348106 A1 | 12/2016 | Harper et al. |

FOREIGN PATENT DOCUMENTS

| | | |
|---|---|---|
| EP | 1144623 | 10/2001 |
| EP | 1214945 | 6/2002 |
| WO | 1990014090 | 11/1990 |
| WO | 199401550 | 1/1994 |
| WO | 199407529 | 4/1994 |
| WO | 199932619 | 7/1999 |
| WO | 199949029 | 9/1999 |
| WO | 200044895 | 8/2000 |
| WO | 200129058 | 4/2001 |
| WO | 200149844 | 7/2001 |
| WO | 200170949 | 9/2001 |
| WO | 200175164 | 10/2001 |
| WO | 200244321 | 6/2002 |
| WO | 200255692 | 7/2002 |
| WO | 200255693 | 7/2002 |
| WO | 200306477 | 1/2003 |
| WO | 200308573 | 1/2003 |
| WO | 200310180 | 2/2003 |
| WO | 200322052 | 3/2003 |
| WO | 2003023015 | 3/2003 |
| WO | 2003048362 | 6/2003 |
| WO | 2003080807 | 10/2003 |
| WO | 2004013280 | 2/2004 |
| WO | 2004013355 | 2/2004 |
| WO | 2004042027 | 5/2004 |
| WO | 2004047872 | 6/2004 |
| WO | 2004058940 | 7/2004 |
| WO | 2005105995 | 11/2005 |
| WO | 2006031267 | 3/2006 |
| WO | 2006083800 | 8/2006 |

OTHER PUBLICATIONS

Abdelgany, et al., Hum. Mol Genet., 2003, 12:2637-2644.
Adelman, et al., DNA, 1983, 2:183.
Agrawal, TIBTech, 1996, 14:376-387.
Alisky, et al., Am J Pharmacogenomics, 4(1):45-51 (2004).
Alisky, et al., Hum Gen Ther., 2000, 11:2315.
Alisky, et al., NeuroReport, 2000, 11:2669.
Altschul, et al., JMB, 1990, 215:403.
Altschul, et al., Nucleic Acids Res. 1997, 25:3389.
Ambrose, et al., Somat Cell Mol Genet., 1994, 20:27-38.
Ancellin, et al., The Journal of Biological Chemistry, 2002, 277:6667-6675.
Anderson, et al., Gene Ther., 2000, 7(12):1034-1038.
Anderson, "Human Gene Therapy", Nature, 1998, 392:25-30.
Andreason and Evans, Biotechniques, 1988, 6:650.
Augood, et al., Ann. Neurol., 1999, 46:761-769.
Augood, et al., Neurology, 2002, 59:445-448.
Bass, "The Short Answer", Nature, 2001, 411:428-429.
Bates, et al., Curr Opin Neurol., 2003, 16:465-470.
Batzer, et al., Nucl. Acids Res., 1991, 19:508.
Baulcombe, Plant Mol. Biol., 1996, 32:79-88.
Behr, et al., PNAS, 1989, 86:6982.
Bernstein, et al., Nature, 2001, 409:363-366.
Bertrand, et al., RNA, 1997 3(1):75-88.
Bledsoe, et al., NatBiot, 2000, 18:964.
Boado, et al., J Pharmacol Exp Ther. 2000, 295(1):239-243.
Boden, "Enhanced gene silencing of HIV-1 specific siRNA using microRNA designed hairpins", Nucleic Acids Res, 32, 1154-1158, (2004).
Branch, TIBS, 1998, 23:45-50.
Brantl, Biochimica et Biophyscia Acta, 2002, 1575:15-25.
Brash, et al., Molec. Cell. Biol., 1987, 7:2031.
Breakefield, et al., Neuron, 2001, 31:9-12.
Bridge, et al., Nat Genet., 2003, 34:263-264.
Brooks, et al., "Functional correction of established central nervous system deficits in an animal model of lysosomal storage disease with feline immunodeficiency virus-based vectors", PNAS 99(9), 6216-6221 (2002).
Brummelkamp, et al., Cancer Cell, 2002, 2:243-247.

(56) References Cited

OTHER PUBLICATIONS

Brummelkamp, et al., "A system for stable expression of short interfering RNAs in mammalian cells", Science, vol. 296, pp. 550-553, 2002.
Burright, et al., Cell, 1995, 82:937-948.
Capecchi, Cell, 1980, 22:479.
Caplen, et al., Hum. Mol. Genet., 2002, 11(2):175-184.
Caplen, et al., PNAS, 2001, 98:9742-9747.
Carter, et al., J Neurosci., 1999, 19(8):3248-3257.
Cemal, et al., Hum. Mol. Genet., 2002, 11(9):1075-1094.
Chai, et al., Hum. Mol. Genet., 1999, 8:673-682.
Chai, et al., J. Neurosci., 1999, 19:10338-10347.
Chan, et al., Hum Mol Genet., 2000, 9(19):2811-2820.
Check, Nature, 2002, 417:779.
Check, Nature, 2004, 432, 136.
Chen, et al., Cell, 2003, 113(4):457-468.
Chiu and Rana, Mol. Cell., 2002, 10(3):549-561.
Clemens, et al., PNAS, 2000, 97:6499-6503.
Cogoni, et al., Antonie Van Leeuwenhoek, 1994, 65:205-209.
Corpet, et al., Nucl. Acids Res., 1988, 16:10881.
Holen, et al., "Positional effects of short interfering RNAs targeting the human coagulation trigger Tissue Factor", Nucleic Acids Res, 30(8), pp. 1757-6617, 2002.
Holland, et al., PNAS, 1987, 84:8662.
Hornykiewicz, et al., N. Engl. J. Med., 1986, 315:347-353.
Houlden, et al., Neurology, 2001, 56(12):1702-1706.
Huang, et al., CABIOS, 1992, 8:155.
Hutton, et al., Nature, 1998, 393:702-705.
Jacque, et al., Nature, 2002, 418(6896):435-438.
Johnston, Nature, 1990, 346:776.
Kao, et al., J. Biol. Chem., 2004, 279:1942-1949.
Karlin and Altschul, PNAS, 1990, 87:2264.
Karlin and Altschul, PNAS, 1993, 90:5873.
Kato, et al., J Biol Chem., 2001, 76(24):21809-21820.
Kawasaki, et al., Nucleic Acids Res., 2003, 31(2):700-707.
Kennerdell, et al., Cell:95, 1017-1026 (1998).
Kennerdell, et al., Nat Biotechnol. 2000;18(8):896-898.
Ketting, et al., Nature, 2000, 404:296-298.
Khvorova, et al., 2003, Cell, 115:505.
Kisielow, et al., Biochem. J., 2002, 363:1-5.
Kitabwalla and Ruprecht, N. Engl. J. Med., 2002, 347:1364-1367.
Klein, et al., Ann. Neurol., 2002, 52:675-679.
Klein, et al., Curr. Opin. Neurol., 2002, 4:491-497.
Konakova, et al., Arch. Neurol., 2001, 58:921-927.
Koseki, et al., J. Virol., 1999, 73:1868-1877.
Krichevsky and Kosik, PNAS, 2002, 99(18):11926-11929.
Kunath, et al., Nat Biotechnol, 2003, 21:559-561.
Kunkel, PNAS, 1985, 82:488.
Kunkel, et al., "Rapid and Efficient Site-Specific Mutagenesis without Phenotypic Selection", Meth. Enzymol., 154(19):367-382 (1987).
Kustedjo, et al., J. Biol. Chem., 2000, 275:27933-27939.
Laccone, et al., Hum. Mutat., 1999, 13(6):497-502.
Lai, et al., PNAS, 1989, 86:10006.
Larrick and Burck, "Gene Therapy", Application of Molecular Biology, 1999, Elsevier Science Publishing Co., Inc., New York, p. 71-104.
Lawn, et al., Nucleic Acids Res., 1981, 9:6103.
Lee, et al., Annu Rev Neurosci., 2001, 24:1121-1159.
Lee, et al., Cell, 2004, 117:69-81.
Lee, et al., Nature Biotechnology, 2002, 19:500-505.
Leger, et al., J. Cell. Sci., 1994, 107:3403-3412.
Leung, et al., Neurogenetics, 2001, 3:133-143.
Lewis, et al., Science, 2001, 293(5534):1487-1491.
Lin, et al., Hum. Mol. Genet., 2001, 10(2):137-144.
Liu, et al., "Specific inhibition of Huntington's disease gene expression by siRNAs in cultured cells", Proc. Japan Acad., 79, Ser. B, No. 10, pp. 293-298, 2003.
Loeffler, et al., J. Neurochem., 1990, 54:1812.
Lotery, et al., Hum Gene Ther., 2002, 13:689-696.

Manche, et al., Mol. Cell Biol., 1992, 12:5238.
Margolis and Ross, Trends Mol. Med., 2001, 7:479-482.
Martinez, et al., Cell, 2002, 110(5):563-574.
Martinez, et al., PNAS, 2002, 99:14849-14854.
McCaffrey, et al., Nature, 2002, 418(6893):38-39.
McManus, et al., Nature Reviews Genetics, 2002, 3(10):737-747.
McManus, et al., RNA, 8, pp. 842-850, 2002.
Meinkoth and Wahl, Anal. Biochem., 1984, 138:267.
Mercola, et al., Cancer Gene Therapy, 1995, 2:47-59.
Meyers and Miller, CABIOS, 1988, 4:11.
Miller, et al., Mol. Cell. Biol., 1990, 10:4239.
Miller, et al., Nucleic Acids Research, 32(2), pp. 661-668, 2004.
Miller, et al., PNAS, 2003, 100:7195-7200.
Minks, et al., J. Biol. Chem., 1979, 254:10180.
Miyagishi, et al., Nature Biotechnology, 2002, 19:497-499.
Miyagishi, et al., "Strategies for generation of an siRNA expression library directed against the human genome", Oligonucleotides, vol. 13, pp. 325-333, 2003.
Molling, J Mol Med., 1997, 75(4):242-246.
Moulder, et al., J. Neurosci., 1999, 19:705-715.
Mullan, et al., "A pathogenic mutation for probable Alzheimer's disease in the APP gene at the N-terminus of beta-amyloid", Nat. Genet. 1: 345-347 (1992).
Nasir, et al., Cell, 1995, 81:811-823.
Needleman and Wunsch, JMB, 1970, 48:443.
Nellemann, et al., Mol Cell Neurosci. 2000;16(4):313-323.
Nykänen, et al., Cell, 2001, 107:309-321.
Oddo, et al., "Triple-transgenic model of Alzheimer's disease with plaques and tangles: intracellular Abeta and synaptic dysfunction", Neuron 39(3), 409-421 (2003).
Ogura and Wilkinson, Genes Cells, 2001, 6:575-597.
Ohtsuka, et al., JBC, 1985, 260:2605.
Okabe, et al., FEBS Lett., 1997, 407:313-319.
Ooboshi, et al., Arterioscler. Thromb. Vasc. Biol., 1997, 17:1786-1792.
Ozelius, Genomics, 1999, 62:377-384.
Ozelius, et al., Nature Genetics, 1997, 17:40-48.
Paddison, Genes and Development, 2002, 16:948-958.
Paddison, et al., PNAS, 2002, 99:1443-1448.
Pardoll, et al., Immunity, 1995, 3(2):165-169.
Paul, "Effective Expression of Smail Interfering RNA in Human Cells", Nature Biotechnology, 29:505-508 (2002).
Paule, et al., Nucleic Acids Research, 2000, 28:1283-1298.
Paulson, et al., Ann. Neurol., 1997, 41(4):453-462.
Pearson, et al., Meth. Mol. Biol., 1994, 24:307.
Pearson and Lipman, PNAS, 1988, 85:2444.
Pham, et al., Cell, 2004, 117:83-94.
Pittman, et al., J. Neurosci., 1993, 13(9):3669-3680.
Poorkaj, et al., Ann. Neurol., 1998, 43:815-825.
Promega siRNA Designer, "SiLentGene U6 Cassette RNA Interference Version 1.1", May 2003, www.promega.com/siRNADesigner/program/default.asp.
Quantin, et al., PNAS, 1992, 89:2581.
Reynolds, et al., Nat. Biotechnol,. 2004, 22:326-30.
Rosenfeld, et al., Science, 1991, 252:431.
Rossolini, et al., Mol. Cell. Probes, 1994, 8:91.
Rubinson, et al., Nature Genetics, 2003, 33:401-406.
Scharfmann, et al., PNAS, 1991, 88:4626.
Schilling, et al., Hum Mol Genet., 1999, 8(3):397-407.
Schilling, et al., Neurobiol Dis., 2001, 8:405-418.
Schramke, et al., Nature, 2005, 435:1275-1279.
Schwartz, et al., Cell, 2003, 115(2):199-208.
Schwartz, et al., Mol. Cell., 2002, 10(3):537-548.
Sharp, Genes and Development, 1999, 13:139-141.
Shi, et al., RNA, 2000, 6:1069-1076.
Shipley, et al., J. Biol. Chem., 1993, 268:12193.
Sisodia, et al., Nat Rev., 2002, 3(4):281-290.
Sledz, et al., Nat Cell Biol., 2003, 5:834-839.
Cortez, et al., Science, 2001, 294:1713-1716.
Couzin, Science, 2004, 306, 1124-1125.
Crea, et al., PNAS, 1978, 75:5765.
Cullen, Nat. Immunol., 2002, 3:597-599.

(56) References Cited

OTHER PUBLICATIONS

Czauderna, et al., "Inducible shRNA expression for application in a prostate cancer mouse model", Nucleic Acids Research, vol. 31, No. 21, e127, Oxford University Press, 2003.
Czauderna, et al., "Structural variations and stabilizing modifications of synthetic siRNAs in mammalian cells", Nucleic Acids Res, 31(11), pp. 2705-2716, 2003.
Dale, et al., "Á test of the model to predict unusually stable RNA hairpin loop stability", RNA, 6, pp. 608-615, 2000.
Davidson, et al., Meth Enzymol, 392:145-173, (2005).
Davidson, et al., The Lancet Neurol., 2004, 3:145-149.
Davidson, et al., "Recombinant adeno-associated virus type 2, 4, and 5 vectors: Transduction of variant cell types and regions in the mammalian central nervous system", PNAS vol. 97 (7), 3428-3432 (2000).
Davidson, et al., "Viral Vectors for Gene Delivery to the Nervous System", Nat Rev., 2003, 4(5):353-364.
Deng, et al., J_Org. Chem., 1999, 64:202-208.
Dillin, PNAS, 2003, 100:6289-6291.
Ding, et al., Aging Cell., 2003, 2:209-217.
Doench, et al., Genes Dev., 2003, 17(4):438-442.
Doheny, et al., Neurology, 2002, 59:1244-1246.
Donze, et al., Nucleic Acids Research, 2002, 30(10):1-4.
Elbashir, et al., EMBO J., 2001, 20(23):6877-6888.
Elbashir, et al., Genes and Development, 2001, 15:188-200.
Elbashir, et al., Nature, 2001, 411:494-498.
Emamian, et al., Neuron, 2003, 38:375-87.
Fahn, et al., Adv. Neurol., 1998, 78:1-10.
Felgner, et al., PNAS., 1987, 84:7413.
Feng, et al., Virology, 2000 25;276(2):271-278.
Fernandez-Funez, et al., Nature, 2000, 408:101-106.
Fire, et al., Nature, 1998, 391:806-811.
Fujigasaki, et al., "CAG repeat expansion in the TATA box-bidning protein gene causes autosomal dominant cerebellar ataxia", Brain, 124, pp. 1939-1947, 2001.
Garrus, et al., Cell, 2001, 107:55-65.
Gaspar, et al., Am. J. Hum. Genet., 2001, 68(2):523-528.
Gitlin, et al., Nature, 2002, 418:430-434.
Goeddel, et al., Nucleic Acids Res., 1980, 8:4057.
Gonzalez-Alegre, et al., Ann Neurol., 2003, 53:781-787.
Gonzalez-Alegre, et al., J Neurosci., 2005; 25(45):10502-9.
Goodchild, et al., Mov. Disord., 2002, 17(5):958, Abstract.
Goto, et al., "Suppression of Huntingtin Gene Expression by siRNA: A Possible Therapeutic Tool for Huntington's Disease", Neurology, 60(5), Suppl 1, p. A286, Abstract P04.055, 2003.
Grishok, et al., Science, 2000, 287:2494-2497.
Hamilton and Baulcombe, Science, 1999, 286:950-952.
Hammond, et al., Nat Rev Genet. 2001;2(2):110-119.
Hammond, et al., Nature, 2000, 404:293-296.
Hannon, Nature, 2002, 418:244-251.
Haque, et al., Exp Neurol. 1997; 144; 139-46.
Harborth, et al., Journal of Cell Science, 2001, 114:4557-4565.
Hardy, et al., "The amyloid hypothesis of Alzheimer's disease: progress and problems on the road to therapeutics", Science, 2002. 297(5580): p. 353-6.
Harper, et al., Meth Mol Biol, 309:219-236 (2005).
Harper, et al., "RNA interference improves motor and neuropathological abnormalities in a Huntington's disease mouse model", PNAS, vol. 102, 5820-5825 (2005).
Hasholt, et al., J Gene Med. 2003;5(6):528-38.
Hewett, et al., Hum. Mol. Gen., 2000, 9:1403-1413.
Higgins, et al., Cabios, 1989, 5:151.
Higgins, et al., Gene, 1988, 73:237.
Hilberg, et al., PNAS, 1987, 84:5232.
Smith, et al., Adv. Appl. Math., 1981, 2:482.
Song, et al., Nat. Med., 2003, 9:347-351.
Stein, et al., J. Virol., 1999, 73:3424-3429.
Stein, et al., RNA, 2003, 9(2):187-192.
Sui, et al., PNAS, 2002, 99:(8)5515-5520.
Svoboda, et al., Development, 2000, 127:4147-4156.
Tabara, et al., Cell, 1999, 99:123-132.
Tanemura, et al., J. Neurosci., 2002, 22(1):133-141.
Tang, et al., Genes Dev., 2003, 17(1):49-63.
Temin, "Retrovirus vectors for gene transfer", Gene Transfer, Kucherlapati R, Ed., pp. 149-187, Plenum, 1986.
Tijsterman, et al., Cell, 2004; 117(1):1-3.
Timmons, et al., Nature, 1998, 395:854.
Tritz, et al., "Screening Promoters for Optimal Expression of Ribozymes", 1999, pp. 115-123, in Intracellular Ribozyme Applications: Principles and Protocols, Horizon Scientific Press.
Trottier, et al., Nature, 1995, 378(6555):403-406.
Turner, et al., Mol. Biotech., 1995, 3:225.
Tuschl, Nat. Biotechnol., 2002, 20:446-448.
Valerio, et al., Gene, 1989, 84:419.
Verma, et al., Nature, 1997, 389:239-242.
Victor, et al., EMBO Reports, 3(1), pp. 50-55,2002.
Viera, et al., Meth. Enzymol., 1987, 153:3.
Wagner, et al., Nature, 1998, 391:744-745.
Walker, et al., Neurology, 2002, 58:120-124.
Waterhouse, et al., PNAS, 1998, 95:13959-13964.
Wianny, et al., Nat. Cell Biol., 2000, 2:70-75.
Xia, et al., Nat Med, 10(8):775-776 (2004).
Xia, et al., Nat. Biotechnol., 2001, 19:640-644.
Xia, "RNAi suppresses polyglutamine-induced neurodegeneration in a model of spinocerebellar ataxia", Nature Medicine, 10, 816-820 (4 supplementary pages), (2004).
Xia, et al., "siRNA-mediated gene silencing in vitro and in vivo", Nature Biotechnology, vol. 20, pp. 1006-1010, 2002.
Xiao, et al., Journal of Virology, 73(5), pp. 3994-4003, 1999.
Yamamoto, et al., Cell, 2000, 101(1):57-66.
Yang, et al., Molecular and Cellular Biology, 2001, 21:7807-7816.
Yu, et al., PNAS., 2002, 99:(9)6047-6052.
Yu, et al., "Mutant Huntingtin causes contex-dependent neurodegenration in mice with Huntington's Disease", Journal of Neuroscience, vol. 23, pp. 2193-2202, 2003.
Zamore, et al., Cell, 2000, 101:25-33.
Zeng, et al., PNAS, 2003, 100(17):9779-9784.
Zeng, et al., RNA, 2003, 9(1), 112-123.
Zoghbi and On, Annu. Rev. Neurosci., 2000, 23:217-247.

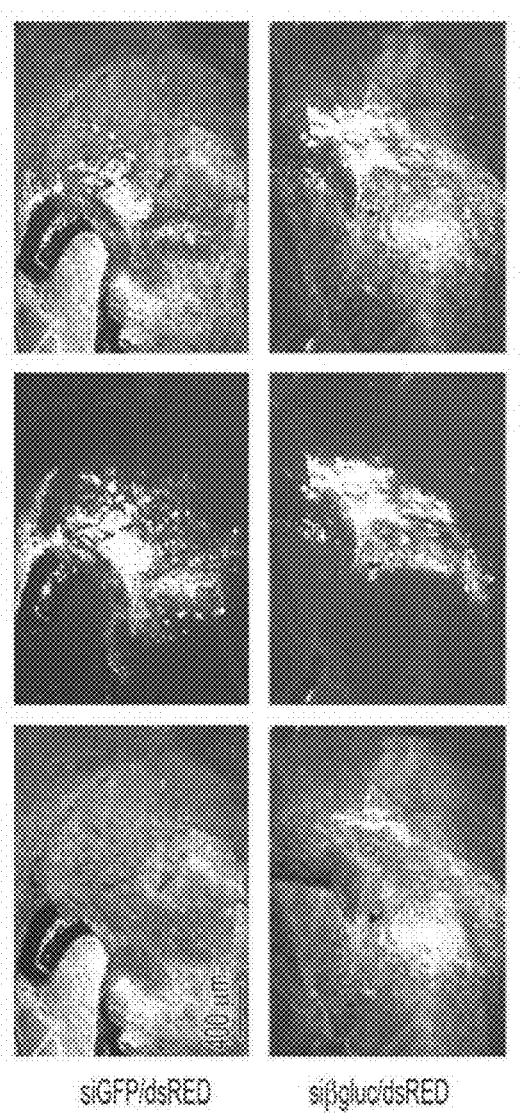

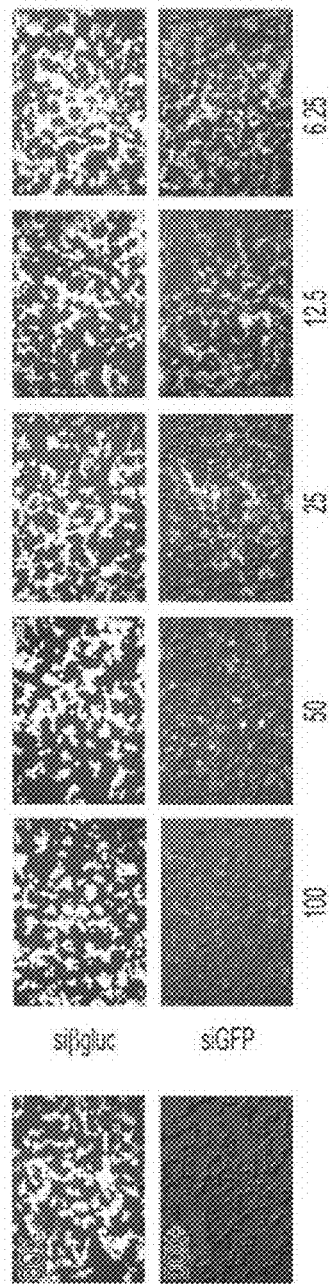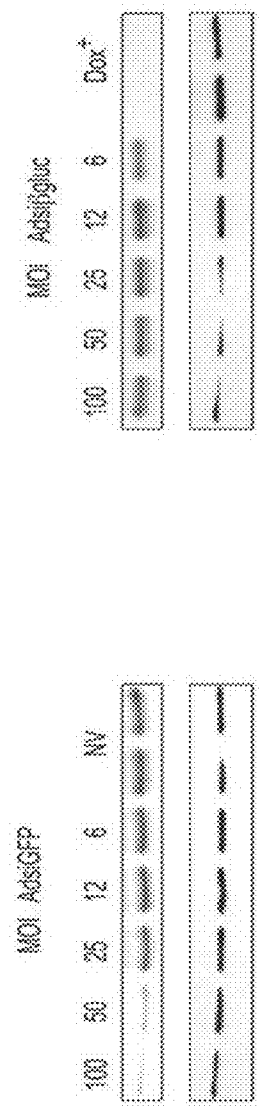
FIG. 3A
FIG. 3B
FIG. 3C

FIG. 17

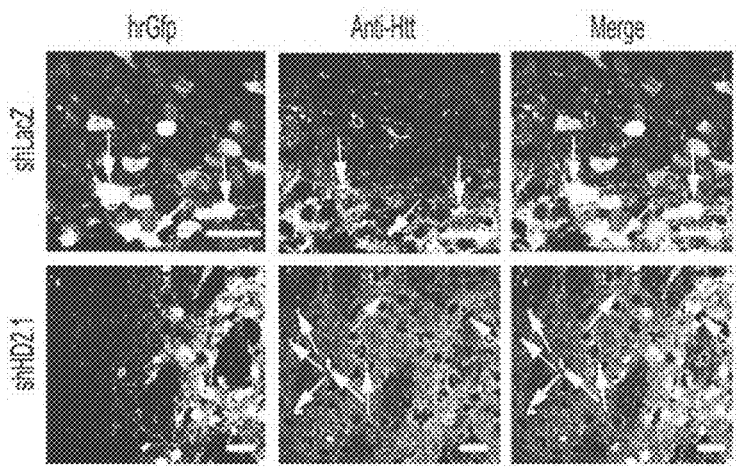
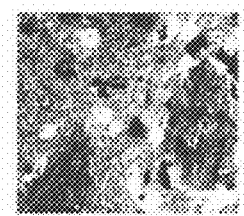
FIG. 28A                FIG. 28B
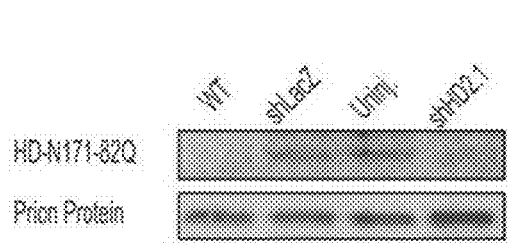
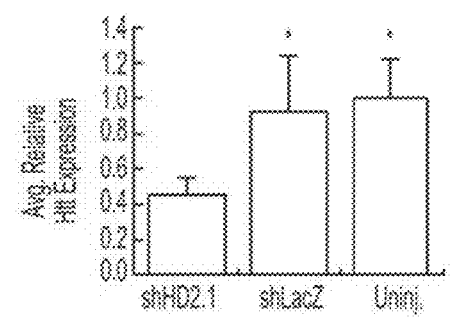
FIG. 28C                FIG. 28D
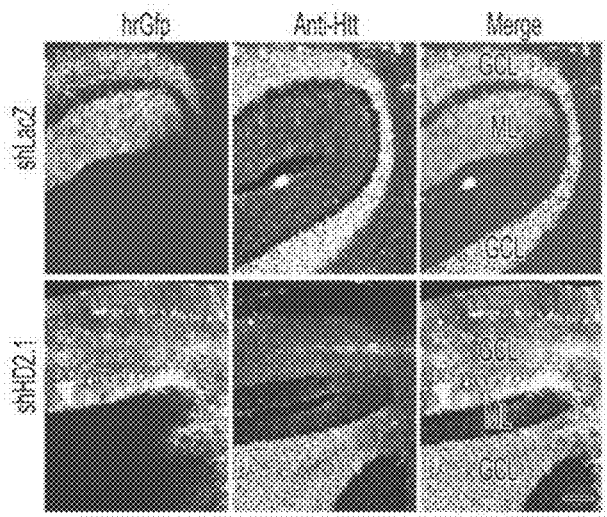
FIG. 28E

FIG. 30

| FIG. 35A |
|---|
| FIG. 35B |
| FIG. 35C |
| FIG. 35D |
| FIG. 35E |
| FIG. 35F |
| FIG. 35G |
| FIG. 35H |
| FIG. 35I |
| FIG. 35J |
| FIG. 35K |
| FIG. 35L |

FIG. 35

Key: Exons are alternating Italics BLUE and regular BLACK text.
M1 = start codon
Underlined nucleotides are sense sequences used to generate shRNAs
Red labeled shRNAs reduce Htt gene expression in HEK293 cells
Yellow highlight is CAG repeat region (only 2 human repeats in this sequence)

ClustalW (v1.4)

1. hHunt normal 19Qs cDNA vs. Mouse huntingtin full-length

```
hHunt normal 19                                     GCTGCCGGGACGGGTCCAAGATGGAC hHunt normal 19    GGCGGCTCAGGTTCTGCTTTTACCTGCGGCCCAGCGCCGCGAGTCGGCCC
Mouse huntingti    CCCATTCATTGCCTTGCTGCTAAGTGGCGCCGCGTAGTGCCAGTAGGCTC M1
hHunt normal 19    GAGGCCTCCGGGGACTGCCGTGCCGGGCGGAGAGCCCATGGCGGACCCT
Mouse huntingti    CAAGTCTTCAGGGTCTGTCCCATCGGGCACGAAGCCGTCATGGCAACCCT     shHD1.3
                        shHD1.1                   shHD1.2 hHunt normal 19    GGAAAAGCTGATGAAGGCCTTCGAGTCCCTCAAGTCCTTCCAGCAGCAAC
Mouse huntingti    GGAAAAGCTGATGAAGGCCTTCGAGTCGCTCAAGTCGTTTCAGCAGCAAC
                   *********************** ** ********** * ********
                             shHD1.4              shHD1.5 hHunt normal 19    AGCCGCCACCGCCGCCGCCGCCGCCGCCTCCTCAGCTTCCTCAGCCG
Mouse huntingti    AGCAGCAGCAGCCACCGCCGCAGCCGCCGCCACC---GCCGCCGCCGCCT
                   *** ** ** ** ******* ********** **     ** ** * ***
                        shHD1.6 hHunt normal 19    CCGCCCAGGCACAGCCGCTGCTGCTCAGCCGCAGCCGCCCCGCCGCC
Mouse huntingti    CCGCCTCAACCCCCTCAGCCGCCGCCTCAGGGGCAGCCGCC---GCCGCC
                   ***** ** * **  ****** *** ***  ********     ******
                              shHD1.7 hHunt normal 19    GCCCCGCCGCCACCCGGCCCGGCTGTGGCTGAGGAGCCGCTGCACCGAC
Mouse huntingti    ACCACCGGCCGCTGCCAGGTCCGGC------AGAGGAACCGCTCACCGAC
                   **  *****   ** ** *****        ***** ***** ******
                                   shHD1.8         shHD1.9 hHunt normal 19    CAAAGAAAGAACTTTCAGCTACCAAGAAAGACCGTGTGAATCATTGTCTG
Mouse huntingti    CAAAGAAGGAACTCTCAGCCACCAAGAAGACCGTGTGAATCATTGTCTA
                   ******* ***** ***** ******** *** ***************
                            ShHD2.1
                      ShHD2.2              ShHD2.3
                                               ShHD2.4
                                              Exon 3 hHunt normal 19    ACAATATGTGAAAACATAGTGGCACAGTCTGTCAGAAATTCTCCAGAATT
Mouse huntingti    ACAATATGTGAAAACATTGTGGCACAGTCTCTCAGAAATTCTCCAGAATT
                   ***************** ************ *******************
                     ShHD2.5             shHD2.6 hHunt normal 19    TCAGAAACTTCTGGCATCGCTATGGAACTTTTTCTGCTGTGCAGTGATG
Mouse huntingti    TCAGAAACTCTTGGCATCGCTATGGAACTGTTTCTGCTGTGCAGTGACC
                   ********* * ***************** ***************** *
                                      shHD3.1 hHunt normal 19 362 ACGCAGAGTCAGATGTCAGGATGGTGGCTGACGAATGCCTCAACAAAGTT
Mouse huntingti    ATGCGCAGTCAGATGTCAGAATGGTGGCTGATGAGTGCCTCAACAAGTC
                   *  ** ************* ********** ** ************
                           Exon 4                    ShHD3.2
hHunt normal 19    ATCAAAGCTTTGATGGATTCTAATCTTCCAAGGTTACAGCTCGAGCTCTA
Mouse huntingti    ATCAAAGCTTTGATGGATTCTAATCTTCCAAGGCTACAGTTAGAGCTCTA
                   ********************************* ***** * ********
                             shHD4.1              Exon 5
hHunt normal 19    TAAGGAAATTAAAAAGAATGGTGCCCCTCGGAGTTTGCGTGCTGCCCTGT
Mouse huntingti    TAAGGAAATTAAAAAGAATGGTGCTCCTCCGAAGTTTGCGTGCTGCCCTGT
                   ************************ ****  ** *****************
```

FIG. 35A

```
hHunt normal 19    GGAGGTTTGCTGAGCTGGCTCACCTGGTTCGGCCTCAGAAATGCAGGCCT
Mouse huntingti    GGAGGTTTGCTGAGCTGGCTCACCTGGTTCGACCTCAGAAGTGCAGGCCT
                   ***************************** ********* ********
                                          Exon 6
hHunt normal 19    TACCTGGTGAACCTTCTGCCGTGCCTGACTCGAACAAGCAAGAGACCCGA
Mouse huntingti    TACCTGGTGAATCTTCTTCCATGCCTGACCCGAACAAGCAAAAGACCGGA
                   ********* *  ******* ****** * hHunt normal 19    AGAATCAGTCCAGGAGACCTTGGCTGCAGCTGTTCCCAAAATTATGGCTT
Mouse huntingti    GGAATCAGTTCAGGAGACCTTGGCTGCAGCTGTTCCTAAAATTATGGCTT
                    ******** ************************** ************
                                                               Exon 7
hHunt normal 19    CTTTTGGCAATTTTGCAAATGACAATGAAATTAAGGTTTTGTTAAAGGCC
Mouse huntingti    CTTTTGGCAATTTCGCAAATGACAATGAAATTAAGGTTCTGTTGAAAGCT
                   *********** ********************   ** hHunt normal 19    TTCATAGCGAACCTGAAGTCAAGCTCCCCCACCATTCGGCGGACAGCGGC
Mouse huntingti    TTCATAGCAAACTGAAGTCAACCTCTCCCACCCGGCGGACAGCAGC
                   ****** * ****** * ****** * ******** hHunt normal 19    TGGATCAGCAGTGAGCATCTGCCAGCACTCAAGAAGGACACAATATTTCT
Mouse huntingti    CGGCTCAGCCGTGAGCATCTGCCAACATTCTAGGAGGACACAGTACTTCT
                    ** ***** ************** ** *** * ******** ** ****
                                                            Exon 8
hHunt normal 19    ATAGTTGGCTACTAAATGTGCTCTTAGGCTTACTCGTTCCTGTCGAGGAT
Mouse huntingti    ACAACTGGCTCCTTAATGTCCTCCTAGGTCTGCTGGTTCCCATGGAAGAA
                   *  *  ***   **** *  *    **   ** hHunt normal 19    GAACACTCCACTCTGCTGATTCTTGGCGTGCTGCTCACCCTGAGGTATTT
Mouse huntingti    GAGCACTCCACTCTCCTGATCCTCGGTGTGTTGCTCACATTGAGGTGTCT
                    ******* *   * ****  **** * * hHunt normal 19    GGTGCCCTTGCTGCAGCAGCAGGTCAAGGACACAAGCCTGAAAGGCAGCT
Mouse huntingti    AGTGCCCTTGCTCCAGCAGCAGGTCAAGGACACAAGTCTAAAAGGCAGCT
                    *********** *********************** ** *********
                                           shHD8.1
hHunt normal 19    TCGGAGTGACAAGGAAAGAAATGGAAGTCTCTCCTTCTGCAGAGCAGCTT
Mouse huntingti    TTGGGGTGACACGGAAAGAAATGGAAGTCTCTCCTTCTACAGAGCAGCTT
                   * ** ****** ************************* ***********
                                   Exon 9
hHunt normal 19    GTCCAGGTTTATGAACTGACGTTACATCATACACAGCACCAAGACCACAA
Mouse huntingti    GTCCAGGTTTATGAACTGACTTTGCATCATACTCAGCACCAAGACCACAA
                   ******************** ** ******** *****************
                   shHD8.2
hHunt normal 19    TGTTGTGACCGGAGCCCCTGGAGCTGTTGCAGCAGCTCTTCAGAACGCCTC
Mouse huntingti    TGTGGTGACAGGGGCACTGGAGCTCCTGCAGCAGCTCTTCCGTACCCCTC
                   *  *   **   ********* *  *  ** hHunt normal 19    CACCCGAGCTTCTGCAAACCCTGACCGCAGTCGGGGGCATTGGGCAGCTC
Mouse huntingti    CACCTGAACTCCTGCAAGCACTGACCACACCAGGAGGGCTTGGGCAGCTC
                   **   **** * ****      *********** hHunt normal 19    ACCGCTGCTAAGGAGGAGTCTGGTGGCCCGAAGCCGTAGTGGGAGTATTGT
Mouse huntingti    ACTCTGGTTCAAGAAGAGGCCCGGGGCCGAGGCCGCAGCGGGAGCATCGT
                   **    * *  ** *** *    * ****** **** ** ***** ** **
                                                  Exon 10
hHunt normal 19    GGAACTTATAGCTGGAGGGGGTTCCTCATGCAGCCCTGTCCTTTCAAGAA
Mouse huntingti    GGAGCTTTTAGCTGGAGGGGGTTCCTCGTGCAGCCCTGTCCTCTCAAGAA
                   *** *** ******************* ************** *******
                        Exon 11
hHunt normal 19    AACAAAAGGCAAAGTGCTCTTAGGAGAAGAAGAAGCCTTGGAGGATGAC
Mouse huntingti    AGCAGAAGGCAAAGTGCTCTTAGGAGAGGAAGAAGCCTTGGAAGATGAC
                   * ** ********************** ************** ******
                                                               Exon 12
hHunt normal 19    TCTGAATCGAGATCGGATGTCAGCAGCTCTGCCTTAACAGCATCTCAGA
Mouse huntingti    TCGGAGTCCAGATCAGATGTCAGCAGCTCAGCCTTTGCAGCCTCTGTGAA
                      * ********** *   * * ** hHunt normal 19    GGATGAGATCAGTGGAGAGCTGGCTGCTTCTTCAGGGGTTCCACTCCAG
Mouse huntingti    GAGTGAGATTGGTGGAGAGCTCGCTGCTTCTTCAGGTGTTTCCACTCCTG
                   * ******* ***********  ************* ***  ****** *
```

```
                    ************ *** ************ ******** *** *
                                                    Exon 18
hHunt normal 19     TGGGAGATTGGATGGGCACCATTAGAACCCTCACACGGAAATACATTTTCT
Mouse huntingti     TTGGTGAGTGGCTGGGCAACATCAGAACCCTGACAGGGAAATACATTTTCT
                    *   *  * ****** ******* ****** hHunt normal 19     TTGGCGGATTGCATTCCTTTGCTGCGGAAAACACTGAAGGATGAGTCTTC
Mouse huntingti     CTGGTGGACTGCATTCCTTTACTGCAGAAAACGTTGAAGGATGAATCTTC
                    *** *** ************ **** ****** ********** *****
                                                    Exon 19
hHunt normal 19     TGTTACTTGCAAGTTAGCCTTGTACAGCTGTGAGGAACTGTGTCATGAGTC
Mouse huntingti     TGTTACTTGCAAGTTGGCTTGTACAGCTGTGAGGCACTGTGTCCTGAGTC
                    *************  ************* **** **** hHunt normal 19     TCTGCAGCAGCAGCTACAGTGAGTTAGGACTGCAGCTGATCATCGATGTG
Mouse huntingti     TTTGCAGCAGCAGCTACAGTGACTTGGGATTACAACTGCTTATTGATATG
                    * *****************  *** *  * hHunt normal 19     CTGACTCTGAGGAACAGTTCCTATTGGCTGGTGAGGACAGAGCTTCTGGA
Mouse huntingti     CTGCCTCTGAAGAACAGCTCCTACTGGCTGCTGAGGACCGAACTGCTGGA
                    *** ****** ****** ***** ****** ******* ** ** *****
                                                    Exon 20
hHunt normal 19     AACCCTTGCAGAGATTGACTTCAGGCTGGTGAGCTTTTGGAGGCAAAAG
Mouse huntingti     CACTCTTGCAGAGATTGACTTCAGGCTCGTGAGTTTTTGGAGGCAAAAG
                    ** ** ********************* ***** *** ***********
                                                    Exon 21
hHunt normal 19     CAGAAAACTTACACAGAGGGGCTCATCATTATACAGGGCTTTTAAAACTG
Mouse huntingti     CAGAAAGTTTACACCGAGGGGCTCATCATTATACAGGGTTTCTAAAACTA
                    ****  *** ******************  ******* hHunt normal 19     CAAGAACGAGTGCTCAATAATGTTGTCATCCATTTGCTTGGAGATGAAGA
Mouse huntingti     CAAGAACGAGTACTCAATAATGTGGTCATTTATTTGCTTGGAGATGAAGA
                    *********** *********** ***** * ******************
                                                              Exon 22
hHunt normal 19     CCCCAGGGGTGCGACATGTTGCCGCAGCATCACTAATTAGGCTTGTCCAA
Mouse huntingti     CCCCAGGGGTTCGACATGTTGCCGCAACATCATTAACAAGGCTTGTCCCAA
                    ******** *********** * *  ******** hHunt normal 19     AGCTGTTTTATAAATGTGACCAAGGACAAGCTGATCCAGTAGTGGCCGTG
Mouse huntingti     AGCTGTTTTACAAGTGTGA<u>CCAAGGACAAGCTGATCCAGT</u>TGTGGCTGTA
                    ********** ** ***** ********************* ***** **
                                                    shHD22.1
hHunt normal 19     GCAAGAGATCAAAGCAGTGTTTACCTGAAACTTCTCATGCATGAGACGCA
Mouse huntingti     GCGAGGGATCAGAGCAGTGTCTACCTGAAGCTCCTCATGCATGAGACCCA
                    ** ** ***** ******** ******** ** ************ **
                                                    Exon 23
hHunt normal 19     GCCTCCATCTCATTTCTCCGTCAGCACAATAACCAGAATATATAGAGGCT
Mouse huntingti     GCCACCATCACACTTTTCTGTCAGCACCATCACCAGAATCTATAGAGGCT
                    * *    ******  ****** ******** hHunt normal 19     ATAACCTACTACCAAGCATAACAGAACGTCACTATGGAAAATAACCTTCA
Mouse huntingti     ATAGCCTTACTGCCAAGTATAACAGATGTCACCATGGAAACAATCTCTCA
                    * *  * **** * **** hHunt normal 19     AGAGTTATTGCAGCAGTTTCTCATGAACTAATACACATCAACCACCAGAGC
Mouse huntingti     AGAGTTGTTGCCGCAGTTTCTCATGAACTCATTACGTCAACAACACGGGC
                    ****** *** ***************** ** ** **** ** ** **
                                                    Exon 24
hHunt normal 19     ACTCACATTTGCATGCTGTGAAGCTTTGTGTCTTCTTTCCACTGCCTTCC
Mouse huntingti     ACTCACATTTGGATGCTGTGAAGCCTTGTGTCTTCTCTCAGCAGCCTTTC
                    *********** ************ *********** **  ** ***** *
                                                    Exon 25
hHunt normal 19     CAGTTTGCATTTGGAGTTTAGGTTGGCACTGTGGAGTGCCTCCACTGAGT
Mouse huntingti     CAGTTTGCACTTGGAGTTTAGGATGCCACTGTGGAGTGCCCCCACTGAGT
                    ******* ********  ************ ****** hHunt normal 19     GCCTCAGATGAGTCTACGAACAGCTCTACCCGTTGGGATGCCCACAATGAT
Mouse huntingti     GCCTCTGATGAGTCCAGGAAGAGCTGCACTGTTGGGATGGCCTCCATGAT
                    *** ****  * **  *****   *** hHunt normal 19     TCTGACCCTGCTCTCGTCAGCTTGGTTCCCATTGGATCTCTCAGCCCATC
Mouse huntingti     TCTCACCCTTGCTTTCATCAGCTTGGTTCCCACTGGATCTCTCAGCCCATC
                    *** ***** *** ** ************** ******************
```

FIG. 35D

```
                                    ***  ***  ****  **  ****************  *******************
                                                                                      Exon 26
hHunt normal 19      AAGATGCTTTGATTTTGGCCCGAAACTTGCTTGCAGCCAGTGCTCCCAAA
Mouse huntingti      AGGATGCCTTGATTTTGGCTGGAAACTTGCTAGCAGCGAGTGCCCCCAAG
                     * *** ***** ******** * ** * *** hHunt normal 19      TCTCTGAGAAGTTCATGGGCCTCTGAAGAAGAAGCCAACCCAGCAGCCAC
Mouse huntingti      TCTCTGAGAAGTTCATGGACCTCTGAAGAAGAAGCCAACTCAGCAGCCAC
                     **************** *************** ******* hHunt normal 19      CAAGCAAGAGGAGGTCTGGCCAGCCCTGGGGGACCGGCCCTGGTGCCCA
Mouse huntingti      CAGACAGGAGGAAATCTGGCCTGCTCTGGGGATCGGACTCTAGTGCCCT
                          ***  ***   ******  *  *    ***** hHunt normal 19      TGGTGGAGCAGCTCTTCTCTCACCTGCTGAAGGTGATTAACATTTGTGCC
Mouse huntingti      TGGTGGAGCAGCTTTTCTCCCACCTGCTGAAGGTGATCAATATCTGTGCT
                     ************* ***** ***************** **  ** *****
                                                                                      Exon 27
hHunt normal 19      CACGTCCTGGATGACGTGGCTCCTGGACCCGCAATAAAGGCAGCCTTGCC
Mouse huntingti      CATGTCTTGGACGATGTGACTCCTGGACCAGCAATCAAGGCAGCCTTGCC
                      * ***  * **** * ************ hHunt normal 19      TTCTCTAACAAACCCCCCTTCTCTAAGTCCCATCCGACGAAAGCGGAAGG
Mouse huntingti      TTCTCTAACAAACCCCCCTTCTCTAAGTCCTATTCGACGGAAAGGGAAGG
                     ****************************   *** * **** hHunt normal 19      AGAAAGAACCAGGAGAACAAGCATCTGTACCGTTGAGTCCCAAGAAAGGC
Mouse huntingti      AGAAAGAACCTGGAGAACAAGCTTCTACTCCAATGAGTCCCAAGAAAGTT
                     ********** *********** ***   **  ** ****************
                                        Exon 28
hHunt normal 19      AGTGAGGCCAGTGCAGCTTCTAGACAATCTGATACCTCAGGTCCTGTTAC
Mouse huntingti      GGTGAGGCCAGTGCAGCCTCTCGACAATCAGACACCTCAGGACCTGTCAC
                     *************** *  *****  ****** * hHunt normal 19      AACAAGTAAATCCTCATCACTGGGGAGTTTCTATCATCTTCCTTCATACC
Mouse huntingti      AGCAAGTAAATCATCCTCACTGGGGAGTTTCTACCATCTCCCCTCCTACC
                     * ********   *************  *    ** hHunt normal 19      TCAAACTGCATGATGTCCTGAAAGCTACACACGCTAACTACAAGGTCACG
Mouse huntingti      TCAAACTGCATGATGTCCTGAAAGCCACTCACGCCAACTATAAGGTCACC
                     ************************* **  *****  *******  *********
                              shHD28.1                             Exon 29
hHunt normal 19      CTGGATCTTCAGAACAGCACGGAAAAGTTTGGAGGGTTTCTCCGCTCAGC
Mouse huntingti      TTAGATCTTCAGAACAGCACTGAAAAGTTTGGGGGGTTCCTGCGCTCTGC
                     * **************** ******  *   ** hHunt normal 19      CTTGGATGTTCTTTCTCAGATACTAGAGCTGGCCACACTGCAGGACATTG
Mouse huntingti      CTTGGACGTCCTTTCTCAGATTCTAGAGCTGGCGACACTGCAGGACATTG
                     ****** ** *********** *********** *****************
                           Exon 30
hHunt normal 19      GGAACTGTGTTGAAGAGATCCTAGGCATACCTGAAATCCTGCTTTAGTCGA
Mouse huntingti      GAAAGTGTGTTGAAGAGGTCCTTGGATACCTGAAATCCTGCTTTAGTCGA
                     *  ** ***********  ****  **  *************************
                                                    shHD30.1   Exon 31
hHunt normal 19      GAACCAATGATGGCAACTGTTTGTGTTCAACAATTGTTGAAGACTCTCTT
Mouse huntingti      GAACCAATGATGGCAACTGTCTGTGTCCAGCAGCTATTGAAGACTCTCTT
                     ****************** *      ************* hHunt normal 19      TGGCACAAACTTGGCCTCCCAGTTTGATGGCTTATCTTCCAACCCCAGCA
Mouse huntingti      TGGCACAAACTTAGCCTCACAGTTTGATGGCTTATCTTCCAACCCCAGCA
                     * **** * ******************************* hHunt normal 19      AGTCACAAGGCCGAGCACAGCGCCTTGGCTCCTCCAGTGTGAGGCCACGC
Mouse huntingti      AGTCTCAGTGCCGAGCTCAGCGCCTTGGCTCTTCAAGTGTGAGGCCGGGC
                     **   ****** *********  ********* * hHunt normal 19      TTGTACCACTACTGCTTCATGGCCCCGTACACCCACTTCACCCAGGCCCT
Mouse huntingti      TTATATCACTACTGCTTCATGGCACCATACACGCACTTCACACAGGCCCT
                       ***************   **  **** ***** * hHunt normal 19      CGCTGACGCCAGCCTGAGGAACATGGTGCAGGCGGAGCAGGAGAACGACA
```

```
Mouse huntingti    GCTGTGGATATCTGGAATCCTCGCCATTCTGAGGGTTCTCATTCCCAGT
                   ********** *  **** ******* ******** hHunt normal 19    CAACTGAAGATATTGTTCTTTCTCGTATTCAGGAGCTCTCCTTCTCTCCG
Mouse huntingti    CAACCGAGGACATTGTTCTTTGTCGTATTCAGGAGCTCTCCTTCTCTCCA
                   **   ****** ************************** hHunt normal 19    TATTTAATCTCCTGTACAGTAATTAATAGGTTAAGAGATGGGGACAGTAC
Mouse huntingti    CACTTGCTCTCCTGTCCAGTGATTAACAGGTTAAGGGGTGGAGGCGGTAA
                     * ** ******** **** ***** ********  * **  *   **
                                        Exon 40
hHunt normal 19    TTCAACGCTAGAAGAACACAGTGAAGGGAAACAAATAAAGAATTTGCCAG
Mouse huntingti    TGTAACACTAGGACAATGCAGCGAAGGGAAACAAA---AGAGTTTGCCAG
                   *  *** ****  **    ***  ***********    *** *******
                                        Exon 40
hHunt normal 19    AAGAAACATTTTCAAGGTTTCTATTACAACTGGTTGGTATTCTTTTAGAA
Mouse huntingti    AAGATACATTCTCAAGRTTTCTTTTACAGCTGGTTGGTATTCTTCTAGAA
                   ** * * * * ********** *** hHunt normal 19    GACATTGTTACAAAACAGCTGAAGGTGGAAATGAGTGAGCAGCAACATAC
Mouse huntingti    GACATCGTTACAAAACAGCTCAAAGTGGACATGAGTGAACAGCAGCATAC
                   *** **********  *** **** * *** hHunt normal 19    TTTCTATTGCCAGGAACTAGGCACACTGCTAATGTGTCTGATCCACATCT
Mouse huntingti    GTTCTACTGCCAAGAGCTAGGCACACTGCTCATGTGTCTGATCCACATAT
                   ***** ****** ** ************** ***************** *
                                         Exon 41
hHunt normal 19    TCAAGTCTGGAATGTTCCGGAGAATCACAGCAGCTGCCCACTAGGCTGTTC
Mouse huntingti    TCAAATCTGGAATGTTCCGGAGAATCACAGCAGCTGCCACTAGACTCTTC
                   ****  ********************************** **** ** **
                                       shHD40.1
hHunt normal 19    CGCAGTGATGGCTCTGTGCGGCAGTTTCTACACCCTGGACAGCTTGAACTT
Mouse huntingti    ACCAGTGATGGCTGTGAAGGCAGCTTCTATACTCTAGAGAGCCTGAATGC
                    ******   ****      *  ** hHunt normal 19    GCGGCTCGTTCCATGATCACCACCCACCCGGCCCTGGTGCTGCTCTGT
Mouse huntingti    ACGGGTCCGATCCATGGTGCCCACGCACCCAGCCCTGGTACTGCTCTGT
                   **   ****** *  ** * *** ******* hHunt normal 19    GTCAGATACTGCTGCTTGTCAACCACACCGACTACCGCTGGTGGGCAGAA
Mouse huntingti    GTCAGATCCTACTTCTCATCAACCACACTGACCACCGGTGGTGGGCAGAG
                   ******* ** ** ** * ********* *** ***** **********
                                           Exon 42
hHunt normal 19    GTGCAGCAGACCCCGAAAAGACACAGTCTGTCCAGCACAAAGTTACTTAG
Mouse huntingti    GTGCAGCAGACCACCAAGAGACACAGTCTGTCCTGCACGAAGTCACTTAA
                   **********     ************   *** * hHunt normal 19    TCCCCAGATGTCTGGAGAAGAGGAGGATTCTGACTTGGCAGCCAAACTTG
Mouse huntingti    CCCCCAGAAGTCTGGCGAAGAGGAGGATTCTGGCTCGGCAGCTCAGCTGG
                   ***** ** *************  ****** * ** * hHunt normal 19    GAATGTGCAATAGAGAAATAGTACGAAGAGGGGCTCTCATTCTCTTCTGT
Mouse huntingti    GAATGTGCAATAGAGAAATAGTGCGAAGAGGGGCCCTTATTCTCTTCTGT
                   ********************** ********** ** ************
                        shHD42.1    Exon 43                shHD42.2
hHunt normal 19    GATTATGTCTGTCAGAACCTCCATGACTCCGAGCACTTAACGTGGCTCAT
Mouse huntingti    GATTATGTCTGTCAGAATCTCCATGACTCAGAACACTTAACATGGCTCAT
                   *************** *******  ****** ***** hHunt normal 19    TGTAAATCACATTCAAGATCTGATCAGCCTTTCCCACGAGCCTCCAGTAC
Mouse huntingti    TGTGAATCACATTCAAGATCTGATCAGCTTGTCTCATGAGCCTCCAGTAC
                   * ********************** *  ** * ************* hHunt normal 19    AGGACTTCATCAGTGCCGTTCATCGGAACTCTGCTGCCAGCGGCCTGTTC
Mouse huntingti    AAGACTTTATTAGTGCCATTCATCGTAATTCTGCAGCTAGTGGTCTTTTT
                   * ***  **** ***  *** hHunt normal 19    ATCCAGGCAATTCAGTCTCGTTGTGAAAAACCTTTCAACTCCAACCATGCT
Mouse huntingti    ATCCAGGCAATTCAGTCTCGCTCTGAAAATCTTTCAACGCCAACCACTCT
                   ******************** * **** **** **  * hHunt normal 19    GAAGAAAACTCTTCAGTGCTTGGAGGGGATCCATCTCAGCCAGTCGGGAG
```

FIG. 35G

```
Mouse huntingti      GAAGAAAACACTTCAGTGCTTGGAAGGCATCCATCTCAGCCAGTCTGGTG
                     ****** *******   ***************  * hHunt normal 19      CTGTGCTCACGCTGTATGTGGACAGGCTTCTGTGCACCCCTTTCCGTGTG
Mouse huntingti      CTGTGCTCACACTATATGTGGACAGGCTCCTGGGCACCCCCTTCCGTGCG
                     ********  ************ * **** ***** * hHunt normal 19      CTGGCTCGCATGGTCGACATCCTTGCTTGTCGCCGGGTAGAAATGCTTCT
Mouse huntingti      CTGGCTCGCATGGTCGACACCCTGGCCTGTCGCCGGGTAGAAATGCTTTT
                     ***************** *  ****************** * hHunt normal 19      GGCTGCAAATTTACAGAGCAGCATGGCCCAGTTGCCAATGGAAGAACTCA
Mouse huntingti      GGCTGCAAATTTACAGAGCAGCATGGCCCAGTTGCCAGAGGAGGAACTAA
                     ************************ ***** * ***** * hHunt normal 19      ACAGAATCCAGGAATACCTTCAGAGCAGCGGGCTCGCTCAGAGACACCAA
Mouse huntingti      ACAGAATCCAAGAACACCTCCAGAACAGTGGGCTTGCACAAAGACACCAA
                     ******** *  *  * ***   * ******** hHunt normal 19      AGGCTCTATTCCCTGCTGGACAGGTTTCGTCTCTCCACCATGCAAGACTC
Mouse huntingti      AGGCTCTATTCACTGCTGGACAGATTCCGACTCTCTACTGTGCAGGACTC
                     ********* *******   **   ** ** hHunt normal 19      ACTTAGTCCCTCTCCTCCAGTCTCTTCCCACCCGCTGGACGGGGATGGGC
Mouse huntingti      ACTTAGCCCCTTGCCCCCAGTCACTTCCCACCCACTGGATGGGGATGGGC
                     **** *  ** ****** ** ******** hHunt normal 19      ACGTGTCACTGGAAACAGTGAGTCCGGACAAAGACTGGTACGTTCATCTT
Mouse huntingti      ACACATCTCTGGAAACAGTGAGTCCAGACAAAGACTGGTACCTCCAGCTT
                     **  * * ************** ************** *  * hHunt normal 19      GTCAAATCCCAGTGTTGGACCAGGTCAGATTCTGCACTGCTGGAAGGTGC
Mouse huntingti      GTCAGATCCCAGTGTTGGACCAGATCAGATTCTGCACTGCTGGAAGGTGC
                     ** ************** ************************ hHunt normal 19      AGAGCTGGTGAATCGGATTCCTGCTGAAGATATGAATGCCTTCATGATGA
Mouse huntingti      AGAGCTGGTCAACCGTATCCCTGCTGAAGATATGAATGACTTCATGATGA
                     *******    ****************  ********* hHunt normal 19      ACTCGGAGTTCAACCTAAGCCTGCTAGCTCCATGCTTAAGCCTAGGGATG
Mouse huntingti      GCTCGGAGTTCAACCTAAGCCTTTTGGCTCCCTGTTTAAGCCTTGGCATG
                     ********************  * ***  *******  *** hHunt normal 19      AGTGAAATTCTGGTGGCCAGAAGAGTGCCCTTTTTGAAGCAGCCCGTGA
Mouse huntingti      AGCGAGATTGCTAATGGCCAAAAGAGTCCCCTCTTTGAAGCAGCCCGTGG
                       *   **** **  ************** hHunt normal 19      GGTGACTCTGGCCCCGTGTGAGCGGCACCGTGCAGCAGCTCCCTGCTGTCC
Mouse huntingti      GGTGATTCTGAACCGGGTGACCAGTGTTGTTCAGCAGCTTCCTGCTGTCC
                     ***   * ****  *  *   *** ******** hHunt normal 19      ATCATGTCTTCCAGCCCGAGCTGCCTGCAGAGCCGGCGGCCTACTGGAGC
Mouse huntingti      ATCAAGTCTTCCAGCCCTTCCTGCCTATAGAGCCCACGGCCTACTGGAAC
                     **  ******* *   **** * ************ * hHunt normal 19      AAGTTGAATGATCTGTTTGGGGATGCTGCACTGTATCAGTCCCTGCCCAC
Mouse huntingti      AAGTTGAATGATCTGCTTGGTGATACCACATCATACCAGTCTCTGACCAT
                     *************  *   *   *** *  ** hHunt normal 19      TCTGGCCCCGGGCCCTGGCACAGTACCTGGTGGTGGTCTCCAAAACTGCCCA
Mouse huntingti      ACTTGCCCGTGCCCTGGCACAGTACCTGGTGGTGCTCTCCAAAGTGCCTG
                       *  ****************** ***** ** hHunt normal 19      GTCATTTGCACCTTCCTCCTGAGAAAGAGAAGGACATTGTGAAATTCGTG
Mouse huntingti      CTCATTTGCACCTTCCTCCTGAGAAGGAGGGGGACACGGTGAAGTTTGTG
                      ********************** *  * * ***  *** hHunt normal 19      GTGGCAACCCTTGAGGCCCTGTCCTGGCATTTGATCCATGAGCAGATCCC
Mouse huntingti      GTAATGACAGTTGAGGCCCTGTCATGGCATTTGATCCATGAGCAGATCCC
                           ****** ********************* hHunt normal 19      GCTGAGTCTGGATCTCCAGGCAGGGCTGGACTGCTGCTGCCTGCCCCTGC
Mouse huntingti      ACTGAGTCTGGACCTCCAAGCCGGGCTAGACTGCTGCTGCCTGGCACTAC
                      *********** ***** ** ***** *************** **
```

FIG. 35H

```
                    ********** ***** ** ***** ****************** ** *
hHunt normal 19     AGCTGCCTGGCCTCTGGAGCGTGGTCTCCTCCACAGAGTTTGTGACCCAC
Mouse huntingti     AGGTGCCTGGCCTCTGGGGGGTGCTGTCCTCCCAGAGTACGTGACTCAT
                     ************* * *** * **** ** * hHunt normal 19     GCCTGCTCCCTCATCTACTGTGTGCACTTCATCCTGGAGGCCGTTGCAGT
Mouse huntingti     GCCTGCTCCCTCATCCATTGTGTGCGATTCATCCTGGAAGCCATTGCAGT
                    *************** * ***** ******** * ******* hHunt normal 19     GCAGCCTGGAGAGCAGCTTCTTAGTCCAGAAAGAAGGACAAATACCCCAA
Mouse huntingti     ACAACCTGGAGACCAGCTTCTCGGTCCTGAAAGCAGGTCACATACTCCAA
                     * ****** ****    *    ** hHunt normal 19     AAGCCATCAGCGAGGAGGAGGAGGAAGTAGATCCAAACACACAGAATCCT
Mouse huntingti     GAGCTGTCAG-------AAAGGAGGAAGTAGACTCAGATATACAAAACCTC
                    *          **********  * *  * hHunt normal 19     AAGTATATCACTGCAGCCTGTGAGATGGTGGCAGAAATGGTGGAGTCTCT
Mouse huntingti     AGTCATGTCACTTCGGCCTGCGAGATGGTGGCAGACATGGTGGAATCCCT
                    *   *** * *** ********** ****  ** hHunt normal 19     GCAGTCGGTGTTGGCCTTGGGTCATAAAAGGAATAGCGGCCGTGCCGGCGT
Mouse huntingti     GCAGTCAGTGCTGGCCTTGGGCCACAAGAGGAACAGCACCCCTGCCTTCAT
                    **** * ********   * *  *  **** * * hHunt normal 19     TTCTCACGCCATTGCTAAGGAACATCATCATCAGCCTGGCCCGCCTGCCC
Mouse huntingti     TTCTCACAGCTGTCGAAGAACATTGTTATCAGTCTGGCCCGACTCCCC
                    ****** * **** * ****** * *** ****  *** hHunt normal 19     CTTGTCAACAGCTACACACGTGTGCCCCACTGGTGTGGAAGCTTGGATG
Mouse huntingti     CTAGTTAACAGCTATACTCGTGTGCCTCCTCTGGTATGGAAACTCGGGTG
                      ******  ******   ** * hHunt normal 19     GTCACCCAAACCGGGAGGGGATTTTGGCACAGCATTCCCTGAGATCCCCG
Mouse huntingti     GTCACCCAAGCCTGGAGGGGATTTTGGCACAGTGTTTCCTGAGATCCCTG
                    *******  *************  ************* * hHunt normal 19     TGGAGTTCCTCCAGGAAAAGGAAGTCTTTAAGGAGTTCATCTACCGCATC
Mouse huntingti     TAGAGTTCCTCCAGGAGAAGGAGATCCTCAAGGAGTTCATCTACCGCATC
                    * ************ *  * ****************** hHunt normal 19     AACACACTAGGCTGGACCAGTCGTACTCAGTTTGAAGAAACTTGGGCCAC
Mouse huntingti     AACACCCTAGGGTGGACCAATCGTACCCAGTTCGAAGAAACTTGGGCCAC
                    *** * *** * * **************** hHunt normal 19     CCTCCTTGGTGTCCTGGTGACGCAGCCCCTCGTGATGGAGCAGGAGGAGA
Mouse huntingti     CCTCCTTGGTGTCCTGGTGACTCAGCCCCTGGTGATGGAACAGGAAGAGA
                    ******************* **** **** * ** hHunt normal 19     GCCCACCAGAAGAAGACACAGAGAGGACCCAGATCAACGTCCTGGCCGTG
Mouse huntingti     GCCCACCAGAGGAAGACACAGAAAGAACCCAGATCCATGTCCTGGCTGTG
                    ******** ******** * * ********** *  ***** * hHunt normal 19     CAGGCCATCACCTCACTGGTGCTCAGTGCAATGACTGTGCCTGTGGCCGG
Mouse huntingti     CAGGCCATCACCTCTCTAGTGCTCAGTGCAATGACCGTGCCTGTGGCTGG
                    ************  *************** ******* hHunt normal 19     CAACCCAGCTGTAAGCTGCTTGGAGCAGCAGCCCCGGAACAAGCCTCTGA
Mouse huntingti     CAATCCAGCTGTAAGCTGCTTGGAGCAACAGCCCCGGAACAAGCCACTGA
                    * ******************* ************  ** hHunt normal 19     AAGCTCTCGACACCAGGTTTGGGAGGAAGCTGAGCATTATCAGAGGGATT
Mouse huntingti     AGGCTCTCGATACCAGATTTGGAAGAAAGCTGAGCATGATCAGAGGGATT
                    * ****** * *  ********* ********** hHunt normal 19     GTGGAGCAAGAGATTCAAGCAATGGTTTCAAAGAGAGAGAATATTGCCAC
Mouse huntingti     GTAGAACAAGAAATCCAAGAGATGGTTTCCCAGAGAGAGAATACTGCCAC
                      ***  **  ****   ******* **** hHunt normal 19     CCATCATTTATATCAGGCATGGGATCCTGTCCCTTCTCTGTCTCCGGCTA
Mouse huntingti     TCACCATTCTCACCAGGCGTGGGATCCTGTCCCTTCTCTGTTACCAGCTA
                    ** ****  * ***** ************************  ** ****
                              Exon 57
```

FIG. 35I

```
hHunt normal 19    CTACAGGTGCCCTCATCAGCCACGAGAAGCTGCTGCTACAGATCAACCCC
Mouse huntingti    CTACAGGTGCTCTTATCAGCCATGACAACAAGCTGCTGCTGCAGATCAACCCA
                   ********** ** ******** ** ************ **********
                                                                   Exon 58
hHunt normal 19    GAGCGGGAGCTGGGGAGCATGAGCTACAAACTCGGCCAGGTGTCCATACA
Mouse huntingti    GAGCGGGAGCCAGGCAACATGAGCTACAAGCTGGGCCAGGTGTCCATACA
                   ********   * **********  ***************** hHunt normal 19    CTCCGTGTGGCTGGGGAACAGCATCACACCCCTGAGGGAGGAGGAATGGG
Mouse huntingti 7880 CTCCGTGTGGCTGGGAAATAACATCACACCCCTGAGAGAGGAGGAATGGG
                   *************** ** * *************** ************
                                                                    shHD58.1
hHunt normal 19    ACGAGGAGGAGGAGGAGGAGGCCGACGCCCCTGCACCTTCGTCACCACCC
Mouse huntingti 7930 ATGAGGAAGAAGAGGAAGAAACTGATGTCCCTGCACCAACGTCACCACCT
                   * ****** ** ***** **  ** * ********* * **********
                   Exon 59           shHD58.2
hHunt normal 19    ACGTCTCCAGTCAACTCCAGGAAACACCGGGCTGGAGTTGACATCCACTC
Mouse huntingti    GTGTCTCCAGTCAATTCCAGAAAACACCGTGCCGGGGTTGATATTCACTC
                    *********** * ****  * *  **** hHunt normal 19    CTGTTCGCAGTTTTTGCTTGAGTTGTACAGCCGCTGGATCCTGCCGTCCA
Mouse huntingti    CTGTTCGCAGTTTCTGCTTGAATTGTACAGCCGATGGATCCTGCCATCCA
                   *********** *** ******* ****** ** hHunt normal 19    GCTCAGCCAGGAGGACCCCGGCCATCCTGATCAGTGAGGTGGTCAGATCC
Mouse huntingti    GTCCAGCCAGAAGGACCCCCGTCATCCTGATCAGTGAAGTGGTTCGATCT
                   *  ******* ******** * *************** ***** ****
                     Exon 60
hHunt normal 19    CTTCTAGTGGTCTCAGACTTGTTCACCGAGCGCAACCAGTTTGAGCTGAT
Mouse huntingti    CTTCTTGTAGTGTCAGACTTATTCACCGAACGTACCCAGTTTGAAATGAT
                   ***   **** ****   ******** ** hHunt normal 19    GTATGTGACGCTGACAGAACTGCGAAGGGTGCACCCTTCAGAAGACGAGA
Mouse huntingti    GTATCTGACGCTGACAGAACTACGAAGAGTGCACCCTTCAGAAGATGAGA
                   ** ************ * ************ ** hHunt normal 19    TCCTCGCTCAGTACCTGGTGCCTGCCACCTGCAAGGCAGCTGCCGTCCTT
Mouse huntingti    TCCTCATTCAGTACCTGGTGCCTGCCACCTGTAAGGCAGCTGCTGTCCTT
                   *****  ************************ ********** ******
                            Exon 61
hHunt normal 19    GGGATGGACAAGGCCGTGGCCGGAGCCTGTCAGCCGCCTGCTGGAGAGCAC
Mouse huntingti    GGAATGGACAAAACTGTGGCAGAGCCAGTCAGCCGCCTACTGGAGAGCAC
                    ******  * ***** * ** ****** ******** hHunt normal 19    GCTCAGGAGCCAGCCACCTGCCCAGCAGGCGTTGGAGCCCCTGCACGGCGTCC
Mouse huntingti    ACTGAGGAGCAGCCACCTGCCCAGCCAGATCGGAGCCCCTGCACGGCATCC
                   *  **** ************* *  ************* hHunt normal 19    TCTATGTGCTGGAGTGCGACCTGCTGGACGACACACTGCCAAGCAGCTCATC
Mouse huntingti    TCTATGTGTTGGAGTGTGACCTCTTGGATGACACTGCAAAGCAGCTCATT
                   ****** *** *  *** * ************* hHunt normal 19    CCGGTCATCAGCCGACTATCTCCTCTCCAACCTGAAAAGGGATCGCCCACTG
Mouse huntingti    CCAGTTGTTAGTGACTATCTGCTGTCCAACCTCAAAGGAATAGCCCACTG
                   ** **  * ** ******** ** ******** *** * ** ********
                              Exon 62
hHunt normal 19    CGTGAACATTCACAGCCAGCAGCACGTACTGGTCATGTGTGCCACTGCGT
Mouse huntingti    CGTGAACATTCACAGCCAGCAGCATGTGCTGGTAATGTGTGCCACTGCTT
                   *********************  *** ************ * hHunt normal 19    TTTACCTCATTGAGAACTATCCTCTGGACGTAGGGCCGGAATTTTCAGCA
Mouse huntingti    TCTACCTGATGGAAAACTACCCTCTGGATGTGGGACCAGAATTTTCAGCA
                   * ***** ** ** ***** ******** ** ** ** ***********
                            Exon 63
hHunt normal 19    TCAATAATACAGATGTGTGGGGTGATCCTGTCTGGAAGTGAGGAGTCCAC
Mouse huntingti    TCTGTGATACAGATGTGTGGAGTAATGCTGTCTGGAAGTGAGGAGTCCAC
                   **   * ***********   ********************* hHunt normal 19    CCCCTCCATCATTTACCACTGTGCCCTCAGAGGCCTGGAGCGGCTCCTGC
Mouse huntingti    CCCCTCCATCATTTACCACTGTGCCCTCCGGGGTCTGGAGCGGCTCCTGC
                   **************************** * ** ****************
```

FIG. 35J

```
                              shHD63.1
hHunt normal 19    TCTCTGAGCAGCTCTCCCGCCTGGATGCAGAATCGCTGGTCAAGCTGAGT
Mouse huntingti    TGTCTGAGCAGCTATCTCGGCTAGACACAGAGTCCTTGGTCAAGCTAAGT
                   * ********** ** ** ** ** **** ** ********** ***

Exon 64
hHunt normal 19    GTGGACAGAGTGAACGTGCACAGCCCGCACCGGGCCATGGCGGCTCTGGG
Mouse huntingti    GTGGACAGAGTGAATGTACAAAGCCCACACAGGGCCATGGCAGCCCTAGG
                   *************   * * ******** hHunt normal 19    CCTGATGCTCACCTGCATGTACACAGGAAAGGAGAAAGTCAGTCCGGGTA
Mouse huntingti    CCTGATGCTCACCTGCATGTACACAGGAAAGGAAAAAGCCAGTCCAGGCA
                   *******************************  **  * hHunt normal 19    GAACTTCAGACCCTAATCCTGCAGCCCCCGACAGCGAGTCAGTGATTGTT
Mouse huntingti    GAGCTTCTGACCCAGCCCTGCTACACCTGACAGCGAGTCTGTGATTGTA
                     *** * ***** *  ******* ****** hHunt normal 19    GCTATGGAGCGGGTATCTGTTCTTTTTGATAGGATCAGGAAAGGCTTTCC
Mouse huntingti    GCTATGGAGCGAGTGTCTGTTCTCTTTGATAGGATCCGCAAGGGATTTCC
                   *********  ****** ********* *   ***** hHunt normal 19    TTGTGAAGCCAGAGTGGTGGCCAGGATCCTGCCCCAGTTTCTAGACGACT
Mouse huntingti    CTGTGAAGCCAGGGTGTGCCAAGGATCCTGCCTCAGTTCCTAGATGACT
                   *********  *** ******** * * ** hHunt normal 19    TCTTCCCACCCCAGGACATCATGAACAAAGTCATCGGAGAGTTTCTGTCC
Mouse huntingti    TCTTTCCACCTCAAGATGTCATGAACAAAGTCATTGGAGAGTTCCTGTCC
                   ** *   ************* **** **** hHunt normal 19    AACCAGCAGCCATACCCCCAGTTCATGGCCACCGTGGTGTATAAGGTGTT
Mouse huntingti    AATCAGCAGCCATACCCACAGTTCATGGCCACTGTTAGTTTACAAGGTTTT
                    ********** **********    *** hHunt normal 19    TCAGACTCTGCACAGCACCGGGCAGTCGTCCATGGTCCGGGACTGGGTCA
Mouse huntingti    TCAGACTCTGCACAGTGCTGGGCAGTCATCCATGGTCCGGGACTGGGTCA
                   *************  ****** ******************** hHunt normal 19    TGCTGTCCCTCTCCAACTTCACGCAGAGGGCCCCGGTCGCCATGGCCACG
Mouse huntingti    TGCTGTCCCTGTCCAACTTCACACAAAGAACTCCAGTTGCCATGGCCATG
                   ******** *******  *     ******** * hHunt normal 19    TGGAGCCTCTCCTGCTTCTTTGTCAGCGCGTCCACCAGCCCGTGGGTCGC
Mouse huntingti    TGGAGCCTCTCCTGCTTCCTTGTTAGCGCATCTACCAGCCCCATGGTTTTC
                   ****************  *  ****** *** * hHunt normal 19    GGCGATCCTCCCACATGTCATCAGCAGGATGGGCAAGCTGGAGCAGGTGG
Mouse huntingti    TGCGATCCTTCCACATGTCATCAGCAGGATGGGCAAACTGGAACAGGTGG
                   ****** ********************** * ***** hHunt normal 19    ACGTGAACCTTTTCTGCCTGGTCGCCACAGACTTCTACAGACACCAGATA
Mouse huntingti    ATGTGAACCTTTTCTCCCTGGTTGCCACAGACTTCTACAGACACCAGATA
                   * *********** * ************************** hHunt normal 19    GAGGAGGAGCTCGACCGCAGGGCCTTCCAGTCTGTGCTTGAGGTGGTTGC
Mouse huntingti    GAGGAGGAATTCGACCGCAGGGCTTTCCAGTCTGTGTTTGAGGTGGTGGC
                   ******  ********* ******* ****** hHunt normal 19    AGCCCCAGGAAGCCCATATCACCGGCTGCTGACTTGTTTACGAAATGTCC
Mouse huntingti    TGCACCAGGAAGTCCATACCACAGGCTGCTTGCTTGTTTGCAAAATGTTC
                   *  ****** * * ******** * ******  * ****** * hHunt normal 19    ACAAGGTCACCACCTGCTGA
Mouse huntingti    ACAAGGTCACCACCTGCTGAGTAGTTCCTGTGGACAAAAGCTGAAAGA
                   ******************** hHunt normal 19    
Mouse huntingti    AGGCAGCTGCTGGGCCTGAGCCTCCAGGAGCCTGCTCCAAGCTTCTGCT hHunt normal 19    
Mouse huntingti    GGGCTGCCTTGGCCGTGCAGGCTTCACTTGTGTCAAGTGGACAGCCAGG
```

FIG. 35K

```
hHunt normal 19
Mouse huntingti        CAATGGCAGGAGTGCTTTGCAATGAGGCTATGCAGGGAACATGCACTAT hHunt normal 19
Mouse huntingti        GTTGGGGTTGAGCCTGAGTCCTGGGTCCTGGCCTCGCTGCAGCTGGTGAC hHunt normal 19
Mouse huntingti        AGTGCTAGGTTGACCAGGTGTTTGTCTTTTTCCTAGTGTTCCCCTGGCCA hHunt normal 19
Mouse huntingti        TAGTCGCCAGGTTGCAGGTGCCCTGGTATGTGGATCAGAAGTCCTAGGCTC hHunt normal 19
Mouse huntingti        CTGCCAGATGGTTCTGAGCCNGCCTGCTCCACTGGGCTGGAGAGCTCCCT hHunt normal 19
Mouse huntingti        CCCACATTTACCCAGTAGGCATACCTGCCACACCAGTGTCTGGACACAAA hHunt normal 19
Mouse huntingti        TGAATGGTGTGTGGGGCTGGAACTGGGGCTGCCAGGTGTCCAGCACCAT hHunt normal 19
Mouse huntingti        TTTCCTTTCTGTGTTTCTTCTCAGGAGTTAAAATTTAATTATATCAGTA hHunt normal 19                              9378
Mouse huntingti        AAGAGATTAATTTTAATGT  9998
```

FIG. 35L

RNA INTERFERENCE SUPPRESSION OF NEURODEGENERATIVE DISEASES AND METHODS OF USE

CLAIM OF PRIORITY

This patent application is a continuation of U.S. patent application Ser. No. 14/931,667, filed on Nov. 3, 2015, which is a continuation of U.S. patent application Ser. No. 13/920,969 filed on Jun. 18, 2013, which issued as U.S. Pat. No. 9,260,716, which is a continuation application of U.S. Ser. No. 12/963,793 filed on Dec. 9, 2010, which issued as U.S. Pat. No. 8,481,710, which is a continuation of U.S. application Ser. No. 11/597,225 filed on May 27, 2008, which is a National Stage application under 35 U.S.C. § 371 and claims benefit under 35 U.S.C. § 119(a) of International Application No. PCT/US2005/019749 having an International Filing Date of Jun. 2, 2005, which is a continuation-in-part application of U.S. application Ser. No. 11/048,627 filed on Jan. 31, 2005, which is a continuation-in-part application of U.S. application Ser. No. 10/738,642 filed on Dec. 16, 2003, and is a continuation-in-part application of U.S. application Ser. No. 10/859,751 filed on Jun. 2, 2004, both of which are continuation-in-part applications of International PCT Application No. PCT/US03/16887 filed on May 26, 2003, which is a continuation-in-part of application U.S. application Ser. No. 10/430,351 filed on May 5, 2003, which is a continuation of U.S. application Ser. No. 10/322,086 filed on Dec. 17, 2002, which is a continuation-in-part application of U.S. application Ser. No. 10/212,322, filed Aug. 5, 2002. The instant application claims the benefit of all the listed applications, which are hereby incorporated by reference herein in their entireties, including the drawings.

STATEMENT REGARDING FEDERALLY SPONSORED RESEARCH

This invention was made with government support under NS044494, NS038712, HD044093, DK054759, and NS022920 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 27, 2008, is named 17023_081US1_SL.txt and is 52.3 KB in size.

BACKGROUND OF THE INVENTION

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis. RNA fragments are the sequence-specific mediators of RNAi. Interference of gene expression by these small interfering RNA (siRNA) is now recognized as a naturally occurring strategy for silencing genes in *C. elegans, Drosophila*, plants, and in mouse embryonic stem cells, oocytes and early embryos.

SUMMARY OF THE INVENTION

The dominant polyglutamine expansion diseases, which include Spinocerebellar ataxia type 1 (SCA1) and Huntington's disease (HD), are progressive, untreatable neurodegenerative disorders. In inducible mouse models of SCA1 and HD, repression of mutant allele expression improves disease phenotypes. Thus, therapies designed to inhibit disease gene expression would be beneficial. In this study, the ability of RNA interference (RNAi) to inhibit polyglutamine-induced neurodegeneration caused by mutant ataxin-1 was evaluated in a mouse model of SCA1. Upon intracerebellar injection, recombinant AAV vectors expressing shRNAs profoundly improved motor coordination, restored cerebellar morphology, and resolved characteristic ataxin-1 inclusions in Purkinje cells of SCA1 mice. The present invention provides methods of using RNAi in vivo to treat dominant neurodegenerative diseases. "Treating" as used herein refers to ameliorating at least one symptom of, curing and/or preventing the development of a disease or a condition.

In certain embodiment of the invention, siRNAs are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when siRNA initiates the degradation of the mRNA transcribed from a gene of interest in a sequence-specific manner via RNA interference, thereby preventing translation of the gene's product (for a review, see Brantl, 2002).

The present invention provides an isolated RNA duplex that has a first strand of RNA and a second strand of RNA, wherein the first strand has at least 15 contiguous nucleotides encoded by shSCA1.F10 (SEQ ID NO:102) or shSCA1.F11 (SEQ ID NO:103), and wherein the second strand is complementary to at least 12 contiguous nucleotides of the first strand. In one embodiment, the first strand of RNA is encoded by shSCA1.F10 or by shSCA1.F11. As used herein the term "encoded by" is used in a broad sense, similar to the term "comprising" in patent terminology. For example, the statement "the first strand of RNA is encoded by SEQ ID NO:102" means that the first strand of RNA sequence corresponds to the RNA sequence transcribed from the DNA sequence indicated in SEQ ID NO:102, but may also contain additional nucleotides at either the 3' end or at the 5' end of the RNA molecule.

The present invention also provides an RNA duplex (under physiological conditions) having a first strand of RNA and a second strand of RNA, wherein the first strand has at least 15 contiguous nucleotides encoded by (a) shHDEx2.1 (5'-AAGAAAGAACTTTCAGCTACC-3', SEQ ID NO:96)), (b) shHDEx2.2 19 nt (5'-AGAACTTTCAGC-TACCAAG-3' (SEQ ID NO:97)), (c) shHDEx2.2 21 nt (5'-AAAGAACTTTCAGCTACCAAG-3' (SEQ ID NO:98)), (d) shHDEx3.1 19 nt (5'-TGCCTCAACAAAGT-TATCA-3' (SEQ ID NO:99)), or (e) shHDEx3.1 21 nt (5'-AATGCCTCAACAAAGTTATCA-3' (SEQ ID NO:100)), (f) siEX58#1 (5'-GAGGAAGAGGAGGAGGC-CGAC-3' (SEQ ID NO:101)), or (g) siEX58#2 (5'-AAGAG-GAGGAGGCCGACGCCC-3' (SEQ ID NO:90)) and wherein the second strand is complementary to at least 12 contiguous nucleotides of the first strand. In further embodiments, the first strand has at least 15 contiguous nucleotides encoded by SEQ ID NO:59, SEQ ID NO:60, SEQ ID NO:63, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, or SEQ ID NO:88, SEQ ID NO:90, SEQ ID NO:96 through SEQ ID NO:101 or SEQ ID NO:106 through SEQ ID NO:142, and wherein the second strand is complementary to at least 12 contiguous nucleotides of the first strand. In one embodiment, the loop structure corresponds to SEQ ID NO:58. In one embodiment, the first strand corresponds to SEQ ID NO:56 and the second strand corresponds to SEQ ID NO:57.

The reference to siRNAs herein is meant to include shRNAs and other small RNAs that can or are capable of modulating the expression of HD gene, for example via RNA interference. Such small RNAs include without limitation, shRNAs and miroRNAs (miRNAs).

In certain embodiments, the RNA duplex described above is between 15 and 30 base pairs in length, such as 19 or 21 base pairs in length. In certain embodiments, the first and/or second strand further comprises an overhang, such as a 3' overhang region, a 5' overhang region, or both 3' and 5' overhang regions. The two strands of RNA in the siRNA may be completely complementary, or one or the other of the strands may have an "overhang region" (i.e., a portion of the RNA that does not bind with the second strand). Such an overhang region may be from 1 to 10 nucleotides in length.

In certain embodiments, in the RNA duplex described above, the first strand and the second strand are operably linked by means of an RNA loop strand to form a hairpin structure to form a duplex structure and a loop structure. In certain embodiments, the loop structure contains from 4 to 10 nucleotides, such as 4, 5 or 6 nucleotides. In certain embodiments, the loop structure corresponds to SEQ ID NO:61 or SEQ ID NO:64.

The present invention further provides expression cassettes containing a nucleic acid encoding at least one strand of the RNA duplex described above. The expression cassette may further contain a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene.

The present invention also provides vectors containing the expression cassettes described above. Examples of appropriate vectors include adenoviral, lentiviral, adeno-associated viral (AAV), poliovirus, HSV, or murine Maloney-based viral vectors. In one embodiment, the vector is an adenoviral vector. In certain embodiments, a vector may contain two expression cassettes, a first expression cassette containing a nucleic acid encoding the first strand of the RNA duplex and a second expression cassette containing a nucleic acid encoding the second strand of the RNA duplex.

The present invention provides cells (such as a mammalian cell) containing the expression cassette or vectors described above. The present invention also provides a non-human mammal containing the expression cassette or vectors described above.

The present invention provides a method of suppressing the accumulation of huntingtin or ataxin-1 in a cell by introducing a ribonucleic acid (RNA) described above into the cell in an amount sufficient to suppress accumulation of huntingtin or ataxin-1 in the cell. In certain embodiments, the accumulation of huntingtin or ataxin-1 is suppressed by at least 10%. The accumulation of huntingtin or ataxin-1 is suppressed by at least 10%, 20%, 30%, 40%, 50%, 60%, 70%, 80%, 90% 95%, or 99%.

The present invention provides a method of preventing cytotoxic effects of mutant huntingtin or ataxin-1 in a cell by introducing a ribonucleic acid (RNA) described above into the cell in an amount sufficient to suppress accumulation of huntingtin or ataxin-1, and wherein the RNA prevents cytotoxic effects of huntingtin or ataxin-1 in the ocular tissue cell.

The present invention provides a method to inhibit expression of a huntingtin or ataxin-1 gene in a cell by introducing a ribonucleic acid (RNA) described above into the cell in an amount sufficient to inhibit expression of the huntingtin or ataxin-1, and wherein the RNA inhibits expression of the huntingtin or ataxin-1 gene. The huntingtin or ataxin-1 is inhibited by at least 10%, 20%, 30%, 40%, 50%, 60%, 70%, 80%, 90% 95%, or 99%.

The present invention provides a method to inhibit expression of a huntingtin or ataxin-1 gene in a mammal (e.g., a human) by (a) providing a mammal containing a neuronal cell, wherein the neuronal cell contains the huntingtin or ataxin-1 gene and the neuronal cell is susceptible to RNA interference, and the huntingtin or ataxin-1 gene is expressed in the neuronal cell; and (b) contacting the mammal with a ribonucleic acid (RNA) or a vector described above, thereby inhibiting expression of the huntingtin or ataxin-1 gene. In certain embodiments, the accumulation of huntingtin or ataxin-1 is suppressed by at least 10%. The huntingtin or ataxin-1 is inhibited by at least 10%, 20%, 30%, 40%, 50%, 60%, 70%, 80%, 90% 95%, or 99%. In certain embodiments, the cell located in vivo in a mammal.

The present invention provides a viral vector comprising a promoter and a micro RNA (miRNA) shuttle containing an embedded siRNA specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with a condition amenable to siRNA therapy, such as a neurodegenerative disease. An example of neurodegenerative diseases is a trinucleotide-repeat disease, such as a disease associated with polyglutamine repeats. These diseases include Huntington's disease or a spinocerebellar ataxia (SCA). Examples of SCA diseases are SCA1, SCA2, SCA3, SCA6, SCA1, or SCA17. The target sequence of the present invention, in certain embodiments, is a sequence encoding ataxin-1 or huntingtin.

The present invention provides a method of preventing cytotoxic effects of neurodegenerative disease in a mammal in need thereof, by introducing the vector encoding a miRNA described in the preceding paragraph into a cell in an amount sufficient to suppress accumulation of a protein associated with the neurodegenerative disease, and wherein the RNA prevents cytotoxic effects of neurodegenerative disease.

The present invention also provides a method to inhibit expression of a protein associated with the neurodegenerative disease in a mammal in need thereof, by introducing the vector encoding a miRNA described above into a cell in an amount sufficient to inhibit expression of the protein associated with the neurodegenerative disease, wherein the RNA inhibits expression of the protein associated with the neurodegenerative disease. The protein associated with the neurodegenerative disease is inhibited by at least 10%, 20%, 30%, 40%, 50%, 60%, 70%, 80%, 90% 95%, or 99%.

This invention relates to compounds, compositions, and methods useful for modulating Huntington's Disease (also referred to as huntingtin, htt, or HD) gene expression using short interfering nucleic acid (siRNA) molecules. This invention also relates to compounds, compositions, and methods useful for modulating the expression and activity of other genes involved in pathways of HD gene expression and/or activity by RNA interference (RNAi) using small nucleic acid molecules. In particular, the instant invention features small nucleic acid molecules, such as short interfering nucleic acid (siRNA), short interfering RNA (siRNA), double-stranded RNA (dsRNA), micro-RNA (miRNA), and short hairpin RNA (shRNA) molecules and methods used to modulate the expression HD genes. A siRNA of the instant invention can be chemically synthesized, expressed from a vector or enzymatically synthesized.

In one embodiment, the present invention provides an AAV-1 expressed siRNA comprising an isolated first strand of RNA of 15 to 30 nucleotides in length and an isolated second strand of RNA of 15 to 30 nucleotides in length, wherein the first or second strand comprises a sequence that is complementary to a nucleotide sequence encoding a mutant Huntington's Disease protein, wherein at least 12 nucleotides of the first and second strands are complementary to each other and form a small interfering RNA (siRNA) duplex under physiological conditions, and wherein the siRNA silences the expression of the nucleotide sequence encoding the mutant Huntington's Disease protein in the cell. In one embodiment, the first or second strand comprises a sequence that is complementary to both a mutant and wild-type Huntington's disease allele, and the siRNA silences the expression of the nucleotide sequence encoding the mutant Huntington's Disease protein and wild-type Huntington's Disease protein in the cell.

In one embodiment, the present invention provides an AAV-1 expressed siRNA comprising an isolated first strand of RNA of 15 to 30 nucleotides in length and an isolated second strand of RNA of 15 to 30 nucleotides in length, wherein the first or second strand comprises a sequence that is complementary to both a nucleotide sequence encoding a wild-type and mutant Huntington's Disease protein, wherein at least 12 nucleotides of the first and second strands are complementary to each other and form a small interfering RNA (siRNA) duplex under physiological conditions, and wherein the siRNA silences the expression of the nucleotide sequence encoding the wild-type and mutant Huntington's Disease protein in the cell. In one embodiment, an AAV-1 vector of the invention is a psuedotyped rAAV-1 vector.

In one embodiment, the present invention provides a mammalian cell containing an isolated first strand of RNA for example corresponding to SEQ ID NO:60, SEQ ID NO:63, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, or SEQ ID NO:88, and an isolated second strand of RNA of 15 to 30 nucleotides in length, wherein the first strand contains a sequence that is complementary to a nucleotide sequence encoding a Huntington's Disease protein (htt), such as wherein at least 12 nucleotides of the first and second strands are complementary to each other and form a small interfering RNA (siRNA) duplex for example under physiological conditions, and wherein the siRNA silences the expression of the Huntington's Disease (HD) gene in the cell, for example by targeting the cleavage of RNA encoded by the HD gene or via translational blocking of the HD gene expression. SEQ ID NO:60 through SEQ ID NO:89 are all represented herein as DNA sequences. However, as used herein when a claim indicates an RNA "corresponding to" it is meant the RNA that has the same sequence as the DNA, except that uracil is substituted for thymine. For example, SEQ ID NO:61 is 5'-GAAGCTTG-3', and the RNA corresponding to this sequence is 5'-GAAGCUUG-3' (SEQ ID NO: 58).

The present invention also provides a mammalian cell containing an expression cassette encoding an isolated first strand of RNA corresponding to, for example, SEQ ID NO:56 or SEQ ID NO:57, and encoding an isolated second strand of RNA of 15 to 30 nucleotides in length, wherein the first or second strand comprises a sequence that is complementary to a nucleotide sequence encoding a Huntington's Disease protein (htt), for example wherein at least 12 nucleotides of the first and second strands are complementary to each other and form a small interfering RNA (siRNA) duplex for example under physiological conditions, and wherein the siRNA silences the expression of the Huntington's Disease gene in the cell, for instance by targeting the cleavage of RNA encoded by the HD gene or via translational blocking of the HD gene expression. The expression cassette may further include a promoter, such as a regulatable promoter or a constitutive promoter. Examples of suitable promoters include without limitation a pol II promoter such as cytomegalovirus (CMV), Rous Sarcoma Virus (RSV), pol III promoters such as U6, and any other pol II or pol III promoter as is known in the art. The expression cassette may further optionally include a marker gene, such as a stuffier fragment comprising a marker gene. The expression cassette may be contained in a vector, such as an adenoviral, lentiviral, adeno-associated viral (AAV), poliovirus, HSV, or murine Maloney-based viral vector. In one embodiment, the first strand corresponds to SEQ ID NO:56 and the second strand corresponds to SEQ ID NO:57.

The present invention provides a small interfering RNA (siRNA) containing a first strand of RNA corresponding to for example SEQ ID NO:56 or SEQ ID NO:57, and a second strand of RNA of 15 to 30 nucleotides in length, wherein the first or second strand comprises a sequence that is complementary to a nucleotide sequence encoding a Huntington's Disease protein (htt), for example wherein at least 12 nucleotides of the first and second strands are complementary to each other and form an siRNA duplex under physiological conditions, wherein the duplex is between 15 and 30 base pairs in length, and wherein the siRNA silences the expression of the Huntington's Disease gene in the cell, for instance via RNA interference.

The present invention provides a method of performing Huntington's Disease gene silencing in a mammal by administering to the mammal an expression cassette encoding an isolated first strand of RNA corresponding to for example SEQ ID NO:56 or SEQ ID NO:57, and encoding an isolated second strand of RNA of 15 to 30 nucleotides in length, wherein the first or second strand comprises a sequence that is complementary to a nucleotide sequence encoding a Huntington's Disease protein (htt), for example wherein at least 12 nucleotides of the first and second strands are complementary to each other and form a small interfering RNA (siRNA) duplex under physiological conditions, and wherein the expression of the siRNA from the expression cassette silences the expression of the Huntington's Disease gene in the mammal, for instance via RNA interference.

The present invention provides an isolated RNA comprising for example SEQ ID NO:59 that functions in RNA interference to a sequence encoding a mutant Huntington's Disease protein (htt).

The present invention provides an isolated RNA duplex comprising a first strand of RNA corresponding to for example SEQ ID NO:56 and a second strand of RNA corresponding to for example by SEQ ID NO:57. The first and/or second strand optionally further include a 3' overhang region, a 5' overhang region, or both 3' and 5' overhang regions, and the overhang region (or regions) can be from 1 to 10 nucleotides in length. Further, the first strand and the second strand can be operably linked by means of an RNA loop strand to form a hairpin structure comprising a duplex structure and a loop structure. This loop structure, if present may be from 4 to 10 nucleotides. In one embodiment, the loop structure corresponds to SEQ ID NO:58 or a portion thereof.

The present invention provides a vector, such as an AAV vector, comprising two expression cassettes, a first expression cassette comprising a nucleic acid encoding the first strand of the RNA duplex corresponding to for example SEQ ID NO:56 and a second expression cassette comprising a nucleic acid encoding the second strand of the RNA duplex corresponding to for example SEQ ID NO:57. The present invention also provides a cell containing this vector. In one embodiment, the cell is a mammalian cell.

The present invention provides a mammalian cell containing an isolated first strand of RNA of 15 to 30 nucleotides in length, and an isolated second strand of RNA of 15 to 30 nucleotides in length, wherein the first strand contains a sequence that is complementary to for example at least 15 nucleotides of RNA encoded by a targeted gene of interest (for example the HD gene), wherein for example at least 12 nucleotides of the first and second strands are complementary to each other and form a small interfering RNA (siRNA) duplex for example under physiological conditions, and wherein the siRNA silences (for example via RNA interference) only one allele of the targeted gene (for example the mutant allele of HD gene) in the cell. The duplex of the siRNA may be between 15 and 30 base pairs in length. The two strands of RNA in the siRNA may be completely complementary, or one or the other of the strands may have an "overhang region" or a "bulge region" (i.e., a portion of the RNA that does not bind with the second strand or where a portion of the RNA sequence is not complementary to the sequence of the other strand). These overhangs may be at the 3' end or at the 5' region, or at both 3' and 5' ends. Such overhang regions may be from 1 to 10 (e.g., 1, 2, 3, 4, 5, 6, 7, 8, 9, 10) or more nucleotides in length. The bulge regions may be at the ends or in the internal regions of the siRNA duplex. Such bulge regions may be from 1-5 (e.g., 1, 2, 3, 4, 5) or more nucleotides long. Such bulge regions may be the bulge regions characteristics of miRNAs. In the present invention, the first and second strand of RNA may be operably linked together by means of an RNA loop strand to form a hairpin structure to form a "duplex structure" and a "loop structure." These loop structures may be from 4 to 10 (e.g., 4, 5, 6, 7, 8, 9, 10) or more nucleotides in length. For example, the loop structure may be 4, 5 or 6 nucleotides long.

The present invention also provides a mammalian cell that contains an expression cassette encoding an isolated first strand of RNA of 15 to 30 nucleotides in length, and an isolated second strand of RNA of 15 to 30 nucleotides in length, wherein the first strand contains a sequence that is complementary to for example at least 15 contiguous nucleotides of RNA encoded by a targeted gene of interest (for example the HD gene), wherein for example at least 12 nucleotides of the first and second strands are complementary to each other and form a small interfering RNA (siRNA) duplex, for example under physiological conditions, and wherein the siRNA silences (for example via RNA interference) only one allele of the targeted gene (for example the mutant allele of HD gene) in the cell. These expression cassettes may further contain a promoter. Such promoters can be regulatable promoters or constitutive promoters. Examples of suitable promoters include a CMV, RSV, pol II or pol III promoter. The expression cassette may further contain a polyadenylation signal, such as a synthetic minimal polyadenylation signal. The expression cassette may further contain a marker gene. The expression cassette may be contained in a vector. Examples of appropriate vectors include adenoviral, lentiviral, adeno-associated viral (AAV), poliovirus, HSV, or murine Maloney-based viral vectors. In one embodiment, the vector is an adenoviral vector or an adeno-associated viral vector.

In the present invention, the alleles of the targeted gene may differ by seven or fewer nucleotides (e.g., 7, 6, 5, 4, 3, 2 or 1 nucleotides). For example the alleles may differ by only one nucleotide. Examples of targeted gene transcripts include transcripts encoding a beta-glucuronidase, TorsinA, Ataxin-3, Tau, or huntingtin. The targeted genes and gene products (i.e., a transcript or protein) may be from different species of organisms, such as a mouse allele or a human allele of a target gene.

The present invention also provides an isolated RNA duplex containing a first strand of RNA and a second strand of RNA, wherein the first strand contains for example at least 15 nucleotides complementary to mutant TorsinA represented for example by SEQ ID NO:55 (5'-GTAAGCA-GAGTGGCTGAGATGACATTTTTCCCCAAAGAG-3'), and wherein the second strand is complementary to for example at least 12 contiguous nucleotides of the first strand. In one embodiment of the invention (mutA-si), the first strand of RNA corresponds to for example SEQ ID NO:49 and the second strand of RNA corresponds to for example SEQ ID NO:50. In an alternative embodiment (mutB-si), the first strand of RNA corresponds to for example SEQ ID NO:51 and the second strand of RNA corresponds to for example SEQ ID NO:52. In another embodiment (mutC-si), the first strand of RNA corresponds to for example SEQ ID NO:53 and second strand of RNA corresponds to for example SEQ ID NO:54. As used herein the term "encoded by" means that the DNA sequence is transcribed into the RNA of interest. This term is used in a broad sense, similar to the term "comprising" in patent terminology. For example, the statement "the first strand of RNA is encoded by SEQ ID NO:49" means that the first strand of RNA sequence corresponds to the DNA sequence indicated in SEQ ID NO:49, but may also contain additional nucleotides at either the 3' end or at the 5' end of the RNA molecule.

The present invention further provides an RNA duplex containing a first strand of RNA and a second strand of RNA, wherein the first strand contains for example at least 15 contiguous nucleotides complementary to mutant Ataxin-3 transcript encoded by SEQ ID NO:8, and wherein the second strand is complementary to for example at least 12 contiguous nucleotides of the first strand. In one embodiment (siC7/8), the first strand of RNA is encoded by SEQ ID NO:19 and the second strand of RNA is encoded by SEQ ID NO: 20. In another embodiment (siC10), the first strand of RNA is encoded by SEQ ID NO:21 and the second strand of RNA is encoded by SEQ ID NO:22.

The present invention further provides an RNA duplex containing a first strand of RNA and a second strand of RNA, wherein the first strand contains for example at least 15 contiguous nucleotides complementary to mutant Tau transcript for example encoded by SEQ ID NO:39 (siA9/C12), and wherein the second strand is complementary to at least 12 contiguous nucleotides of the first strand. The second strand may be encoded for example by SEQ ID NO:40.

The RNA duplexes of the present invention are between 15 and 30 base pairs in length. For example they may be between 19 and 25 base pairs in length or 19-27 base-pairs in length. As discussed above the first and/or second strand further may optionally comprise an overhang region. These overhangs may be at the 3' end or at the 5' overhang region, or at both 3' and 5' ends. Such overhang regions may be from 1 to 10 nucleotides in length. The RNA duplex of the present invention may optionally include nucleotide bulge regions. The bulge regions may be at the ends or in the internal regions of the siRNA duplex. Such bulge regions may be from 1-5 nucleotides long. Such bulge regions may be the bulge regions characteristics of miRNAs. In the present invention, the first and second strand of RNA may be operably linked together by means of an RNA loop strand to form a hairpin structure to form a "duplex structure" and a "loop structure." These loop structures may be from 4 to 10 nucleotides in length. For example, the loop structure may be 4, 5 or 6 nucleotides long.

In the present invention, an expression cassette may contain a nucleic acid encoding at least one strand of the RNA duplex described above. Such an expression cassette may further contain a promoter. The expression cassette may be contained in a vector. These cassettes and vectors may be contained in a cell, such as a mammalian cell. A non-human mammal may contain the cassette or vector. The vector may contain two expression cassettes, the first expression cassette containing a nucleic acid encoding the first strand of the RNA duplex, and a second expression cassette containing a nucleic acid encoding the second strand of the RNA duplex.

In one embodiment, the present invention further provides a method of performing gene silencing in a mammal or mammalian cell by administering to the mammal an isolated first strand of RNA of about 15 to about 30 nucleotides (for example 19-27 nucleotides) in length, and an isolated second strand of RNA of 15 to 30 nucleotides (for example 19-27 nucleotides) in length, wherein the first strand contains for example at least 15 contiguous nucleotides complementary to a targeted gene of interest (such as HD gene), wherein for example at least 12 nucleotides of the first and second strands are complementary to each other and form a small interfering RNA (siRNA) duplex for example under physiological conditions, and wherein the siRNA silences only one or both alleles of the targeted gene (for example the wild type and mutant alleles of HD gene) in the mammal or mammalian cell. In one example, the gene is a beta-glucuronidase gene. The alleles may be murine-specific and human-specific alleles of beta-glucuronidase. Examples of gene transcripts include an RNA transcript complementary to TorsinA, Ataxin-3, huntingtin or Tau. The targeted gene may be a gene associated with a condition amenable to siRNA therapy. For example, the condition amenable to siRNA therapy could be a disabling neurological disorder.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the present invention further provides a method of performing allele-specific gene silencing in a mammal by administering to the mammal an isolated first strand of RNA of 15 to 30 nucleotides in length, and an isolated second strand of RNA of 15 to 30 nucleotides in length, wherein the first strand contains for example at least 15 contiguous nucleotides complementary to a targeted gene of interest, wherein for example at least 12 nucleotides of the first and second strands are complementary to each other and form a small interfering RNA (siRNA) duplex for example under physiological conditions, and wherein the siRNA silences only one allele of the targeted gene in the mammal. The alleles of the gene may differ by seven or fewer base pairs, such as by only one base pair. In one example, the gene is a beta-glucuronidase gene. The alleles may be murine-specific and human-specific alleles of beta-glucuronidase. Examples of gene transcripts include an RNA transcript complementary to TorsinA, Ataxin-3, huntingtin or Tau. The targeted gene may be a gene associated with a condition amenable to siRNA therapy. For example, the condition amenable to siRNA therapy could be a disabling neurological disorder.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

In one embodiment, the present invention further provides a method of substantially silencing both alleles (e.g., both mutant and wild type alleles) of a target gene. In certain embodiments, the targeting of both alleles of a gene target of interest can confer a therapeutic effect by allowing a certain level of continued expression of the wild-type allele while at the same time inhibiting expression of the mutant (e.g., disease associated) allele at a level that provides a therapeutic effect. For example, a therapeutic effect can be achieved by conferring on the cell the ability to express siRNA as an expression cassette, wherein the expression cassette contains a nucleic acid encoding a small interfering RNA molecule (siRNA) targeted against both alleles, and wherein the expression of the targeted alleles are silenced at a level that inhibits, reduces, or prevents the deleterious gain of function conferred by the mutant allele, but that still allows for adequate expression of the wild type allele at a level that maintains the function of the wild type allele. Examples of such wild type and mutant alleles include without limitation those associated with polyglutamine diseases such as Huntington's Disease.

In one embodiment, the present invention further provides a method of substantially silencing a target allele while allowing expression of a wild-type allele by conferring on the cell the ability to express siRNA as an expression cassette, wherein the expression cassette contains a nucleic acid encoding a small interfering RNA molecule (siRNA) targeted against a target allele, wherein expression from the targeted allele is substantially silenced but wherein expression of the wild-type allele is not substantially silenced.

In one embodiment, the present invention provides a method of treating a dominantly inherited disease in an allele-specific manner by administering to a patient in need thereof an expression cassette, wherein the expression cassette contains a nucleic acid encoding a small interfering RNA molecule (siRNA) targeted against a target allele, wherein expression from the target allele is substantially silenced but wherein expression of the wild-type allele is not substantially silenced.

In one embodiment, the present invention provides a method of treating a dominantly inherited disease by administering to a patient in need thereof an expression cassette, wherein the expression cassette contains a nucleic acid encoding a small interfering RNA molecule (siRNA) targeted against both the mutant allele and the wild type allele of the target gene, wherein expression from the mutant allele is substantially silenced at a level that still allows for expression from the wild type allele to maintain its function in the patient.

In one embodiment, the present invention also provides a method of performing allele-specific gene silencing by administering an expression cassette containing a pol II promoter operably-linked to a nucleic acid encoding at least one strand of a small interfering RNA molecule (siRNA) targeted against a gene of interest, wherein the siRNA silences only one allele of a gene.

In one embodiment, the present invention also provides a method of performing gene silencing by administering an expression cassette containing a pol II promoter operably-linked to a nucleic acid encoding at least one strand of a small interfering RNA molecule (siRNA) targeted against a gene of interest, wherein the siRNA silences one or both alleles of the gene.

In one embodiment, the present invention provides a method of performing allele-specific gene silencing in a mammal by administering to the mammal a vector containing an expression cassette, wherein the expression cassette contains a nucleic acid encoding at least one strand of a small interfering RNA molecule (siRNA) targeted against a gene of interest, wherein the siRNA silences only one allele of a gene.

In one embodiment, the present invention provides a method of performing gene silencing in a mammal by administering to the mammal a vector containing an expression cassette, wherein the expression cassette contains a nucleic acid encoding at least one strand of a small interfering RNA molecule (siRNA) targeted against a gene of interest, wherein the siRNA silences one or both alleles of the gene.

In one embodiment, the present invention provides a method of screening of allele-specific siRNA duplexes, involving contacting a cell containing a predetermined mutant allele with an siRNA with a known sequence, contacting a cell containing a wild-type allele with an siRNA with a known sequence, and determining if the mutant allele is substantially silenced while the wild-type allele retains substantially normal activity.

In one embodiment, the present invention provides a method of screening of specific siRNA duplexes, involving contacting a cell containing both a predetermined mutant allele and a predetermined wild-type allele with an siRNA with a known sequence, and determining if the mutant allele is substantially silenced at a level that allows the wild-type allele to retain substantially normal activity.

In one embodiment, the present invention also provides a method of screening of allele-specific siRNA duplexes involving contacting a cell containing a predetermined mutant allele and a wild-type allele with an siRNA with a known sequence, and determining if the mutant allele is substantially silenced while the wild-type allele retains substantially normal activity.

In one embodiment, the present invention also provides a method for determining the function of an allele by contacting a cell containing a predetermined allele with an siRNA with a known sequence, and determining if the function of the allele is substantially modified.

In one embodiment, the present invention further provides a method for determining the function of an allele by contacting a cell containing a predetermined mutant allele and a wild-type allele with an siRNA with a known sequence, and determining if the function of the allele is substantially modified while the wild-type allele retains substantially normal function.

In one embodiment, the invention features a method for treating or preventing Huntington's Disease in a subject or organism comprising contacting the subject or organism with a siRNA of the invention under conditions suitable to modulate the expression of the HD gene in the subject or organism whereby the treatment or prevention of Huntington's Disease can be achieved. In one embodiment, the HD gene target comprises a mutant HD allele (e.g., an allele comprising a trinucleotide (CAG) repeat expansion). In one embodiment, the HD gene target comprises both HD allele (e.g., an allele comprising a trinucleotide (CAG) repeat expansion and a wild type allele). The siRNA molecule of the invention can be expressed from vectors as described herein or otherwise known in the art to target appropriate tissues or cells in the subject or organism.

In one embodiment, the invention features a method for treating or preventing Huntington's Disease in a subject or organism comprising, contacting the subject or organism with a siRNA molecule of the invention via local administration to relevant tissues or cells, such as brain cells and tissues (e.g., basal ganglia, striatum, or cortex), for example, by administration of vectors or expression cassettes of the invention that provide siRNA molecules of the invention to relevant cells (e.g., basal ganglia, striatum, or cortex). In one embodiment, the siRNA, vector, or expression cassette is administered to the subject or organism by stereotactic or convection enhanced delivery to the brain. For example, U.S. Pat. No. 5,720,720 provides methods and devices useful for stereotactic and convection enhanced delivery of reagents to the brain. Such methods and devices can be readily used for the delivery of siRNAs, vectors, or expression cassettes of the invention to a subject or organism, and is incorporated by reference herein in its entirety. US Patent Application Nos. 2002/141980; 2002/0114780; and 2002/0187127 all provide methods and devices useful for stereotactic and convection enhanced delivery of reagents that can be readily adapted for delivery of siRNAs, vectors, or expression cassettes of the invention to a subject or organism, and are incorporated by reference herein in their entirety. Particular devices that may be useful in delivering siRNAs, vectors, or expression cassettes of the invention to a subject or organism are for example described in US Patent Application No. 2004/0162255, which is incorporated by reference herein in its entirety. The siRNA molecule of the invention can be expressed from vectors as described herein or otherwise known in the art to target appropriate tissues or cells in the subject or organism.

In one embodiment, a viral vector of the invention is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-8. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped rAAV are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See for example Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.). As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from any of several AAV serotypes, including without limitation, AAV-1, AAV-2, AAV-3, AAV-4, AAV-5, AAV6, or AAV8, and the AAV ITRS are derived form AAV serotype 2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art Dong, J.-Y. et al. (Nov. 10, 1996). "Quantitative Analysis of the Packaging Capacity of Recombinant Adeno-Associated Virus,"

*Human Gene Ther.* 7(17):2101-2112 and U.S. Pat. No. 6,596,535 herein incorporated in its entirety. In some embodiments of the invention the DNA molecules for use in the AAV vectors will contain multiple copies of the identical siRNA sequence. As used herein the term multiple copies of an siRNA sequences means at least 2 copies, at least 3 copies, at least 4 copies, at least 5 copies, at least 6 copies, at least 7 copies, at least 8 copies, at least 9 copies, and at least 10 copies. In some embodiments the DNA molecules for use in the AAV vectors will contain multiple siRNA sequences. As used herein the term multiple=Si RNA sequences means at least 2 siRNA sequences, at least 3 siRNA sequences, at least 4 siRNA sequences, at least 5 siRNA sequences, at least 6 siRNA sequences, at least 7 siRNA sequences, at least 8 siRNA sequences, at least 9 siRNA sequences, and at least 10 siRNA sequences. In some embodiments suitable DNA vectors of the invention will contain a sequence encoding the siRNA molecule of the invention and a stuffer fragment. Suitable stuffer fragments of the invention include sequences known in the art including without limitation sequences which do not encode an expressed protein molecule; sequences which encode a normal cellular protein which would not have deleterious effect on the cell types in which it was expressed; and sequences which would not themselves encode a functional siRNA duplex molecule.

In one embodiment, suitable DNA molecules for use in AAV vectors will be less than about 5 kilobases (kb) in size and will include, for example, a stuffer sequence and a sequence encoding a siRNA molecule of the invention. For example, in order to prevent any packaging of AAV genomic sequences containing the rep and cap genes, a plasmid containing the rep and cap DNA fragment may be modified by the inclusion of a stuffer fragment as is known in the art into the AAV genome which causes the DNA to exceed the length for optimal packaging. Thus, the helper fragment is not packaged into AAV virions. This is a safety feature, ensuring that only a recombinant AAV vector genome that does not exceed optimal packaging size is packaged into virions. An AAV helper fragment that incorporates a stuffer sequence can exceed the wild-type genome length of 4.6 kb, and lengths above 105% of the wild-type will generally not be packaged. The stuffer fragment can be derived from, for example, such non-viral sources as the Lac-Z or beta-galactosidase gene.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMB promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl$_2$, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge, Nature (1981) 292:756; Nambair et al. Science (1984) 223:1299; Jay et al. J. Biol. Chem. (1984) 259:6311.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Feigner et al. (1987) Proc. Natl. Acad. Sci. USA 84:7413-7417), and nucleic acid delivery using high-velocity microprojectiles (Klein et al. (1987) Nature 327:70-73).

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present invention. Particularly, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a particularly convenient platform in which to produce rAAV virions.

In one embodiment, host cells containing the above-described AAV expression vectors are rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97-129; and Kotin, R. M. (1994) Human Gene Therapy 5:793-801. Suitable homologues of the AAV rep coding region include the human herpesvirus 6 (HHV-6) rep gene which is also known to mediate AAV-2 DNA replication (Thomson et al. (1994) Virology 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

In one embodiment, both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

In one embodiment, the host cell (or packaging cell) is rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In one embodiment, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) J. Virol. 40:241-247; McPherson et al. (1985) Virology 147:217-222; Schlehofer et al. (1986) Virology 152:110-117.

In one embodiment, accessory functions are provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions. See, for example, International Publication No. WO 97/17548, published May 15, 1997.

In one embodiment, nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, N. (1992) Curr. Topics. Microbiol and Immun. 158:97-129. Specifically, early adenoviral gene regions E1a, E2a, E4, VAI RNA and, possibly, E1b are thought to participate in the accessory process. Janik et al. (1981) Proc. Natl. Acad. Sci. USA 78:1925-1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990), supra., Schlehofer et al. (1986) Virology 152:110-117.

In one embodiment, as a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

In one embodiment, following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60.degrees C. for, e.g., 20 minutes or more. This treatment effectively inactivates only the helper virus since AAV is extremely heat stable while the helper adenovirus is heat labile. The resulting rAAV virions are then ready for use for DNA delivery to the CNS (e.g., cranial cavity) of the subject.

Methods of delivery of viral vectors include, but are not limited to, intra-arterial, intramuscular, intravenous, intranasal and oral routes. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, the rAAV virions are formulated into pharmaceutical compositions and will generally be administered parenterally, e.g., by intramuscular injection directly into skeletal or cardiac muscle or by injection into the CNS.

In one embodiment, viral vectors of the invention are delivered to the CNS via convection-enhanced delivery (CED) systems that can efficiently deliver viral vectors, e.g., AAV, over large regions of a subject's brain (e.g., striatum and/or cortex). As described in detail and exemplified below, these methods are suitable for a variety of viral vectors, for instance AAV vectors carrying therapeutic genes (e.g., siRNAs).

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat PD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIGS. 2A-C. Viral vectors expressing siRNA reduce expression from transgenic and endogenous alleles in vivo. Recombinant adenovirus vectors were prepared from the siGFP and siβgluc shuttle plasmids described in FIG. 1. (A) Fluorescence microscopy reveals diminution of eGFP expression in vivo. In addition to the siRNA sequences in the E1 region of adenovirus, RFP expression cassettes in E3 facilitate localization of gene transfer. Representative photomicrographs of eGFP (left), RFP (middle), and merged images (right) of coronal sections from mice injected with adenoviruses expressing siGFP (top panels) or siβgluc (bottom panels) demonstrate siRNA specificity in eGFP transgenic mice striata after direct brain injection. (B) Full coronal brain sections (1 mm) harvested from AdsiGFP or Adsiβgluc injected mice were split into hemisections and both ipsilateral (il) and contralateral (cl) portions evaluated by western blot using antibodies to GFP. Actin was used as an internal control for each sample. (C) Tail vein injection of recombinant adenoviruses expressing siβgluc directed against mouse β-glucuronidase (AdsiMuβgluc) reduces endogenous β-glucuronidase RNA as determined by Northern blot in contrast to control-treated (Adsiβgal) mice.

FIGS. 3A-D. siGFP gene transfer reduces Q19-eGFP expression in cell lines. PC12 cells expressing the polyglutamine repeat Q19 fused to eGFP (eGFP-Q19) under tetracycline repression (A, bottom left) were washed and dox-free media added to allow eGFP-Q19 expression (A, top left). Adenoviruses were applied at the indicated multiplicity of infection (MOI) 3 days after dox removal. (A) eGFP fluorescence 3 days after adenovirus-mediated gene transfer of Adsiβgluc (top panels) or AdsiGFP (bottom panels). (B, C) Western blot analysis of cell lysates harvested 3 days after infection at the indicated MOIs demonstrate a dose-dependent decrease in GFP-Q19 protein levels. NV, no virus. Top lanes, eGFP-Q19. Bottom lanes, actin loading controls. (D) Quantitation of eGFP fluorescence. Data represent mean total area fluorescence±standard deviation in 4 low power fields/well (3 wells/plate).

FIG. 10, are from the region boxed.

Figure 11:
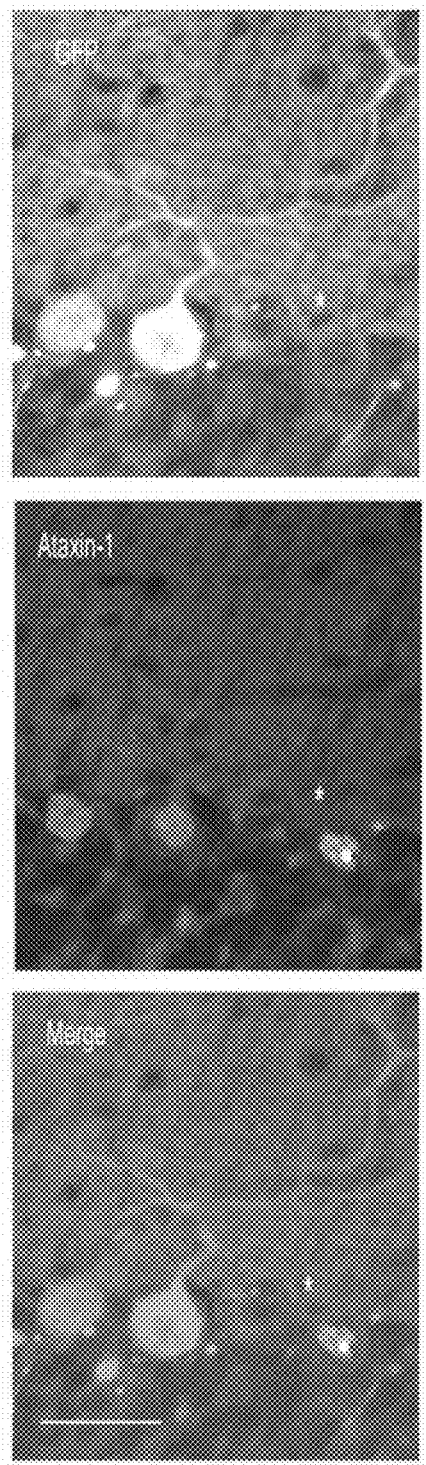

see also FIG. 11). Numbers in lower left refer to % intranuclear inclusion-positive Purkinje cells in ~400 cells scored.

FIG. 11. Reductions in ataxin-1 inclusions in SCA1 mice requires transduction. Sections from SCA1 mice injected 9 weeks earlier with AAVshSCA1.F10mi were evaluated for hrGFP expression to identify transduced cells, and ataxin-1 inclusions using IF, as described in the Methods and to the legend of FIG. 4. The photomicrographs demonstrate that ataxin-1 inclusions are noted in untransduced cells, but not transduced cells, from AAVshSCA1.F10mi-treated mice Bar=25 µm.

Figure 12:
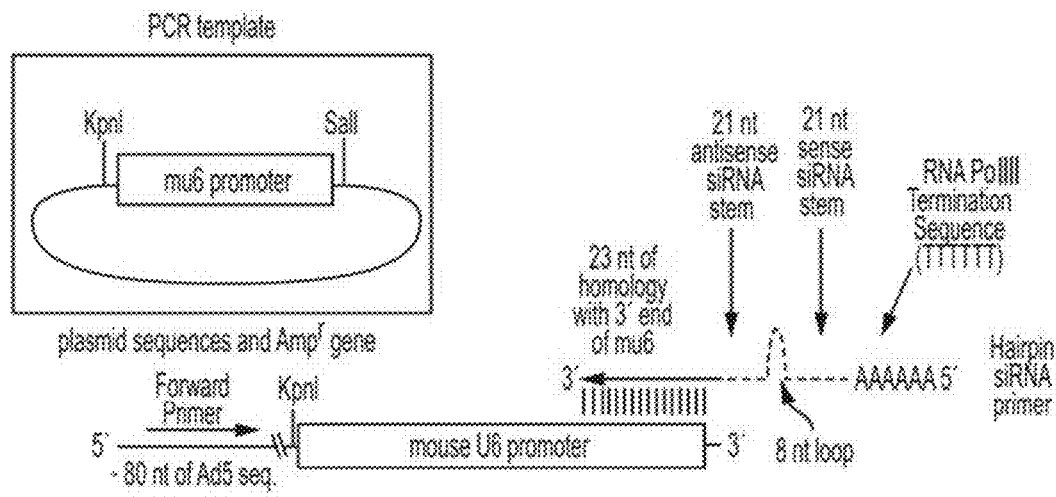

FIG. 12. PCR method for cloning hairpins. A 79 nt primer is used with the Ampr template. Pfu and DMSO are used in the amplification reaction. Products are ligated directly into pCR-Blunt Topo (Invitrogen) and Kanr resistant colonies picked and sequenced. Positive clones can be used directly.

Figure 13:
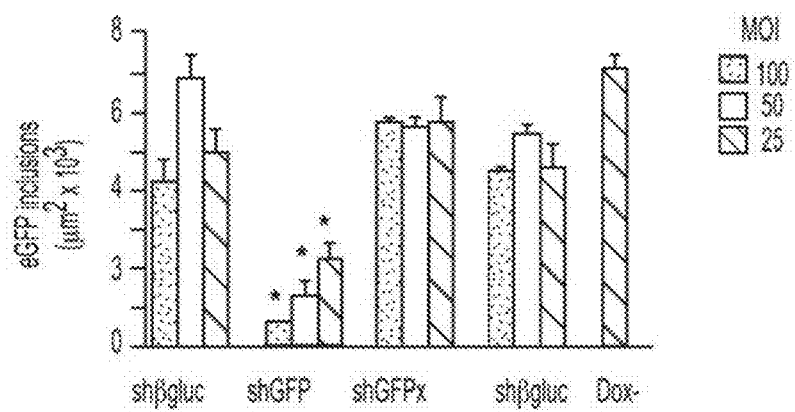

FIG. 13. Reduction of eGFP inclusions after transduction with 25, 50 or 100 viruses/cell into cultures with pre-formed aggregates. Note dose-dependent response with shGFP vectors only.

Figure 14:
Figure 14:
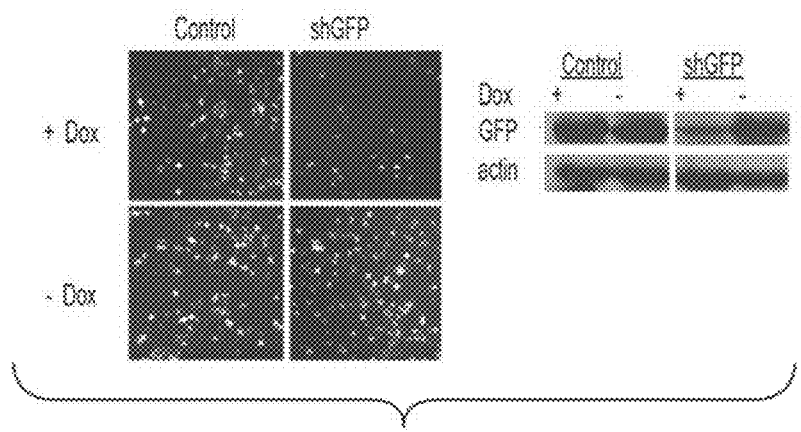

FIG. 14. Regulated RNAi. Two Teto2 sequences were placed up- and down-stream of the TATA box of the H1 promoter element (cartoon). Either control shRNA or shGFP was placed into the cassette for expression of hairpins. Plasmids expressing GFP and the hairpin constructs were transfected into a cell line expressing the TetR (tet-repressor). GFP fluorescence (left panels) or western blot (right panels) was evaluated in the absence (TetR binding) or presence (TetR off) of doxycycline.

Figure 15:
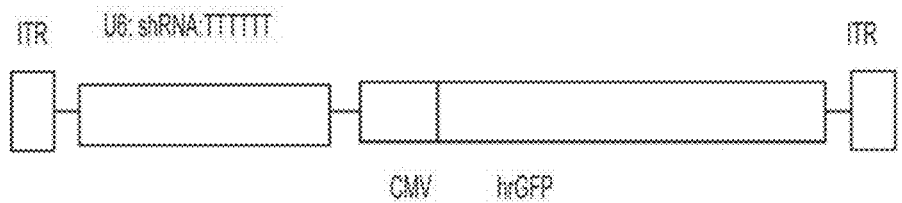

FIG. 15. Top, FIV construct. Bottom, AAV construct. Both express the hrGFP reporter so that transduced cells can be readily evaluated for shRNA efficacy (as in FIGS. 3 and 4).

FIGS. 16A-F. RNAi-mediated suppression of expanded CAG repeat containing genes. Expanded CAG repeats are not direct targets for preferential inactivation (A), but a linked SNP can be exploited to generate siRNA that selectively silences mutant ataxin-3 expression (B-F). (A) Schematic of cDNA encoding generalized polyQ-fluorescent protein fusions. Bars indicate regions targeted by siRNAs. HeLa cells co-transfected with Q80-GFP, Q19-RFP and the indicated siRNA. Nuclei are visualized by DAPI staining (blue) in merged images. (B) Schematic of human ataxin-3 cDNA with bars indicating regions targeted by siRNAs. The targeted SNP (G987C) is shown in color. In the displayed siRNAs, red or blue bars denote C or G respectively. In this Figure, CAGCAGCAGCAGGGGGACCTATCAGGAC is SEQ ID NO:7, and
CAGCAGCAGCAGCGGGACCTATCAGGAC is SEQ ID NO:8. (C) Quantitation of fluorescence in Cos-7 cells transfected with wild type or mutant ataxin-3-GFP expression plasmids and the indicated siRNA. Fluorescence from cells co-transfected with siMiss was set at one. Bars depict mean total fluorescence from three independent experiments+/−standard error of the mean (SEM). (D) Western blot analysis of cells co-transfected with the indicated ataxin-3 expression plasmids (top) and siRNAs (bottom). Appearance of aggregated, mutant ataxin-3 in the stacking gel (seen with siMiss and siG10) is prevented by siRNA inhibition of the mutant allele. (E) Allele specificity is retained in the simulated heterozygous state. Western blot analysis of Cos-7 cells cotransfected with wild-type (atx-3-Q28-GFP) and mutant (atx-Q166) expression plasmids along with the indicated siRNAs. (Mutant ataxin-3 detected with 1C2, an antibody specific for expanded polyQ, and wild-type ataxin-3 detected with anti-ataxin-3 antibody.) (F) Western blot of Cos-7 cells transfected with Atx-3-GFP expression plasmids and plasmids encoding the indicated shRNA. The negative control plasmid, phU6-LacZi, encodes siRNA specific for LacZ. Both normal and mutant protein were detected with anti-ataxin-3 antibody. Tubulin immunostaining shown as a loading control in panels (D)-(F).

Figure 17:
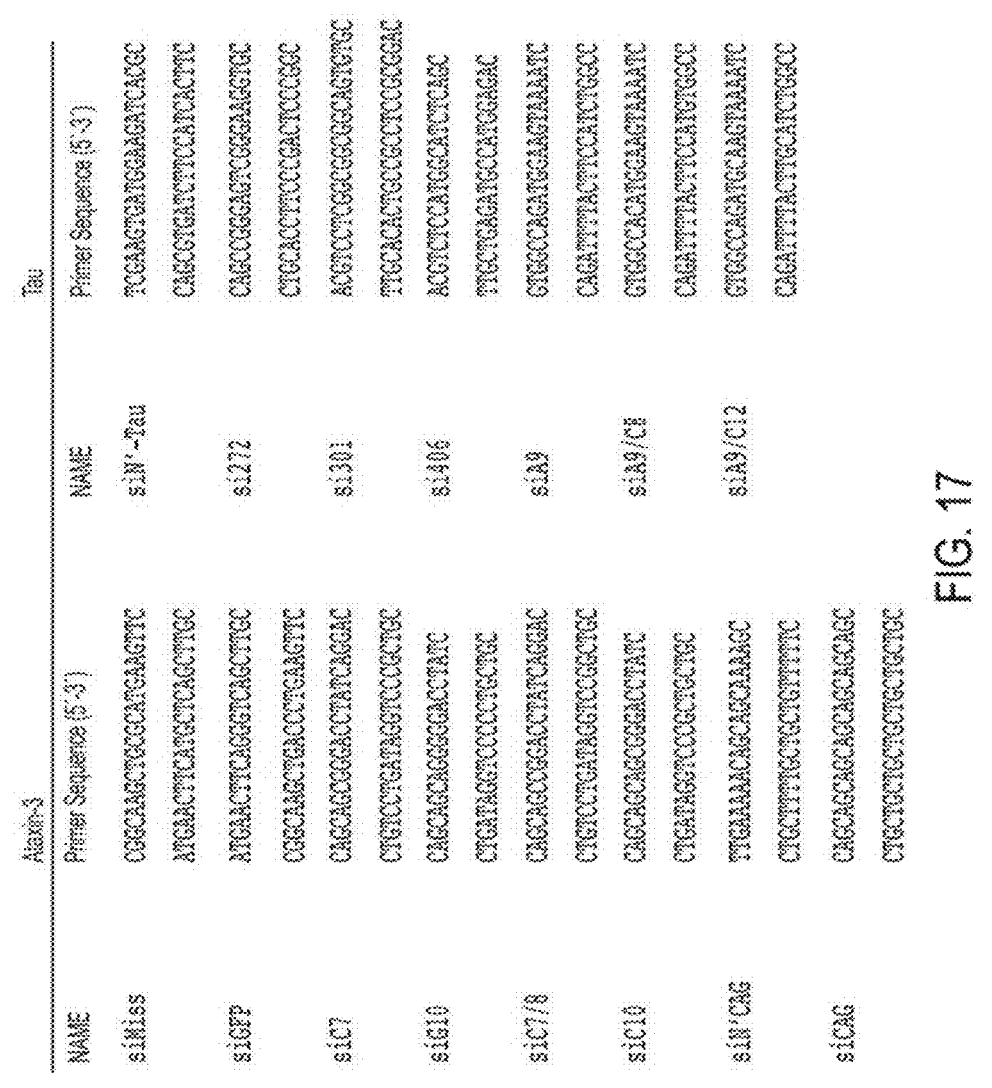

FIG. 17. Primer sequences (SEQ ID NOS: 11-40, respectively, in order of appearance) for in vitro synthesis of siRNAs using T7 polymerase. All primers contain the following T7 promoter sequence at their 3' ends: 5'-TATAGT-GAGTCGTATTA-3' (SEQ ID NO:9). The following primer was annealed to all oligos to synthesize siRNAs: 5'-TAATACGACTCACTATAG-3' (SEQ ID NO:10).

Figure 18A:
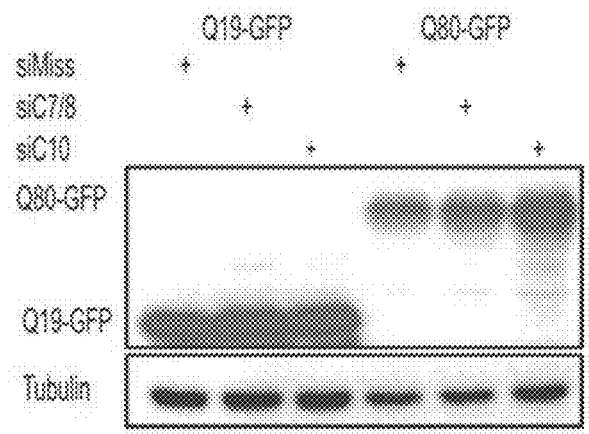
Figure 18B:
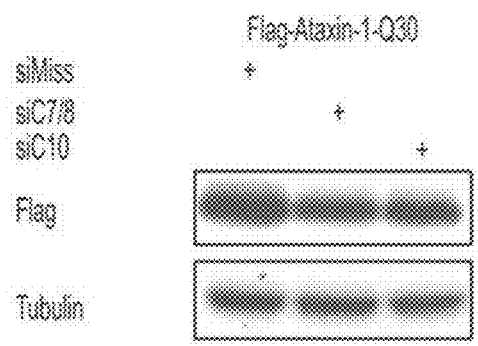

FIGS. 18A-B. Inclusion of either two (siC7/8) or three (siC10) CAG triplets at the 5' end of ataxin-3 siRNA does not inhibit expression of unrelated CAG repeat containing genes. (A) Western blot analysis of Cos-7 cells transfected with CAG repeat-GFP fusion proteins and the indicated siRNA. Immunostaining with monoclonal anti-GFP antibody (MBL) at 1:1000 dilution. (B) Western blot analysis of Cos-7 cells transfected with Flag-tagged ataxin-1-Q30, which is unrelated to ataxin-3, and the indicated siRNA. Immunostaining with anti-Flag monoclonal antibody (Sigma St. Louis, Mo.) at 1:1000 dilution. In panels (A) and (B), lysates were collected 24 hours after transfection. Tubulin immunostaining shown as a loading control.

FIGS. 19A-D. shRNA-expressing adenovirus mediates allele-specific silencing in transiently transfected Cos-7 cells simulating the heterozygous state. (A) Representative images of cells cotransfected to express wild type and mutant ataxin-3 and infected with the indicated adenovirus at 50 multiplicities of infection (MOI). Atx-3-Q28-GFP (green) is directly visualized and Atx-3-Q166 (red) is detected by immunofluorescence with 1C2 antibody. Nuclei visualized with DAPI stain in merged images. An average of 73.1% of cells co-expressed both ataxin-3 proteins with siMiss. (B) Quantitation of mean fluorescence from 2 independent experiments performed as in (A). (C) Western blot analysis of viral-mediated silencing in Cos-7 cells expressing wild type and mutant ataxin-3 as in (A). Mutant ataxin-3 detected with 1C2 antibody and wild-type human and endogenous primate ataxin-3 detected with anti-ataxin-3 antibody. (D) shRNA-expressing adenovirus mediates allele-specific silencing in stably transfected neural cell lines. Differentiated PC12 neural cells expressing wild type (left) or mutant (right) ataxin-3 were infected with adenovirus (100 MOI) engineered to express the indicated hairpin siRNA. Shown are Western blots immunostained for ataxin-3 and GAPDH as loading control.

Figure 20A:
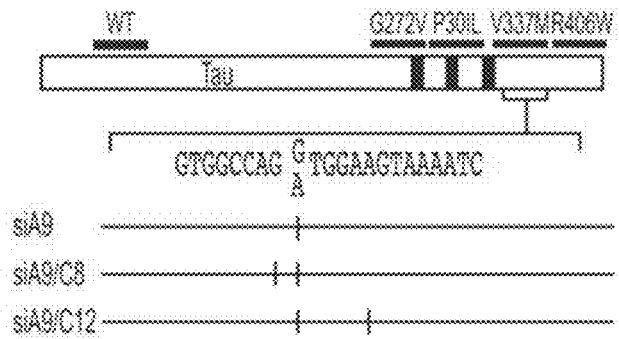
Figure 20B:
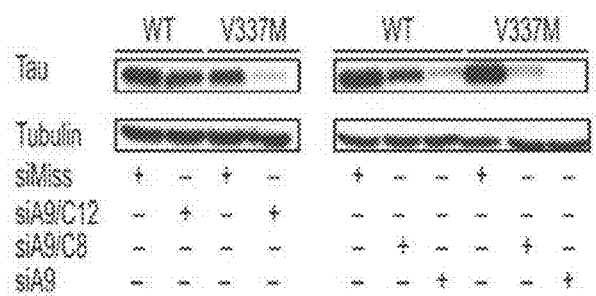
Figure 20C:
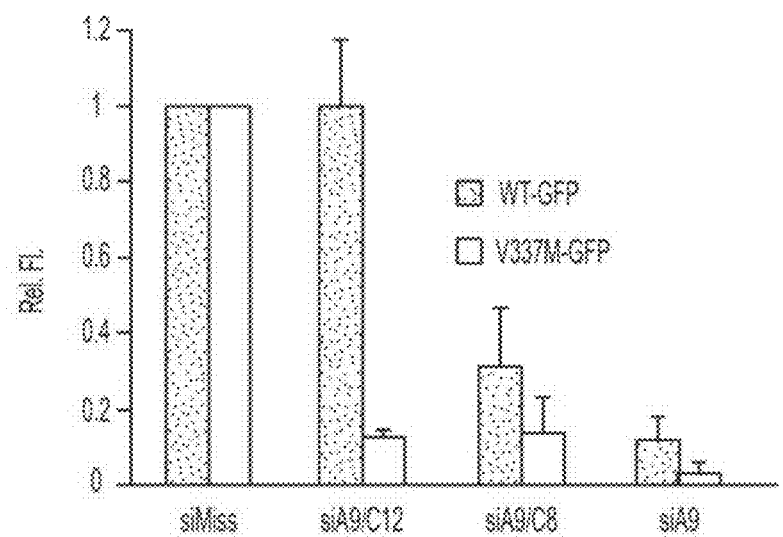

FIGS. 20A-C. Allele-specific siRNA suppression of a missense Tau mutation. (A) Schematic of human tau cDNA with bars indicating regions and mutations tested for siRNA suppression. Of these, the V337M region showed effective suppression and was further studied. Vertical bars represent microtubule binding repeat elements in Tau. In the displayed siRNAs, blue and red bars denote A and C respectively. In this Figure, GTGGCCAGATGGAAGTAAAATC is SEQ ID NO:35, and GTGGCCAGGTGGAAGTAAAATC is SEQ ID NO:41. (B) Western blot analysis of cells co-transfected with WT or V337M Tau-EGFP fusion proteins and the indicated siRNAs. Cells were lysed 24 hr after transfection and probed with anti-tau antibody. Tubulin immunostaining is shown as loading control. (C) Quantitation of fluorescence in Cos-7 cells transfected with wild type tau-EGFP or mutant V337M tau-EGFP expression plasmids and the indicated siRNAs. Bars depict mean fluorescence and SEM from three independent experiments. Fluorescence from cells co-transfected with siMiss was set at one.

Figure 21A:
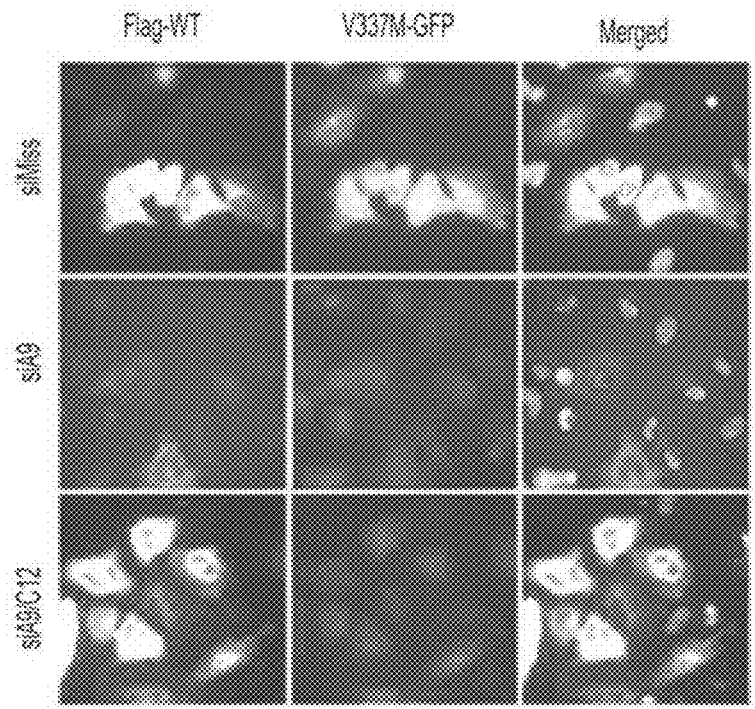
Figure 21B:
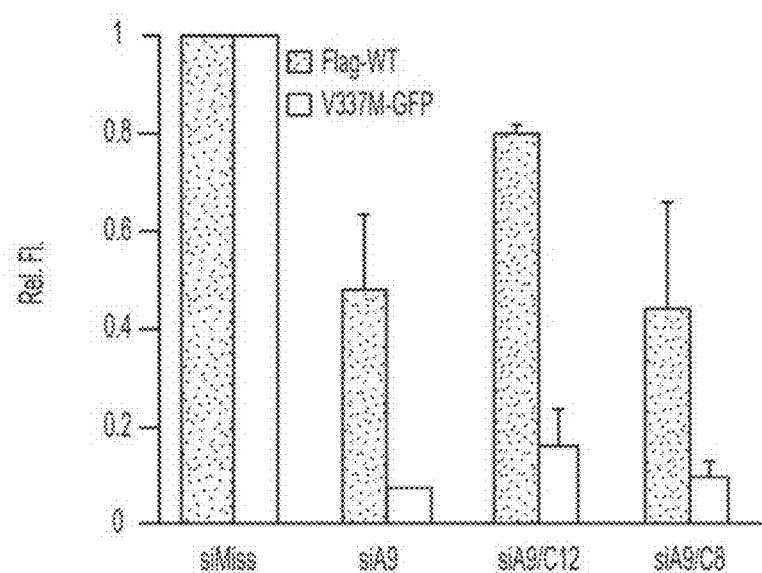
Figure 21C:
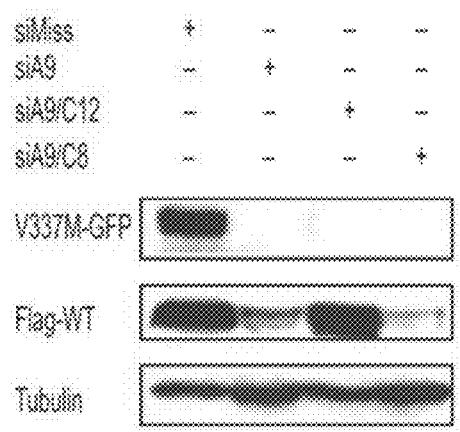

FIGS. 21A-C. Allele-specific silencing of Tau in cells simulating the heterozygous state. (A) Representative fluorescent images of fixed Hela cells co-transfected with flag-tagged WT-Tau (red), V337M-Tau-GFP (green), and the indicated siRNAs. An average of 73.7% of cells co-expressed both Tau proteins with siMiss. While siA9 suppresses both alleles, siA9/C12 selectively decreased expression of mutant Tau only. Nuclei visualized with DAPI stain in merged images. (B) Quantitation of mean fluorescence from 2 independent experiments performed as in (A). (C) Western blot analysis of cells co-transfected with Flag-WT-Tau and V337M-Tau-EGFP fusion proteins and the indicated siRNAs. Cells were lysed 24 hr after transfection and probed with anti-tau antibody. V337M-GFP Tau was differentiated based on reduced electrophoretic mobility due to the addition of GFP. Tubulin immunostaining is shown as a loading control.

Figure 22:
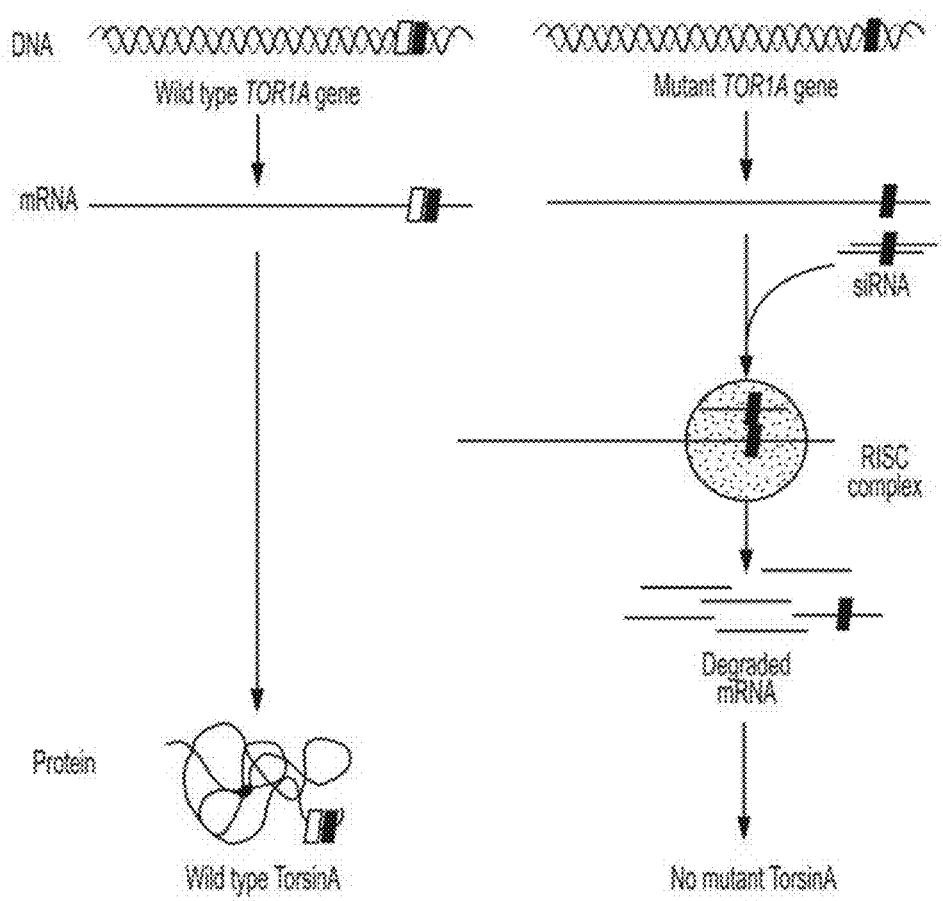

FIG. 22. Schematic diagram of allele-specific silencing of mutant TorsinA by small interfering RNA (siRNA). In the disease state, wild type and mutant alleles of TOR1A are both transcribed into mRNA. siRNA with sequence identical to the mutant allele (deleted of GAG) should bind mutant mRNA selectively and mediate its degradation by the RNA-induced silencing complex (RISC) (circle). Wild type mRNA, not recognized by the mutant-specific siRNA, will remain and continue to be translated into normal TorsinA. The two adjacent GAG's in wild type TOR1A alleles are shown as two parallelograms, one of which is deleted in mutant TOR1A alleles.

Figure 23:
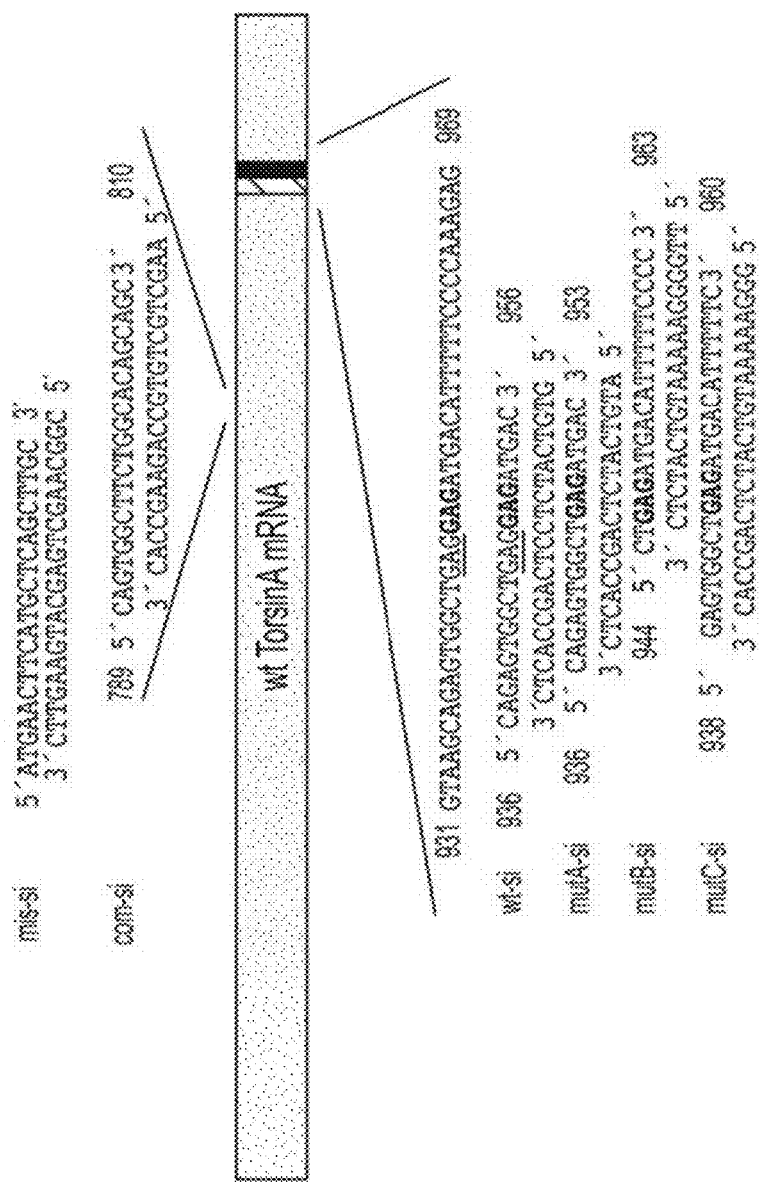

FIG. 23. Design and targeted sequences of siRNAs (SEQ ID NOS: 42-54, respectively, in order of appearance). Shown are the relative positions and targeted mRNA sequences for each primer used in this study. Mis-siRNA (negative control) does not target TA; com-siRNA targets a sequence present in wild type and mutant TA; wt-siRNA targets only wild type TA; and three mutant-specific siRNAs (Mut A, B, C). preferentially target mutant TA. The pair of GAG codons near the c-terminus of wild type mRNA are shown in underlined gray and black, with one codon deleted in mutant mRNA.

FIGS. 24A-E. siRNA silencing of TAwt and TAmut in Cos-7 cells. (A) Western blot results showing the effect of different siRNAs on GFP-TAwt expression levels. Robust suppression is achieved with wt-siRNA and com-siRNA, while the mutant-specific siRNAs MutA, (B) and (C) have modest or no effect on GFP-TAwt expression. Tubulin loading controls are also shown. (B) Similar experiments with cells expressing HA-TAmut, showing significant suppression by mutant-specific siRNAs and com-siRNA but no suppression by the wild type-specific siRNA, wt-siRNA. (C) Quantification of results from at least three separate experiments as in A and B. (D) Cos-7 cells transfected with GFP-TAwt or GFP-TAmut and different siRNAs visualized under fluorescence microscopy (200×). Representative fields are shown indicating allele-specific suppression. (E) Quantification of fluorescence signal from two different experiments as in D.

Figure 25A:
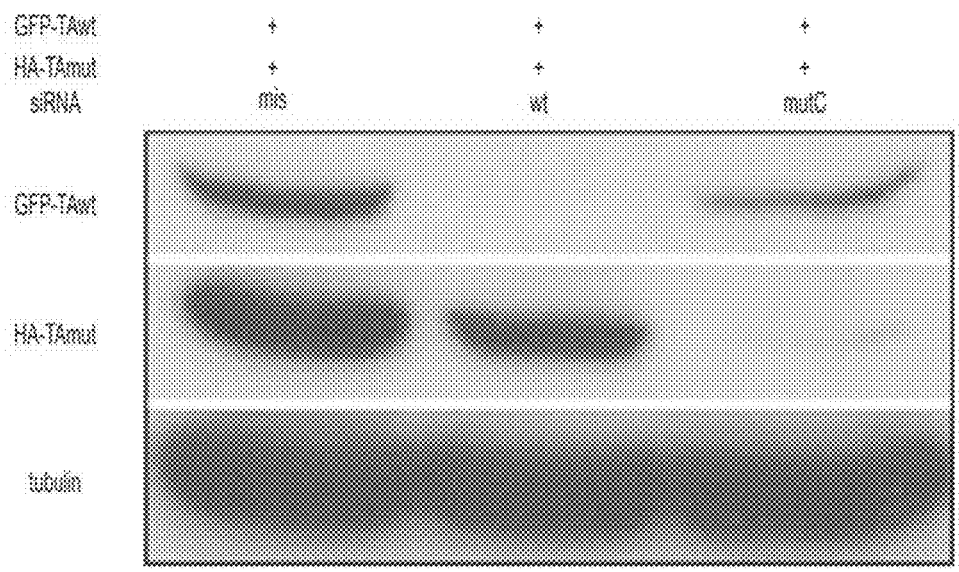
Figure 25B:
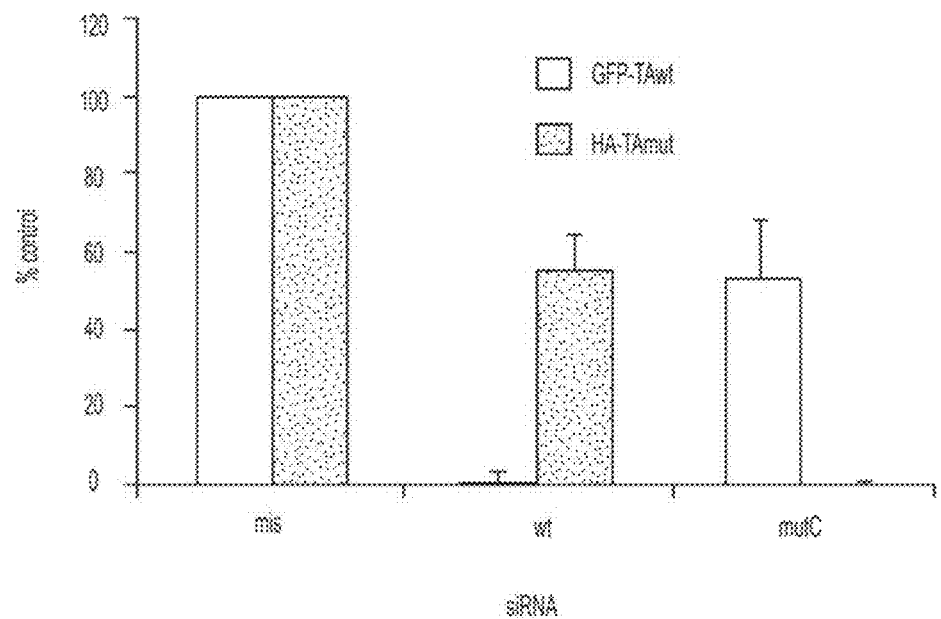

FIGS. 25A-B. Allele-specific silencing by siRNA in the simulated heterozygous state. Cos-7 cells were cotransfected with plasmids encoding differentially tagged TAwt and TAmut, together with the indicated siRNA. (A) Western blot results analysis showing selective suppression of the targeted allele by wt-siRNA or mutC-siRNA. (B) Quantification of results from three experiments as in (A).

FIGS. 26A-E. RNAi reduces human huntingtin expression in vitro. (A) RNA sequence of shHD2.1 (SEQ ID NO: 59). The 21 nucleotide antisense strand is cognate to nucleotides 416-436 of human htt mRNA (Genbank #NM 00211). (B and C) Northern and western blots demonstrate shHD2.1 mediated reduction of HD-N171-82Q mRNA and protein expression, 48 h post-transfection of target- and shRNA-expressing plasmids. GAPDH and actin serve as loading controls. (D) Western blots show that shHD2.1 inhibits expression of full-length human huntingtin protein, 48 h post-transfection. (E) ShHD2.1 induces dose-dependent reduction of human htt mRNA. Cells were transfected with shLacZ- or shHD2.1-expressing plasmids in the indicated amounts. Relative htt expression was determined by quantitative PCR 24 h later. SEQ ID NO:56 is 5'-AAGAAAGAACUUUCAGCUACC-3'. SEQ ID NO:57 is 5'-GGUAGCUGAAAGUUCUUUCUU-3'. SEQ ID NO:58 is 5'-GAAGCUUG-3'. SEQ ID NO:59 is 5'-AAGAAAGAACUUUCAGCUACCGAAGC-UUGGGUAGCUGAAAGUUCUUUCUUUUU UU-3'.

Figure 27A:
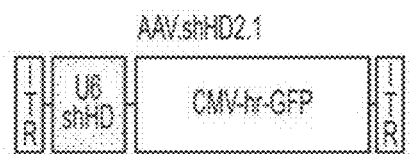
Figure 27B:
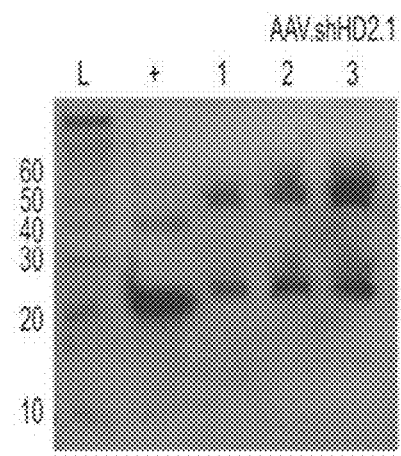
Figure 27C:
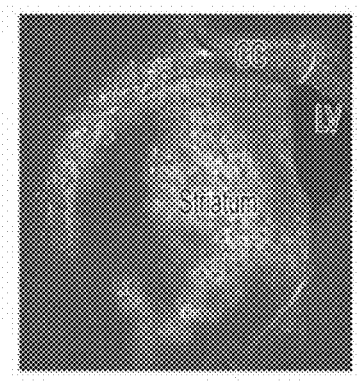

FIGS. 27A-C. AAV.shHD2.1 delivers widespread RNAi expression to mouse striatum. (A) AAV.shHD2.1 viral vector. ITR, inverted terminal repeat. (B) Northern blot showing shHD2.1 transcripts are expressed in vivo. Processed antisense (lower band) and unprocessed (upper band) shHD2.1 transcripts in three different AAV.shHD2.1-injected mice. L, ladder; +, positive control oligo. Blot was probed with radiolabeled sense probe. (C) Typical AAV1 transduction pattern (hrGFP) in mouse brain. CC, corpus callosum; LV, lateral ventricle.

FIGS. 28A-E. AAV.shHD2.1 eliminates accumulation of huntingtin-reactive neuronal inclusions and reduces HD-N171-82Q mRNA in vivo. (A) Representative photomicrographs show htt-reactive inclusions (arrows) in HD striatal cells transduced with AAV.shLacZ-, but not AAV.shHD2.1. Scale bar, 20 µm. (B) Higher magnification photomicrograph from a (bottom, right) showing lack of htt-reactive inclusions in cells transduced by AAV.shHD2.1. * serves as a marker for orientation. Scale bar, 20 µm. (C) Representative western blot demonstrates decreased HD-N171-82Q expression in mouse striata transduced with AAV.shHD2.1 compared to uninjected or AAV.shLacZ-injected striata. Prion protein was used as a loading control to normalize for tissues expressing the HD-N171-82Q transgene. (D) AAV.shHD2.1-treated HD mice showed a 55% average reduction in HD-N171-82Q mRNA compared to AAV.shLacZ or uninjected HD mice. Data are means+ S.E.M. relative to uninjected HD samples. *, difference from AAV.shHD2.1 samples, $p<0.05$ (ANOVA). (E) Mice were injected directly into cerebellum with AAV.shHD2.1 or AAV.shLacZ. Cerebellar sections confirm that AAV.shHD2.1, but not AAV.shLacZ, reduces htt immunoreactivity. GCL, granule cell layer; ML, molecular layer. Scale bar, 100 µm.

Figure 29A:
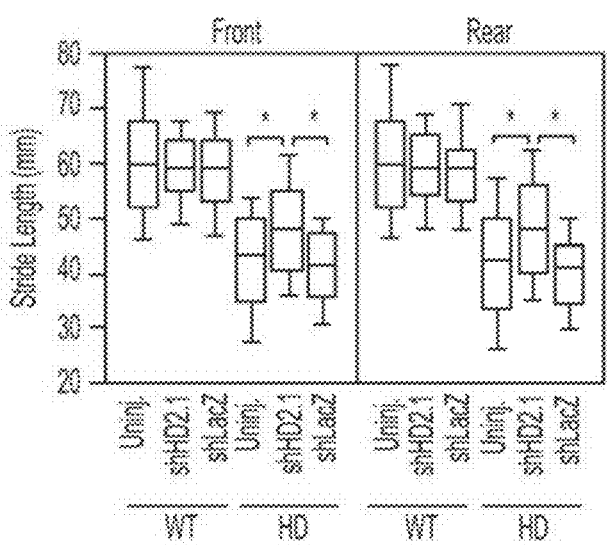
Figure 29B:
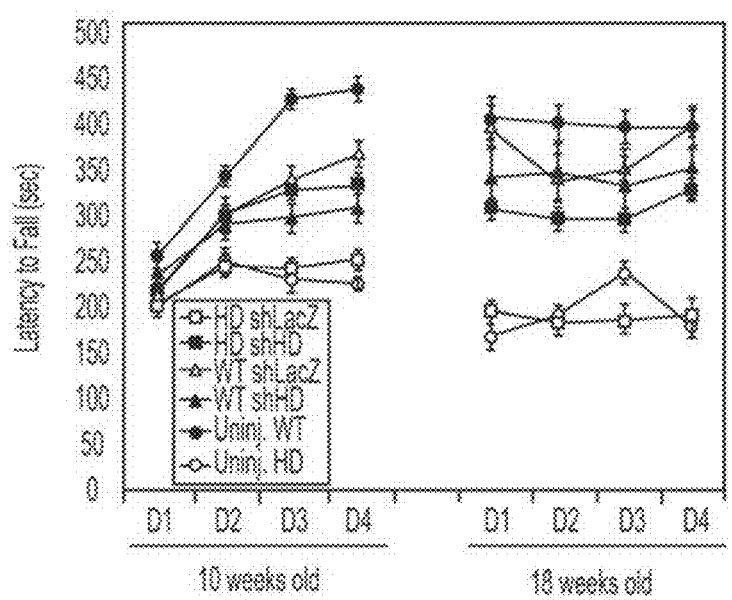

FIGS. 29A-B. AAV.shHD2.1 improves behavioral deficits in HD-N171-82Q mice. (A) Box plot. Bilateral striatal delivery of AAV.shHD2.1 improves stride length in HD-N171-82Q mice. HD mice had significantly shorter stride lengths compared to WT. AAV.shHD2.1 mediated significant gait improvement relative to control-treated HD mice. *, $p<0.0001$ (ANOVA, Scheffe post-hoc). (B) Bilateral striatal delivery of AAV.shHD2.1 significantly improves rotarod performance in HD-N171-82Q mice. Only AAV.sh-LacZ-injected and uninjected HD-N171-82Q declined significantly with time. Data are means±S.E.M.

Figure 30:
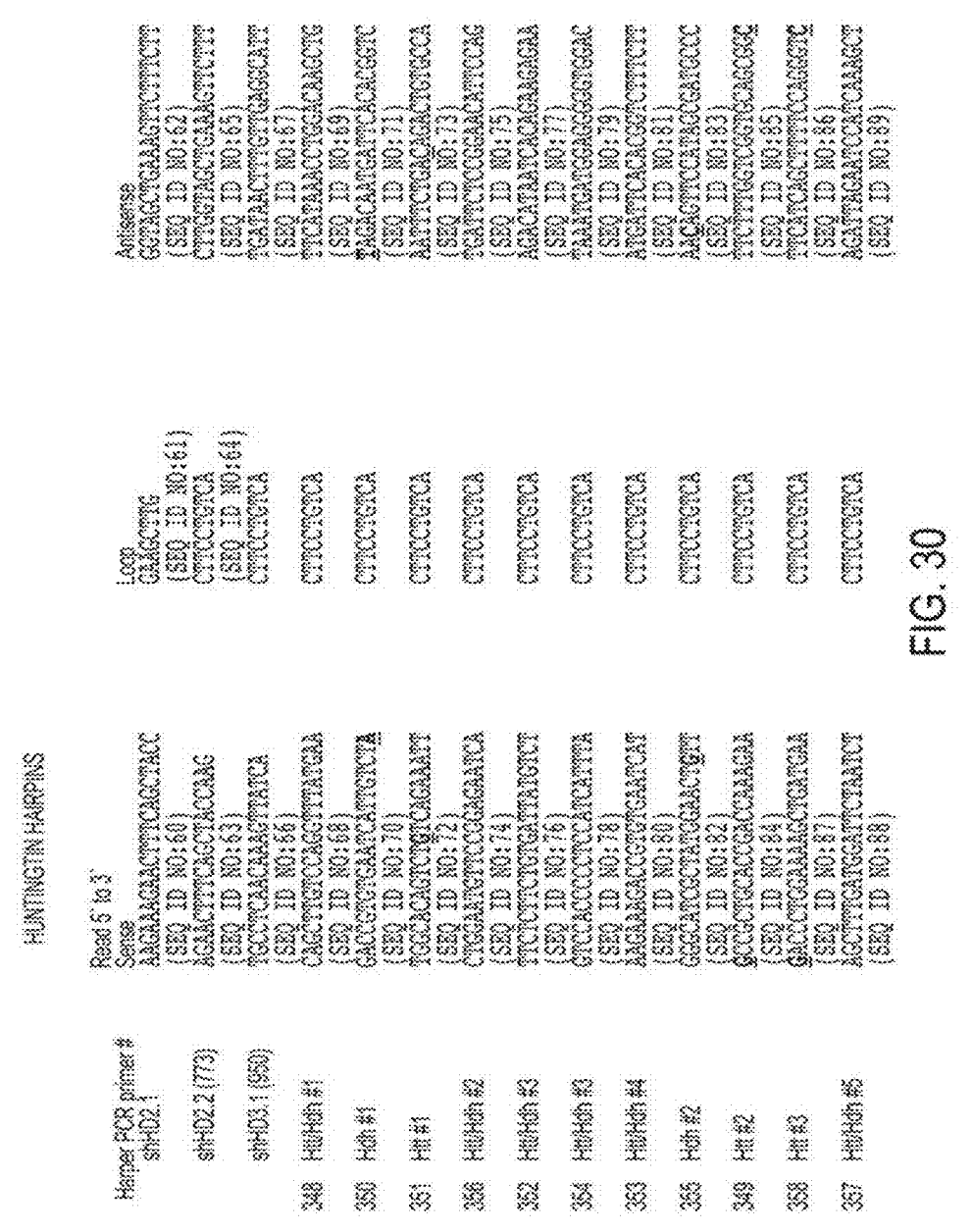

FIG. 30. DNA sequences of huntingtin hairpins (SEQ ID NOS: 60-89). The bases that are underlined indicate changes from the native huntingtin sequence.

Figure 31:
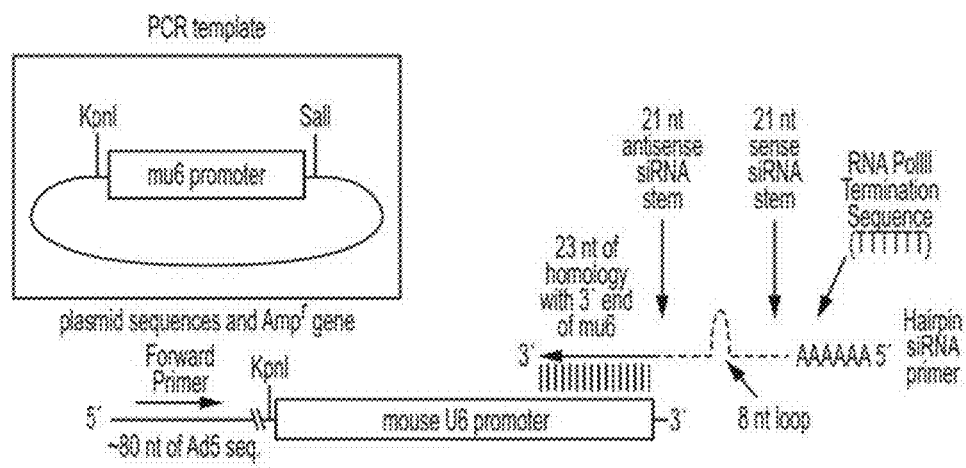

FIG. 31. PCR method for cloning hairpins. A 79 nt primer is used with the Ampr template. Pfu and DMSO are used in the amplification reaction. Products are ligated directly into pCR-Blunt Topo (Invitrogen) and Kanr resistant colonies picked and sequenced. Positive clones can be used directly.

Figure 32:
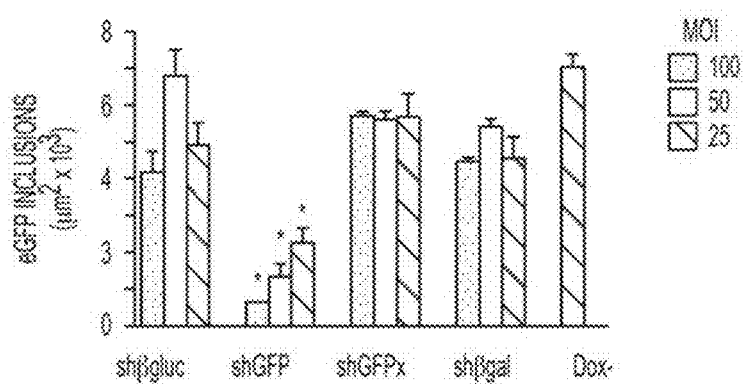

FIG. 32. Reduction of eGFP inclusions after transduction with 25, 50 or 100 viruses/cell into cultures with pre-formed aggregates. Note dose-dependent response with shGFP vectors only.

Figure 33:
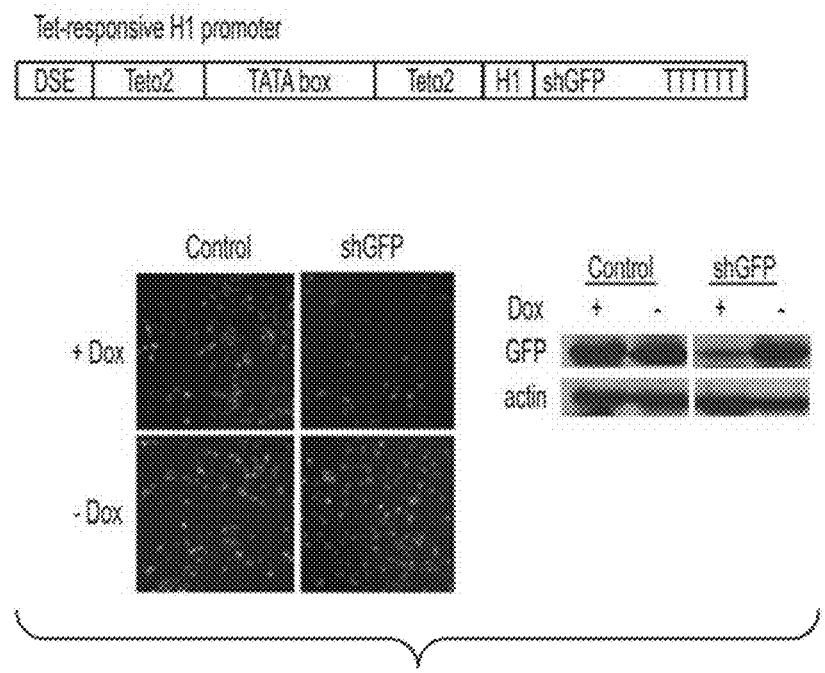

FIG. 33. Regulated RNAi. Two Teto2 sequences were placed up- and down-stream of the TATA box of the H1 promoter element (cartoon). Either control shRNA or shGFP was placed into the cassette for expression of hairpins. Plasmids expressing GFP and the hairpin constructs were transfected into a cell line expressing the TetR (tet-repressor). GFP fluorescence (left panels) or western blot (right panels) was evaluated in the absence (TetR binding) or presence (TetR off) of doxycycline.

Figure 34:
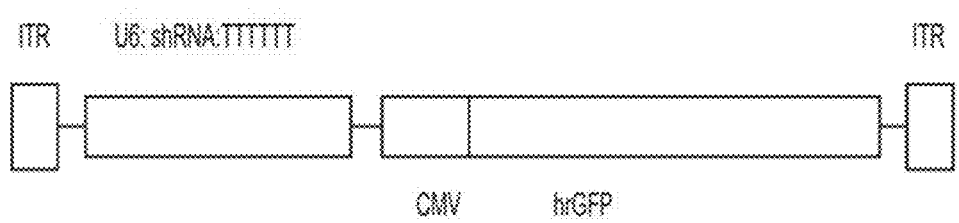

FIG. 34. Top, FIV construct. Bottom, AAV construct. Both express the hrGFP reporter so that transduced cells can be readily evaluated for shRNA efficacy (as in FIGS. 3 and 4).

Figure 35C:
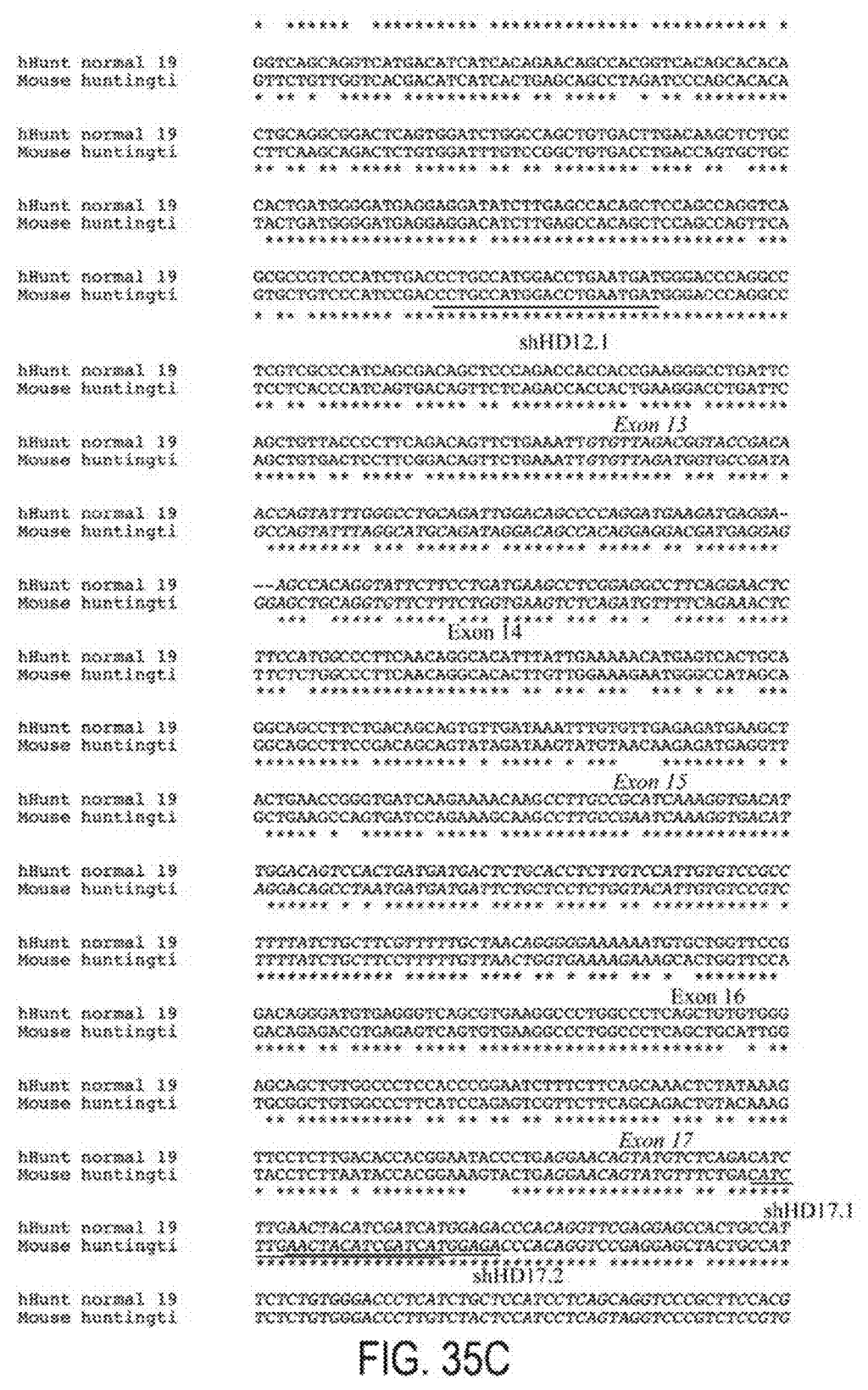

FIGS. 35A-L. siRNA molecules specific for regions of the HD gene. shHD sequences disclosed as SEQ ID NOS: 106-115, 145, 116-141, 146 and 142, respectively, in order of appearance. Human and mouse huntington sequences disclosed as SEQ ID NOS: 143 and 144, respectively.

DETAILED DESCRIPTION OF THE INVENTION

Modulation of gene expression by endogenous, noncoding RNAs is increasingly appreciated as a mechanism playing a role in eukaryotic development, maintenance of chromatin structure and genomic integrity (McManus, 2002). Recently, techniques have been developed to trigger RNA interference (RNAi) against specific targets in mammalian cells by introducing exogenously produced or intracellularly expressed siRNAs (Elbashir, 2001a, 2001b, 2001c; Brummelkamp, 2002). These methods have proven to be quick, inexpensive and effective for knockdown experiments in vitro and in vivo (Elbashir, 2001a, 2001b, 2001c; Brummelkamp, 2002; McCaffrey, 2002; Xia, 2002). The ability to accomplish selective gene silencing has led to the hypothesis that siRNAs might be employed to suppress gene expression for therapeutic benefit (Xia, 2002; Jacque, 2002; Gitlin, 2002).

RNA interference is now established as an important biological strategy for gene silencing, but its application to mammalian cells has been limited by nonspecific inhibitory effects of long double-stranded RNA on translation. Moreover, delivery of interfering RNA has largely been limited to administration of RNA molecules. Hence, such administration must be performed repeatedly to have any sustained effect. The present inventors have developed a delivery mechanism that results in specific silencing of targeted genes through expression of small interfering RNA (siRNA). The inventors have markedly diminished expression of exogenous and endogenous genes in vitro and in vivo in brain and liver, and further apply this novel strategy to a model system of a major class of neurodegenerative disorders, the polyglutamine diseases, to show reduced polyglutamine aggregation in cells. This strategy is generally useful in reducing expression of target genes in order to model biological processes or to provide therapy for dominant human diseases.

Disclosed herein is a strategy that results in substantial silencing of targeted alleles via siRNA. Use of this strategy results in markedly diminished in vitro and in vivo expression of targeted alleles. This strategy is useful in reducing expression of targeted alleles in order to model biological processes or to provide therapy for human diseases. For example, this strategy can be applied to a major class of neurodegenerative disorders, the polyglutamine diseases, as is demonstrated by the reduction of polyglutamine aggregation in cells following application of the strategy. As used herein the term "substantial silencing" means that the mRNA of the targeted allele is inhibited and/or degraded by the presence of the introduced siRNA, such that expression of the targeted allele is reduced by about 10% to 100% as compared to the level of expression seen when the siRNA is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of an allele when an siRNA has not been introduced to a cell.

Dominantly inherited diseases, including polyQ neurodegenerative disorders, are ideal candidates for siRNA-based therapy. The polyQ neurodegenerative disorders include at least nine inherited disorders caused by CAG repeat expansions that encode polyQ in the disease protein. PolyQ expansion confers a dominant toxic property on the mutant protein that is associated with aberrant accumulation of the disease protein in neurons (Zoghbi, 2000). All polyQ diseases are progressive, ultimately fatal disorders that typically begin in adulthood. Huntington disease (HD) is the best known polyQ disease, but at least seven hereditary ataxias and one motor neuron disease are also due to CAG repeat/polyQ expansion. Although the clinical features and patterns of neuronal degeneration differ among the diseases, increasing evidence suggests that polyQ diseases share important pathogenic features. In particular, expansion of the CAG repeat/polyQ domain confers upon the encoded protein a dominant toxic property. Thus as a therapeutic strategy, efforts to lower expression of the mutant gene product prior to cell death could be highly beneficial to patients.

Dominantly inherited diseases are ideal candidates for siRNA-based therapy. To explore the utility of siRNA in inherited human disorders, the present inventors employed cellular models to test whether mutant alleles responsible for these dominantly-inherited human disorders could be specifically targeted. First, three classes of dominantly inherited, untreatable neurodegenerative diseases were examined: polyglutamine (polyQ) neurodegeneration in MJD/SCA3, Huntington's disease and frontotemporal dementia with parkinsonism linked to chromosome 17 (FTDP-17). Machado-Joseph disease is also known as Spinocerebellar Ataxia Type 3 (The HUGO official name is MJD). The gene involved is MJD1, which encodes for the protein ataxin-3 (also called Mjd1p). Huntington's disease is due to expansion of the CAG repeat motif in exon 1 of huntingtin. In 38% of patients a polymorphism exists in exon 58 of the huntingtin gene, allowing for allele specific targeting. Frontotemporal dementia (sometimes with parkinonism, and linked to chromosome 17, so sometimes called FTDP-17) is due to mutations in the MAPT1 gene that encodes the protein tau.

The polyQ neurodegenerative disorders include at least nine diseases caused by CAG repeat expansions that encode polyQ in the disease protein. PolyQ expansion confers a dominant toxic property on the mutant protein that is associated with aberrant accumulation of the disease protein in neurons (Zoghbi, 2000). In FTDP-17, Tau mutations lead to the formation of neurofibrillary tangles accompanied by neuronal dysfunction and degeneration (Poorkaj, 1998; Hutton, 1998). The precise mechanisms by which these mutant proteins cause neuronal injury are unknown, but considerable evidence suggests that the abnormal proteins themselves initiate the pathogenic process (Zoghbi, 2000). Accordingly, eliminating expression of the mutant protein by siRNA or other means slows or prevents disease (Yamamoto, 2000). However, because many dominant disease genes also encode essential proteins (e.g. Nasir, 1995) siRNA-mediated approaches were developed that selectively inactivate mutant alleles, while allowing continued expression of the wild type proteins ataxin-3 and huntingtin.

Second, the dominantly-inherited disorder DYT1 dystonia was studied. DYT1 dystonia is also known as Torsion dystonia type 1, and is caused by a GAG deletion in the TOR1A gene encoding torsinA. DYT1 dystonia is the most common cause of primary generalized dystonia. DYT1 usually presents in childhood as focal dystonia that progresses to severe generalized disease (Fahn, 1998; Klein, 2002a). With one possible exception (Leung, 2001; Doheny, 2002; Klein, 2002), all cases of DYT1 result from a common GAG deletion in TOR1A, eliminating one of two adjacent glutamic acids near the C-terminus of the protein TorsinA (TA) (Ozelius, 1997). Although the precise cellular function of TA is unknown, it seems clear that mutant TA (TAmut) acts through a dominant-negative or dominant-toxic mechanism (Breakefield, 2001).

Several characteristics of DYT1 make it an ideal disease in which to use siRNA-mediated gene silencing as therapy. Of greatest importance, the dominant nature of the disease suggests that a reduction in mutant TA, whatever the precise pathogenic mechanism proves to be, is helpful. Moreover, the existence of a single common mutation that deletes a full three nucleotides suggested it might be feasible to design siRNA that specifically targets the mutant allele and is applicable to all affected persons. Finally, there is no effective therapy for DYT1, a relentless and disabling disease.

As outlined in the strategy in FIG. 11, the inventors developed siRNA that would specifically eliminate production of protein from the mutant allele. By exploiting the three base pair difference between wild type and mutant alleles, the inventors successfully silenced expression of the mutant protein (TAmut) without interfering with expression of the wild type protein (TAwt). Because TAwt may be an essential protein it is critically important that efforts be made to silence only the mutant allele. This allele-specific strategy has obvious therapeutic potential for DYT1 and represents a novel and powerful research tool with which to investigate the function of TA and its dysfunction in the disease state.

Expansions of poly-glutamine tracts in proteins that are expressed in the central nervous system can cause neurodegenerative diseases. Some neurodegenerative diseases are caused by a $(CAG)_n$ repeat that encodes poly-glutamine in a protein include Huntington disease (HD), spinocerebellar ataxia (SCA1, SCA2, SCA3, SCA6, SCA7), spinal and bulbar muscular atrophy (SBMA), and dentatorubropallidoluysian atrophy (DRPLA). In these diseases, the polyglutamine expansion in a protein confers a novel toxic property upon the protein. Studies indicate that the toxic property is a tendency for the disease protein to misfold and form aggregates within neurons.

CAG triplet repeat expansion in exon 1 of Hdh causes Huntington's disease. Clinical characteristics of HD include progressive loss of striatal neurons and later, cortical thinning. Adult patients show choreiform movements, impaired coordination, progressive dementia and other psychiatric disturbances. The symptoms of juvenile HD patients include bradykinesia, dystonia and seizures. HD is a uniformly fatal disease, with death occurring one to two decades after disease onset.

The Hdh locus is on chromosome 4, spans 180 kb over 67 exons and encodes the protein huntingtin (htt). In non-HD individuals, the CAG repeat region is less than 35 CAG repeats. Expansions of 36 to ~50 repeats, or greater than ~50, cause late or early onset disease, respectively. The inverse correlation of repeat length with age of disease onset is a common characteristic of the CAG repeat disorders, and one that is recapitulated in mouse models. Evidence indicates that HD also may be a dose-dependent process. For example, in transgenic mouse models of polyQ disease, phenotypic severity usually correlates with expression levels of the disease protein, and homozygous transgenic mice develop disease more rapidly than heterozygous mice. In addition, the very rare human cases of homozygosity for polyQ disease suggest that disease severity correlates with the level of disease protein expression, again supporting the notion that reducing mutant protein expression would be clinically beneficial.

The function of htt is not known. It is clear from mouse models, however, that it is required during gastrulation, neurogenesis and in postnatal brain. Htt knock-out mice die during development. Also, removal of htt via Cre recombinase-mediated excision of a floxed Hdh allele causes progressive postnatal neurodegeneration. A CAG expansion introduced into the mouse allele (a knock-in) does not impair neurogenesis unless wildtype htt expression is reduced from normal levels, suggesting that the expanded allele does not impair wildtype htt function in neurogenesis. In adult mice mutant htt causes progressive depletion of normal htt. Htt is important in vesicle trafficking, NMDA receptor modulation, and regulation of BDNF transcription, and the expression of many genes is affected in the CNS of HD mice.

The therapeutic promise of silencing the mutant gene (and its toxic property) is best demonstrated in a tetracycline-regulated mouse model of HD (Yamamoto 2000). When mutant htt is inducibly expressed in these mice, pathological and behavioral features of the disease develop over time, including the characteristic formation of neuronal inclusions and abnormal motor behavior (Yamamoto 2000, Orr 2000). However, when expression of the transgene is repressed in affected mice, the pathological and behavioral features of disease fully resolve (Yamamoto 2000). This result indicates that if expression of mutant polyQ protein can be halted, protein clearance mechanisms within neurons can eliminate the aggregated mutant protein, and possibly normalize mutant htt-induced changes. It also suggests that gene silencing approaches may be beneficial even for individuals with fairly advanced disease.

One of skill in the art can select additional target sites for generating siRNA specific for other alleles beyond those specifically described in the experimental examples. Such allele-specific siRNAs made be designed using the guidelines provided by Ambion (Austin, Tex.). Briefly, the target cDNA sequence is scanned for target sequences that had AA di-nucleotides. Sense and anti-sense oligonucleotides are generated to these targets (AA+3' adjacent 19 nucleotides) that contained a G/C content of 35 to 55%. These sequences are then compared to others in the human genome database to minimize homology to other known coding sequences (BLAST search).

To accomplish intracellular expression of the therapeutic siRNA, an RNA molecule is constructed containing two complementary strands or a hairpin sequence (such as a 21-bp hairpin) representing sequences directed against the gene of interest. The siRNA, or a nucleic acid encoding the siRNA, is introduced to the target cell, such as a diseased brain cell. The siRNA reduces target mRNA and protein expression.

The construct encoding the therapeutic siRNA is configured such that the one or more strands of the siRNA are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, allowing for diminished target-gene expression in the cell.

It was surprising that a pol II promoter would be effective. While small RNAs with extensive secondary structure are routinely made from Pol III promoters, there is no a priori reason to assume that small interfering RNAs could be expressed from pol II promoters. Pol III promoters terminate in a short stretch of Ts (5 or 6), leaving a very small 3' end and allowing stabilization of secondary structure. Polymerase II transcription extends well past the coding and polyadenylation regions, after which the transcript is cleaved. Two adenylation steps occur, leaving a transcript with a tail of up to 200 As. This string of As would of course completely destabilize any small, 21 base pair hairpin. Therefore, in addition to modifying the promoter to minimize sequences between the transcription start site and the siRNA sequence (thereby stabilizing the hairpin), the inventors also extensively modified the polyadenylation sequence to test if a very short polyadenylation could occur. The results, which were not predicted from prior literature, showed that it could.

The present invention provides an expression cassette containing an isolated nucleic acid sequence encoding a small interfering RNA molecule (siRNA) targeted against a gene of interest. The siRNA may form a hairpin structure that contains a duplex structure and a loop structure. The loop structure may contain from 4 to 10 nucleotides, such as 4, 5 or 6 nucleotides. The duplex is less than 30 nucleotides in length, such as from 19 to 25 nucleotides. The siRNA may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene or stuffer sequences. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to siRNA therapy. Examples of such conditions include neurodegenerative diseases, such as a trinucleotide-repeat disease (e.g., polyglutamine repeat disease). Examples of these diseases include Huntington's disease or several spinocerebellar ataxias. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest. The expression cassette may be contained in a vector, such as a viral vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest.

The present method also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as a small interfering RNA molecule (siRNA) targeted against a gene of interest.

I. Small Interfering RNA (siRNA)

A "small interfering RNA" or "short interfering RNA" or "siRNA" or "short hairpin RNA" or "shRNA" is a RNA duplex of nucleotides that is targeted to a nucleic acid sequence of interest, for example, ataxin-1 or huntingtin (htt). As used herein, the term "siRNA" is a generic term that encompasses the subset of shRNAs. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1 or huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression. RNAi involving the use of siRNA has been successfully applied to knockdown the expression of specific genes in plants, *D. melanogaster, C. elegans*, trypanosomes, planaria, hydra, and several vertebrate species including the mouse. For a review of the mechanisms proposed to mediate RNAi, please refer to Bass et al., 2001 Elbashir, 2001a, 2001b, 2001c; or Brantl, 2002.

According to a method of the present invention, the expression of huntingtin or atxain-1 can be modified via RNAi. For example, the accumulation of huntingtin or ataxain-1 can be suppressed in a cell. The term "suppressing" refers to the diminution, reduction or elimination in the number or amount of transcripts present in a particular cell. For example, the accumulation of mRNA encoding huntingtin or atxain-1 can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in one or both alleles of huntingtin or atxain-1. A mutant huntingtin or atxain-1 may be disease-causing, i.e., may lead to a disease associated with the presence of huntingtin or atxain-1 in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. Arr isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

A "foreign" gene refers to a gene not normally found in the host organism that has been introduced by gene transfer.

The terms "protein," "peptide" and "polypeptide" are used interchangeably herein.

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous gene", "heterologous DNA sequence", "exogenous DNA sequence", "heterologous RNA sequence", "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation of Meinkoth and Wahl (1984); Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993). Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference (for a review, see Brantl, 2002). In some embodiments, gene silencing may be allele-specific. "Allele-specific" gene silencing refers to the specific silencing of one allele of a gene.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. For example, the expression may be reduced by 10, 20, 30, 40, 50, 60, 70, 80, 90, 95, or even 99%. Knock-down of gene expression can be directed by the use of dsRNAs or siRNAs. For example, "RNA interference (RNAi)," which can involve the use of siRNA, has been successfully applied to knockdown the expression of specific genes in plants, D. melanogaster, C. elegans, trypanosomes, planaria, hydra, and several vertebrate species including the mouse. For a review of the mechanisms proposed to mediate RNAi, please refer to Bass et al., 2001, Elbashir et al., 2001 or Brantl 2002.

"RNA interference (RNAi)" is the process of sequence-specific, post-transcriptional gene silencing initiated by siRNA. RNAi is seen in a number of organisms such as Drosophila, nematodes, fungi and plants, and is believed to be involved in anti-viral defense, modulation of transposon activity, and regulation of gene expression. During RNAi, siRNA induces degradation of target mRNA with consequent sequence-specific inhibition of gene expression.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. Examples of shRNA specific for huntington are encoded by the DNA sequences provided in FIGS. 20A-C. The "sense" and "antisense" sequences can be used with or without the loop region indicated to form siRNA molecules. Other loop regions can be substituted for the examples provided in this chart. As used herein, the term siRNA is meant to be equivalent to other terms used to describe nucleic acid molecules that are capable of mediating sequence specific RNAi, for example, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetic silencing. For example, siRNA molecules of the invention can be used to epigenetically silence genes at both the post-transcriptional level or the pre-transcriptional level. In a non-limiting example, epigenetic modulation of gene expression by siRNA molecules of the invention can result from siRNA mediated modification of chromatin structure or methylation pattern to alter gene expression (see, for example, Verdel et al., 2004, *Science*, 303, 672-676; Pal-Bhadra et al., 2004, *Science*, 303, 669-672; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237). In another non-limiting example, modulation of gene expression by siRNA molecules of the invention can result from siRNA mediated cleavage of RNA (either coding or non-coding RNA) via RISC, or alternately, translational inhibition as is known in the art.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Treating" as used herein refers to ameliorating at least one symptom of, curing and/or preventing the development of a disease or a condition.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA1, and SCA17), spinal and bulbar muscular atrophy (SBMA), dentatorubropallidoluysian atrophy (DRPLA). An example of a neurological disorder that does not appear to result in atrophy is DYT1 dystonia.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

II. Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an siRNA. Such an isolated siRNA may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art as described by Adelman et al. (1983). Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13mp18 and M13mp19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

There are well-established criteria for designing siRNAs (see, e.g., Elbashire et al., 2001a, 2001b, 2001c). Details can be found in the websites of several commercial vendors such as Ambion, Dharmacon and Oligoengine. However, since the mechanism for siRNAs suppressing gene expression is not entirely understood and siRNAs selected from different regions of the same gene do not work as equally effective, very often a number of siRNAs have to be generated at the same time in order to compare their effectiveness.

III. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein. For example, Sambrook and Russell, infra, provides suitable methods of construction.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed above, a "transfected", or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell", comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

IV. Methods for Introducing the Expression Cassettes of the Invention into Cells The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta□-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In one embodiment of the present invention, an expression cassette may contain a pol II promoter that is operably linked to a nucleic acid sequence encoding a siRNA. Thus, the pol II promoter, i.e., a RNA polymerase II dependent promoter, initiates the transcription of the siRNA. In another embodiment, the pol II promoter is regulatable.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the siRNA may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

In one embodiment, a pol II promoter that effectively directs the expression of the siRNA in the cell type, organelle, and organism chosen for expression will be employed. Those of ordinary skill in the art of molecular biology generally know the use of promoters for protein expression, for example, see Sambrook and Russell (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

V. Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells. Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector (Brooks et al. (2002); Alisky et al. (2000a)) or an AAV vector. For example, one may use AAV5 (Davidson et al. (2000); Alisky et al. (2000a)). Also, one may apply poliovirus (Bledsoe et al. (2000)) or HSV vectors (Alisky et al. (2000b)).

Application of siRNA is generally accomplished by transfection of synthetic siRNAs, in vitro synthesized RNAs, or plasmids expressing short hairpin RNAs (shRNAs). More recently, viruses have been employed for in vitro studies and to generate transgenic mouse knock-downs of targeted genes (Hannon 2002, Rubinson 2003, Kunath 2003). Recombinant adenovirus, adeno-associated virus (AAV) and feline immunodeficiency virus (FIV) can be used to deliver genes in vitro and in vivo (Alisky 2000, Davidson 2000, Brooks 2000). Each has its own advantages and disadvantages (Davidson 2003). Adenoviruses are double stranded DNA viruses with large genomes (36 kb) and have been engineered by my laboratory and others to accommodate expression cassettes in distinct regions. We used recombinant adenoviruses expressing siRNAs to demonstrate successful viral-mediated gene suppression in brain (Xia 2002).

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively, three of which have been evaluated in the brain (Davidson 2000, Passini 2003, Skorupa 1999, Frisella 2001, Xiao 1997, During 1998). An important consideration for the present application is that AAV5 transduces striatal and cortical neurons, and is not associated with any known pathologies.

Adeno associated virus (AAV) is a small nonpathogenic virus of the parvoviridae family (for review see Muzyczka, N. 1992. Curr Top Microbiol Immunol 158: 97-129; see also U.S. Pat. No. 6,468,524). AAV is distinct from the other members of this family by its dependence upon a helper virus for replication. In the absence of a helper virus, AAV may integrate in a locus specific manner into the q arm of chromosome 19 (Kotin et al., (1990) Proc. Natl. Acad. Sci. (USA) 87: 2211-2215). The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date seven serologically distinct AAVs have been identified and five have been isolated from humans or primates and are referred to as AAV types 1-5 (Arella et al Handbook of Parvoviruses. Vol. 1. ed. P. Tijssen. Boca Raton, Fla., CRC Press, 1990). The most extensively studied of these isolates is AAV type 2 (AAV2). The genome of AAV2 is 4680 nucleotides in length and contains two open reading frames (ORFs). The left ORF encodes the non-structural Rep proteins, Rep40, Rep 52, Rep68 and Rep 78, which are involved in regulation of replication and transcription in addition to the production of single-stranded progeny genomes. Furthermore, two of the Rep proteins have been associated with the possible integration of AAV genomes into a region of the q arm of human chromosome 19. Rep68/78 have also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV2 virion is a non-enveloped, icosohedral particle approximately 25 nm in diameter, consisting of three related proteins referred to as VP1,2 and 3. The right ORF encodes the capsid proteins, VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles.

The following features of AAV have made it an attractive vector for gene transfer. AAV vectors have been shown in vitro to stably integrate into the cellular genome; possess a broad host range; transduce both dividing and non dividing cells in vitro and in vivo and maintain high levels of expression of the transduced genes. Viral particles are heat stable, resistant to solvents, detergents, changes in pH, temperature, and can be concentrated on CsCl gradients. Integration of AAV provirus is not associated with any long term negative effects on cell growth or differentiation. The ITRs have been shown to be the only cis elements required for replication, packaging and integration and may contain some promoter activities.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, psuedotyped retroviral vectors, and adenoviral vectors.

Also provided by this invention are variant AAV vectors. For example, the sequence of a native AAV, such as AAV5, can be modified at individual nucleotides. The present invention includes native and mutant AAV vectors. The present invention further includes all AAV serotypes.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons (Brooks 2002, Lotery 2002), and transduction can be directed to different cell types by pseudotyping, the process of exchanging the viruses native envelope for an envelope from another virus (Kang 2002, Stein 2001).

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

VI. Diseases and Conditions Amenable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state. An example of a targetable polymorphism that is not itself a mutation is the polymorphism in exon 58 associated with Huntington's disease.

Single nucleotide polymorphisms comprise most of the genetic diversity between humans. The major risk factor for developing Alzheimer's disease is the presence of a particular polymorphism in the apolipoprotein E gene.

Single nucleotide polymorphisms comprise most of the genetic diversity between humans, and that many disease genes, including the HD gene in Huntington's disease, contain numerous single nucleotide or multiple nucleotide polymorphisms that could be separately targeted in one allele vs. the other. The major risk factor for developing Alzheimer's disease is the presence of a particular polymorphism in the apolipoprotein E gene.

A. Gene Defects

A number of diseases caused by gene defects have been identified. For example, this strategy can be applied to a major class of disabling neurological disorders. For example this strategy can be applied to the polyglutamine diseases, as is demonstrated by the reduction of polyglutamine aggregation in cells following application of the strategy. The neurodegenerative disease may be a trinucleotide-repeat disease, such as a disease associated with polyglutamine repeats, including Huntington's disease, and several spinocerebellar ataxias. Additionally, this strategy can be applied to a non-degenerative neurological disorder, such as DYT1 dystonia.

B. Acquired Pathologies

As used herein, "acquired pathology" refers to a disease or syndrome manifested by an abnormal physiological, biochemical, cellular, structural, or molecular biological state. For example, the disease could be a viral disease, such as hepatitis or AIDS.

C. Cancers

The condition amenable to gene silencing therapy alternatively can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

VII. Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of siRNA may be accomplished through the administration of the nucleic acid molecule encoding the siRNA (see, for example, Feigner et al., U.S. Pat. No. 5,580,859, Pardoll et al. 1995; Stevenson et al. 1995; Moiling 1997; Donnelly et al. 1995; Yang et al. II; Abdallah et al. 1995). Pharmaceutical formulations, dosages and routes of administration for nucleic acids are generally disclosed, for example, in Feigner et al., supra.

The present invention envisions treating a disease, for example, a neurodegenerative disease, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

EXAMPLE 1 siRNA-Mediated Silencing of Genes Using Viral Vectors

In this Example, it is shown that genes can be silenced in an allele-specific manner. It is also demonstrated that viral-mediated delivery of siRNA can specifically reduce expression of targeted genes in various cell types, both in vitro and in vivo. This strategy was then applied to reduce expression of a neurotoxic polyglutamine disease protein. The ability of viral vectors to transduce cells efficiently in vivo, coupled with the efficacy of virally expressed siRNA shown here, extends the application of siRNA to viral-based therapies and in vivo targeting experiments that aim to define the function of specific genes.

Experimental Protocols

Generation of the expression cassettes and viral vectors. The modified CMV (mCMV) promoter was made by PCR amplification of CMV by primers 5'-AAGGTACCAGATCTTAGTTATTAATAGTAATCAATTACGG-3' (SEQ ID NO:1) and 5'-GAATCGATGCATGCCTCGAGACGGTTCACTAAACCAGCTCTGC-3' (SEQ ID NO:2) with peGFPN1 plasmid (purchased from Clontech, Inc) as template. The mCMV product was cloned into the KpnI and ClaI sites of the adenoviral shuttle vector pAd5KnpA, and was named pmCMVknpA. To construct the minimal polyA cassette, the oligonucleotides, 5'-CTAGAACTAGTAATAAAGGATCCTTTATTTTCATTGGATCCGTGTGTTGGTTTTTTGTGTGCGGCCGCG-3' (SEQ ID NO:3) and 5'-TCGACGCGGCCGCACACAAAAAACCAACACACGGATCC AAT- GAAAATAAAGGATCCTTTATTACTAGTT-3' (SEQ ID NO:4), were used. The oligonucleotides contain SpeI and SalI sites at the 5' and 3' ends, respectively. The synthesized polyA cassette was ligated into SpeI, SalI digested pmCM-VKnpA. The resultant shuttle plasmid, pmCMVmpA was used for construction of head-to-head 21 bp hairpins of eGFP (bp 418 to 438), human β-glucuronidase (bp 649 to 669), mouse β-glucuronidase (bp 646 to 666) or E. coli β-galactosidase (bp 1152-1172). The eGFP hairpins were also cloned into the Ad shuttle plasmid containing the commercially available CMV promoter and polyA cassette from SV40 large T antigen (pCMVsiGFPx). Shuttle plasmids were co-transfected into HEK293 cells along with the adenovirus backbones for generation of full-length Ad genomes. Viruses were harvested 6-10 days after transfection and amplified and purified as described (Anderson 2000).

Northern blotting. Total RNA was isolated from HEK293 cells transfected by plasmids or infected by adenoviruses using TRIZOL® Reagent (Invitrogen™ Life Technologies, Carlsbad, Calif.) according to the manufacturer's instruction. RNAs (30 µg) were separated by electrophoresis on 15% (wt/vol) polyacrylamide-urea gels to detect transcripts, or on 1% agarose-formaldehyde gel for target mRNAs analysis. RNAs were transferred by electroblotting onto hybond N+ membrane (Amersham Pharmacia Biotech). Blots were probed with $^{32}$P-labeled sense (5'-CACAAGCTGGAGTACAACTAC-3' (SEQ ID NO:5)) or antisense (5'-GTACTTGTACTCCAGCTTTGTG-3' (SEQ ID NO:6)) oligonucleotides at 37° C. for 3 h for evaluation of siRNA transcripts, or probed for target mRNAs at 42° C. overnight. Blots were washed using standard methods and exposed to film overnight. In vitro studies were performed in triplicate with a minimum of two repeats.

In vivo studies and tissue analyses. Mice were injected into the tail vein (n=10 per group) or into the brain (n=6 per group) as described previously (Stein 1999) with the virus doses indicated. Animals were sacrificed at the noted times and tissues harvested and sections or tissue lysates evaluated for β-glucuronidase expression, eGFP fluorescence, or β-galactosidase activity using established methods (Xia 2001). Total RNA was harvested from transduced liver using the methods described above.

Cell lines. PC12 tet off cell lines (Clontech Inc., Palo Alto, Calif.) were stably transfected with a tetracycline regulatable plasmid into which was cloned GFPQ19 or GFPQ80 (Chai 1999a). For GFP–Q80, clones were selected and clone 29 chosen for regulatable properties and inclusion formation. For GFP–Q19 clone 15 was selected for uniformity of GFP expression following gene expression induction. In all studies 1.5 µg/ml dox was used to repress transcription. All experiments were done in triplicate and were repeated 4 times.

Results and Discussion

Figure 1A:
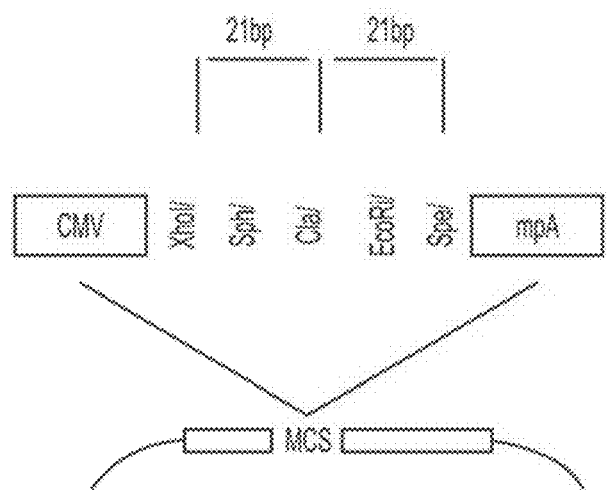
FIGS. 1A-J. siRNA expressed from CMV promoter constructs and in vitro effects. (A) A cartoon of the expression plasmid used for expression of functional siRNA in cells. The CMV promoter was modified to allow close juxtaposition of the hairpin to the transcription initiation site, and a minimal polyadenylation signal containing cassette was constructed immediately 3' of the MCS (mCMV, modified CMV; mpA, minipA). (B, C) Fluorescence photomicrographs of HEK293 cells 72 h after transfection of pEGFPN1 and pCMVβgal (control), or pEGFPN1 and pmCMVsiGFPmpA, respectively. (D) Northern blot evaluation of transcripts harvested from pmCMVsiGFPmpA (lanes 3, 4) and pmCMVsiβgalmpA (lane 2) transfected HEK293 cells. Blots were probed with $^{32}$P-labeled sense oligonucleotides. Antisense probes yielded similar results (not shown). Lane 1, $^{32}$P-labeled RNA markers. AdsiGFP infected cells also possessed appropriately sized transcripts (not shown). (E) Northern blot for evaluation of target mRNA reduction by siRNA (upper panel). The internal control GAPDH is shown in the lower panel. HEK293 cells were transfected with pEGFPN1 and pmCMVsiGFPmpA, expressing siGFP, or plasmids expressing the control siRNA as indicated. pCMVeGFPx, which expresses siGFPx, contains a large poly(A) cassette from SV40 large T and an unmodified CMV promoter, in contrast to pmCMVsiGFPmpA shown in (A). (F) Western blot with anti-GFP antibodies of cell lysates harvested 72 h after transfection with pEGFPN1 and pCMVsiGFPmpA, or pEGFPN1 and pmCMVsiβglucmpA. (G, H) Fluorescence photomicrographs of HEK293 cells 72 h after transfection of pEGFPN1 and pCMVsiGFPx, or pEGFPN1 and pmCMVsiβglucmpA, respectively. (I, J) siRNA reduces expression from endogenous alleles. Recombinant adenoviruses were generated from pmCMVsiβglucmpA and pmCMVsiGFPmpA and purified. HeLa cells were infected with 25 infectious viruses/cell (MOI=25) or mock-infected (control) and cell lysates harvested 72 h later. (I) Northern blot for β-glucuronidase mRNA levels in Adsiβgluc and AdsiGFP transduced cells. GAPDH was used as an internal control for loading. (J) The concentration of β-glucuronidase activity in lysates quantified by a fluorometric assay. (Stein1999).
Figure 1B:
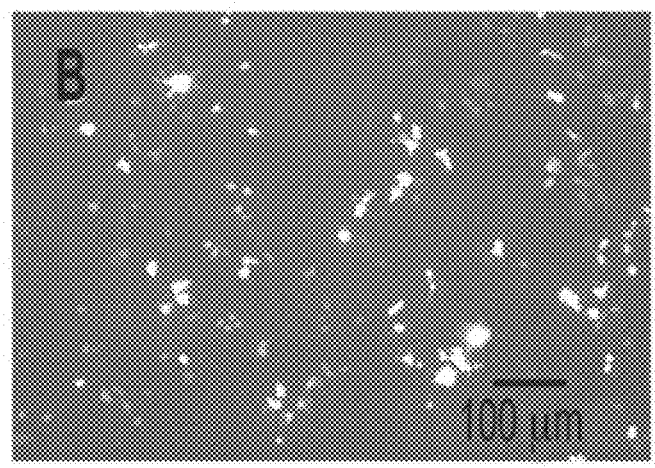
Figure 1C:
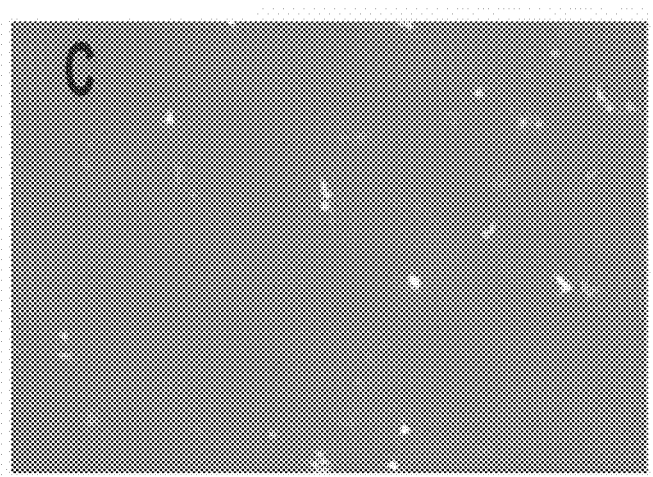
Figure 1D:
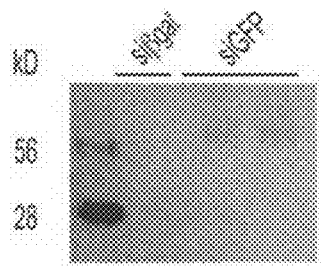
Figure 1E:
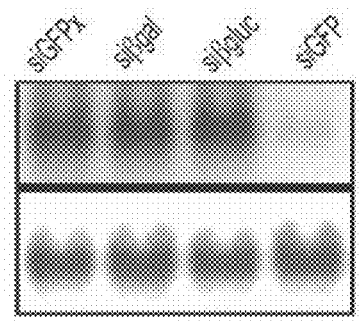
Figure 1F:
Figure 1G:
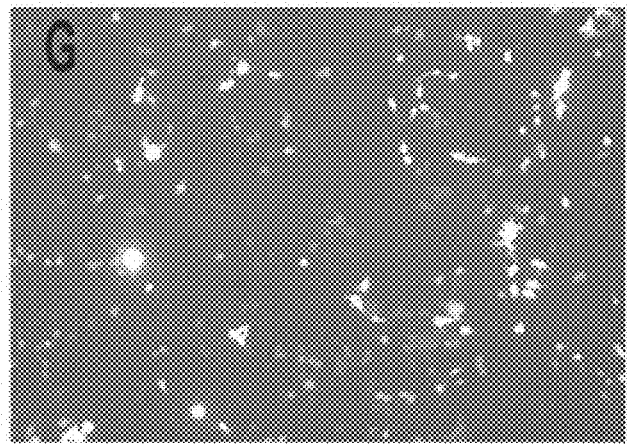
Figure 1H:
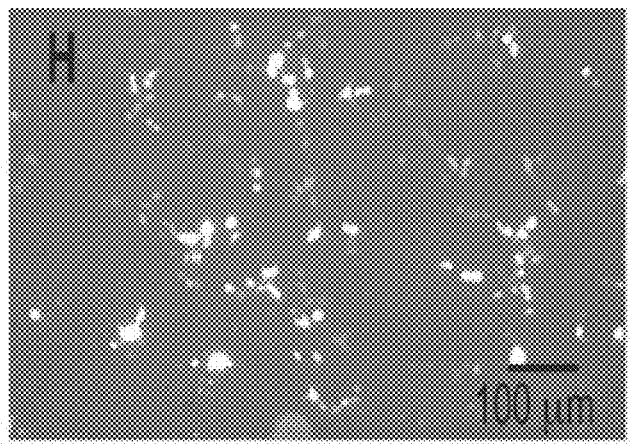

To accomplish intracellular expression of siRNA, a 21-bp hairpin representing sequences directed against eGFP was constructed, and its ability to reduce target gene expression in mammalian cells using two distinct constructs was tested. Initially, the siRNA hairpin targeted against eGFP was placed under the control of the CMV promoter and contained a full-length SV-40 polyadenylation (polyA) cassette (pCMVsiGFPx). In the second construct, the hairpin was juxtaposed almost immediate to the CMV transcription start site (within 6 bp) and was followed by a synthetic, minimal polyA cassette (FIG. 1A, pmCMVsiGFPmpA) (Experimental Protocols), because we reasoned that functional siRNA would require minimal to no overhangs (Caplan 2001; Nykänen 2001). Co-transfection of pmCMVsiGFPmpA with pEGFPN1 (Clontech Inc) into HEK293 cells markedly reduced eGFP fluorescence (FIG. 1C). pmCMVsiGFPmpA transfection led to the production of an approximately 63 bp RNA specific for eGFP (FIG. 1D), consistent with the predicted size of the siGFP hairpin-containing transcript. Reduction of target mRNA and eGFP protein expression was noted in pmCMVsiGFPmpA-transfected cells only (FIG. 1E, F). In contrast, eGFP RNA, protein and fluorescence levels remained unchanged in cells transfected with pEGFPN1 and pCMVsiGFPx (FIG. 1E, G), pEGFPN1 and pCMVsiβglucmpA (FIG. 1E, F, H), or pEGFPN1 and pCMVsiβgalmpA, the latter expressing siRNA against E. coli β-galactosidase (FIG. 1E). These data demonstrate the specificity of the expressed siRNAs.

Constructs identical to pmCMVsiGFPmpA except that a spacer of 9, 12 and 21 nucleotides was present between the transcription start site and the 21 bp hairpin were also tested. In each case, there was no silencing of eGFP expression (data not shown). Together the results indicate that the spacing of the hairpin immediate to the promoter can be important for functional target reduction, a fact supported by recent studies in MCF-7 cells (Brummelkamp 2002).

Figure 1I:
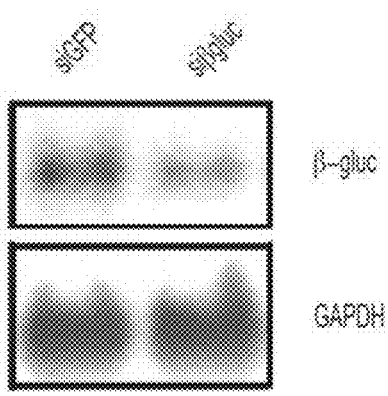
Figure 1J:
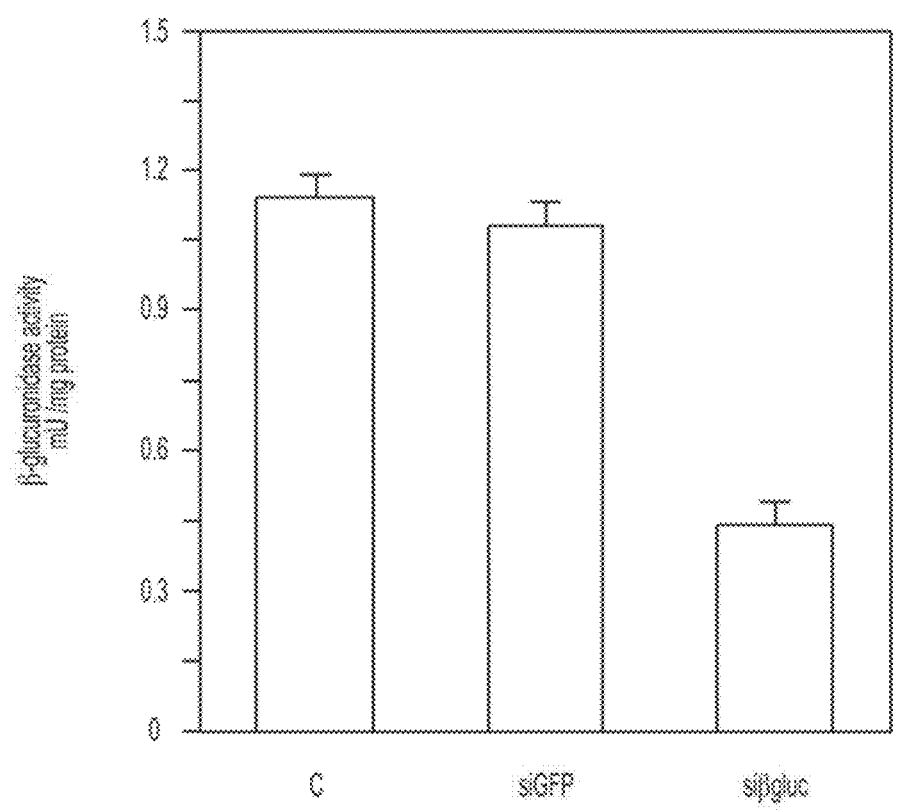

Recombinant adenoviruses were generated from the siGFP (pmCMVsiGFPmpA) and siβgluc (pmCMVsiβglucmpA) plasmids (Xia 2001; Anderson 2000) to test the hypothesis that virally expressed siRNA allows for diminished gene expression of endogenous targets in vitro and in vivo. HeLa cells are of human origin and contain moderate levels of the soluble lysosomal enzyme β-glucuronidase. Infection of HeLa cells with viruses expressing siβgluc caused a specific reduction in human β-glucuronidase mRNA (FIG. 1I) leading to a 60% decrease in β-glucuronidase activity relative to siGFP or control cells (FIG. 1J). Optimization of siRNA sequences using methods to refine target mRNA accessible sequences (Lee 2002) could improve further the diminution of β-glucuronidase transcript and protein levels.

The results in FIG. 1A-J are consistent with earlier work demonstrating the ability of synthetic 21-bp double stranded RNAs to reduce expression of target genes in mammalian cells following transfection, with the important difference that in the present studies the siRNA was synthesized intracellularly from readily available promoter constructs. The data support the utility of regulatable, tissue or cell-specific promoters for expression of siRNA when suitably modified for close juxtaposition of the hairpin to the transcriptional start site and inclusion of the minimal polyA sequence containing cassette (see, Methods above).

Figure 2B:

To evaluate the ability of virally expressed siRNA to diminish target-gene expression in adult mouse tissues in vivo, transgenic mice expressing eGFP (Okabe 1997) were injected into the striatal region of the brain with 1×10$^7$ infectious units of recombinant adenovirus vectors expressing siGFP or control siβgluc. Viruses also contained a dsRed expression cassette in a distant region of the virus for unequivocal localization of the injection site. Brain sections evaluated 5 days after injection by fluorescence (FIG. 2A) or western blot assay (FIG. 2B) demonstrated reduced eGFP expression. Decreased eGFP expression was confined to the injected hemisphere (FIG. 2B). The in vivo reduction is promising, particularly since transgenically expressed eGFP is a stable protein, making complete reduction in this short time frame unlikely. Moreover, evaluation of eGFP levels was done 5 days after injection, when inflammatory changes induced by the adenovirus vector likely enhance transgenic eGFP expression from the CMV enhancer (Ooboshi 1997).

Figure 2C:
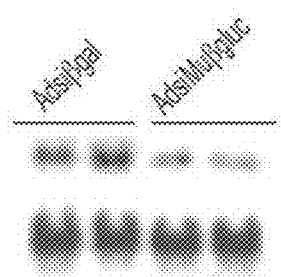

It was next tested whether virus mediated siRNA could decrease expression from endogenous alleles in vivo. Its ability to decrease β-glucuronidase activity in the murine liver, where endogenous levels of this relatively stable protein are high, was evaluated. Mice were injected via the tail vein with a construct expressing murine-specific siβgluc (AdsiMuβgluc), or the control viruses Adsiβgluc (specific for human β-glucuronidase) or Adsiβgal. Adenoviruses injected into the tail vein transduced hepatocytes as shown previously (Stein 1999). Liver tissue harvested 3 days later showed specific reduction of target β-glucuronidase RNA in AdsiMuβgluc treated mice only (FIG. 2C). Fluorometric enzyme assay of liver lysates confirmed these results, with a 12% decrease in activity from liver harvested from AdsiMuβgluc injected mice relative to Adsiβgal and Adsiβgluc treated ones (p<0.01; n=10). Interestingly, sequence differences between the murine and human siRNA constructs are limited, with 14 of 21 bp being identical. These results confirm the specificity of virus mediated siRNA, and indicate that allele-specific applications are possible. Together, the data are the first to demonstrate the utility of siRNA to diminish target gene expression in brain and liver tissue in vivo, and establish that allele-specific silencing in vivo is possible with siRNA.

Figure 3D:
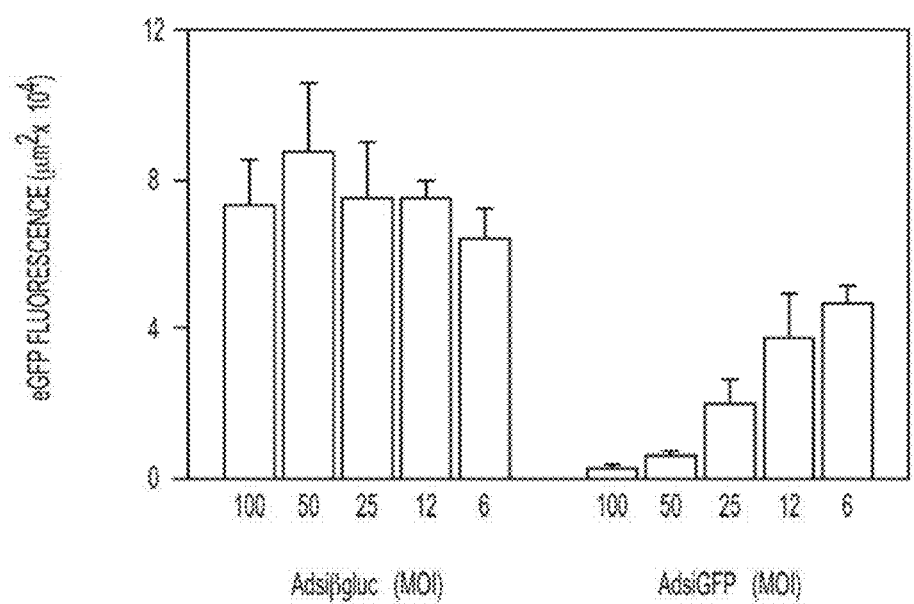

One powerful therapeutic application of siRNA is to reduce expression of toxic gene products in dominantly inherited diseases such as the polyglutamine (polyQ) neurodegenerative disorders (Margolis 2001). The molecular basis of polyQ diseases is a novel toxic property conferred upon the mutant protein by polyQ expansion. This toxic property is associated with disease protein aggregation. The ability of virally expressed siRNA to diminish expanded polyQ protein expression in neural PC-12 clonal cell lines was evaluated. Lines were developed that express tetracycline-repressible eGFP-polyglutamine fusion proteins with normal or expanded glutamine of 19 (eGFP-Q19) and 80 (eGFP-Q80) repeats, respectively. Differentiated, eGFP-Q19-expressing PC12 neural cells infected with recombinant adenovirus expressing siGFP demonstrated a specific and dose-dependent decrease in eGFP-Q19 fluorescence (FIG. 3A, C) and protein levels (FIG. 3B). Application of Adsiβgluc as a control had no effect (FIG. 3A-C). Quantitative image analysis of eGFP fluorescence demonstrated that siGFP reduced GFPQ19 expression by greater than 96% and 93% for 100 and 50 MOI respectively, relative to control siRNA (FIG. 3C). The multiplicity of infection (MOI) of 100 required to achieve maximal inhibition of eGFP-Q19 expression results largely from the inability of PC12 cells to be infected by adenovirus-based vectors. This barrier can be overcome using AAV- or lentivirus-based expression systems (Davidson 2000; Brooks 2002).

Figure 4A:
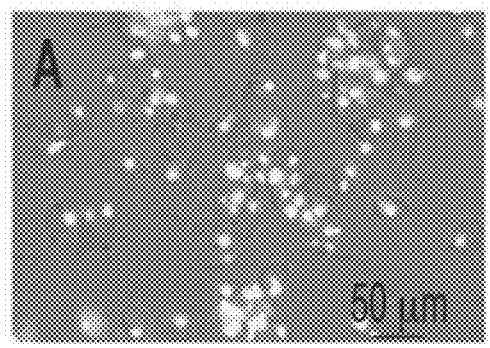
FIGS. 4A-G. siRNA mediated reduction of expanded polyglutamine protein levels and intracellular aggregates. PC12 cells expressing tet-repressible eGFP-Q80 fusion proteins were washed to remove doxycycline and adenovirus vectors expressing siRNA were applied 3 days later. (A-D) Representative punctate eGFP fluorescence of aggregates in mock-infected cells (A), or those infected with 100 MOI of Adsiβgluc (B), AdsiGFPx (C) or Adsiβgal (D). (E) Three days after infection of dox-free eGFP-Q80 PC12 cells with AdsiGFP, aggregate size and number are notably reduced. (F) Western blot analysis of eGFP-Q80 aggregates (arrowhead) and monomer (arrow) following Adsiβgluc or AdsiGFP infection at the indicated MOIs demonstrates dose dependent siGFP-mediated reduction of GFP-Q80 protein levels. (G) Quantification of the total area of fluorescent inclusions measured in 4 independent fields/well 3 days after virus was applied at the indicated MOIs. The data are mean±standard deviation.
Figure 4B:
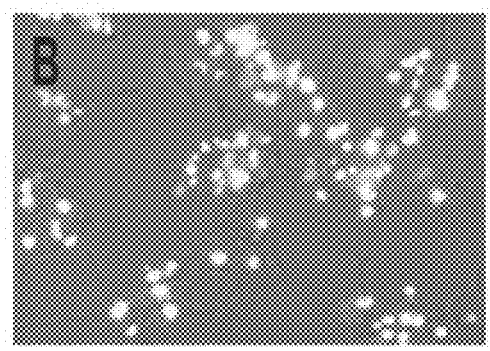
Figure 4C:
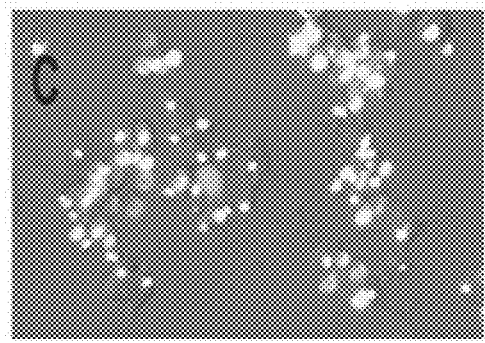
Figure 4D:
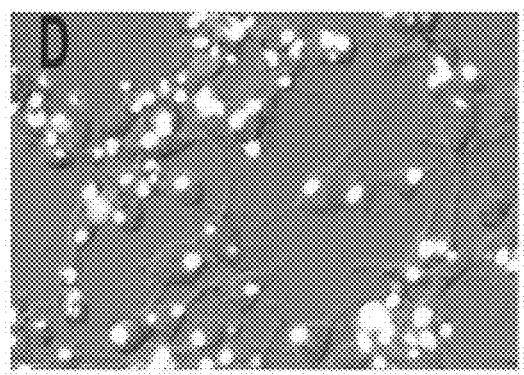
Figure 4E:
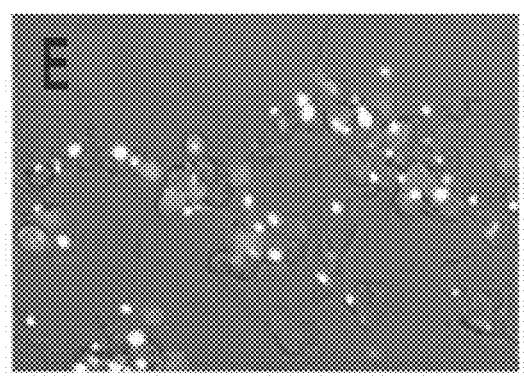
Figure 4F:
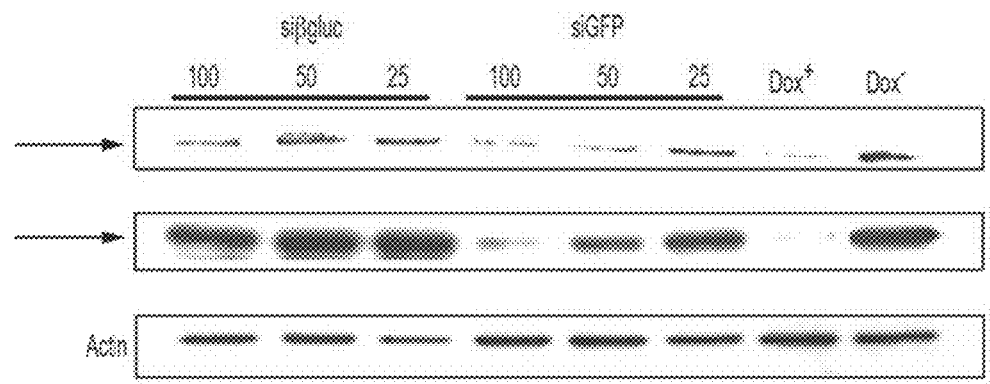
Figure 4G:
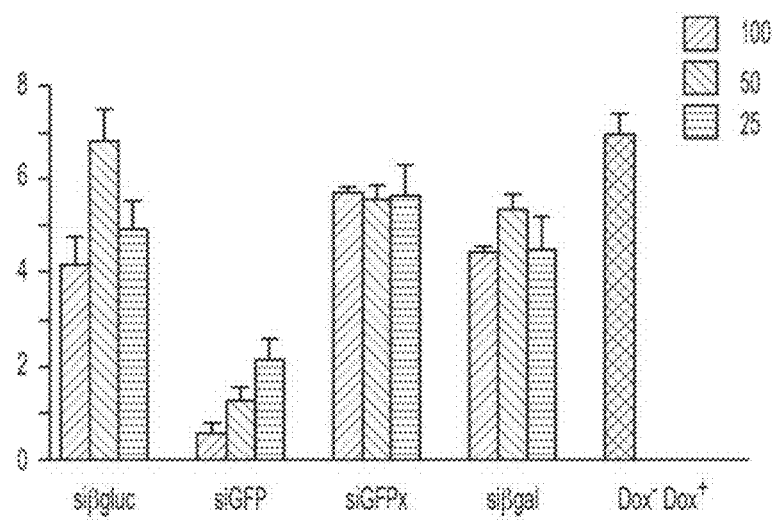

To test the impact of siRNA on the size and number of aggregates formed in eGFP-Q80 expressing cells, differentiated PC-12/eGFP-Q80 neural cells were infected with AdsiGFP or Adsiβgluc 3 days after doxycycline removal to induce GFP-Q80 expression. Cells were evaluated 3 days later. In mock-infected control cells (FIG. 4A), aggregates were very large 6 days after induction as reported by others (Chai 1999a; Moulder 1999). Large aggregates were also seen in cells infected with Adsiβgluc (FIG. 4B), AdsiGFPx, (FIG. 4C, siRNA expressed from the normal CMV promoter and containing the SV40 large T antigen polyadenylation cassette), or Adsiβgal (FIG. 4D). In contrast, polyQ aggregate formation was significantly reduced in AdsiGFP infected cells (FIG. 4E), with fewer and smaller inclusions and more diffuse eGFP fluorescence. AdsiGFP-mediated reduction in aggregated and monomeric GFP-Q80 was verified by Western blot analysis (FIG. 4F), and quantitation of cellular fluorescence (FIG. 4G). AdsiGFP caused a dramatic and specific, dose-dependent reduction in eGFP-Q80 expression (FIG. 4F, G).

It was found that transcripts expressed from the modified CMV promoter and containing the minimal polyA cassette were capable of reducing gene expression in both plasmid and viral vector systems (FIGS. 1-4). The placement of the hairpin immediate to the transcription start site and use of the minimal polyadenylation cassette was of critical importance. In plants and Drosophila, RNA interference is initiated by the ATP-dependent, processive cleavage of long dsRNA into 21-25 bp double-stranded siRNA, followed by incorporation of siRNA into a RNA-induced silencing complex that recognizes and cleaves the target (Nykänen 2001; Zamore 2000; Bernstein 2001; Hamilton 1999; Hammond 2000). Viral vectors expressing siRNA are useful in determining if similar mechanisms are involved in target RNA cleavage in mammalian cells in vivo.

In summary, these data demonstrate that siRNA expressed from viral vectors in vitro and in vivo specifically reduce expression of stably expressed plasmids in cells, and endogenous transgenic targets in mice. Importantly, the application of virally expressed siRNA to various target alleles in different cells and tissues in vitro and in vivo was demonstrated. Finally, the results show that it is possible to reduce polyglutamine protein levels in neurons, which is the cause of at least nine inherited neurodegenerative diseases, with a corresponding decrease in disease protein aggregation. The ability of viral vectors based on adeno-associated virus (Davidson 2000) and lentiviruses (Brooks 2002) to efficiently transduce cells in the CNS, coupled with the effectiveness of virally-expressed siRNA demonstrated here, extends the application of siRNA to viral-based therapies and to basic research, including inhibiting novel ESTs to define gene function.

EXAMPLE 2 siRNA Specific for Huntingtin's Disease

The present inventors have developed huntingtin siRNA focused on two targets. One is non-allele specific (siHDexon2), the other is targeted to the exon 58 codon deletion, the only known common intragenic polymorphism in linkage dysequilibirum with the disease mutation (Ambrose et al, 1994). Specifically, 92% of wild type huntingtin alleles have four GAGs in exon 58, while 38% of RD patients have 3 GAGs in exon 58. To assess a siRNA targeted to the intragenic polymorphism, PC6-3 cells were transfected with a full-length huntingtin containing the exon 58 deletion. Specifically, PC6-3 rat pheochromocytoma cells were co-transfected with CMV-human Htt (37Qs) and U6 siRNA hairpin plasmids. Cell extracts were harvested 24 hours later and western blots were performed using 15 μg total protein extract. Primary antibody was an anti-huntingtin monoclonal antibody (MAB2166, Chemicon) that reacts with human, monkey, rat and mouse Htt proteins.

Figure 5A:
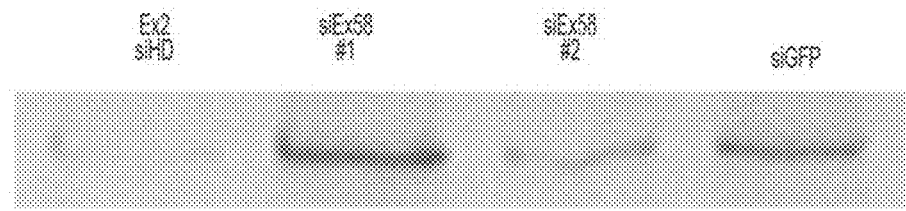
FIGS. 5A-B. (A) Allele-specific silencing of mutant huntingtin by siRNA. PC6-3 cells were co-transfected with plasmids expressing siRNA specific for the polymorphism encoding the transcript for mutant huntingtin. (B) The original target for testing hairpins with putative specificity for the 3 GAG-repeat disease linked polymorphism, shEx58.1 and shEx58.2. In this preliminary test, shEx58.1 is best.
Figure 5B:
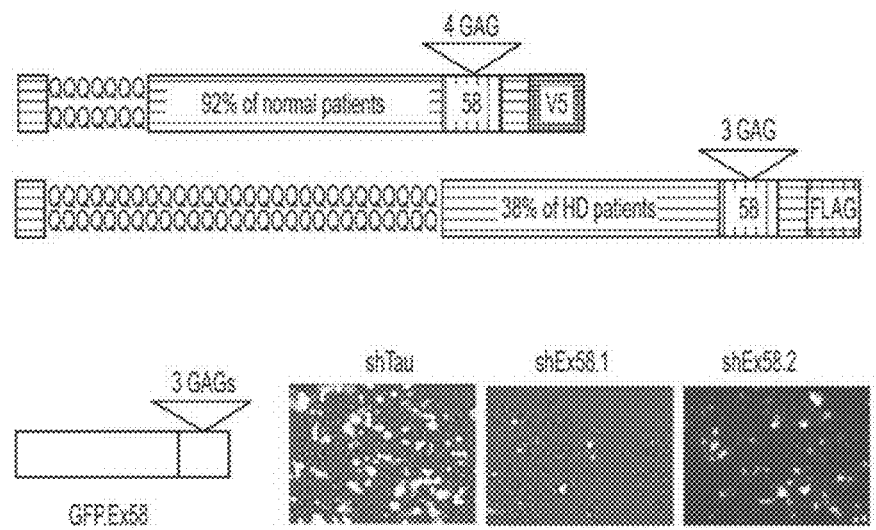

As seen in FIGS. 5A-B, the siRNA lead to silencing of the disease allele. As a positive control, a non-allele specific siRNA targeted to exon 2 of the huntingtin gene was used. siRNA directed against GFP was used as a negative control. It was noted that siEx58#2 functional. The sequence for siEX58#2 is the following: 5'-AAGAGGAGGAGGC-CGACGCCC-3' (SEQ ID NO:90). siEX58#1 was only minimally functional.

EXAMPLE 3 siRNA Specific for SCA1

Spinocerebellar ataxia type 1 (SCA1) is a dominantly inherited, progressive neurodegenerative disease caused by an expanded polyglutamine tract in ataxin-1. SCA1 is one of at least nine neurodegenerative diseases caused by polyglutamine expansion, which includes Huntington's disease (HD) and several other ataxias (On 1993, Zoghbi 1995). SCA1 is characterized by progressive ataxia, cerebellar atrophy, and loss of cerebellar Purkinje cells and brainstem neurons. A feature common to all polyglutamine diseases, and many other neurodegenerative diseases, is the formation of intracellular aggregates containing the disease protein, molecular chaperones, and components of the ubiquitin-proteasome pathway (On 1993, Zoghbi 1995). In SCA1, as in many other polyQ diseases, the inclusions are intranuclear (Skinner 1997).

Disease allele expansion ranges from 44 to 82 glutamines in SCA1, with repeat length inversely correlated to age of disease onset (Zoghbi 1995). Work in *Drosophila* models and transgenic mice demonstrate that the expansion confers a toxic gain of function on ataxin-1 (Fernandez-Funez 2000, Burright 1995, Klement 1998). Recent work has also shown that phosphorylation of serine 776 of ataxin-1 by AKT, but not nuclear aggregation, is required for SCA1 pathogenesis (Emamian 2003, Chen 2003). Together, work in these model organisms has identified manipulation of molecular chaperones, or inhibition of AKT phosphorylation of ataxin-1, as potential therapeutic routes (Fernandez-Funez 2000, Emamian 2003, Cummings 1998). As yet, however, there is no effective therapy for SCA1 or the other dominant neurodegenerative diseases caused by polyglutamine expansion.

Inhibition of mutant allele expression provides a direct approach to SCA1 therapy. In past years, antisense- or ribozyme-based techniques held promise in culture systems, but proved difficult to translate to animal models. More recently, gene silencing through RNA interference (RNAi) has emerged as a powerful method to reduce target gene expression in cell culture and, importantly, in brain (Caplen 2002, Miller 2003, Xia 2002, Davidson 2004). In the present experiments, the inventors tested whether the introduction of viral vectors expressing short hairpin RNAs (shRNAs) directed against the transgenic human mutant ataxin-1 gene would reduce pathology and ataxia in a mouse SCA1 model.

Vector construction and in vitro screening. Different target sites (F1 to F11) were made based on the 2.4 kb human ataxin-1 ORF (gene accession number: X79204). Sites were as follows: F1, bp 144-64; F2 bp 576-96; F3, bp 679-99; F4, 1334-54; F5, bp 490-510; F6, bp 2250-70; F7, bp 18-38; F8, bp 863-82; F9, bp 1876-96; F10, bp574-94; F11, bp 670-90. *E. coli* β-galactosidase (bp 1152-1172) was used as control shRNA. Hairpins with loops 5'-ACTAGT-3' (SEQ ID NO:104), or 5'-CTTCCTGTCA-3' (SEQ ID NO:105) from mir23, were cloned into vectors containing the human U6 promoter, or the modified CMV promoter, by a two-step method as previously described (Xia 2002).

Flag-tagged ataxin-1 with normal (30Q) or expanded (82Q) polyglutamine regions were cloned into the AAV shuttle plasmid for testing hairpin silencing. Plasmids expressing hairpins and plasmids expressing ataxin-1 were co-transfected into HEK 293 cells or PC6-3 cells (4:1 ratio, hairpin to target), and cells lysed 48 to 72 h later. Western blots with anti-Flag were done to assess ataxin-1 levels. Actin was used a loading control.

Quantitative RT-PCR. HEK293 cells were transfected (Lipofectamine-2000, Invitrogen) with shLacZ, shScaI.F10 (571-592, ScaI-shSCA1.F10, 5'-GGACACAAGGCT-GAGCAGCAG-3' (SEQ ID NO:102)), or shScaI.F11 (595-615, HScaI-shSCA1.F11, 5'-CAGCAGCACCTCAGCA-GGGCTGCAGGATTAGTCAACCACCTCAGCAGGG CT-3' (SEQ ID NO:103)) and a human ScaI expression plasmid in 2:1, 4:1, or 8:1 molar ratios of shRNA:ScaI. RNA was harvested 24 hours post-transfection using Trizol reagent (Invitrogen). Following DNase treatment (DNA-free, Ambion), random-primed, first-strand cDNA was generated from 1 mg total RNA (Taqman Reverse Transcription Reagents, Applied Biosystems) according to the manufacturer's protocol. cDNA was diluted four-fold and then used as template for real-time PCR. Taqman Assays were performed on an ABI Prism 7000 Sequence Detection System using Taqman 2× Universal PCR Master Mix (Applied Biosystems) and Applied Biosystems Assays-on-Demand Taqman primers/probe sets specific for human ScaI and mammalian rRNA. Relative gene expression was determined using the relative standard curve method (Applied Biosystems User Bulletin #2). Human ScaI expression levels were normalized to rRNA levels and all samples were calibrated to the shLacZ 8:1 sample.

AAV vectors. pAAVshLacZ and pAAVshSCA1 contain human U6 driven hairpins and CMV-hrGFP-SV40 polyA expression cassettes cloned between two AAV2 ITR sequences. Flanking the AAV provirus are left and right arm sequences from the Baculovirus *Autographa californica*, which are used to generate recombinant Bacmid DNA through homologous recombination in *E. coli*. Recombinant Baculovirus were generated as described in the Bac-to-Bac Baculovirus Expression System (InVitrogen), and AAV virus was purified as described in Urabe et al (Urabe 2002). AAV titers were determined by DNA slot blot using an hrGFP-specific radiolabeled probe.

AAV injections. Injections into cerebella were as described by Alisky et al. (Alisky 2000), except that injections were administered 1 mm lateral to the midline, with a total of 3 μl injected into three separate sites. Transduction was targeted to midline lobules IV/V, with transduction spreading anterior-posterior to lobules III and VI, respectively. Virus titers were ~1 ×1012 vector genomes/ml as assessed by Q-PCR.

Northern Analysis. Total RNA was isolated using TRIZOL® Reagent (InVitrogen™ Life Technologies, Carlsbad, Calif.) according to the manufacturer's instructions. RNAs (30 mg) were separated by electrophoresis on 15% (wt/vol) polyacrylamide-urea gels to detect transcripts. RNAs were transferred by electroblotting onto Hybond N+ membranes (Amersham Pharmacia Biotech). Blots were probed with 32P-labeled sense oligonucleotides at 36° C. for 3 h for evaluation of transcripts. Blots were washed in 2×SSC twice for 15 min at 36° C. and exposed to film overnight (Miyagishi 2002).

Immunohistochemistry and quantitation. Mice were perfused and fixed overnight with 4% paraformaldehyde in 0.2M phosphate buffer (pH 7.4). Tissues were cryoprotected by immersion in 25% sucrose and frozen in O.C.T. compound (Sakura Finetek U.S.A. Inc, Torrance, Calif.). Sagittal cryostat sections (10 um) were cut and mounted onto gelatin-coated slides. For calbindin staining, no unmasking procedure was used. Ataxin-1 staining was done as described (Skinner 1997). Sections were analyzed using a Leica DM RBE and images acquired with a SPOT RT camera and associated software (Diagnostics Instruments, Sterling Heights, Mich.). Measurement of molecular layer thickness and quantitation of Purkinje cells were done using BioQuant system software (R & M Biometrics, Nashville, Tenn.) (Williams 1988).

Rotarod analysis. The Rotarod (Ugo Basile Biological Research Apparatus, model 7650) was used for these studies. Five-week-old mice were habituated on the rotarod for 4 min, and then tested for 4 consecutive days, 4 trials per day (~30 minutes rest between trial). Mice were retested two weeks after intracerebellar injection, and every two weeks until sacrifice at 16 wks. Additional groups of animals were tested out to 20 weeks. For each trial, the rod was accelerated from 4 to 40 rpm over 5 min, then maintained at 40 rpm until trial completion. Latency to fall (or if they hung on or rotated for two consecutive rotations without running) was recorded for each mouse. Any mouse remaining on the apparatus for 500 sec. was removed and scored as 500 sec.

Results

Optimization of Ataxin-1-Targeting shRNAs

Figure 6A:
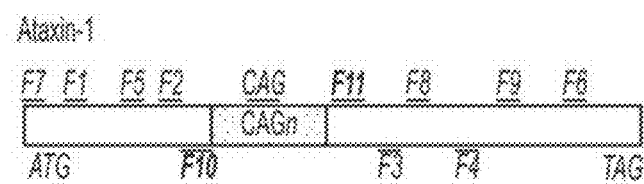
FIGS. 6A-F. Silencing ataxin-1. (A) Cartoon of the ataxin-1 cDNA and regions tested for silencing (lines). The CAG repeat region is indicated. The most effective hairpins identified, F10 and F11, are bolded. (B) Screening of shSCA1s for ataxin-1 silencing. HEK 293 cells were transfected with shRNA- and ataxin-1-expressing plasmids (4:1 ratio), and FLAG-tagged ataxin-1 (ataxin-1FLAG) expression was screened by western blot two days later. Actin was used as a loading control. ShLacZ was included as a negative hairpin control. Data shown are from U6-expressed shRNAs. (C) Dose dependent decline in hSCA-1 mRNA as assessed by Q-RTPCR. HEK 293 cells were transfected with shRNA- and ataxin-1-expressing plasmids at the ratios indicated, and RNA isolated 24 hrs later. RNA levels were measured by Q-PCR as described in the methods. (D) Comparison of mCMV- and U6-expressed shRNAs in neuronal cells. PC6-3 cells were transfected with plasmids expressing the indicated shRNAs, and expression of ataxin assessed 2 days later by western blot. shCAG was targeted to the CAG repeat region and was used as a positive control for silencing (E) The loop from miR23 improves silencing from the hU6 promoter. HEK 293 cells were transfected with plasmids expressing the indicated hairpins and ataxin-1FLAG, and silencing evaluated 2 days later by western blot. The loop improves silencing of shSCA1.F10 and shSCA1.F11. (F) shSCA1.F11 and shSCA1.F11 silence mutant (Q82) ataxin-1. HEK 293 cells were transfected with plasmids expressing the indicated hairpins, and a plasmid expressing human ataxin-1 with an expanded poly(Q) tract (FLAG-tagged). Silencing of the human mutant ataxin-1 was assessed by western blot 2 days later.
Figure 6B:
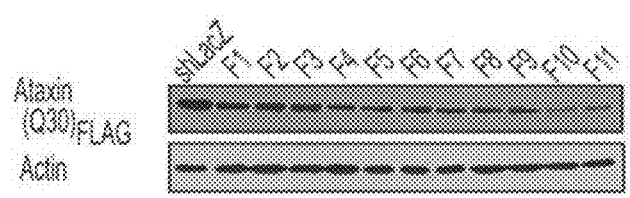
Figure 6C:
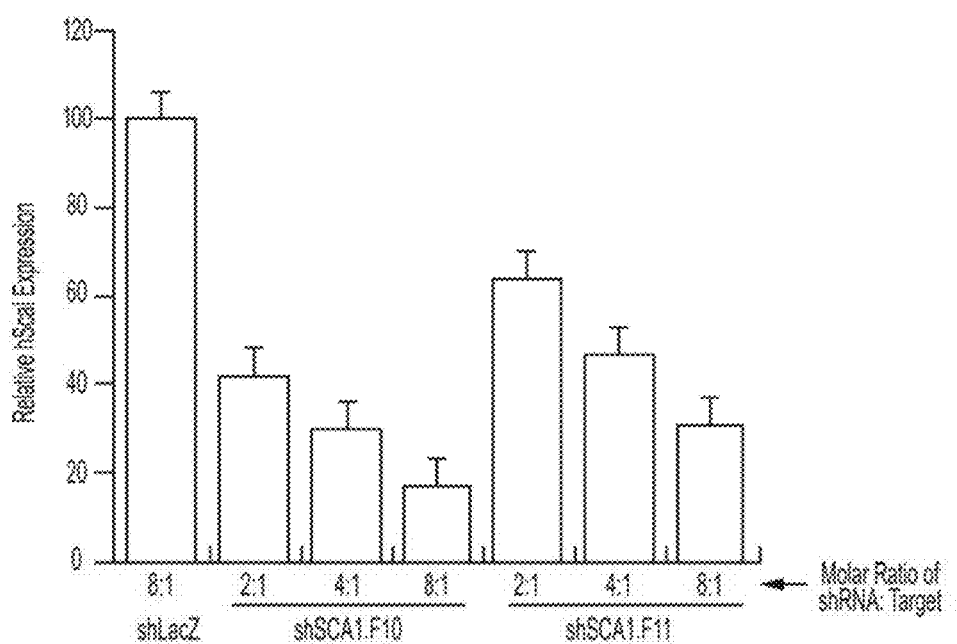
Figure 6D:
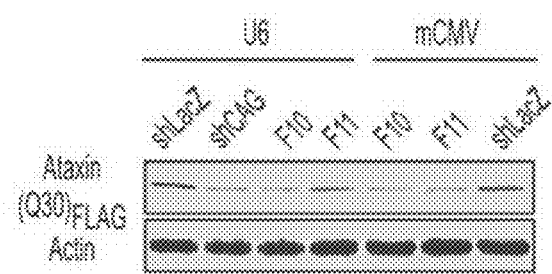

To accomplish RNAi for ataxin-1, the inventors developed short hairpins (shRNA) directed to the human 2.4 kb ataxin-1 cDNA for primary screening in vitro. Short hairpin RNA (shRNA)-expressing plasmids were co-transfected into HEK 293 cells with ataxin-1 (FLAG-tagged) expression plasmids. Candidate hairpin sequences expressed from pol III (human U6; hU6) and pol II (modified CMV; mCMV) (Xia 2002) promoters were tested. The initial screen of hairpins directed against ataxin-1 sequences dispersed along the ataxin-1 cDNA (FIG. 6A) was unsuccessful regardless of promoter (0 of 4 tested). An expanded evaluation identified two constructs (shSCA1.F10 and shSCA1.F11; 2 of 7 tested) that reduced RNA levels up to 80% and ataxin-1 protein levels by 50-60% (FIG. 6B, 6C). Q-PCR analysis showed that shSCA1.F10- and shSCA1.F11-mediated silencing of the ataxin-1 transcript was dose dependent (FIG. 6C). To determine if shSCA1s were functional in neural cells the inventors used PC6-3 cells, a PC-12 cell derivative that displays more uniform neuronal phenotypes (Pittman 1993). PC6-3 cells were transfected with AAV shuttle vectors expressing shSCA1.F10, shSCA1.F11, or control shRNAs, and silencing of ataxin-1 expression was assessed by western blot. Interestingly, mCMV-expressed shSCA1.F11 appeared more efficient than the same construct expressed from the hU6 promoter (FIG. 6D).

Figure 6E:
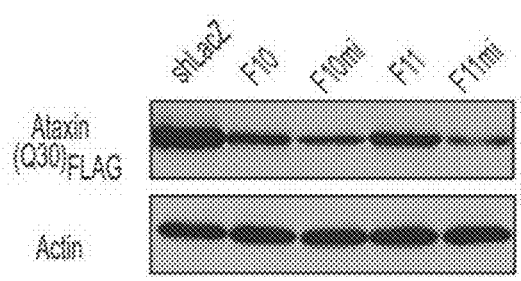
Figure 6F:
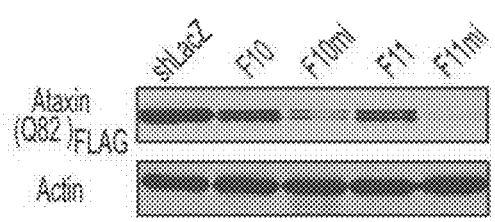

A recent study by Kawasaki and colleagues (Kawasaki 2003) suggested that one caveat of Pol III-based promoters for expressing shRNAs is inefficient export of transcripts to the cytoplasm. Replacement of the loop structure of their shRNAs with those derived from endogenously expressed miRNAs improved nuclear export and gene silencing (Kawasaki 2003). To test if similar modifications improved Pol III-directed expression of shRNAs for ataxin-1 silencing, the loops of hairpins from shSCA1.F10 and shSCA1.F11, (originally 5'-ACTAGT-3' (SEQ ID NO:104)), were replaced with the loop from miR23 (5'-CTTCCTGTCA-3' (SEQ ID NO:105); designated F10mi). While there was no effect of the miRNA loop on CMV-shRNA-based silencing (not shown), miR23 loops improved the silencing activity of Pol III-expressed shSCA1.F10 and shSCA1.F11 against normal human ataxin-1 (FIG. 6E) and importantly, human ataxin-1 with an 82Q expansion (FIG. 6F).

Effects of shSCA1 on Motor Coordination in SCA1 Transgenic Mice

Figure 7A:
FIGS. 7A-D. AAV vectors for shRNA expression in vivo. (A) Cartoon of AAV construct. The construct for shSCA.F11mi and shLacZ expression was similar except that shSCA1.F10mi was replaced with shSCA.F11mi or shLacZ sequences, respectively. Note that the hrGFP expression cassette is distinct from the shRNA expression cassette. (B) AAVshSCA1 with hrGFP reporter leads to extensive transduction of cerebellar Purkinje cells (Purkinje cell layer denoted by arrowheads). Wildtype mice were injected with AAVshSCA1.F10mi (left panel) or injected with saline (right panel) and sacrificed 3 weeks later to evaluate eGFP expression. g, granule cell layer; m, molecular layer. Bar=100 µm. (C) shSCA1 and shLacZ transcripts are expressed in vivo. Wildtype mice were injected with AAVshLacZ or AAVshSCA1.F10mi, and RNA isolated from cerebella 10 days later. Northern blots were probed with 32P-labeled oligonucleotides specific for the antisense strand of the hairpin. L, RNA ladder; (sizes indicated at left). Lanes, 2 and 3, RNA from AAVshSCA1.F10mi and AAVshLacZ transduced brains, respectively. The arrowhead denotes the unprocessed transcript, the arrow the processed siRNA. (D) Rotarod performance of wildtype (triangles) and SCA1 (squares) mice treated with shRNA-expressing AAV1s or mock infected, as indicated in the legend. Mice were injected with virus or saline at age 7 weeks and re-tested every two weeks (weeks 5, 11, 15, and 21 are shown). From weeks 11-21 significant differences in performance between AAVshSCA1 and AAVshLacZ treated SCA1 mice were noted (P<0.001). There were no significant differences between wildtype mice treated with shLacZ (not shown), shSCA1.F10mi or saline. For week 5, n=10 and 11 for shSCA1 and shLacZ treated SCA1 mice, respectively; n=6 and 5 for shSCA1 and control treated age-matched wildtype littermates, respectively. For weeks 7-21, n=14 and 12 for shSCA1 and shLacZ treated SCA1 mice, respectively; n=12 and 11 for shSCA1 and control treated age-matched wildtype littermates, respectively; n=9 for saline injected SCA1 mice. WT mice given shLacZ were not significantly different than WT mice treated with saline, shSCA1, or left untreated (data not shown).
Figure 7B:
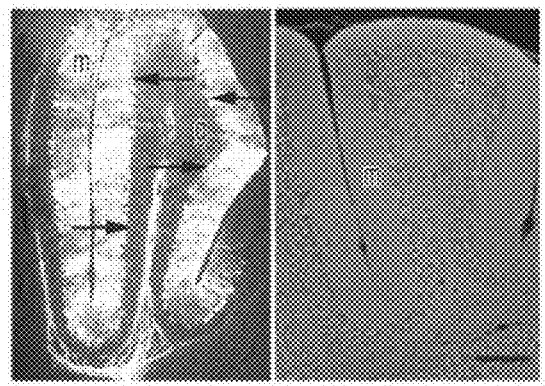
Figure 7C:
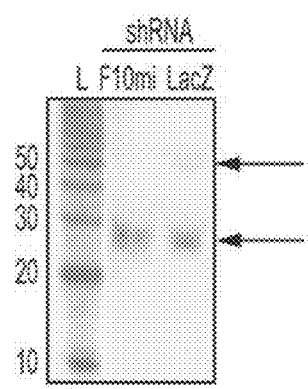

The inventors next generated recombinant adeno-associated virus serotype 1 (AAV1) expressing shSCA1.F10mi and shSCA1.F11mi to evaluate hairpin efficacy in the transgenic mouse model of SCA1 (denoted AAVshSCA1.F10mi or AAVshSCA1.F11mi). The virus was also engineered to express the hrGFP reporter for detection of transduced cells (FIG. 7A). In SCA1 mice, transgenic human disease allele (ataxin-1-Q82) expression is confined to the cerebellar Purkinje cells by PCP-2, a Purkinje cell-specific promoter (Burright 1995, Clark 1997). Thus the inventors initially tested AAV1's ability to transduce Purkinje cells, since its transduction profile in cerebella was unknown. As shown in FIG. 7B, AAVshSCA1 readily transduces Purkinje cells. Northern blot of RNA harvested from cerebella 10 days after viral injection also showed that shRNAs are expressed in vivo (FIG. 7C). The fast expression kinetics from AAV1 is similar to AAV serotype 5, which also shows tropism for Purkinje cells (Alisky 2000).

Figure 7D:
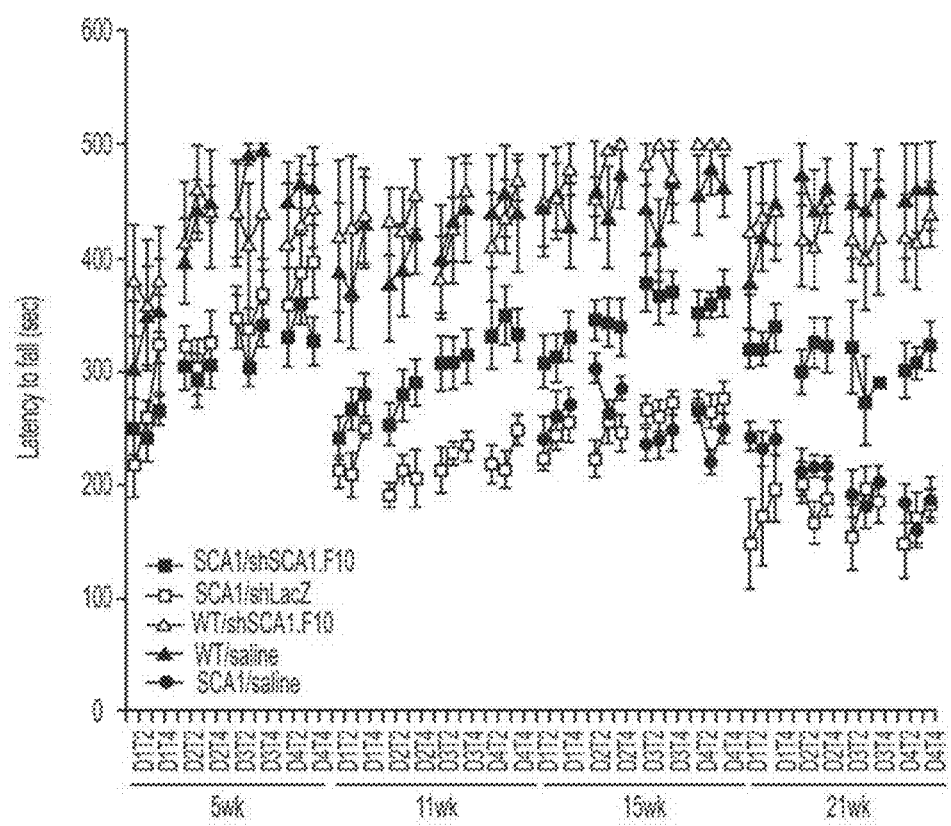

Heterozygous SCA1 transgenic mice display many of the characteristics of human SCA1, including progressive ataxia, Purkinje cell degeneration, and thinning of cerebellar molecular layers. The rotarod test for motor performance is a valid indicator of the progressive ataxia; proper foot placement in response to a changing environment (i.e., the rotating rod) challenges the cerebellum. To determine the effects of AAVshSCA1, or AAVs expressing control hairpins (AAVshLacZ), on the ataxic phenotype, mice were analyzed for baseline rotarod performance, followed by injection at 7 weeks of age with shRNA-expressing viruses into midline cerebellar lobules. Rotorod analyses were repeated every two weeks until sacrifice. Mock-transduced animals (saline injection) were also assessed. The data in FIG. 7D demonstrate that transduction with viruses expressing shSCA1.F10mi, but not shLacZ, significantly improves SCA1 mice motor performance. Also of note is the observation that expression of shSCA1.F10mi did not negatively affect the rotarod performance of wildtype mice, indicating that intracellular expression of shRNAs is not overtly toxic to Purkinje cells.

Improved Neuropathology in shSCA1-Expressing Purkinje Cells

The inventors next tested if the improved rotarod performance was attributable to improvements in neuropathology. The progressive pathological changes in SCA1 transgenic mice have been well characterized, and include intranuclear inclusions of ataxin-1, Purkinje cell dendritic pruning, Purkinje cell loss and concomitant thinning of the cerebellar molecular layer (Burright 1995).

Figure 8A:
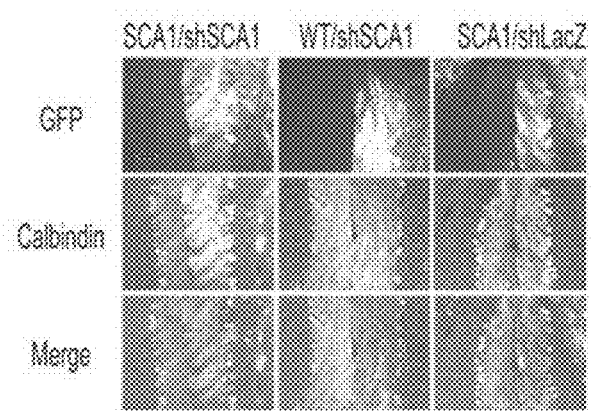
FIGS. 8A-C. SCA1 neuropathology is improved by shRNAs directed to ataxin-1. (A) SCA and wildtype mice were injected with AAVshSCA1.F10mi or AAVshLacZ at week 7, and sacrificed 9 weeks later for cerebellar pathology. Calbindin immunofluorescence (IF) (middle panels) and hrGFP expression (top panels) were evaluated. Merged images (bottom panels) demonstrate that hrGFP+ molecular layers from AAVshSCA-injected SCA1 mice have calbindin staining similar to wildtype mice. Panels are representative of 100 or 40 sections evaluated for AAVshSCA1.F10mi-treated SCA1 or wildtype mice, respectively, and 80 sections from AAVshLacZ-treated mice. Bar in upper left panel=50 µm and is representative of all images. (B) The molecular layer width in transduced (solid bars), and untransduced (open bars) lobules from wildtype and SCA1 mice was measured. The data demonstrate significant protection following shSCA1.F10mi therapy. **, P<0.001. Numbers below bars refer to numbers of sections measured/group. Molecular layer widths from wildtype mice given AAVs expressing shLacZ or shSCA1.F10mi were indistinguishable and were pooled for comparison to SCA1 mice cerebella (designated shRNA). (C) Photomicrographs shown in A.

Cerebellar lobules from SCA1 and wildtype mice injected with AAVshLacZ or AAVshSCA1 were evaluated for hrGFP expression and calbindin staining to assess if shSCA1 reduced the progressive thinning of the molecular layer in SCA1 transgenic mice. FIG. 8A shows representative sections from virus-injected mice cerebella. The juxtaposition of untransduced regions (hrGFP−) to transduced ones (hrGFP+) allowed for direct comparisons of the effects of shSCA1. Calbindin staining remained robust in hrGFP+ molecular layers from SCA1 transgenic mice treated with AAVshSCA1, but was notably diminished in untransduced areas. HrGFP+ molecular layers from SCA1 transgenic mice injected with AAVshLacZ showed reduced calbindin staining, indistinguishable from untransduced layers. In wildtype mice injected with AAVshSCA1 (FIG. 8A), AAVshLacZ or saline (not shown), calbindin staining was uniform in all regions examined. The data show that shSCA1-mediated improvements are confined to transduced neurons.

Figure 8B:
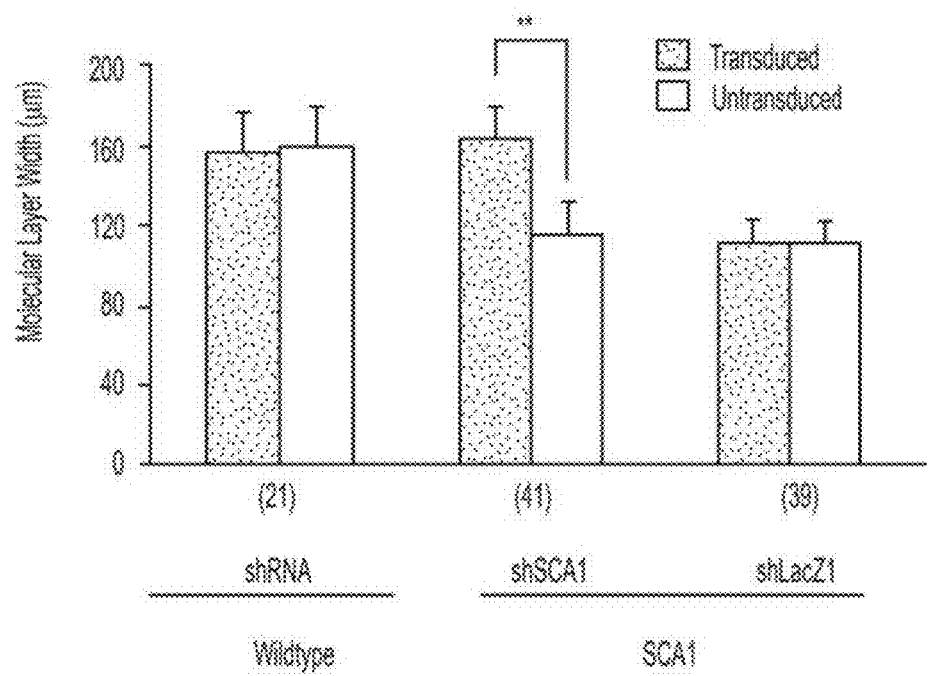
Figure 8C:
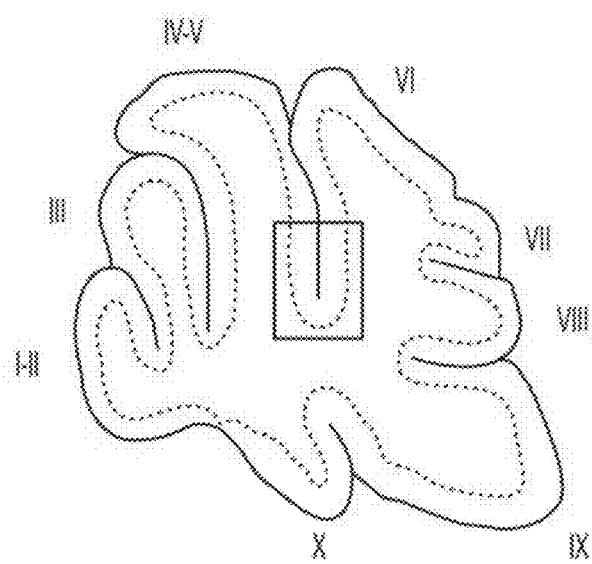

Molecular layer widths were quantified in wildtype mice and SCA1 transgenic mice treated with AAV. FIG. 8B confirms the morphological observation that expression of shRNAs did not affect the molecular layers of wildtype mice. The data also show that molecular layer widths in hrGFP+ regions from shSCA1-treated SCA1 mice (162

µm±16) are indistinguishable from wildtype controls (untransduced, 158 µm±20; AAVshSCA1 treated, 156 µm±20), in contrast to the markedly thinned molecular layer in SCA1 mice given AAVshLacZ (109 µm±12), or mock injected (109 µm±11).

Figure 9:
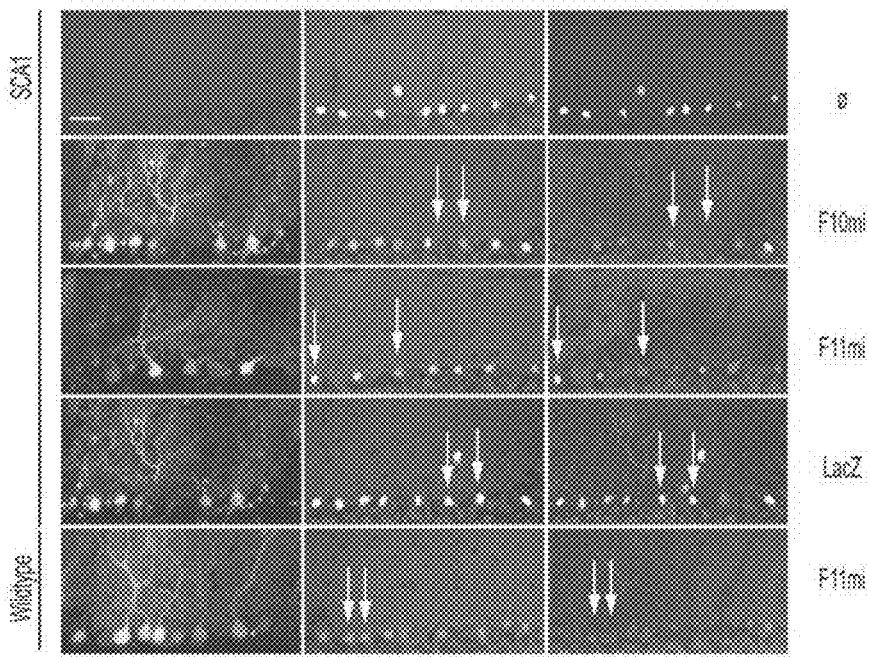
FIG. 9. Effects of shSCA1.F10mi and shSCA1.F11mi on ataxin-1 expression in mice cerebella. SCA1 transgenic or wildtype mice were injected with the indicated shRNA-expressing AAVs, and cerebella harvested 1 week later and processed for hrGFP fluorescence, and ataxin-1 IF. The top panels are from untreated SCA1 mice. The arrowheads in the middle and merged panels depict pairs of Purkinje cells, one transduced (hrGFP+), and one untransduced (hrGFP−), highlighting the extent of reduction in transgenic ataxin-1 (Q82) expression from mice injected with AAVshSCA1.F10mi and AAVshSCA1.F11mi, but not AAVshLacZ. Mouse ataxin-1 IF is weak, but notable, in wildtype mice (lower middle panel), and its expression is not reduced following shSCA1.F11mi-treatment. Bar=25 µm and refers to all panels.

The inventors next determined the effects of AAVshSCA1 on human ataxin-1 expression and the formation of ataxin-1 nuclear inclusions. In cerebella from SCA1 mice harvested 1 week after injection of AAVshSCA1.F10 or AAVshSCA1.F11, ataxin-1 immuno-reactivity was markedly reduced in transduced (hrGFP+) relative to non-transduced (GFP−) cells (FIG. 9). There was no effect of transduction on ataxin-1 levels in mock or AAVshLacZ treated SCA1 mice.

Figure 10A:
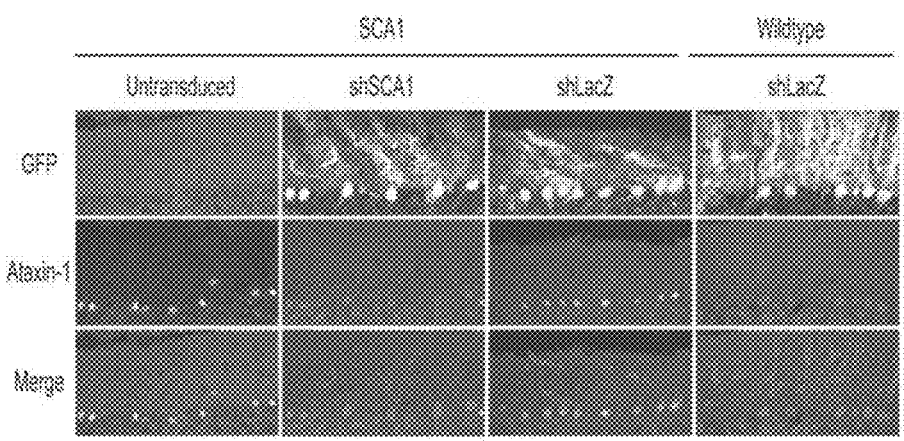
FIGS. 10A-B. RNAi reduces intranuclear inclusions in transduced cells. (A) Inclusions in transduced (hrGFP+) vs. untransduced cells. Brains from SCA1 and wildtype mice were harvested 9 weeks after gene transfer (16 weeks of age) and processed to evaluate hrGFP fluorescence and ataxin-1 IF. Bar=25 µm and is representative of all images. (B) Higher magnification of merged hrGFP and ataxin-1 positive cells. There are punctate ataxin-1 inclusions and robust nuclear staining in untransduced (Un) or AAVshLacZ transduced SCA1 Purkinje cells (top and bottom, respectively), but not AAVshSCA1.F10mi transduced ones (middle panel.
Figure 10B:
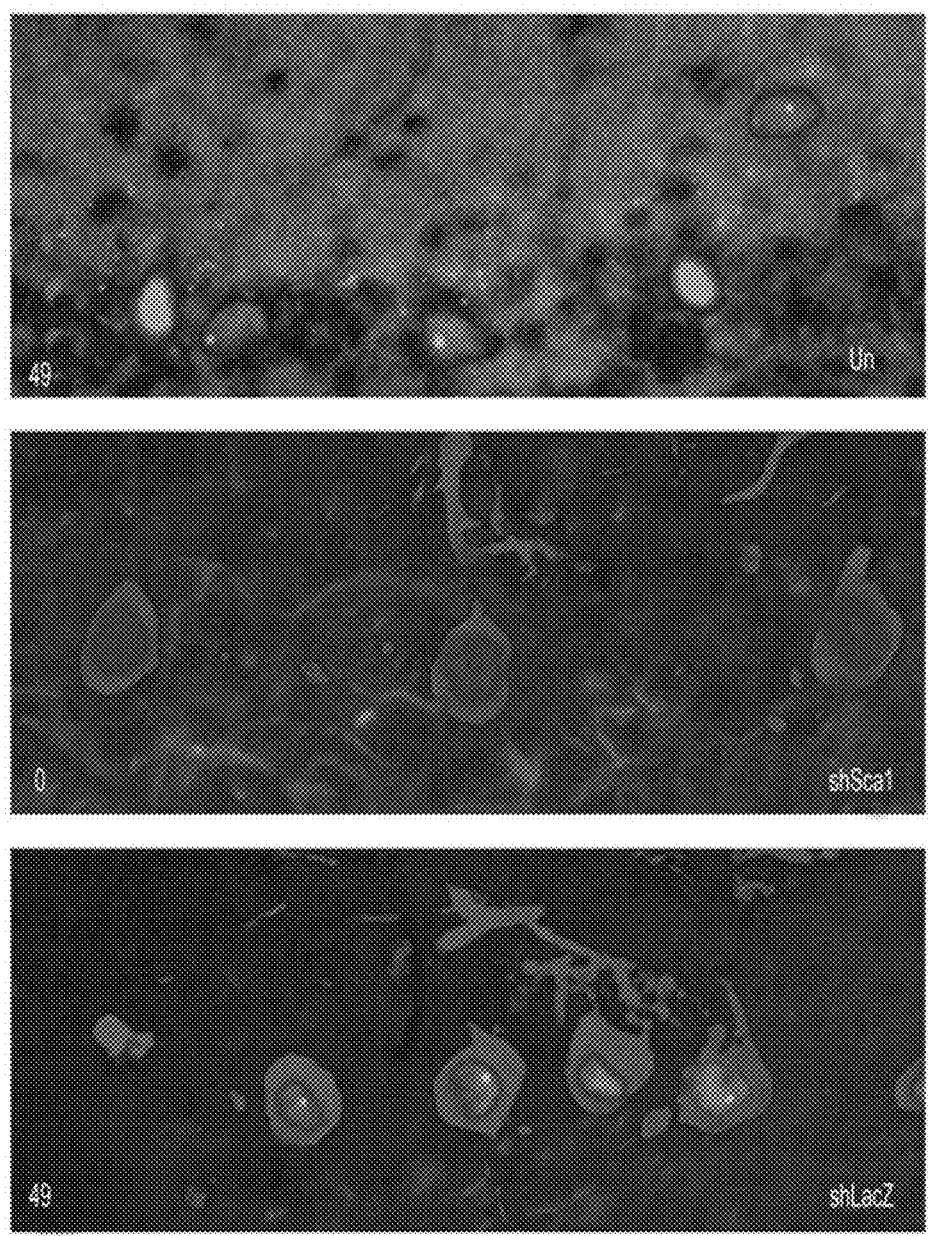

Prior work in the Orr and Zoghbi laboratories (Clark 1997) established that mutant ataxin-1 forms single intranuclear inclusions in ~50% of Purkinje cells at 16 weeks of age. In tissues from SCA1 mice harvested 9 weeks after injection of saline or AAVshLacZ, ataxin-1 immunofluorescence (IF) was robust and present throughout Purkinje cell nuclei. The inventors found punctate intranuclear inclusions in 49% of cells (FIG. 10A left panels; FIG. 10B top panel), independent of their transduction status. In contrast, transduced (hrGFP+) cells from AAVshSCA I treated mice displayed greatly diminished ataxin-1 nuclear staining, with complete resolution of inclusions in transduced cells (FIGS. 10A, 10B and FIG. 11).

Discussion

The present results demonstrate in vivo efficacy of RNAi and support the utility of RNAi gene therapy for SCA1 and other polyglutamine neurodegenerative diseases. In the SCA1 mouse model, cerebellar delivery of AAV1 vectors expressing ataxin-1-targeting shRNAs reduced ataxin-1 expression in Purkinje cells, improved motor performance and normalized the cerebellar pathology in transduced regions. In these studies, the inventors directed delivery to midline cerebellar lobules because of their importance in axial and gait coordination in mammals. In tissues harvested 9 weeks after injection, the inventors found near 100% transduction of targeted lobules, with a transduction efficiency of 5-10% of all cerebellar Purkinje cells. This supports that directed correction could have a major impact on human disease characteristics.

SCA1 mice show progressive neurodegenerative disease similar to SCA1 patients. In recent work using an inducible mouse model of SCA1, reversal of disease phenotypes was more difficult as the disease progressed, suggesting that earlier treatments will be more beneficial (Zu 2004). In the inducible SCA1 model, inhibition of mutant ataxin-1 expression at week 12 led to rotarod performance improvements.

The intranuclear, ataxin-1 inclusions are characteristic of SCA1 patient brain tissue and SCA1 mice cerebellar Purkinje cells (Burright 1995). The inventors found complete resolution of inclusions in transduced cells, which correlated with improved neuropathology. In the inducible SCA1 model, inclusions resolved several days after inhibition of mutant allele expression. AAV1 expressed shRNAs reduced mutant ataxin-1 expression as early as one week after introduction of vector, indicating that shSCA1-mediated inhibition of ataxin-1 (Q82) expression could improve disease-associated neuropathological changes almost immediately after gene transfer.

In the inventors' initial in vitro screen, it was difficult to identify effective shRNAs for ataxin-1 silencing. The two functional shRNAs discovered by the inventors flanked the CAG repeat region. The generalizability of this finding was tested in studies targeting a mutant huntingtin and found that the CAG-repeat expansion in huntingtin did not confer accessibility to RNAi. Interestingly, shRNAs shSca1.F10 and shSCA.F11 adhere less well to the model criteria (Reynolds 2004) than those that did not reduce ataxin-1 expression. This suggests the potential requirement for screening many hairpins (perhaps up to 20) prior to identifying one suitably potent for gene silencing.

Heterozygous SCA1 mice provide a tool for allele-specific silencing of the disease gene; SCA1 mice retain two wildtype ataxin-1 genes in addition to the human disease transgene. In SCA1 patients, however, shSCA1 would target both the disease and the wildtype allele. For SCA1 this may not be problematic because ataxin-1 knock out mice do not display cerebellar or brainstem pathology and have only mild ataxia measured by rotarod performance. Moreover, shRNAs probably do not reduce mRNA and protein levels to zero. The significant but non-ablative reduction of ataxin-1 would enable cellular machinery to 'catch up' with existent inclusions.

In summary, the inventors have shown that RNAi therapy can dramatically improve cellular and behavioral characteristics in a mouse model of a human dominant neurodegenerative disease, SCA1. The present findings have relevance to other polyglutamine-repeat disorders including Huntington's disease, and neurodegenerative disorders such as Alzheimer's disease, where inhibiting expression of a disease-linked protein would directly protect, or even reverse, disease phenotypes.

EXAMPLE 4

Huntington's Disease (HD)

Huntington's disease (HD) is one of several dominant neurodegenerative diseases that result from a similar toxic gain of function mutation in the disease protein: expansion of a polyglutamine (polyQ)-encoding tract. It is well established that for HD and other polyglutamine diseases, the length of the expansion correlates inversely with age of disease onset. Animal models for HD have provided important clues as to how mutant huntingtin (htt) induces pathogenesis. Currently, no neuroprotective treatment exists for HD. RNA interference has emerged as a leading candidate approach to reduce expression of disease genes by targeting the encoding mRNA for degradation.

As discussed in Example 3 above, short hairpin RNAs (shRNAs) were generated that significantly inhibited human htt expression in cell lines. Importantly, the shRNAs were designed to target sequences present in HD transgenic mouse models. The present studies test the efficacy of the shRNAs in HD mouse models by determining if inclusions and other pathological and behavioral characteristics that are representative of HD can be inhibited or reversed. In a transgenic model of inducible HD, pathology and behavior improved when mutant gene expression was turned off. These experiments show that RNAi can prevent or reverse disease.

Although the effect of partial reduction of wildtype htt in adult neurons is unknown, it is advantageous to target only mutant htt for degradation, if possible. One polymorphism in linkage disequilibrium with HD has been identified in the coding sequence for htt, and others are currently being investigated. Disease allele-specific RNAi are designed using approaches that led to allele specific silencing for other neurogenetic disease models. This would allow directed silencing of the mutant, disease-causing expanded allele, leaving the normal allele intact.

Constitutive expression of shRNA can prevent the neuropathological and behavioral phenotypes in a mouse model of Spinocerebellar Ataxia type I, a related polyQ disease. However, the constitutive expression of shRNA may not be necessary, particularly for pathologies that take many years to develop but may be cleared in a few weeks or months. For this reason, and to reduce long-term effects that may arise if nonspecific silencing or activation of interferon responses is noted, controlled expression may be very important. In order to regulate RNAi for disease application, doxycycline-responsive vectors have been developed for controlled silencing in vitro.

HD researchers benefit from a wealth of animal models including six transgenic and four knock-in mouse models (Bates 2003). Expression is from the endogenous human promoter, and the CAG expansion in the R6 lines ranges from 110 to approximately 150 CAGs. The R6/2 line is the most extensively studied line from this work. R6/2 mice show aggressive degenerative disease, with age of symptom onset at 8-12 weeks, and death occurring at 10 to 13 weeks. Neuronal intranuclear inclusions, a hallmark of HD patient brain, appear in the striatum and cortex of the R6/2 mouse (Meade 2002).

Adding two additional exons to the transgene and restricting expression via the prion promoter led to an HD mouse model displaying important HD characteristics but with less aggressive disease progression (Shilling 1999, Shilling 2001). The Borchelt model, N171-82Q, has greater than wildtype levels of RNA, but reduced amounts of mutant protein relative to endogenous htt. N171-82Q mice show normal development for the first 1-2 months, followed by failure to gain weight, progressive incoordination, hypokinesis and tremors. There are statistically significant differences in the rotarod test, alterations in gait, and hindlimb clasping. Mice show neuritic pathology characteristic of human HD. Unlike the Bates model, there is limited neuronal loss.

Detloff and colleagues created a mouse knock-in model with an extension of the endogenous mouse CAG repeat to approximately 150 CAGs. This model, the CHL2 line, shows more aggressive phenotypes than prior mouse knock-in models containing few repeats (Lin 2001). Measurable neurological deficits include clasping, gait abnormalities, nuclear inclusions and astrogliosis.

The present studies utilize the well-characterized Borchelt mouse model (N171-82Q, line 81), and the Detloff knock-in model, the CHL2 line. The initial targets for htt silencing were focused on sequences present in the N171-82Q transgene (exons 1-3). The use of this model was advantageous in the preliminary shRNA development because the RNAi search could focus on only the amino-terminal encoding sequences rather than the full length 14 kb mRNA. FIG. 12 depicts the one-step cloning approach used to screen hairpins (Harper 2004). No effective shRNAs were found in exon 1, but several designed against exon 2, denoted shHDEx2.1 (5'-AAGAAAGAACTTTCAGCTACC-3', SEQ ID NO:96), shHDEx2.2 19 nt (5'-AGAACTTTCAGCTAC-CAAG-3' (SEQ ID NO:97)), or shHDEx2.2 21 nt 5'-AAAGAACTTTCAGCTACCAAG-3' (SEQ ID NO:98)) and exon 3 (shHDEx3.1 19 nt 5'-TGCCTCAACAAAGT-TATCA-3' (SEQ ID NO:99) or shHDEx3.1 21 nt 5'-AAT-GCCTCAACAAAGTTATCA-3' (SEQ ID NO:100)) sequences were effective. In co-transfection experiments with shRNA expressing plasmids and the N171-82Q transcript target, shHDEx2.1 reduced N171-Q82 transcript levels by 80%, and protein expression by 60%.

In transient transfection assays shHDex2.1 did not silence a construct spanning exons 1-3 of mouse htt containing a 79 CAG repeat expansion, the mouse equivalent of N171-82Q. Next shHDEx2 into NIH 3T3 cells were transfected to confirm that endogenous mouse htt, which is expressed in NIH 3T3 cells, would not be reduced. Surprisingly, shHDEx2.1 and shHDEx3.1 silenced full-length mouse htt. In contrast, shHDEx2.2 silenced only the human N171-82Q transgene.

Yamamoto and colleagues and others have demonstrated that preformed inclusions can resolve (Yamamoto 2000). To test if RNAi could also reduce preformed aggregates, the inventors used a neuronal cell line, which, upon induction of Q80-eGFP expression, showed robust inclusion formation (Xia 2002). Cells laden with aggregates were mock-transduced, or transduced with recombinant virus expressing control shRNA, or shRNAs directed against GFP. The inventors found dramatic reduction in aggregates as assessed by fluorescence. Quantification showed dose dependent effects (FIG. 13) that were corroborated by western blot (Xia 2002).

As indicated in Example 1 above, viral vectors expressing siRNAs can mediate gene silencing in the CNS (Xia 2002). Also, as indicated in Example 3 above, these studies were extended to the mouse model of spinocerebellar ataxia type 1 (SCA1). The data are important as they demonstrate that shRNA is efficacious in the CNS of a mouse model of human neurodegenerative disease. The data also support that shRNA expression in brain is not detrimental to neuronal survival.

shRNAs can target the exon 58 polymorphism. As described in Example 2 above, a polymorphism in htt exon 58 is in linkage disequilibrium with HD (Ambrose 1994). Thirty eight percent of the HD population possesses a 3-GAG repeat in exon 58, in contrast to the 4-GAG repeat found in 92% of non-HD patients. The polymorphism likely has no affect on htt, but it provides a target for directing gene silencing to the disease allele. As indicated in Example 2 above, in experiments to test if allele-specific silencing for HD was possible, plasmids were generated that expressed shRNAs that were specific for the exon 58 polymorphism. The exon 58 3-GAG-targeting shRNAs were functional.

Developing vectors for control of RNAi in vivo. As demonstrated above, shRNA expressed from viral vectors is effective at directing gene silencing in brain. Also, viral vectors expressing shSCA1 inhibited neurodegeneration in the SCA1 mouse model. ShRNA expression was constitutive in both instances. However, constitutive expression may not be necessary, and could exacerbate any noted nonspecific effects. The present inventors have developed and tested several doxycycline-regulated constructs. The construct depicted in FIG. 14 showed strong suppression of target gene (GFP) expression after addition of doxycycline and RNAi induction.

RNAi can Protect, and/or Reverse, the Neuropathology in Mouse Models of Human Huntington's Disease Two distinct but complimentary mouse models are used, the N171-82Q transgenic and CHL2 knock-in mice. The former express a truncated NH2-terminal fragment of human htt comprising exons 1-3 with an 82Q-repeat expansion. The knock-in expresses a mutant mouse allele with a repeat size of ~150. Neither shows significant striatal or cortical cell loss. Both therefore are suitable models for the early stages of HD. They also possess similarities in mid- and end-stage neuropathological phenotypes including inclusions, gliosis, and motor and behavioral deficits that will permit comparison and validation. On the other hand, the differences inherent in the two models provide unique opportunities for addressing distinct questions regarding RNAi therapy. For example, N171-82Q transgenic mice have relatively early disease onset. Thus efficacy can be assessed within a few months, in contrast to 9 months or more in the CHL2 line. Because the data showed that shHDEx2.2 targets the human transgene and not mouse HD, evaluate disease-allele specific silencing in N171-82Q mice is evaluated. In contrast, the CHL2 knock-in is important for testing how reducing expression of both the mutant and wildtype alleles impacts on the HD phenotype. Finally, both models should be investigated because any therapy for HD should be validated in two relevant disease models.

siRNA Against Human Htt Protects Against Inclusion Formation in N171-82Q Mice

The data show that it is possible to silence the human N171-82Q transgene in vitro, and work in reporter mice and SCA1 mouse models demonstrated efficacy of RNAi in vivo in brain. shHDEx2.2 constructs, expressed from two vector systems with well-established efficacy profiles in CNS, are now tested for their capacity to reduce mutant transgenic allele expression in vivo. Further, the impact of shHDEx2.2 on inclusion formation is assessed. Inclusions may not be pathogenic themselves, but they are an important hallmark of HD and their presence and abundance correlates with severity of disease in many studies.

Recombinant feline immunodeficiency virus (FIV) and adeno-associated virus (AAV) expressing shHDs are injected into N171-82Q. The levels of shHDs expressed from FIV and AAV are evaluated, as is the ability to reduce htt mRNA and protein levels in brain, and subsequently affect inclusion formation.

Mice. N171-82Q mice developed by Borchelt and colleagues are used for these experiments (Shilling 1999, Shilling 2001). The colony was set up from breeders purchased from Jackson Laboratories (N171-82Q, line 81) and are maintained as described (Shilling 1999, Shilling 2001). F1 pups are genotyped by PCR off tail DNA, obtained when tagging weaned litters.

IC2 and EM48 have been used previously to evaluate N171-82Q transgene expression levels in brain by immunohistochemistry (IHC) and western blot (Zhou 2003, Trottier 1995). EM48 is an antibody raised against a GST-NH2 terminal fragment of htt that detects both ubiquitinated and non-ubiquitinated htt-aggregates (Li 2000), and the IC2 antibody recognizes long polyglutamine tracts (Trottier 1995). By 4 weeks N171-82Q mice show diffuse EM48-positive staining in striata, hippocampus, cerebellar granule cells, and cortical layers IV and V (Shilling 1999, Shilling 2001). The present experiments focus on the striatum and cortex because they are the major sites of pathology in human HD. TUNEL positivity and GFAP immunoreactivity are also significant in striatal sections harvested from 3 month old N171-82Q mice (Yu 2003). At 4 months, punctate nuclear and cytoplasmic immunoreactivity is also seen (Yu 2003).

Viruses. It is difficult to directly compare the two viruses under study at equivalent doses; FIV is enveloped and can be concentrated and purified, at best, to titers of $5 \times 10^8$ infectious units/ml (iu/ml). FIV psuedotyped with the vesicular stomatitis glycoprotein (VSVg) are used because of its tropism for neurons in the striatum (Brooks 2002). In contrast, AAV is encapsidated and can be concentrated and purified to titers ranging from $1 \times 10^9$ to $1 \times 10^{11}$ iu/ml, with $1 \times 10^{10}$ titers on average. AAV serotype 5 is used because it is tropic for neurons in striatum and cortex, our target brain regions. Also, it diffuses widely from the injection site (Alisky 2000, Davidson 2000). Ten-fold dilutions of FIV and AAV generally results in a greater than 10-fold drop in transduction efficiency, making comparisons at equal titers, and dose escalation studies, unreasonable. Thus, both viruses are tested at the highest titers routinely available to get a fair assessment of their capacities for efficacy in N171-82Q mice. All viruses express the humanized *Renilla reniformis* green fluorescent protein (hrGFP) reporter transgene in addition to the shRNA sequence (FIG. 15). This provides the unique opportunity to look at individual, transduced cells, and to compare pathological improvements in transduced vs. untransduced cells.

Injections. Mice are placed into a David Kopf frame for injections. Mice are injected into the striatum (5 microliters; 100 nl/min) and the cortex (3 microliters; 75 nl/min) using a Hamilton syringe and programmable Harvard pump. The somatosensory cortex is targeted from a burr hole at −1.5 mm from Bregma, and 1.5 mm lateral. Depth is 0.5 mm. The striatum is targeted through a separate burr hole at +1.1 mm from Bregma, 1.5 mm lateral and 2 mm deep. Only the right side of the brain is injected, allowing the left hemisphere to be used as a control for transgene expression levels and presence or absence of inclusions.

Briefly, groups of 4 week-old mice heterozygous for the N171-82Q transgene and their age-matched wildtype littermates are injected with FIV (FIV groups are VSVg.FIV.shHDEx2.2, VSVg.FIVshlacZ, VSVg.hrGFP, saline) or AAV (AAV groups are AAV5.shHDEx2.2, AAV5shlacZ, AAV5hrGFP, saline) (n=18/group; staggered injections because of the size of the experiment). [Names of shHDEx2.2 and shlacZ expressing viruses have been shortened from shlacZ.hrGFP, for example, to make it easier to read—but all vectors express hrGFP as reporter.] Nine mice/group are sacrificed at 12 weeks of age to assess the extent of transduction (eGFP fluorescence; viral copy number/brain region), shRNA expression (northern for shRNAs, and inhibition of expression of the transgenic allele (QPCR and western blot). The remaining groups are sacrificed at 5 months of age. This experimental set up is repeated (to n=6/group) to confirm results and test inter-experiment variability.

All mice in all groups are weighed bi-weekly (every other week) after initial weekly measurements. N171-82Q mice show normal weight gain up to approximately 6 weeks, after which there are significant differences with their wildtype littermates.

PCR Analyses. Brains are harvested from mice sacrificed at 12 weeks of age, and grossly evaluated for GFP expression to confirm transduction. The cortex and striatum from each hemisphere is dissected separately, snap frozen in liquid N2, pulverized with a mortar and pestle, and resuspended in Trizol (Gibco BRL). Separate aliquots are used for Q-RTPCR for N171-82Q transgenes and DNA PCR for viral genomes. A coefficient of correlation is determined for transgene silencing relative to viral genomes for both vector systems, for the regions analyzed and compared to contralateral striata and mice injected with control vectors or saline.

The RNA harvested is used to evaluate activation of interferon-responsive genes. Bridges et al (Bridges 2003) and Sledz and colleagues (Sledz 2003) found activation of 2'S' oligo(A) polymerase (OAS) in cell culture with siRNAs and shRNAs, the latter expressed from lentivirus vectors. Gene expression changes are assessed using QPCR for OAS, Stat1, interferon-inducible transmembrane proteins 1 and 2 and protein kinase R (PKR). PKR activation is an initial trigger of the signaling cascade of the interferon response.

Protein analyses. A second set of 3 brains/group are harvested for protein analysis. Regions of brains are micro dissected as described above, and after pulverization are resuspended in extraction buffer (50 mM Tris, pH 8.0, 150 mM NaCl, 1% NP-40, 0.5% deoxycholate, 0.1% SDS, 1 mM BetaME, 1× complete protease inhibitor cocktail) for analysis by western blot. HrGFP expression are evaluated and correlated to diminished levels of soluble N171-82Q using anti-GFP and antibodies to the NH2-terminal region of htt (EM48) or the polyglutamine tract (IC2).

Histology. Histology is done on the remaining animals. Mice are perfused with 2% paraformaldehyde in PBS, brains blocked to remove the cerebellum, post-fixed ON, and then cryoprotected in 30% sucrose. Full coronal sections (40 µm) of the entire cerebrum are obtained using a Microtome (American Products Co #860 equipped with a Super Histo Freeze freezing stage). Briefly, every section is collected, and sections 1-6 are placed into 6 successive wells of a 24-well plate. Every 400 microns, two sections each of 10 microns are collected for Nissl and H&E staining. The process is repeated.

EM-48 immuno-staining reveals diffuse nuclear accumulations in N171-82Q mice as early as 4 weeks of age. In 6 mo. old mice inclusions are extensive (Shilling 2001). The increase in cytoplasmic and nuclear EM48 immuno-reactivity, and in EM48 immuno-reactive inclusions over time allow quantitative comparisons between transduced and untransduced cells. Again, control values are obtained from mice injected with shlacZ-expressing vectors, saline injected mice, and wt mice. The contralateral region is used as another control, with care taken to keep in mind the possibility of retrograde and anterograde transport of virus from the injection site.

Quantitation of nuclear inclusions is done using BioQuant™ software in conjunction with a Leitz DM RBE upright microscope equipped with a motorized stage (Applied Scientific Instruments). Briefly, floating sections are stained with anti-NeuN (AMCA secondary) and EM48 antibodies (rhodamine secondary) followed by mounting onto slides. The regions to be analyzed are outlined, and threshold levels for EM48 immunoreactivity set using sections from control injected mice. A minimum of 50 hrGFP– positive and hrGFP negative neurons cells are evaluated per slide (5 slides/mouse), and inclusion intensity measured (arbitrary units). This is done for both striata and cortices. To quantitate cytoplasmic inclusions, the striatum is outlined and total EM48 aggregate density measured. Threshold values are again done using control hemispheres and control injected mice.

Additional wells of sections are stained with anti-GFAP, anti-neurofilament, and the lectin GSA to assay for viral or viral+hairpin induced gliosis, neuritic changes, and microglial activation, respectively. GFAP-stained brain sections from N171-82Q mice show gliosis by 4 months (Yu 1998), although earlier time points have not been reported.

Stereology. In a separate experiment on N171-82Q mice and wt mice, unbiased stereology using BioQuant™ software is done to assess transduction efficiency. Stereology allows for an unbiased assessment of efficiency of transduction (number of cells transduced/input). AAV5 (AAV5hrGFP, AAV5shHD.hrGFP) and FIV (VSVg.FIVhrGFP, VSVg.FIVshHD.hrGFP) transduction efficiency is compared in the striatum and somatosensory cortex in HD and wildtype mice, with n=5 each. Mice are harvested at 12 and 20 weeks. The cerebrum is sectioned in its entirety and stored at −20° C. until analysis. Briefly, six weeks after gene transfer with VSVg.FIVhrGFP (n=3) or AAV5hrGFP (n=3), every section of an HD mouse cerebrum is mounted and an initial assessment of the required numbers of sections and grid and dissector size done using the coefficient of error (as determined by Martheron's quadratic approximation formula) as a guide.

The 171-82Q HD mouse model has important neuropathological and behavioral characteristics relevant to HD. Onset of disease occurs earlier than HD knock-in or YAC transgenic models, allowing an initial, important assessment of the protective effects of RNAi on the development of neuropathology and dysfunctional behavior, without incurring extensive long term housing costs. Admittedly, disease onset is slower and less aggressive than the R6/2 mice created by Bates and colleagues (Mangiarini 1996), but the R6/2 line is difficult to maintain and disease is so severe that it may be less applicable and less predicative of efficacy in clinical trials.

N171-82Q mice (n=6/group) and age-matched littermates (n=6/group) are be weighed twice a month from 4 wks on, and baseline rotarod tests performed at 5 and 7 weeks of age. Numbers of mice per group are as described in Schilling et al (Shilling 1999) in which statistically significant differences between N171-82Q and wildtype littermates were described. At 7 weeks of age (after testing is complete), AAV (AAVshHDEx2.2, AAVshlacZ, AAVhrGFP, saline) or FIV (FIVshEx2.2, FIVshlacZ, FIVhrGFP, saline) is injected bilaterally into the striatum and cortex. Rotarod tests are repeated at 3-week intervals starting at age 9 weeks, until sacrifice at 6 months. The clasping behavior is assessed monthly starting at 3 months.

Behavioral testing. N171-82Q mice are given four behavioral tests, all of which are standard assays for progressive disease in HD mouse models. The tests allow comparisons of behavioral changes resulting from RNAi to those incurred in HD mouse models given other experimental therapies. For example, HD mice given cystamine or creatine therapy showed delayed impairments in rotarod performance, and in some cases delayed weight loss (Ferrante 2000, Dedeoglu 2002, Dedeogu 2003) In addition to the rotarod, which is used to assay for motor performance and general neurological dysfunction, the activity monitor allows assessment of the documented progressive hypoactivity in N171-82Q mice. The beam analysis is a second test of motor performance that has also been used in RD mice models (Carter 1999). Clasping, a phenotype of generalized neurological dysfunction, is straightforward and takes little time. Clasping phenotypes were corrected in R. Hen's transgenic mice possessing an inducible mutant htt.

Accelerated rotarod. N171-82Q and age-matched littermates are habituated to the rotarod at week 4, and 4 trials per day for 4 days done on week 5 and 7, and every 3 weeks hence using previously described assays (Shilling 1999, Clark 1997) in use in the lab. Briefly, 10 min trials are run on an Economex rotarod (Columbus Instruments) set to accelerate from 4 to 40 rpm over the course of the assay. Latency to fall is recorded and averages/group determined and plotted. Based on prior work (Shilling 1999) 6 mice will give sufficient power to assess significance.

Clasping behavior. Normal mice splay their limbs when suspended, but mice with neurological deficits can exhibit the opposite, with fore and hind limbs crunched into the abdomen (clasping). All mice are suspended and scored for clasping monthly. The clasp must be maintained for at least 30 sec. to be scored positive.

Activity monitor. Most HD models demonstrate hypokinetic behavior, particularly later in the disease process. This can be measured in several ways. One of the simplest methods is to monitor home cage activity with an infrared sensor (AB-system 4.0, Neurosci Co., LTD). Measurements are taken over 3 days with one day prior habituation to the testing cage (standard 12-hour light/dark cycle). Activity monitoring is done at 12, 17, and 20 and 23 weeks of age.

Beam walking. N171Q-82Q and age matched littermates are assayed for motor performance and coordination using a series of successively more difficult beams en route to an enclosed safety platform. The assay is as described by Carter et al (Carter 1999). Briefly, 1 meter-length beams of 28, 17 or 11 mm diameter are placed 50 cm above the bench surface. A support stand and the enclosed goal box flank the ends. Mice are trained on the 11 mm beam at 6 weeks of age over 4 days, with 3 trials per day. If mice can traverse the beam in <20 sec. trials are initiated. A trial is then run on each beam, largest to smallest, with a 60 sec cutoff/beam and one minute rest between beams. A second trial is run and the mean scores of the two trials evaluated.

RNAi cannot replace neurons; it only has the potential to protect non-diseased neurons, or inhibit further progression of disease at a point prior to cell death. N171-82Q mice do not show noticeable cellular loss, and is therefore an excellent model of early HD in humans. The general methodology is the similar to that described above, except that the viruses are injected at 4 months, when N171-82Q mice have measurable behavioral dysfunction and inclusions. Animals are sacrificed at end stage disease or at 8 months, whichever comes first. Histology, RNA and protein in harvested brains are analyzed as described above.

It is important to confirm the biological effects of virally expressed shHDs in a second mouse model, as it is with any therapy. The Detloff knock-in mouse (the CHL2 line, also notated as HdhCAGQ150) is used as a second model of early HD disease phenotypes. These mice have a CAG expansion of approximately 150 units, causing brain pathologies similar to HD including gliosis and neural inclusions in the cortex and striatum. They also show progressive motor dysfunction and other behavioral manifestations including rotarod deficits, clasping, gait abnormalities and hypoactivity.

Heterozygous CHL2 mice express the mutant and wildtype allele at roughly equivalent levels, and shRNAs directed against mouse HD silence both transcripts. shmHDEx2.1 causes reductions in gene expression, but not complete silencing. Disease severity in mouse models is dependent on mutant htt levels and CAG repeat length.

The inventors created shmHDEx2 (shRNA for murine HD) directed against a region in mouse exon 2 that reduces expression of the full-length mouse Hdh transcript in vitro. Transduction of neurons with shmHDEx2-expressing viruses, and its impacts on neuropathological progression, behavioral dysfunction and the appearance of EM48 immuno-reactive inclusions in CHL2 mice is tested. shmHD- or shlacZ-expressing vectors in CHL2 and wildtype brain is tested. In this experiment, virus is injected into the striatum of wt or CRL2 mice (10/group) using the coordinates described above, at 3 months of age. Two months later mice are sacrificed and brains removed and processed for RNA (n=5/group) and protein (n=5).

A second study tests the vectors in the Detloff model. Briefly, 15 mice per group are injected into the striatum and cortex at 3 months of age with AAV (AAVshmHD, AAVshlacZ, AAVhrGFP, saline) or FIV (VSVg.FIV.shmHD, VSVg.FIVshlacZ, VSVg.FIVhrGFP, saline) expressing the transgenes indicated. To assess the impact of RNAi, activity performed. The mice are sacrificed at 16-18 months of age and five brains/group are processed for histology and sections banked in 24-well tissue culture plates. The remaining brains are processed for RNA (n=6) and protein analysis (n=5). Northern blots or western blots are required to analyze wildtype and mutant htt expression because the only distinguishing characteristic is size.

Development of Effective Allele-Specific siRNAs

Mutant htt leads to a toxic gain of function, and inhibiting expression of the mutant allele has a profound impact on disease (Yamamoto 2000). Also, selectively targeting the disease allele would be desirable if non-disease allele silencing is deleterious. At the present time, there is one documented disease linked polymorphism in exon 58 (Lin 2001). Most non-HD individuals have 4 GAGs in Hdh exon 58 while 38% of HD patients have 3 GAGs. As described above, RNAi can be accomplished against the 3-GAG repeat.

Prior work by the inventors showed the importance of using full-length targets for testing putative shRNAs. In some cases, shRNAs would work against truncated, but not full-length targets, or vice-versa. Thus, it is imperative that testable, full-length constructs are made to confirm allele-specific silencing. The V5 and FLAG tags provide epitopes to evaluate silencing at the mRNA and protein levels. This is important as putative shRNAs may behave as miRNAs, leading to inhibition of expression but not message degradation.

Designing the siRNAs. Methods are known for designing siRNAs (Miller 2003, Gonzalez-Alegre 2003, Xia 2002, Kao 2003). Information is also know about the importance of maintaining flexibility at the 5' end of the antisense strand for loading of the appropriate antisense sequence into the RISC complex (Khvorova 2003 Schwarz 2003). DNA sequences are generated by PCR. This method allows the rapid generation of many candidate shRNAs, and it is significantly cheaper than buying shRNAs. Also, the inserts can be cloned readily into our vector shuttle plasmids for generation of virus. The reverse primer is a long oligonucleotide encoding the antisense sequence, the loop, the sense sequence, and a portion of the human U6 promoter. The forward primer is specific to the template in the PCR reaction. PCR products are cloned directly into pTOPO blunt from InVitrogen, plasmids transformed into DH5a, and bacteria plated onto Kanr plates (the PCR template is Ampr). Kanr clones are picked and sequenced. Sequencing is done with an extended 'hot start' to allow effective read-through of the hairpin. Correct clones are transfected into cells along with plasmids expressing the target or control sequence (HttEx58.GAG3V5 and HttEx58.GAG4FLAG, respectively) and silencing evaluated by western blot. Reductions in target mRNA levels are assayed by Q-RTPCR. The control for western loading is neomycin phosphotransferase or hrGFP, which are expressed in the target-containing plasmids and provide excellent internal controls for transfection efficiency. The control for Q-RTPCR is HPRT.

Cell lines expressing targets with the identified polymorphism or control wildtype sequences are created. Target gene expression are under control of an inducible promoter. PC6-3, Tet repressor (TetR+) cells, a PC-12 derivative with a uniform neuronal phenotype (Xia 2002) are used. PC6-3 cells are transfected with plasmids expressing HDEx58.GAG3V5 (contains neo marker) and HDEx58GAG4FLG (contains puro marker), and G418+/puromycin+ positive clones selected and characterized for transcript levels and htt-V5 or htt-Flag protein levels.

FIV vectors expressing the allele specific shRNAs are generated and used to test silencing in the inducible cell lines. FIV vectors infect most epithelial and neuronal cell lines with high efficiency and are therefore useful for this purpose. They also efficiently infect PC6-3 cells. AAV vectors are currently less effective in in vitro screening because of poor transduction efficiency in many cultured cell lines.

Cells are transduced with 1 to 50 infectious units/cell in 24-well dishes, 3 days after induction of mutant gene expression. Cells are harvested 72 h after infection and the effects on HDEx58.GAG3V5 or HDEx58GAG4FLG expression monitored.

EXAMPLE 5

Micro RNAi-Therapy for Polyglutamine Disease

Post-transcriptional gene silencing occurs when double stranded RNA (dsRNA) is introduced or naturally expressed in cells. RNA interference (RNAi) has been described in plants (quelling), nematodes, and *Drosophila*. This process serves at least two roles, one as an innate defense mechanism, and another developmental (Waterhouse 2001 Fire 1999, Lau 2001, Lagos-Quintana 2001, Lee 2001). RNAi may regulate developmental expression of genes via the processing of small, temporally expressed RNAs, also called microRNAs (Knight 2001, Grishok 2001). Harnessing a cell's ability to respond specifically to small dsRNAs for target mRNA degradation has been a major advance, allowing rapid evaluation of gene function (Gonczy 2000, Fire 1998, Kennerdell 1998, Hannon 2002, Shi 2003, Sui 2002).

Most eukaryotes encode a substantial number of small noncoding RNAs termed micro RNAs (miRNAs) (Zeng 2003, Tijsterman 2004, Lee 2004, Pham 2004). mir-30 is a 22-nucleotide human miRNA that can be naturally processed from a longer transcript bearing the proposed miR-30 stem-loop precursor. mir-30 can translationally inhibit an mRNA-bearing artificial target sites. The mir-30 precursor stem can be substituted with a heterologous stem, which can be processed to yield novel miRNAs and can block the expression of endogenous mRNAs.

Huntington's disease (HD) and Spinocerebellar ataxia type I (SCA1) are two of a class of dominant, neurodegenerative diseases caused by a polyglutamine (polyQ) expansion. The mutation confers a toxic gain of function to the protein, with polyQ length predictive of age of onset and disease severity. There is no curative or preventative therapy for HD or SCA1, supporting the investigation of novel strategies. As described above, the inventors showed that gene silencing by RNA interference (RNAi) can be achieved in vitro and in vivo by expressing short hairpin RNAs (shRNAs) specific for mRNAs encoding ataxin-1 or huntingtin. Currently, strong, constitutive polIII promoters (U6 and H1) are used to express shRNAs, which are subsequently processed into functional small interfering RNAs (siRNAs). However, strong, constitutive expression of shRNAs may be inappropriate for diseases that take several decades to manifest. Moreover, high-level expression may be unnecessary for sustained benefit, and in some systems may induce a non-specific interferon response leading to global shut-down of gene expression. The inventors therefore generated polII-expressed microRNAs (miRNAs) as siRNA shuttles as an alternative strategy. Due to their endogenous nature, miRNA backbones may prevent the induction of the interferon response.

Using human mir-30 as a template, miRNA shuttles were designed that upon processing by dicer released siRNAs specific for ataxin-1. Briefly, the constructs were made by cloning a promoter (such as an inducible promoter) and an miRNA shuttle containing an embedded siRNA specific for a target sequence (such as ataxin-1) into a viral vector. By cloning the construct into a viral vector, the construct can be effectively introduced in vivo using the methods described in the Examples above. Constructs containing polII-expressed miRNA shuttles with embedded ataxin-1-specific siRNAs were co-transfected into cells with GFP-tagged ataxin-1, and gene silencing was assessed by fluorescence microscopy and western analysis. Dramatic arid dose-dependent gene silencing relative to non-specific miRNAs carrying control siRNAs was observed. This polII-based expression system exploits the structure of known miRNAs and supports tissue-specific as well as inducible siRNA expression, and thus, serves as a unique and powerful alternative to dominant neurodegenerative disease therapy by RNAi.

Briefly, the constructs were made by cloning a promoter (such as an inducible promoter) and an miRNA shuttle containing an embedded siRNA specific for a target sequence (such as ataxin-1) into a viral vector. By cloning the construct into a viral vector, the construct can be effectively introduced in vivo using the methods described in the Examples above.

EXAMPLE 6 siRNA Suppression of Genes Involved in MJD/SCA3 and FTDP-17

Modulation of gene expression by endogenous, noncoding RNAs is increasingly appreciated to play a role in eukaryotic development, maintenance of chromatin structure and genomic integrity. Recently, techniques have been developed to trigger RNA interference (RNAi) against specific targets in mammalian cells by introducing exogenously produced or intracellularly expressed siRNAs. These methods have proven to be quick, inexpensive and effective for knockdown experiments in vitro and in vivo. The ability to accomplish selective gene silencing has led to the hypothesis that siRNAs might be employed to suppress gene expression for therapeutic benefit.

Dominantly inherited diseases are ideal candidates for siRNA-based therapy. To explore the utility of siRNA in inherited human disorders, the inventors employed cellular models to test whether we could target mutant alleles causing two classes of dominantly inherited, untreatable neurodegenerative diseases: polyglutamine (polyQ) neurodegeneration in MJD/SCA3 and frontotemporal dementia with parkinsonism linked to chromosome 17 (FTDP-17). The polyQ neurodegenerative disorders consist of at least nine diseases caused by CAG repeat expansions that encode polyQ in the disease protein. PolyQ expansion confers a dominant toxic property on the mutant protein that is associated with aberrant accumulation of the disease protein in neurons. In FTDP-17, Tau mutations lead to the formation of neurofibrillary tangles accompanied by neuronal dysfunction and degeneration. The precise mechanisms by which these mutant proteins cause neuronal injury are unknown, but considerable evidence suggests that the abnormal proteins themselves initiate the pathogenic process. Accordingly, eliminating expression of the mutant protein by siRNA or other means should, in principle, slow or even prevent disease. However, because many dominant disease genes may also encode essential proteins, the inventors sought to develop siRNA-mediated approaches that selectively inactivate mutant alleles while allowing continued expression of the wild type protein.

Methods siRNA Synthesis. In vitro siRNA synthesis was previously described (Donze 2000). Reactions were performed with desalted DNA oligonucleotides (IDT Coralville, Iowa) and the AmpliScribeT7 High Yield Transcription Kit (Epicentre Madison, Wis.). Yield was determined by absorbance at 260 nm. Annealed siRNAs were assessed for double stranded character by agarose gel (1% w/v) electrophoresis and ethidium bromide staining. Note that for all siRNAs generated in this study the most 5' nucleotide in the targeted cDNA sequence is referred to as position 1 and each subsequent nucleotide is numbered in ascending order from 5' to 3'.

Plasmid Construction. The human ataxin-3 cDNA was expanded to 166 CAG's by PCR (Laccone 1999). PCR products were digested at BamHI and KpnI sites introduced during PCR and ligated into BglII and KpnI sites of pEGFP–N1 (Clontech) resulting in full-length expanded ataxin-3 fused to the N-terminus of EGFP. Untagged Ataxin-3-Q166 was constructed by ligating a PpuMI-NotI ataxin-3 fragment (3' of the CAG repeat) into Ataxin-3-Q166-GFP cut with PpuMI and NotI to remove EGFP and replace the normal ataxin-3 stop codon. Ataxin-3-Q28-GFP was generated as above from pcDNA3.1-ataxin-3-Q28. Constructs were sequence verified to ensure that no PCR mutations were present. Expression was verified by Western blot with anti-ataxin-3 (Paulson 1997) and GFP antibodies (MBL). The construct encoding a flag tagged, 352 residue tau isoform was previously described (Leger 1994). The pEGFP–tau plasmid was constructed by ligating the human tau cDNA into pEGFP–C2 (Clontech) and encodes tau with EGFP fused to the amino terminus. The pEGFP–tauV337M plasmid was derived using site-directed mutagenesis (QuikChange Kit, Stratagene) of the pEFGP-tau plasmid.

Cell Culture and Transfections. Culture of Cos-7 and HeLa cells has been described (Chai 1999b). Transfections with plasmids and siRNA were performed using Lipofectamine Plus (LifeTechnologies) according to the manufacturer's instructions. For ataxin-3 expression 1.5 µg plasmid was transfected with 5 µg in vitro synthesized siRNAs. For Tau experiments 1 µg plasmid was transfected with 2.5 µg siRNA. For expression of hairpin siRNA from the phU6 constructs, 1 µg ataxin-3 expression plasmid was transfected with 4 µg phU6-siC10i or phU6-siG10i. Cos-7 cells infected with siRNA-expressing adenovirus were transfected with 0.5 µg of each expression plasmid.

Stably transfected, doxycycline-inducible cell lines were generated in a subclone of PC12 cells, PC6-3, because of its strong neural differentiation properties (Pittman 1993B). A PC6-3 clone stably expressing Tet repressor plasmid (provided by S. Strack, Univ. of Iowa), was transfected with pcDNA5/TO-ataxin-3(Q28) or pcDNA5/TO-ataxin-3 (Q166) (Invitrogen). After selection in hygromycin, clones were characterized by Western blot and immunofluorescence. Two clones, PC6-3-ataxin3(Q28)#33 and PC6-3-ataxin3(Q166)#41, were chosen because of their tightly inducible, robust expression of ataxin-3.

siRNA Plasmid and Viral Production. Plasmids expressing ataxin-3 shRNAs were generated by insertion of head-to-head 21 bp hairpins in phU6 that corresponded to siC10 and siG10 (Xia 2002).

Recombinant adenovirus expressing ataxin-3 specific shRNA were generated from phU6-C10i (encoding C10 hairpin siRNA) and phU6si-G10i (encoding G10 hairpin siRNA) as previously described (Xia 2002, Anderson 2000).

Western Blotting and Immunofluorescence. Cos-7 cells expressing ataxin-3 were harvested 24-48 hours after transfection (Chai 1999b). Stably transfected, inducible cell lines were harvested 72 hours after infection with adenovirus. Lysates were assessed for ataxin-3 expression by Western blot analysis as previously described (Chai 1999b), using polyclonal rabbit anti-ataxin-3 antisera at a 1:15,000 dilution or 1C2 antibody specific for expanded polyQ tracts (Trottier 1995) at a 1:2,500 dilution. Cells expressing Tau were harvested 24 hours after transfection. Protein was detected with an affinity purified polyclonal antibody to a human tau peptide (residues 12-24) at a 1:500 dilution. Anti-alpha-tubulin mouse monoclonal antibody (Sigma St. Louis, Mo.) was used at a 1:10,000 dilution and GAPDH mouse monoclonal antibody (Sigma St. Louis, Mo.) was used at a 1:1,000 dilution.

Immunofluorescence for ataxin-3 (Chai 1999b) was carried out using 1C2 antibody (Chemicon International Temecula, Calif.) at 1:1,000 dilution 48 hours after transfection. Flag-tagged, wild type tau was detected using mouse monoclonal antibody (Sigma St. Louis, Mo.) at 1:1,000 dilution 24 hours after transfection. Both proteins were detected with rhodamine conjugated secondary antibody at a 1:1,000 dilution.

Fluorescent Imaging and Quantification. Fixed samples were observed with a Zeiss Axioplan fluorescence microscope. Digital images were collected on separate red, green and blue fluorescence channels using a SPOT digital camera. Images were assembled and overlaid using Adobe Photoshop 6.0. Live cell images were collected with a Kodak MDS 290 digital camera mounted to an Olympus (Tokyo, Japan) CK40 inverted microscope. Fluorescence was quantitated by collecting 3 non-overlapping images per well at low power (10×). Pixel count and intensity for each image was determined using Bioquant Nova Prime software (BIOQUANT Image Analysis Corporation). Background was subtracted by quantitation of images from cells of equivalent density under identical fluorescent illumination. Mock transfected cells were used to assess background fluorescence for all experiments and were stained with appropriate primary and secondary antibodies for simulated heterozygous experiments. Average fluorescence is reported from 2 to 3 independent experiments. The mean of 2 to 3 independent experiments for cells transfected with the indicated expression plasmid and siMiss was set at one. Errors bars depict variation between experiments as standard error of the mean. In simulated heterozygous experiments, a blinded observer scored cells with a positive fluorescence signal for expression of wild type, mutant or both proteins in random fields at high power for two independent experiments. More than 100 cells were scored in each experiment and reported as number of cells with co-expression divided by total number of transfected cells.

Results

Figure 16A:
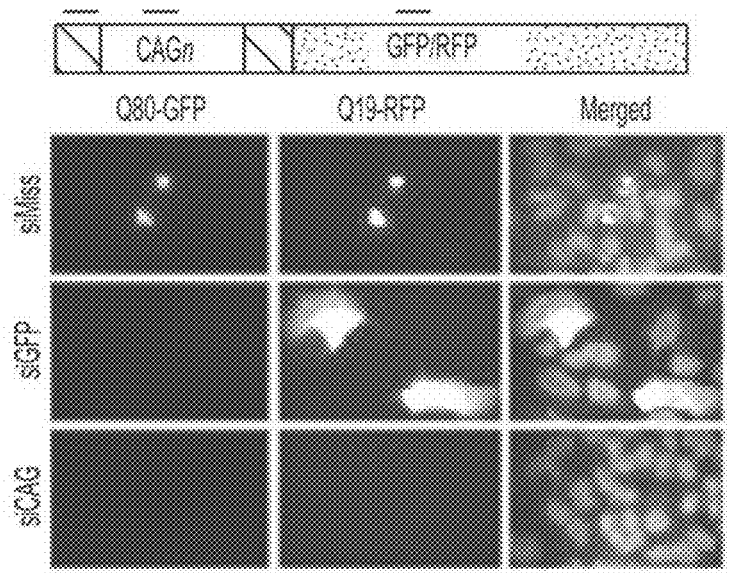

Direct Silencing of Expanded Alleles. The inventors first attempted suppression of mutant polyQ expression using siRNA complementary to the CAG repeat and immediately adjacent sequences to determine if the expanded repeat differentially altered the susceptibility of the mutant allele to siRNA inhibition (FIG. 17). HeLa cells were transfected with various in vitro synthesized siRNAs (Danze 2002) and plasmids encoding normal or expanded polyQ fused to red or green fluorescent protein, respectively (Q19-RFP and Q80-GFP) (FIG. 16A). In negative control cells transfected with Q80-GFP, Q19-RFP and a mistargeted siRNA (siMiss), Q80-GFP formed aggregates (Onodera 1997) which recruited the normally diffuse Q19-RFP (FIG. 16A). When the experiment was performed with siRNA targeted to GFP as a positive control for allele specific silencing, Q80-GFP expression was nearly abolished while Q19-RFP continued to be expressed as a diffusely distributed protein (FIG. 16A). When Q19-RFP and Q80-GFP were co-transfected with siRNA directly targeting the CAG repeat (siCAG) (FIG. 16A) or an immediately adjacent 5' region (data not shown), expression of both proteins was efficiently suppressed.

Figure 16B:
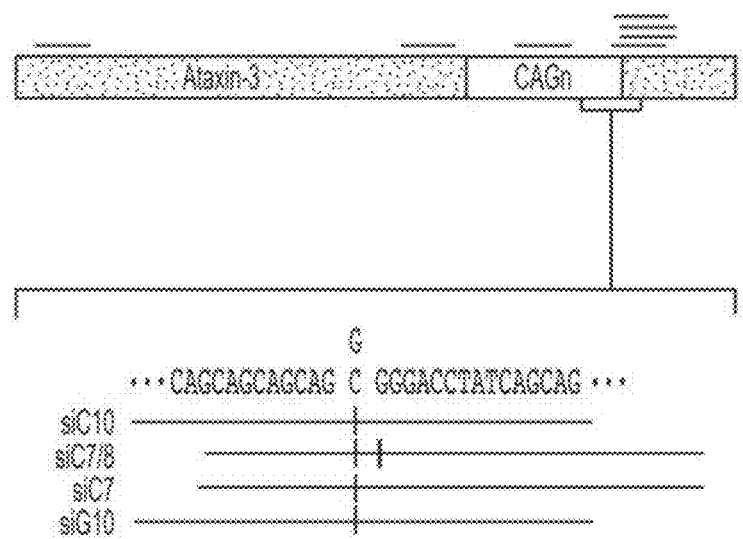

To test whether siRNA could selectively silence expression of a full-length polyQ disease protein, siRNAs were designed that target the transcript encoding ataxin-3, the disease protein in Machado-Joseph Disease, also known as Spinocerebellar Ataxia Type 3 (MJD/SCA3) (Zoghbi 2000) (FIG. 16B). In transfected cells, siRNA directed against three separate regions—the CAG repeat, a distant 5' site, or a site just 5' to the CAG repeat (siN'CAG)—resulted in efficient, but not allele-specific, suppression of ataxin-3 containing normal or expanded repeats (data not shown). Consistent with an earlier study using longer dsRNA (Caplen 2002) the present results show that expanded CAG repeats and adjacent sequences, while accessible to RNAi, may not be preferential targets for silencing.

Figure 16C:
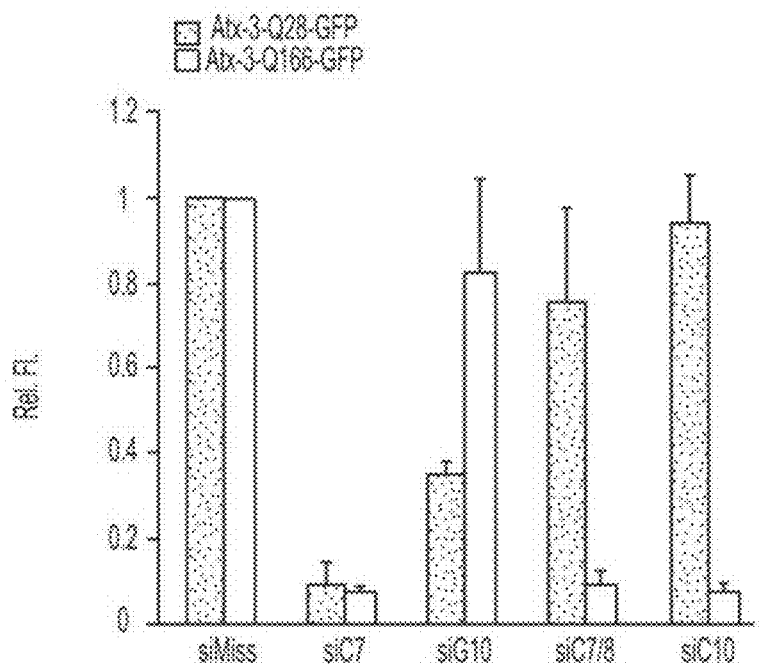
Figure 16D:
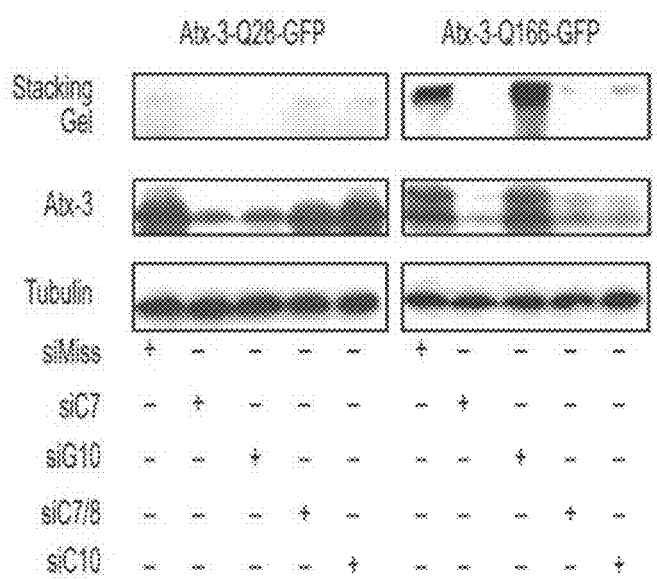

Allele-Specific Silencing of the Mutant PolyQ Gene in MJD/SCA3. In further efforts to selectively inactivate the mutant allele the inventors took advantage of a SNP in the MJD1 gene, a G to C transition immediately 3' to the CAG repeat (G987C) (FIG. 16B). This SNP is in linkage disequilibrium with the disease-causing expansion, in most families segregating perfectly with the disease allele. Worldwide, 70% of disease chromosomes carry the C variant (Gaspar 2001). The present ataxin-3 expression cassettes, which were generated from patients (Paulson 1997), contain the C variant in all expanded ataxin-3 constructs and the G variant in all normal ataxin-3 constructs. To test whether this G-C mismatch could be distinguished by siRNA, siRNAs were designed that included the last 2 CAG triplets of the repeat followed by the C variant at position 7 (siC7) (FIG. 17 and FIG. 16B), resulting in a perfect match only for expanded alleles. Despite the presence of a single mismatch to the wild type allele, siC7 strongly inhibited expression of both alleles (FIG. 16C,D). A second G-C mismatch was then introduced at position 8 such that the siRNA contained two mismatches as compared to wild type and only one mismatch as compared to mutant alleles (siC7/8). The siC7/8 siRNA effectively suppressed mutant ataxin-3 expression, reducing total fluorescence to an average 8.6% of control levels, with only modest effects on wild type ataxin-3 (average 75.2% of control). siC7/8 also nearly eliminated the accumulation of aggregated mutant ataxin-3, a pathological hallmark of disease (Chan 2000) (FIG. 16D).

To optimize differential suppression, siRNAs were designed containing a more centrally placed mismatch. Because the center of the antisense strand directs cleavage of target mRNA in the RNA Induced Silencing Complex (RISC) complex (Elbashir 2001c), it was reasoned that central mismatches might more efficiently discriminate between wild type and mutant alleles. siRNAs were designed that place the C of the SNP at position 10 (siC10), preceded by the final three triplets in the CAG repeat (FIG. 17 and FIG. 16B). In transfected cells, siC10 caused allele-specific suppression of the mutant protein (FIG. 16C,D). Fluorescence from expanded Atx-3-Q166-GFP was dramatically reduced (7.4% of control levels), while fluorescence of Atx-3-Q28-GFP showed minimal change (93.6% of control; FIG. 16C,D). Conversely, siRNA engineered to suppress only the wild type allele (siG10) inhibited wild type expression with little effect on expression of the mutant allele (FIG. 16C,D). Inclusion of three CAG repeats at the 5' end of the siRNA did not inhibit expression of Q19-GFP, Q80-GFP, or full-length ataxin-1-Q30 proteins that are each encoded by CAG repeat containing transcripts (FIG. 18A-B).

Figure 16E:
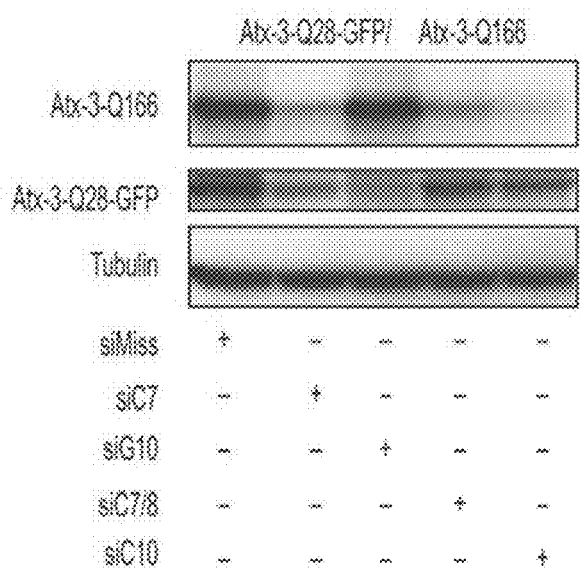

In the disease state, normal and mutant alleles are simultaneously expressed. In plants and worms, activation of RNAi against one transcript results in the spread of silencing signals to other targets due to RNA-dependent RNA polymerase (RDRP) activity primed by the introduced RNA (Fire 1998, Tang 2003). Although spreading has not been detected in mammalian cells and RDRP activity is not required for effective siRNA inhibition (Chiu 2002, Schwarz 2002, Martinez 2002), most studies have used cell-free systems in which a mammalian RDRP could have been inactivated. If triggering the mammalian RNAi pathway against one allele activates cellular mechanisms that also silence the other allele, then siRNA applications might be limited to non-essential genes. To test this possibility, the heterozygous state was simulated by co-transfecting Atx-3-Q28-GFP and Atx-3-Q166 and analyzing suppression by Western blot. As shown in FIG. 16E each siRNA retained the specificity observed in separate transfections: siC7 inhibited both alleles, siG10 inhibited only the wild type allele, and siC7/8 and siC10 inhibited only mutant allele expression.

Figure 16F:
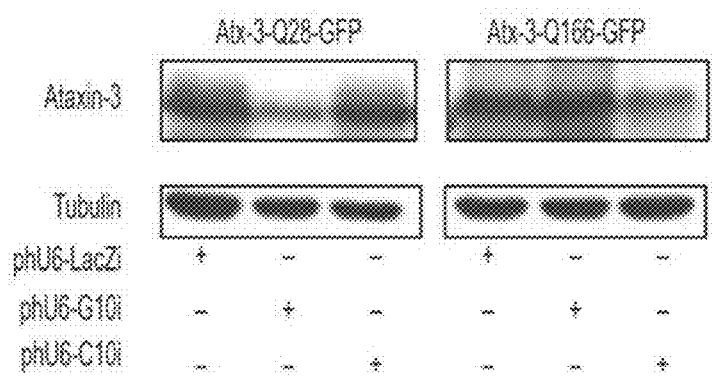

Effective siRNA therapy for late onset disease will likely require sustained intracellular expression of the siRNA. Accordingly, the present experiments were extended to two intracellular methods of siRNA production and delivery: expression plasmids and recombinant virus (Brummelkamp 2002, Xia 2002). Plasmids were constructed expressing siG10 or siC10 siRNA from the human U6 promoter as a hairpin transcript that is processed intracellularly to produce siRNA (Brummelkamp 2002, Xia 2002). When co-transfected with ataxin-3-GFP expression plasmids, phU6-G10i and phU6-C10i-siRNA plasmids specifically suppressed wild type or mutant ataxin-3 expression, respectively (FIG. 16F).

Figure 19A:
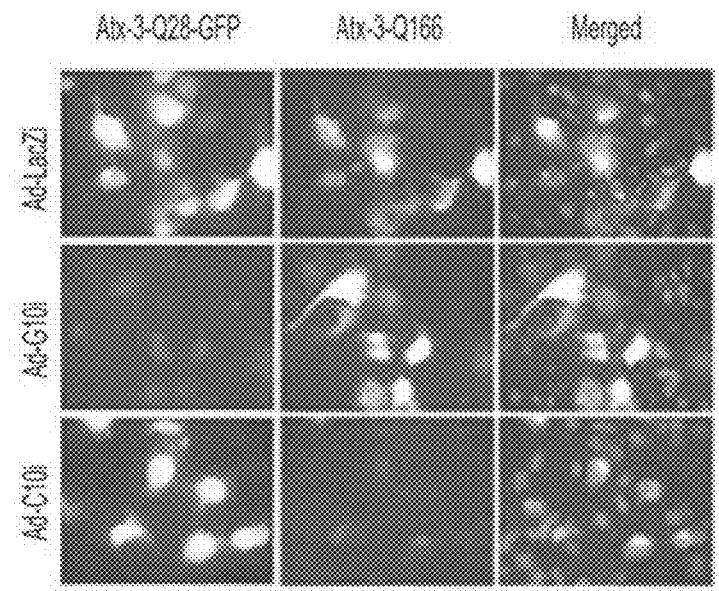
Figure 19B:
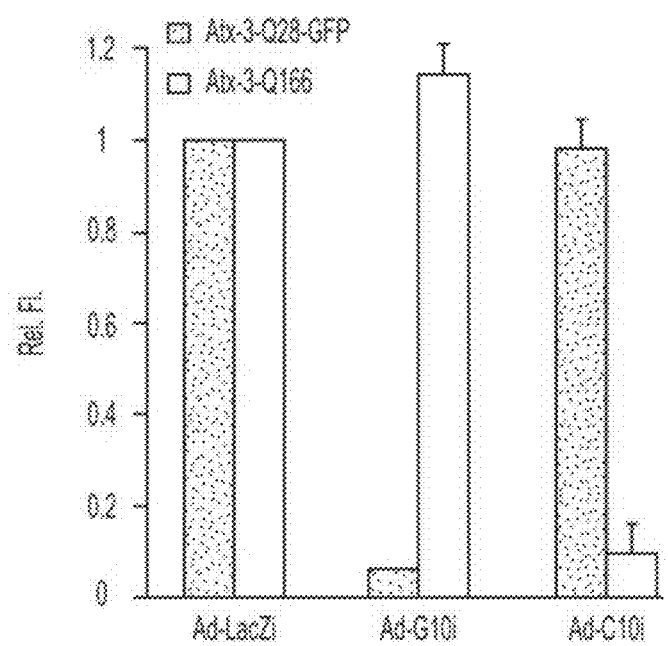
Figure 19C:
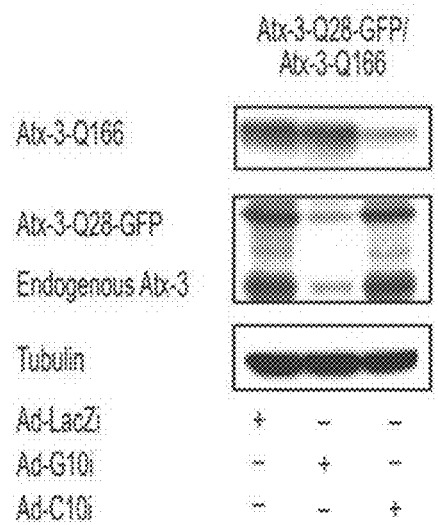

This result encouraged the inventors to engineer recombinant adenoviral vectors expressing allele-specific siRNA (Xia 2002). Viral-mediated suppression was tested in Cos-7 cells transiently transfected with both Atx-3-Q28-GFP and Atx-3-Q166 to simulate the heterozygous state. Cos-7 cells infected with adenovirus encoding siG10, siC10 or negative control siRNA (Ad-G10i, Ad-C10i, and Ad-LacZi respectively) exhibited allele-specific silencing of wild type ataxin-3 expression with Ad-G10i and of mutant ataxin-3 with Ad-C10i (FIG. 19A,B,C). Quantitation of fluorescence (FIG. 19B) showed that Ad-G10i reduced wild type ataxin-3 to 5.4% of control levels while mutant ataxin-3 expression remained unchanged. Conversely, Ad-C10i reduced mutant ataxin-3 fluorescence levels to 8.8% of control and retained 97.4% of wild type signal. These results were confirmed by Western blot where it was further observed that Ad-G10i virus decreased endogenous (primate) ataxin-3 while Ad-C10i did not (FIG. 19C).

Figure 19D:
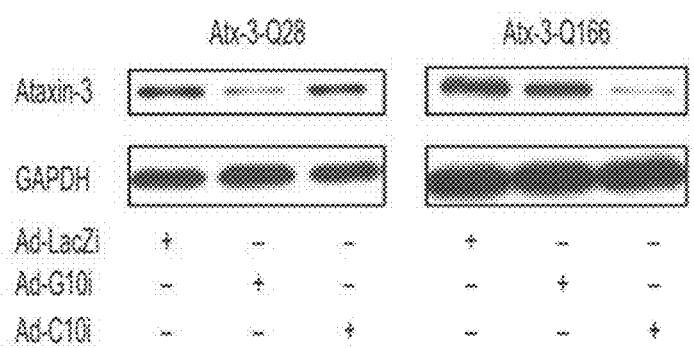

Viral mediated suppression was also assessed in differentiated PC12 neural cell lines that inducibly express normal (Q28) or expanded (Q166) mutant ataxin-3. Following infection with Ad-G10i, Ad-C10i, or Ad-LacZi, differentiated neural cells were placed in doxycycline for three days to induce maximal expression of ataxin-3. Western blot analysis of cell lysates confirmed that the Ad-G10i virus suppressed only wild type ataxin-3, Ad-C10i virus suppressed only mutant ataxin-3, and Ad-LacZi had no effect on either normal or mutant ataxin-3 expression (FIG. 19D).

Thus, siRNA retains its efficacy and selectivity across different modes of production and delivery to achieve allele-specific silencing of ataxin-3.

Allele-Specific Silencing of a Missense Tau Mutation. The preceding results indicate that, for DNA repeat mutations in which the repeat itself does not present an effective target, an associated SNP can be exploited to achieve allele-specific silencing. To test whether siRNA works equally well to silence disease-causing mutations directly, the inventors targeted missense Tau mutations that cause FTDP-17 (Poorkaj 1998, Hutton 1998). A series of 21-24 nt siRNAs were generated in vitro against four missense FTDP-17 mutations: G272V, P301L, V337M, and R406W (FIG. 17 and FIG. 20A). In each case the point mutation was placed centrally, near the likely cleavage site in the RISC complex (position 9, 10 or 11) (Laccone 1999). A fifth siRNA designed to target a 5' sequence in all Tau transcripts was also tested. To screen for siRNA-mediated suppression, the inventors co-transfected GFP fusions of mutant and wild type Tau isoforms together with siRNA into Cos-7 cells. Of the five targeted sites, the inventors obtained robust suppression with siRNA corresponding to V337M (FIG. 17 and FIG. 20A) (Poorkaj 1998, Hutton 1998), and thus focused further analysis on this mutation. The V337M mutation is a G to A base change in the first position of the codon (GTG to ATG), and the corresponding V337M siRNA contains the A missense change at position 9 (siA9). This intended V337M-specific siRNA preferentially silenced the mutant allele but also caused significant suppression of wild type Tau (FIG. 20B,C).

Based on the success of this approach with ataxin-3, the inventors designed two additional siRNAs that contained the V337M (G to A) mutation at position 9 as well as a second introduced G-C mismatch immediately 5' to the mutation (siA9/C8) or three nucleotides 3' to the mutation (siA9/C12), such that the siRNA now contained two mismatches to the wild type but only one to the mutant allele. This strategy resulted in further preferential inactivation of the mutant allele. One siRNA, siA9/C12, showed strong selectivity for the mutant tau allele, reducing fluorescence to 12.7% of control levels without detectable loss of wild type Tau (FIG. 20B,C). Next, we simulated the heterozygous state by co-transfecting V337M-GFP and flag-tagged WT-Tau expression plasmids (FIG. 21A, B, C). In co-transfected HeLa cells, siA9/C12 silenced the mutant allele (16.7% of control levels) with minimal alteration of wild type expression assessed by fluorescence (FIG. 21A) and Western blot (FIG. 21B). In addition, siA9 and siA9/C8 displayed better allele discrimination than we had observed in separate transfections, but continued to suppress both wild type and mutant tau expression (FIG. 21A,B,C).

Discussion

Despite the rapidly growing siRNA literature, questions remain concerning the design and application of siRNA both as a research tool and a therapeutic strategy. The present study, demonstrating allele-specific silencing of dominant disease genes, sheds light on important aspects of both applications.

Because many disease genes encode essential proteins, development of strategies to exclusively inactivate mutant alleles is important for the general application of siRNA to dominant diseases. The present results for two unrelated disease genes demonstrate that in mammalian cells it is possible to silence a single disease allele without activating pathways analogous to those found in plants and worms that result in the spread of silencing signals (Fire 1998, Tang 2003).

In summary, siRNA can be engineered to silence expression of disease alleles differing from wild type alleles by as little as a single nucleotide. This approach can directly target missense mutations, as in frontotemporal dementia, or associated SNPs, as in MJD/SCA3. The present stepwise strategy for optimizing allele-specific targeting extends the utility of siRNA to a wide range of dominant diseases in which the disease gene normally plays an important or essential role. One such example is the polyglutamine disease, Huntington disease (HD), in which normal RD protein levels are developmentally essential (Nasir 1995). The availability of mouse models for many dominant disorders, including MJD/SCA3 (Cemal 2002), HD (Lin 2001), and FTDP-17 (Tanemura 2002), allows for the in vivo testing of siRNA-based therapy for these and other human diseases.

EXAMPLE 7

Therapy for DYT1 Dystonia: Allele-Specific Silencing of Mutant TorsinA

DYT1 dystonia is the most common cause of primary generalized dystonia. A dominantly inherited disorder, DYT1 usually presents in childhood as focal dystonia that progresses to severe generalized disease. With one possible exception, all cases of DYT1 result from a common GAG deletion in TOR1A, eliminating one of two adjacent glutamic acids near the C-terminus of the protein TorsinA (TA). Although the precise cellular function of TA is unknown, it seems clear that mutant TA (TAmut) acts through a dominant-negative or dominant-toxic mechanism. The dominant nature of the genetic defect in DYT1 dystonia suggests that efforts to silence expression of TAmut should have potential therapeutic benefit.

Several characteristics of DYT1 make it an ideal disease in which to explore siRNA-mediated gene silencing as potential therapy. Of greatest importance, the dominant nature of the disease suggests that a reduction in mutant TA, whatever the precise pathogenic mechanism proves to be, will be helpful. Moreover, the existence of a single common mutation that deletes a full three nucleotides suggests it may be feasible to design siRNA that will specifically target the mutant allele and will be applicable to all affected persons. Finally, there is no effective therapy for DYT1, a relentless and disabling disease. Thus, any therapeutic approach with promise needs to be explored. Because TAwt may be an essential protein, however, it is critically important that efforts be made to silence only the mutant allele.

In the studies reported here, the inventors explored the utility of siRNA for DYT1. As outlined in the strategy in FIG. 22, the inventors sought to develop siRNA that would specifically eliminate production of protein from the mutant allele. By exploiting the three base pair difference between wild type and mutant alleles, the inventors successfully silenced expression of TAmut without interfering with expression of the wild type protein (TAwt).

Methods siRNA design and synthesis Small-interfering RNA duplexes were synthesized in vitro according to a previously described protocol (Donze 2002), using AmpliScribeT7 High Yield Transcription Kit (Epicentre Technologies) and desalted DNA oligonucleotides (IDT). siRNAs were designed to target different regions of human TA transcript: 1) an upstream sequence common to both TAwt and TAmut (com-siRNA); 2) the area corresponding to the mutation with either the wild type sequence (wt-siRNA) or the mutant sequence positioned at three different places (mutA-siRNA, mutB-siRNA, mutC-siRNA); and 3) a negative control siRNA containing an irrelevant sequence that does not target any region of TA (mis-siRNA). The design of the primers and targeted sequences are shown schematically in FIG. 23. After in vitro synthesis, the double stranded structure of the resultant RNA was confirmed in 1.5% agarose gels and RNA concentration determined with a SmartSpect 3000 UV Spectrophotometer (BioRad).

Plasmids pcDNA3 containing TAwt or TAmut cDNA were kindly provided by Xandra Breakefield (Mass General Hospital, Boston, Mass.). This construct was produced by cloning the entire coding sequences of human TorsinA (1-332), both wild-type and mutant (GAG deleted), into the mammalian expression vector, pcDNA3 (Clontech, Palo Alto, Calif.). Using PCR based strategies, an N-terminal hemagglutinin (HA) epitope tag was inserted into both constructs. pEGFP-C3-TAwt was kindly provided by Pullanipally Shashidharan (Mt Sinai Medical School, NY). This construct was made by inserting the full-length coding sequence of wild-type TorsinA into the EcoRI and BamHI restriction sites of the vector pEGFP-C3 (Clontech). This resulted in a fusion protein including eGFP, three "stuffer" amino acids and the 331 amino acids of TorsinA. HA-tagged TAmut was inserted into the ApaI and SalI restriction sites of pEGFP-C1 vector (Clontech), resulting in a GFP-HA-TAmut construct.

Cell culture and transfections Methods for cell culture of Cos-7 have been described previously (Chai 1999b). Transfections with DNA plasmids and siRNA were performed using Lipofectamine Plus (LifeTechnologies) according to the manufacturer's instructions in six or 12 well plates with cells at 70-90% confluence. For single plasmid transfection, 1 µg of plasmid was transfected with 5 µg of siRNA. For double plasmid transfection, 0.75 µg of each plasmid was transfected with 3.75 µg of siRNA.

Western Blotting and Fluorescence Microscopy. Cells were harvested 36 to 48 hours after transfection and lysates were assessed for TA expression by Western Blot analysis (WB) as previously described (Chai 1999b). The antibody used to detect TA was polyclonal rabbit antiserum generated against a TA-maltose binding protein fusion protein (kindly provided by Xandra Breakefield) at a 1:500 dilution. Additional antibodies used in the experiments described here are the anti-HA mouse monoclonal antibody 12CA5 (Roche) at 1:1,000 dilution, monoclonal mouse anti-GFP antibody (MBL) at 1:1,000 dilution, and for loading controls, anti α-tubulin mouse monoclonal antibody (Sigma) at 1:20,000 dilution.

Fluorescence visualization of fixed cells expressing GFP-tagged TA was performed with a Zeiss Axioplan fluorescence microscope. Nuclei were visualized by staining with 5 µg/ml DAPI at room temperature for 10 minutes. Digital images were collected on separate red, green and blue fluorescence channels using a Diagnostics SPOT digital camera. Live cell images were collected with a Kodak MDS 290 digital camera mounted on an Olympus CK40 inverted microscope equipped for GFP fluorescence and phase contrast microscopy. Digitized images were assembled using Adobe Photoshop 6.0.

Western Blot and Fluorescence Quantification. For quantification of WB signal, blots were scanned with a Hewlett Packard ScanJet 5100C scanner. The pixel count and intensity of bands corresponding to TA and α-tubulin were measured and the background signal subtracted using Scion Image software (Scion Corporation). Using the α-tubulin signal from control lanes as an internal reference, the TA signals were normalized based on the amount of protein loaded per lane and the result was expressed as percentage of TA signal in the control lane. Fluorescence quantification was determined by collecting three non-overlapping images per well at low power (10×), and assessing the pixel count and intensity for each image with Bioquant Nova Prime software (BIOQUANT Image Analysis Corporation). Background fluorescence, which was subtracted from experimental images, was determined by quantification of fluorescence images of untransfected cells at equivalent confluence, taken under identical illumination and exposure settings.

Results

Expression of Tagged TorsinA Constructs. To test whether allele-specific silencing could be applied to DYT1, a way to differentiate TAwt and TAmut proteins needed to be developed. Because TAwt and TAmut display identical mobility on gels and no isoform-specific antibodies are available, amino-terminal epitope-tagged TA constructs and GFP-TA fusion proteins were generated that would allow distinguishing TAwt and TAmut. The use of GFP-TA fusion proteins also facilitated the ability to screen siRNA suppression because it allowed visualization of TA levels in living cells over time.

In transfected Cos-7 cells, epitope-tagged TA and GFP-TA fusion protein expression was confirmed by using the appropriate anti-epitope and anti-TA antibodies. Fluorescence microscopy in living cells showed that GFP-TAwt and GFP-TAmut fusion proteins were expressed diffusely in the cell, primarily in the cytoplasm, although perinuclear inclusions were also seen. It is important to note that these construct were designed to express reporter proteins in order to assess allele-specific RNA interference rather than to study TA function. The N-terminal epitope and GFP domains likely disrupt the normal signal peptide-mediated translocation of TA into the lumen of the endoplasmic reticulum, where TA is thought to function. Thus, while these constructs facilitated expression analysis in the studies described here, they are of limited utility for studying TA function.

Figure 24A:
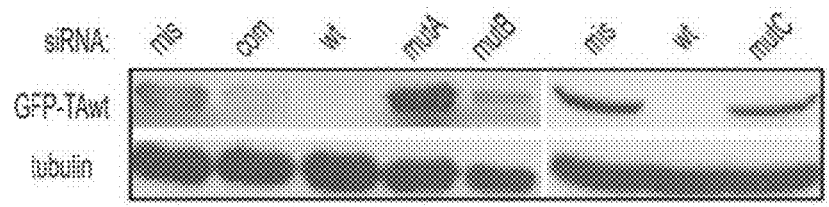
Figure 24B:
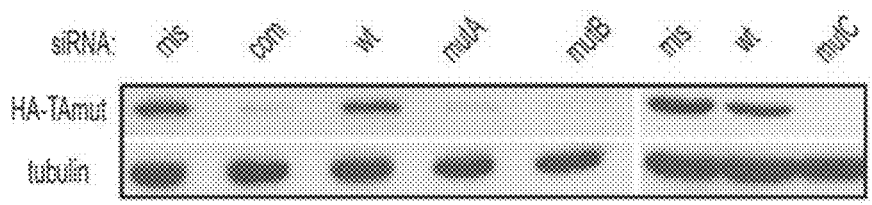
Figure 24C:
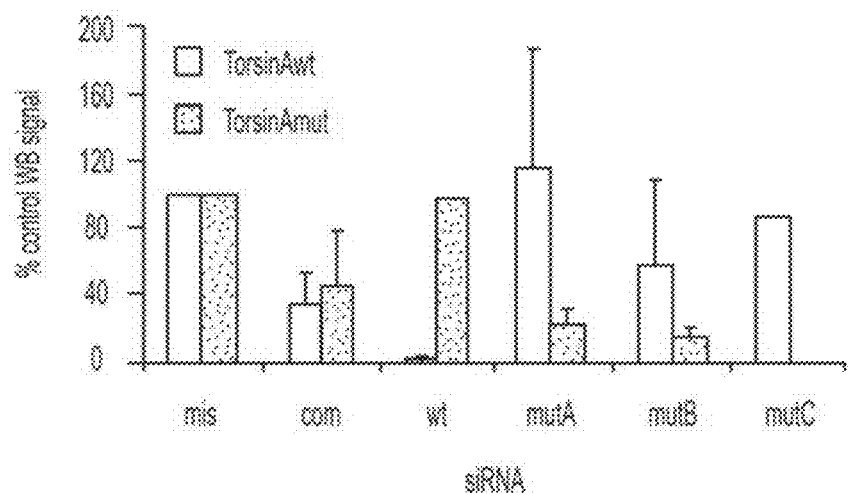
Figure 24D:
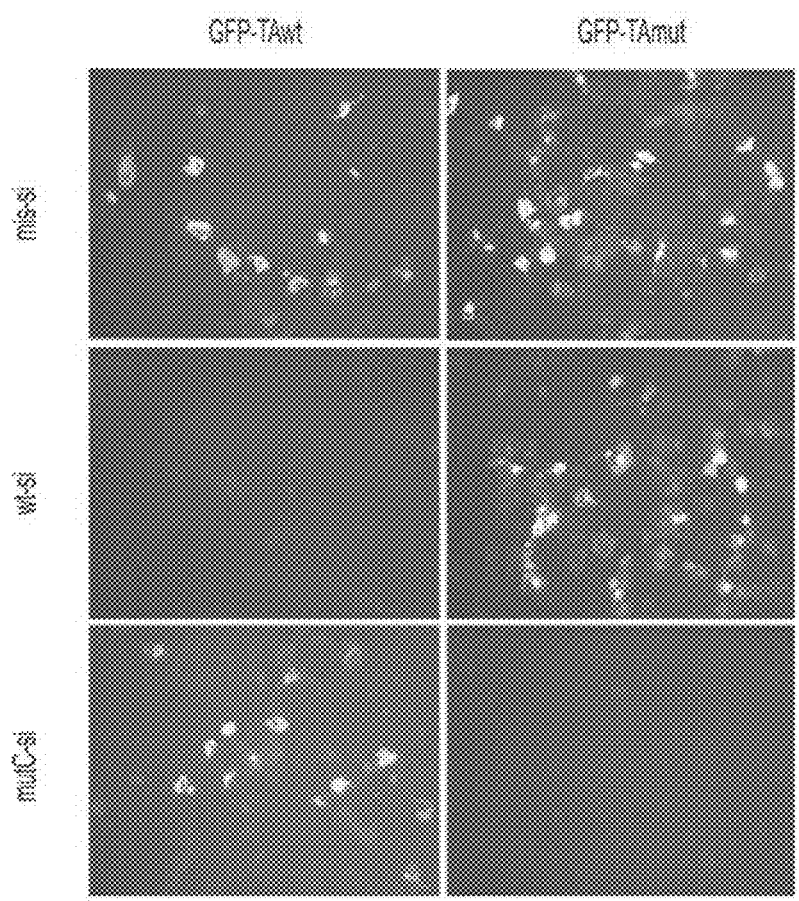
Figure 24E:
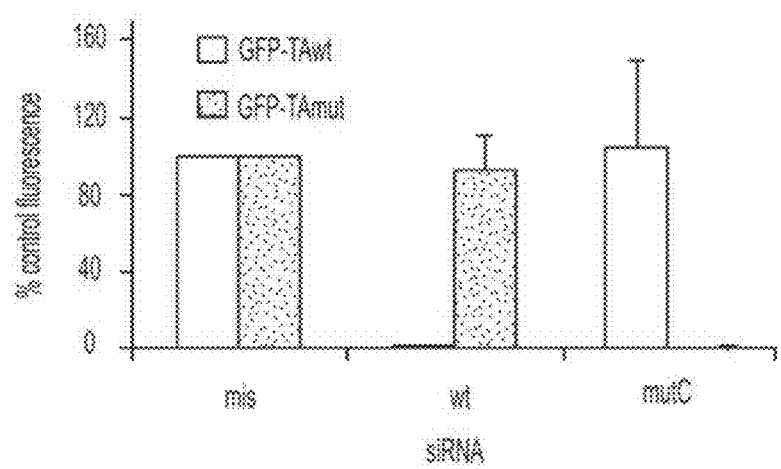

Silencing TorsinA with siRNA. Various siRNAs were designed to test the hypothesis that siRNA-mediated suppression of TA expression could be achieved in an allele-specific manner (FIG. 23). Because siRNA can display exquisite sequence specificity, the three base pair difference between mutant and wild type TOR1A alleles might be sufficient to permit the design of siRNA that preferentially recognizes mRNA derived from the mutant allele. Two siRNAs were initially designed to target TAmut (mutA-siRNA and mutB-siRNA) and one to target TAwt (wt-siRNA). In addition, a positive control siRNA was designed to silence both alleles (com-siRNA) and a negative control siRNA of irrelevant sequence (mis-siRNA) was designed. Cos-7 cells were first cotransfected with siRNA and plasmids encoding either GFP-TAwt or untagged TAwt at a siRNA to plasmid ratio of 5:1. With wt-siRNA, potent silencing of TAwt expression was observed to less than 1% of control levels, based on western blot analysis of cell lysates (FIGS. 24A and 24C). With com-siRNA, TAwt expression was suppressed to ~30% of control levels. In contrast, mutA-siRNA did not suppress TAwt and mutB-siRNA suppressed TAwt expression only modestly. These results demonstrate robust suppression of TAwt expression by wild type-specific siRNA but not mutant-specific siRNA.

To assess suppression of TAmut, the same siRNAs were cotransfected with plasmids encoding untagged or HA-tagged TAmut. With mutA-siRNA or mutB-siRNA, marked, though somewhat variable, suppression of TAmut expression was observed as assessed by western blot analysis of protein levels (FIGS. 24B and 24C). With com-siRNA, suppression of TAmut expression was observed similar to what was observed with TAwt expression. In contrast, wt-siRNA did not suppress expression of TAmut. Thus differential suppression of TAmut expression was observed by allele-specific siRNA in precisely the manner anticipated by the inventors.

To achieve even more robust silencing of TAmut, a third siRNA was engineered to target TAmut (mutC-siRNA, FIG. 23). MutC-siRNA places the GAG deletion more centrally in the siRNA duplex. Because the central portion of the antisense strand of siRNA guides mRNA cleavage, it was reasoned that placing the GAG deletion more centrally might enhance specific suppression of TAmut. As shown in FIGS. 24A-E, mutC-siRNA suppressed TAmut expression more specifically and robustly than the other mut-siRNAs tested. In transfected cells, mutC-siRNA suppressed TAmut to less than 0.5% of control levels, and had no effect on the expression of TAwt.

To confirm allele-specific suppression by wt-siRNA and mutC-siRNA, respectively, the inventors cotransfected cells with GFP-TAwt or GFP-TAmut together with mis-siRNA, wt-siRNA or mutC-siRNA. Levels of TA expression were assessed 24 and 48 hours later by GFP fluorescence, and quantified the fluorescence signal from multiple images was quantified. The results (FIGS. 24D and 24E) confirmed the earlier western blots results in showing potent, specific silencing of TAwt and TAmut by wt-siRNA and mutC-siRNA, respectively, in cultured mammalian cells.

Allele-Specific Silencing in Simulated Heterozygous State. In DYT1, both the mutant and wild type alleles are expressed. Once the efficacy of siRNA silencing was established, the inventors sought to confirm siRNA specificity for the targeted allele in cells that mimic the heterozygous state of DYT1. In plants and *Caenorhabditis elegans*, RNA-dependent RNA polymerase activity primed by introduction of exogenous RNA can result in the spread of silencing signals along the entire length of the targeted mRNA (Fire 1998, Tang 2003). No evidence for such a mechanism has been discovered in mammalian cells (Schwarz 2002, Chiu 2002). Nonetheless it remained possible that silencing of the mutant allele might activate cellular processes that would also inhibit expression from the wild type allele. To address this possibility, Cos-7 cells were cotransfected with both GFP-TAwt and HA-TAmut, and suppression by mis-siRNA, wt-siRNA or mutC-siRNA was assessed. As shown in FIGS. 25A-B, potent and specific silencing of the targeted allele (either TAmut or TAwt) to levels less than 1% of controls was observed, with only slight suppression in the levels of the non-targeted protein. Thus, in cells expressing mutant and wild type forms of the protein, siRNA can suppress TAmut while sparing expression of TAwt.

Discussion

In this study the inventors succeeded in generating siRNA that specifically and robustly suppresses mutant TA, the defective protein responsible for the most common form of primary generalized dystonia. The results have several implications for the treatment of DYT1 dystonia. First and foremost, the suppression achieved was remarkably allele-specific, even in cells simulating the heterozygous state. In other words, efficient suppression of mutant TA occurred without significant reduction in wild type TA. Homozygous TA knockout mice die shortly after birth, while the heterozygous mice are normal (Goodchild 2002), suggesting an essential function for TA. Thus, therapy for DYT1 needs to eliminate the dominant negative or dominant toxic properties of the mutant protein while sustaining expression of the normal allele in order to prevent the deleterious consequences of loss of TA function. Selective siRNA-mediated suppression of the mutant allele fulfills these criteria without requiring detailed knowledge of the pathogenic mechanism.

An appealing feature of the present siRNA therapy is applicable to all individuals afflicted with DYT1. Except for one unusual case (Leung 2001, Doheny 2002, Klein 2002b), all persons with DYT1 have the same (GAG) deletion mutation (Ozelius 1997, Ozelius 1999). This obviates the need to design individually tailored siRNAs. In addition, the fact that the DYT1 mutation results in a full three base pair difference from the wild type allele suggests that siRNA easily distinguishes mRNA derived from normal and mutant TOR1A alleles.

It is important to recognize that DYT1 is not a fully penetrant disease (Fahn 1998, Klein 2002a). Even when expressed maximally, mutant TA causes significant neurological dysfunction less than 50% of the time. Thus, even partial reduction of mutant TA levels might be sufficient to lower its pathological brain activity below a clinically detectable threshold. In addition, the DYT1 mutation almost always manifests before age 25, suggesting that TAmut expression during a critical developmental window is required for symptom onset. This raises the possibility that suppressing TAmut expression during development might be sufficient to prevent symptoms throughout life. Finally, unlike many other inherited movement disorders DYT1 is not characterized by progressive neurodegeneration. The clinical phenotype must result primarily from neuronal dysfunction rather than neuronal cell death (Hornykiewicz 1986, Walker 2002, Augood 2002, Augood 1999). This suggests the potential reversibility of DYT1 by suppressing TAmut expression in overtly symptomatic persons.

EXAMPLE 8

RNA Interference Improves Motor and Neuropathological Abnormalities in a Huntington's Disease Mouse Model Huntington's disease (HD) is one of nine dominant neurodegenerative diseases resulting from polyglutamine repeat expansions (CAG codon, Q) in exon 1 of HD, leading to a toxic gain of function on the protein huntingtin (htt) (The Huntington's Disease Collaborative Research Group (1993) Cell 72, 971-83; Gusella et al., (2000) Nat Rev Neurosci 1, 109-15). Hallmark HD characteristics include cognitive and behavioral disturbance, involuntary movements (chorea), neuronal inclusions, and striatal and cortical neurodegeneration (Gusella et al., (2000) Nat Rev Neurosci 1, 109-15). Htt alleles containing greater than 35 CAG repeats generally cause HD, with age-at-onset correlating inversely with expansion length, a common characteristic of the polyglutamine repeat disorders. The disease usually develops in mid-life, but juvenile-onset cases can occur with CAG repeat lengths greater than 60. Death typically occurs 10-15 years after symptom onset. Currently, no preventative treatment exists for HD.

Therapies aimed at delaying disease progression have been tested in HD animal models. For example, beneficial effects have been reported in animals treated with substances that increase transcription of neuroprotective genes (histone deacetylase) (Ferrante et al., (2003) J Neurosci 23, 9418-27); prevent apoptosis (caspase inhibitors)(Ona et al., (1999) Nature 399, 263-7); enhance energy metabolism (coenzyme Q/remacemide, creatine) (Ferrante et al., (2002) J Neurosci 22, 1592-9; Andreassen et al., (2001) Neurobiol Dis 8, 479-91); and inhibit the formation of polyglutamine aggregates (trehalose, Congo red, cystamine) (Tanaka et al., (2004) Nat Med 10, 148-54; Karpuj et al., (2002) Nat Med 8, 143-9; Sanchez et al., (2003) Nature 421, 373-9). These approaches target downstream and possibly indirect effects of disease allele expression. In contrast, no therapies have been described that directly reduce mutant huntingtin gene expression, thereby targeting the fundamental, underlying pathological insult.

The therapeutic promise of silencing mutant htt expression was demonstrated in a tetracycline-regulated mouse model of HD (Yamamoto et al., (2000) Cell 101, 57-66). When mutant htt was inducibly expressed, pathological and behavioral features of the disease developed, including the characteristic neuronal inclusions and abnormal motor behavior. Upon repression of transgene expression in affected mice, pathological and behavioral features resolved. Thus, reduction of htt expression using RNAi may allow protein clearance mechanisms within neurons to normalize mutant htt-induced changes. We hypothesize that directly inhibiting the expression of mutant htt will slow or prevent HD-associated symptom onset in a relevant animal model.

Screening of putative therapies for HD has benefited from the existence of several HD mouse models (Beal et al., (2004) Nat Rev Neurosci 5, 373-84; Levine et al., (2004) Trends Neurosci 27, 691-7). HD-like phenotypes are displayed in knock-in mice (Lin et al., (2001) Hum Mol Genet 10, 137-44; Menalled et al., (2003) J Comp Neurol 465, 11-26), drug-induced models (McBride et al., (2004) J Comp Neurol 475, 211-9) and transgenic mice expressing full-length mutant huntingtin (e.g. YAC-transgenic mice) (Hodgson et al., (1999) Neuron 23, 181-92; Slow et al., (2003) Hum Mol Genet 12, 1555-67; Reddy et al., (1998) Nat Genet 20, 198-202) or an N-terminal fragment of htt (Yamamoto et al., (2000) Cell 101, 57-66; Mangiarini et al., (1996) Cell 87(3), 493-506; Schilling et al., (1999) Hum Mol Genet 8(3), 397-407). Mice expressing truncated N-terminal fragments of huntingtin have been valuable for proof-of-principle evaluation of therapies because they show rapidly progressive motor abnormalities and striatal neuropathology, phenotypes which do not develop or develop very late in knock-in or YAC transgenic mice. Mice expressing truncated forms of huntingtin thus replicate more severe forms of the disease. The present inventors tested if RNA interference (RNAi) induced by short hairpin RNAs (shRNAs) (Dykxhoorn et al., (2003) Nat Rev Mol Cell Biol 4, 457-67) could reduce expression of mutant htt and improve HD-associated abnormalities in a transgenic mouse model of HD. It was found that RNAi directed against mutant human huntingtin (htt) reduced htt mRNA and protein expression in cell culture and in HD mouse brain. It is important to note that htt gene silencing improved behavioral and neuropathological abnormalities associated with HD.

Materials and Methods

Figure 26A:
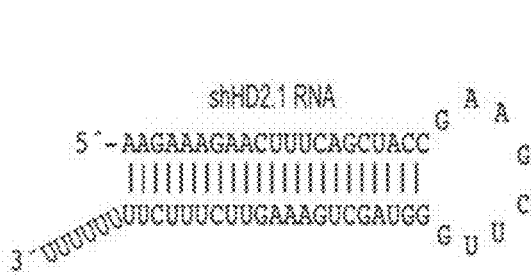

Plasmids and Adeno-Associated Virus (AAV) Construction. Myc-tagged HD-N171-82Q was expressed from a pCMV-HD-N171-82Q plasmid (Schilling et al., (1999) Hum Mol Genet 8(3), 397-407). PCR (Pfu polymerase, Stratagene) was used to amplify the U6 promoter along with shRNAs targeting human huntingtin (shHD2.1; FIG. 26A), eGFP (shGFP) (Xia et al., (2002) Nat Biotechnol 20, 1006-1010); or *E. coli* β-galactosidase (bp 1152-1172; shLacZ). PCR products were cloned, verified by sequencing and inserted into pAAV.CMV.hrGFP, which contains AAV-2 ITRs, a CMV-hrGFP–SV40 polyA reporter cassette, and sequences used for homologous recombination into baculovirus (Urabe et al., (2002) Hum Gene Ther 13, 1935-1943). Recombinant AAV serotype 1 capsid vectors were generated as described (Urabe et al., (2002) Hum Gene Ther 13, 1935-1943). AAV titers were determined by quantitative PCR and/or DNA slot blot and were $5 \times 10^{12}$ vector genomes/ml.

Animals. All animal studies were approved by the University of Iowa Animal Care and Use Committee. HD-N171-82Q mice were purchased from Jackson Laboratories, Inc. (Schilling et al., (1999) Hum Mol Genet 8(3), 397-407; Schilling et al., (2001) Neurobiol Dis 8, 405-18) and maintained on a B6C3F1/J background. Heterozygous and age-matched wildtype littermates were used for the experiments, as indicated.

Northern blots. HEK293 cells were transfected (Lipofectamine-2000; Invitrogen) with pCMV-HD-N171-82Q and plasmids expressing shHD2.1, shGFP, or shLacZ at shRNA:target ratios of 8:1. Forty-eight hours post-transfection, RNA was harvested (Trizol Reagent; Invitrogen) and 10 □g were assessed northern blot (NorthernMax; Ambion) using probes to human htt or human GAPDH. Band intensities were quantified using a phosphorimager (Storm 860 instrument and ImageQuant v1.2 software, Molecular Dynamics).

For in vivo studies, total RNA was isolated from hrGFP–positive striata. Thirty μg RNA was run on 15% polyacrylamide-urea gels, transferred to Hybond N+ membranes (Amersham Pharmacia), then probed with $^{32}$P-labeled sense oligonucleotides at 36° C. for 3 h, washed in 2× SSC (36° C.), and exposed to film.

Western blots. HEK293 cells were transfected as described with shHD2.1 or shGFP singly or in combination with pCMV-HD-N171-82Q. Forty-eight hours later, cells were lysed to recover total protein. Western blots were incubated with anti-myc (1:5,000; Invitrogen), anti full-length human htt (1:5,000; MAB2166; Chemicon), or anti-human β-actin (1:5,000; Clone AC-15; Sigma) followed by HRP-coupled goat anti-mouse or goat anti-rabbit secondary antibodies (1:20,000 and 1:100,000, respectively; Jackson Immunochemicals). Blots were developed using ECL-Plus reagents (Amersham Biosciences). For evaluation of transduced brain, 3 week old mice were injected as described and protein was harvested from striata 2 weeks later. Twenty-five μg were run on SDS-PAGE gels as described, transferred to nitrocellulose, then probed with antibodies to detect human htt (1:500, mEM48; Gift from X. J. Li) and mouse prion protein (1:40,000; Chemicon International). Secondary antibody incubations were performed as described above.

Quantitative RT-PCR

In vitro shRNA dose response. HEK293 cells were transfected with 0 (mock), 10, 100, or 1000 ng of shLacZ or shHD2.1 and RNA was harvested 24 h later. Following DNase treatment (DNA-Free, Ambion), random-primed, first strand cDNA was generated from 500 ng total RNA (Taqman™ Reverse Transcription Reagents, Applied Biosystems) according to manufacturer's protocol. Taqman™ Assays were performed on an ABI Prism 7000 Sequence Detection System using Taqman™ 2× Universal PCR Master Mix (Applied Biosystems) and Taqman™ primers/probe sets specific for human htt and mammalian rRNA (Applied Biosystems). Relative gene expression was determined using the relative standard curve method.

In vivo huntingtin mRNA expression. Striata were dissected from 5.5 month old mice, snap frozen in liquid nitrogen, and pulverized. cDNA was generated as described above. Relative gene expression was assayed using Taqman™ primers/probe sets specific for human htt and mammalian rRNA or Assays-By-Design Taqman™ primers/probes specific for mouse huntingtin (mHdh; Applied Biosystems). All values were calibrated to contralateral, uninjected striata. For human huntingtin detection; shHD2.1 samples, n=8 striata; shLacZ, n=7; uninjected, n=4. For mouse Hdh detection; injected HD samples, n=4; uninjected samples n=2.

AAV Injections

All animal procedures were pre-approved by the University of Iowa Animal Care and Use Committee. AAV Injections were performed in 4 week old mice using the following parameters (coordinates are reported with respect to the bregma): Striatal: 0.5 mm anterior, 2.5 mm lateral, 2.5 mm depth, 5 µl/site, 250 nl/min infusion rate. Cerebellar: 0.1 mm depth, 1 µl/site, 250 nl/min infusion rate.

Behavioral Analysis

Stride length measurements. Mice injected bilaterally at 4 weeks of age were analyzed at 4 months of age. Analyses were performed as described previously (Carter et al., (1999) J Neurosci 19, 3248) with some modifications. Specifically, mice were allowed to walk across a paper-lined chamber measuring 100 cm long, 10 cm wide, with 10 cm high walls into an enclosed box. Mice were given one practice run and were then tested three times to produce three separate footprint tracings, totaling 42 measurements each for front and rear footprints per mouse. Measurements were averaged and data presented as box plots. ANOVA with Scheffe's post-hoc test was performed to determine statistical significance. Uninjected mice, n=4; injected WT, n=3; injected N171-82Q, n=6 mice.

Rotarod performance test. Two separate experimental cohorts of mice were injected at 4 weeks of age and tested on the rotarod (Model 7650, Ugo Basile Biological Research Apparatus) at 10 and 18 weeks of age as previously described (Xia et al., (2004) Nat Med 10, 816-820). Data from trials 2-4 for each day are presented as means±S.E.M. Uninjected WT, n=6; shLacZ WT, n=5, shHD2.1 WT, n=6; uninjected N171-82Q, n=5; shLacZ N171-82Q, n=10; shHD2.1 N171-82Q, n=11). Reported values are means±S.E.M.

Immunofluorescence

Forty µm free-floating coronal sections were stained with mEM48 antibody (1:500; 24 h, 4° C.), followed by Alexa-568 labeled goat anti-mouse secondary antibody (1:200; 4 h, room temp; Molecular Probes). Sections were mounted onto slides, covered in Gel/Mount (Biomeda Corp) and images were captured using fluorescent microscopy (Leica DM RBE or Zeiss confocal) equipped with a CCD-camera (SPOT RT, Diagnostics Instruments).

Results shHD2.1 Reduces Human Huntingtin Expression In Vitro

Figure 26B:
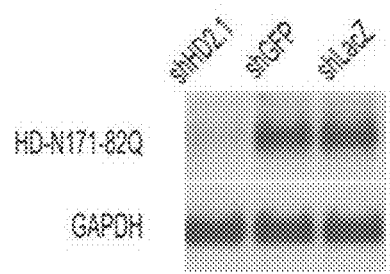
Figure 26C:
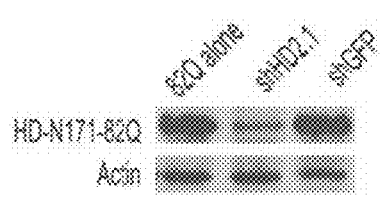

In vitro screening was used to identify effective shRNAs directed against a CMV-promoter transcribed HD-N171-82Q mRNA, which is identical to the pathogenic truncated huntingtin fragment transgene present in HD-N171-82Q mice (Schilling et al., (1999) Hum Mol Genet 8(3), 397-407). Hairpin constructs targeting sequences in human exons 1-3 were evaluated by co-transfection. One htt-targeted shRNA, shHD2.1 (FIG. 26A), reduced HD-N171-82Q mRNA and protein levels by ~85 and ~55% respectively, relative to control shRNA treated samples (FIG. 26B, C). Interestingly, none of the shRNAs tested that targeted exon 1 were functional under these conditions and in this system. Additional siRNAs can be screened as described herein to identify functional siRNAs targeting exon 1 of the HD gene.

Figure 26D:
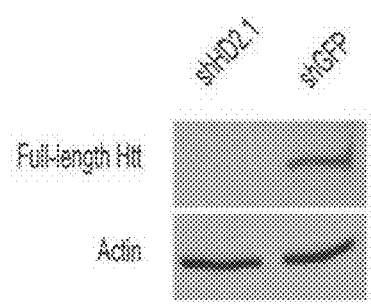
Figure 26E:
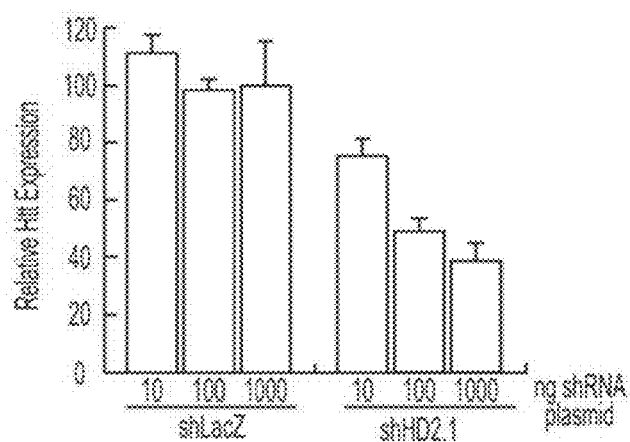

To test if shHD2.1 could silence endogenous full-length human htt expression, HEK 293 cells were transfected with plasmids expressing shHD2.1 or shGFP. ShHD2.1, but not control shRNAs, directed gene silencing of endogenous htt mRNA and protein (FIGS. 26D, E). This system can be readily used to screen additional siRNAs targeting the HD gene.

Expression of shRNA in Mouse Brain

Next, the inventors tested U6 promoter-transcribed shHD2.1 expression in vivo and determined its effects on HD-associated symptoms in mice. This pol III dependent promoter has not previously been evaluated in striata for sustained expression in vivo, although shRNAs have been expressed in brain using either the pol II-dependent CMV promoter in striatum (Xia et al., (2002) Nat Biotechnol 20, 1006-1010) or the H1 promoter in cerebellar degeneration models (Xia et al., (2004) Nat Med 10, 816-820). U6 promoter-driven shHD2.1, and the control hairpin shLacZ, were cloned into adeno-associated virus (AAV) shuttle plasmids that contained a separate CMV-humanized Renilla green fluorescent protein (hrGFP) reporter cassette (FIG. 27A). High-titer AAV1 particles (AAV.shHD2.1 and AAV.shLacZ), which have broad neuronal tropism, were generated (Urabe et al., (2002) Hum Gene Ther 13, 1935-1943), and hairpin expression was assessed after injection into mouse striatum. The N171-82Q mouse model was used because shHD2.1 targets sequences in exon 2, precluding use of the R6/2 transgenic model, which expresses only exon 1 of the HD gene. As shown in FIG. 27B, precursor and processed shRNAs (~50 nt and 21 nt, respectively) were expressed three weeks after transduction, indicating sustained expression and appropriate processing of shRNAs in the striatum. Analysis of coronal brain sections from injected mice showed widespread transduction (FIG. 27C; hrGFP fluorescence) up to 5 months post-injection.

AAV.shHD2.1 Reduces HD-N171-82Q Expression In Vivo

The inventors next investigated the effects of RNAi on the characteristic HD-associated neuronal inclusions and HD-N171-82Q mRNA levels in vivo. Tissues were harvested from end-stage HD-N171-82Q mice (~5.5 months of age) because striatal inclusions are less robust at earlier ages in this model. In striata from HD-N171-82Q mice injected with AAV.shHD2.1, htt-reactive inclusions were absent in transduced cells compared to untransduced regions (FIG. 28A, lower panels; FIG. 28B). Conversely, abundant inclusions were detected in transduced regions from AAV.shLacZ-injected HD mice (FIG. 28A, upper panels). No inclusions were observed in WT mice (data not shown). In addition, western analysis revealed that soluble HD-N171-82Q monomer was decreased in mouse striata transduced with AAV.shHD2.1 compared to uninjected or AAV.shLacZ-injected controls (FIG. 28C). The reduction in protein levels detected by immunohistochemistry and western blot was due to decreased transgene expression. HD-N171-82Q mRNA was reduced 51% to 55% in AAV.shHD2.1-injected HD mice relative to AAV.shLacZ-injected or uninjected HD mice (FIG. 28D). AAV.shHD2.1 and AAV.shLacZ had no effect on endogenous mouse htt expression (Avg. mHDH expression: Uninjected HD, 1.00±0.09; Uninjected WT, 1.13±0.04; AAV.shLacZ injected HD, 1.10±0.08; AAV.shHD2.1 injected HD, 1.08±0.05).

Neuronal inclusions in HD-N171-82Q striata are variable. Inclusions may be present in as few as 10% and up to 50% of all striatal neurons in different end-stage HD-N171-82Q mice (Schilling et al., (1999) Hum Mol Genet 8(3), 397-407). In contrast, robust and widespread EM48-positive inclusions are present in cerebellar granule cells by ~3 months of age [(Schilling et al., (1999) Hum Mol Genet 8(3), 397-407) and FIG. 28A-E], and cerebellar HD-N171-

82Q mRNA levels are ~8 fold higher relative to striatum (QPCR, data not shown). This high-level cerebellar expression is partially attributable to the transcriptional profile of the prion promoter driving HD-N171-82Q transgene expression (Schilling et al., (1999) Hum Mol Genet 8(3), 397-407). Cerebellar inclusions are not typically found in brains of adult-onset HD patients. However, cerebellar pathology has been reported in juvenile onset HD cases, which are the most severe forms of the disease, and interestingly, in Hdh140 knock-in mice as early as 4 months of age (Menalled et al., (2003) J Comp Neurol 465, 11-26; Nance et al., (2001) Ment Retard Dev Disabil Res Rev 7, 153-7; Fennema-et al., (2004) Neurology 63, 989-95; Seneca et al., (2004) Eur J Pediatr.; Byers et al., (1973) Neurology 23, 561-9; Wheeler et al., (2002) Hum Mol Genet 11, 633-40). The abundant inclusions in HD-N171-82Q cerebellar neurons provide a second target for assessing the effects of AAV.shHD2.1 on target protein levels. Direct cerebellar injections were done into a separate cohort of mice, and HD-N171-82Q expression examined by immunofluorescence. Together the data show that AAV.shHD2.1, but not control AAV.shLacZ, reduces mutant htt expression and prevents formation of the disease-associated neuronal inclusions.

Striatal Delivery of AAV.shHD2.1 Improves Established Behavioral Phenotypes

The effects of shRNA treatment on established behavioral deficits and animal weight were tested. RNAi directed to striatum did not normalize the notable weight differences between HD-N171-82Q and WT mice (shHD2.1-injected, 22.7±3.8 g; shLacZ, 22.6±2.8 g; compared to age-matched wild-type mice (shHD2.1, 26.3±0.4; shLacZ, 27.3±5.8), confirming that intracerebral injection confines RNAi therapy to the site of application (Schilling et al., (1999) Hum Mol Genet 8(3), 397-407; Xia et al., (2004) Nat Med 10, 816-820). However, significant improvements in stride length measurements and rotarod deficits were noted.

Stride length and rotarod tests were performed on uninjected mice, and mice injected bilaterally into striatum with AAVshHD2.1 or AAVshLacZ. As shown in FIG. 29A, HD-N171-82Q mice display significantly shorter stride lengths than those of wild-type (WT) mice, consistent with prior work (Menalled et al., (2003) J Comp Neurol 465, 11-26; Carter et al., (1999) J Neurosci 19, 3248; Wheeler et al., (2002) Hum Mol Genet 11, 633-40). Gait deficits in AAV.shHD2.1-treated HD-N171-82Q mice were significantly improved compared to AAV.shLacZ-treated (improvements for front and rear strides, 13 and 15%, respectively; $p<0.0001$) and uninjected HD-N171-82Q mice (front and rear strides, 14 and 18%, respectively; $p<0.0001$). Gait improvements did not fully resolve, as all HD-N171-82Q groups remained significantly different than their age-matched WT littermates. There was no effect of AAV.shLacZ or AAV.shHD2.1 expression on stride lengths of WT mice.

The accelerating rotarod test was used to confirm the beneficial behavioral effects of RNAi targeted to the mutant human HD allele (Schilling et al., (1999) Hum Mol Genet 8(3), 397-407). Mice were left uninjected, or were injected bilaterally into the striatum with AAV.shLacZ or AAV.shHD2.1 at 4 weeks of age, followed by rotarod analyses at 10- and 18-weeks of age (FIG. 29B). By 10 weeks, uninjected and AAV.shLacZ-injected HD mice show impaired performance relative to all other groups, and continued to demonstrate significantly reduced performance over the course of the study ($p<0.05$ relative to all other groups). It is important to note that HD mice treated with AAVshHD2.1 showed dramatic behavioral improvements relative to control-treated HD mice ($p<0.0008$) (FIG. 29B). AAV.shLacZ-treated HD mice showed a 22% decline ($p<0.005$; ANOVA), while AAV.shHD2.1-treated HD mice displayed a modest, non-significant 3% drop in rotarod performance between 10 and 18 weeks of age. There was a partial normalization of rotarod deficits in HD mice injected with AAV.shHD2.1 compared to WT mice that was consistent with the gait analyses.

The inventors found no decline in stride length or rotarod performance between WT mice left untreated, or those injected with shRNA-expressing AAVs (FIG. 29A,B). However, at 10 weeks, there was a dramatic difference in rotarod performance between uninjected WT and all groups of injected WT mice, which resolved by 18 weeks of age. These data suggest that there was some detrimental effect of direct brain injection on rotarod performance from which the mice recovered over time. These data suggest that RNAi expression in mammalian brain had no overt negative impact on motor behavior (FIG. 29A,B).

Discussion

The inventors have shown that motor and neuropathological abnormalities in a relevant HD mouse model are significantly improved by reducing striatal expression of a pathogenic huntingtin allele using AAV1-delivered shRNA. The inventors have previously shown that RNAi can improve neuropathology and behavioral deficits in a mouse model of spino-cerebellar ataxia type 1 (SCA1) (Xia et al., (2004) Nat Med 10, 816-820), a dominant neurodegenerative disorder that affects a population of neurons distinct from those degenerating in HD.

The shHD2.1 hairpin sequence reduced huntingtin expression in vitro and in vivo, and it is important to note, the present northern blot data suggest that the processed active guide strand was protected by RISC in vivo. The activity of the shRNAs could be improved using recently described rules for optimal shRNA design (Reynolds et al., (2004) Nat Biotechnol 22, 326-30; Schwarz et al., (2003) Cell 115, 199-208; Khvorova et al., (2003) Cell 115, 505; Ui-Tei et al., (2004) Nucleic Acids Res 32, 936-48).

Prior work demonstrated an essential role for huntingtin in embryogenesis and postnatal neurogenesis (Nasir et al., (1995) Cell 81, 811-23; Duyao et al., (1995) Science 269, 407-10; White et al., (1997) Nat Genet 17, 404-10; Dragatsis et al., (2000) Nat Genet 26, 300-6). However the effect of partial reduction of normal huntingtin expression in adult, post-mitotic neurons in vivo is unknown. In the current study, shHD2.1 reduced expression of a mutant, disease-causing human htt transgene, but had no effect on normal mouse huntingtin expression due to sequence differences between mouse and human genes. In HD patients, shHD2.1 would be expected to reduce expression of both the mutant and normal huntingtin alleles. The present data show that HD-like symptoms can be improved by even a partial reduction of mutant htt expression, suggesting that complete elimination of mutant allele expression may not be required.

In summary, the inventors have shown that RNAi can dramatically improve HD-associated abnormalities, including pathological and behavioral deficits, in a HD mouse model.

EXAMPLE 9

Huntington's Disease (HD)

Huntington's disease (HD) is one of several dominant neurodegenerative diseases that result from a similar toxic gain of function mutation in the disease protein: expansion of a polyglutamine (polyQ)-encoding tract. It is well established that for HD and other polyglutamine diseases, the length of the expansion correlates inversely with age of disease onset. Animal models for HD have provided important clues as to how mutant huntingtin (htt) induces pathogenesis. Currently, no neuroprotective treatment exists for HD. RNA interference has emerged as a leading candidate approach to reduce expression of disease genes by targeting the encoding mRNA for degradation.

Short hairpin RNAs (shRNAs) were generated that significantly inhibited human htt expression in cell lines. Importantly, the shRNAs were designed to target sequences present in HD transgenic mouse models. The present studies test the efficacy of the shRNAs in HD mouse models by determining if inclusions and other pathological and behavioral characteristics that are representative of HD can be inhibited or reversed. In a transgenic model of inducible HD, pathology and behavior improved when mutant gene expression was turned off. These experiments show that RNAi can prevent or reverse disease.

Although the effect of partial reduction of wildtype htt in adult neurons is unknown, it is advantageous to target only mutant htt for degradation, if possible. One polymorphism in linkage disequilibrium with HD has been identified in the coding sequence for htt, and others are currently being investigated. Disease allele-specific RNAi are designed using approaches that led to allele specific silencing for other neurogenetic disease models. This would allow directed silencing of the mutant, disease-causing expanded allele, leaving the normal allele intact.

Constitutive expression of shRNA can prevent the neuropathological and behavioral phenotypes in a mouse model of Spinocerebellar Ataxia type I, a related polyQ disease. However, the constitutive expression of shRNA may not be necessary, particularly for pathologies that take many years to develop but may be cleared in a few weeks or months. For this reason, and to reduce long-term effects that may arise if nonspecific silencing or activation of interferon responses is noted, controlled expression may be very important. In order to regulate RNAi for disease application, doxycycline-responsive vectors have been developed for controlled silencing in vitro.

HD researchers benefit from a wealth of animal models including six transgenic and four knock-in mouse models (Bates 2003). Expression is from the endogenous human promoter, and the CAG expansion in the R6 lines ranges from 110 to approximately 150 CAGs. The R6/2 line is the most extensively studied line from this work. R6/2 mice show aggressive degenerative disease, with age of symptom onset at 8-12 weeks, and death occurring at 10 to 13 weeks. Neuronal intranuclear inclusions, a hallmark of HD patient brain, appear in the striatum and cortex of the R6/2 mouse (Meade 2002).

Adding two additional exons to the transgene and restricting expression via the prion promoter led to an HD mouse model displaying important HD characteristics but with less aggressive disease progression (Shilling 1999, Shilling 2001). The Borchelt model, N171-82Q, has greater than wildtype levels of RNA, but reduced amounts of mutant protein relative to endogenous htt. N171-82Q mice show normal development for the first 1-2 months, followed by failure to gain weight, progressive incoordination, hypokinesis and tremors. There are statistically significant differences in the rotarod test, alterations in gait, and hindlimb clasping. Mice show neuritic pathology characteristic of human HD. Unlike the Bates model, there is limited neuronal loss.

Detloff and colleagues created a mouse knock-in model with an extension of the endogenous mouse CAG repeat to approximately 150 CAGs. This model, the CHL2 line, shows more aggressive phenotypes than prior mouse knock-in models containing few repeats (Lin 2001). Measurable neurological deficits include clasping, gait abnormalities, nuclear inclusions and astrogliosis.

The present studies utilize the well-characterized Borchelt mouse model (N171-82Q, line 81), and the Detloff knock-in model, the CHL2 line. The initial targets for htt silencing were focused on sequences present in the N171-82Q transgene (exons 1-3). The use of this model was advantageous in the preliminary shRNA development because the RNAi search could focus on only the amino-terminal encoding sequences rather than the full length 14 kb mRNA. FIG. 31 depicts the one-step cloning approach used to screen hairpins (Harper 2004). No effective shRNAs were found in exon 1, but several designed against exon 2, denoted shHDEx2.1 (5'-AAGAAAGAACTTTCAGCTACC-3', SEQ ID NO:91), shHDEx2.2 19 nt (5'-AGAACTTTCAGCTAC-CAAG-3' (SEQ ID NO:92)), or shHDEx2.2 21 nt 5'-AAAGAACTTTCAGCTACCAAG-3' (SEQ ID NO:93)) and exon 3 (shHDEx3.1 19 nt 5'-TGCCTCAACAAAGT-TATCA-3' (SEQ ID NO:94) or shHDEx3.1 21 nt 5'-AAT-GCCTCAACAAAGTTATCA-3' (SEQ ID NO:95)) sequences were effective. In co-transfection experiments with shRNA expressing plasmids and the N171-82Q transcript target, shHDEx2.1 reduced N171-Q82 transcript levels by 80%, and protein expression by 60%.

In transient transfection assays shHDex2.1 did not silence a construct spanning exons 1-3 of mouse htt containing a 79 CAG repeat expansion, the mouse equivalent of N171-82Q. Next shHDEx2 into NIH 3T3 cells were transfected to confirm that endogenous mouse htt, which is expressed in NIH 3T3 cells, would not be reduced. Surprisingly, shHDEx2.1 and shHDEx3.1 silenced full-length mouse htt. In contrast, shHDEx2.2 silenced only the human N171-82Q transgene.

Yamamoto and colleagues and others have demonstrated that preformed inclusions can resolve (Yamamoto 2000). To test if RNAi could also reduce preformed aggregates, the inventors used a neuronal cell line, which, upon induction of Q80-eGFP expression, showed robust inclusion formation (Xia 2002). Cells laden with aggregates were mock-transduced, or transduced with recombinant virus expressing control shRNA, or shRNAs directed against GFP. The inventors found dramatic reduction in aggregates as assessed by fluorescence. Quantification showed dose dependent effects (FIG. 32) that were corroborated by western blot (Xia 2002).

As indicated in Example 1 above, viral vectors expressing siRNAs can mediate gene silencing in the CNS (Xia 2002). Also, these studies were extended to the mouse model of spinocerebellar ataxia type 1 (SCA1). The data are important as they demonstrate that shRNA is efficacious in the CNS of a mouse model of human neurodegenerative disease. The data also support that shRNA expression in brain is not detrimental to neuronal survival.

shRNAs can target the Exon 58 polymorphism. As described in Example 4 above, a polymorphism in htt exon 58 is in linkage disequilibrium with HD (Ambrose 1994). Thirty eight percent of the HD population possesses a 3-GAG repeat in exon 58, in contrast to the 4-GAG repeat found in 92% of non-HD patients. The polymorphism likely has no affect on htt, but it provides a target for directing gene silencing to the disease allele. As indicated in Example 4 above, in experiments to test if allele-specific silencing for HD was possible, plasmids were generated that expressed shRNAs that were specific for the exon 58 polymorphism. The exon 58 3-GAG-targeting shRNAs were functional.

Developing vectors for control of RNAi in vivo. As demonstrated above, shRNA expressed from viral vectors is effective at directing gene silencing in brain. Also, viral vectors expressing shSCA1 inhibited neurodegeneration in the SCA1 mouse model. ShRNA expression was constitutive in both instances. However, constitutive expression may not be necessary, and could exacerbate any noted nonspecific effects. The present inventors have developed and tested several doxycycline-regulated constructs. The construct depicted in FIG. 33 showed strong suppression of target gene (GFP) expression after addition of doxycycline and RNAi induction.

RNAi can Protect, and/or Reverse, the Neuropathology in Mouse Models of Human Huntington's Disease Two distinct but complimentary mouse models are used, the N171-82Q transgenic and CRL2 knock-in mice. The former express a truncated NH2-terminal fragment of human htt comprising exons 1-3 with an 82Q-repeat expansion. The knock-in expresses a mutant mouse allele with a repeat size of ~150. Neither shows significant striatal or cortical cell loss. Both therefore are suitable models for the early stages of HD. They also possess similarities in mid- and end-stage neuropathological phenotypes including inclusions, gliosis, and motor and behavioral deficits that will permit comparison and validation. On the other hand, the differences inherent in the two models provide unique opportunities for addressing distinct questions regarding RNAi therapy. For example, N171-82Q transgenic mice have relatively early disease onset. Thus efficacy can be assessed within a few months, in contrast to 9 months or more in the CHL2 line. Because the data showed that shHDEx2.2 targets the human transgene and not mouse HD, evaluate disease-allele specific silencing in N171-82Q mice is evaluated. In contrast, the CHL2 knock-in is important for testing how reducing expression of both the mutant and wildtype alleles impacts on the HD phenotype. Finally, both models should be investigated because any therapy for HD should be validated in two relevant disease models.

siRNA Against Human Htt Protects Against Inclusion Formation in N171-82Q Mice

The data show that it is possible to silence the human N171-82Q transgene in vitro, and work in reporter mice and SCA1 mouse models demonstrated efficacy of RNAi in vivo in brain. shHDEx2.2 constructs, expressed from two vector systems with well-established efficacy profiles in CNS, are now tested for their capacity to reduce mutant transgenic allele expression in vivo. Further, the impact of shHDEx2.2 on inclusion formation is assessed. Inclusions may not be pathogenic themselves, but they are an important hallmark of HD and their presence and abundance correlates with severity of disease in many studies.

Recombinant feline immunodeficiency virus (FIV) and adeno-associated virus (AAV) expressing shHDs are injected into N171-82Q. The levels of shHDs expressed from FIV and AAV are evaluated, as is the ability to reduce htt mRNA and protein levels in brain, and subsequently affect inclusion formation.

Mice. N171-82Q mice developed by Borchelt and colleagues are used for these experiments (Shilling 1999, Shilling 2001). The colony was set up from breeders purchased from Jackson Laboratories (N171-82Q, line 81) and are maintained as described (Shilling 1999, Shilling 2001). F1 pups are genotyped by PCR off tail DNA, obtained when tagging weaned litters.

IC2 and EM48 have been used previously to evaluate N171-82Q transgene expression levels in brain by immunohistochemistry (IHC) and western blot (Zhou 2003, Trottier 1995). EM48 is an antibody raised against a GST-NH2 terminal fragment of htt that detects both ubiquitinated and non-ubiquitinated htt-aggregates (Li 2000), and the IC2 antibody recognizes long polyglutamine tracts (Trottier 1995). By 4 weeks N171-82Q mice show diffuse EM48-positive staining in striata, hippocampus, cerebellar granule cells, and cortical layers IV and V (Shilling 1999, Shilling 2001). The present experiments focus on the striatum and cortex because they are the major sites of pathology in human HD. TUNEL positivity and GFAP immunoreactivity are also significant in striatal sections harvested from 3 month old N171-82Q mice (Yu 2003). At 4 months, punctate nuclear and cytoplasmic immunoreactivity is also seen (Yu 2003).

Viruses. It is difficult to directly compare the two viruses under study at equivalent doses; FIV is enveloped and can be concentrated and purified, at best, to titers of $5\times10^8$ infectious units/ml (iu/ml). FIV psuedotyped with the vesicular stomatitus glycoprotein (VSVg) are used because of its tropism for neurons in the striatum (Brooks 2002). In contrast, AAV is encapsidated and can be concentrated and purified to titers ranging from $1\times10^9$ to $1\times10^{11}$ iu/ml, with $1\times10^{10}$ titers on average. AAV serotype 5 is used because it is tropic for neurons in striatum and cortex, our target brain regions. Other serotypes of AAV, such as AAV-1 may also be used to neurons in striatum and cortex. Also, it diffuses widely from the injection site (Alisky 2000, Davidson 2000). Ten-fold dilutions of FIV and AAV generally results in a greater than 10-fold drop in transduction efficiency, making comparisons at equal titers, and dose escalation studies, unreasonable. Thus, both viruses are tested at the highest titers routinely available to get a fair assessment of their capacities for efficacy in N171-82Q mice. All viruses express the humanized *Renilla reniformis* green fluorescent protein (hrGFP) reporter transgene in addition to the shRNA sequence (FIG. 34). This provides the unique opportunity to look at individual, transduced cells, and to compare pathological improvements in transduced vs. untransduced cells.

Injections. Mice are placed into a David Kopf frame for injections. Mice are injected into the striatum (5 microliters; 100 nl/min) and the cortex (3 microliters; 75 nl/min) using a Hamilton syringe and programmable Harvard pump. The somatosensory cortex is targeted from a burr hole at −1.5 mm from Bregma, and 1.5 mm lateral. Depth is 0.5 mm. The striatum is targeted through a separate burr hole at +1.1 mm from Bregma, 1.5 mm lateral and 2 mm deep. Only the right side of the brain is injected, allowing the left hemisphere to be used as a control for transgene expression levels and presence or absence of inclusions.

Briefly, groups of 4 week-old mice heterozygous for the N171-82Q transgene and their age-matched wildtype littermates are injected with FIV (FIV groups are VSVg.FIV.shHDEx2.2, VSVg.FIVshlacZ, VSVg.hrGFP, saline) or AAV (AAV groups are AAV5.shHDEx2.2, AAV5shlacZ, AAV5hrGFP, saline) (n=18/group; staggered injections because of the size of the experiment). Names of shHDEx2.2 and shlacZ expressing viruses have been shortened from shlacZ.hrGFP, for example, to make it easier to read, but all vectors express hrGFP as reporter. Nine mice/group are sacrificed at 12 weeks of age to assess the extent of transduction (eGFP fluorescence; viral copy number/brain region), shRNA expression (northern for shRNAs, and inhibition of expression of the transgenic allele (QPCR and western blot). The remaining groups are sacrificed at 5 months of age. This experimental set up is repeated (to n=6/group) to confirm results and test inter-experiment variability.

All mice in all groups are weighed bi-weekly (every other week) after initial weekly measurements. N171-82Q mice show normal weight gain up to approximately 6 weeks, after which there are significant differences with their wildtype littermates.

PCR Analyses. Brains are harvested from mice sacrificed at 12 weeks of age, and grossly evaluated for GFP expression to confirm transduction. The cortex and striatum from each hemisphere is dissected separately, snap frozen in liquid N2, pulverized with a mortar and pestle, and resuspended in Trizol (Gibco BRL). Separate aliquots are used for Q-RTPCR for N171-82Q transgenes and DNA PCR for viral genomes. A coefficient of correlation is determined for transgene silencing relative to viral genomes for both vector systems, for the regions analyzed and compared to contralateral striata and mice injected with control vectors or saline.

The RNA harvested is used to evaluate activation of interferon-responsive genes. Bridges et al (Bridges 2003) and Sledz and colleagues (Sledz 2003) found activation of 2'5' oligo(A) polymerase (OAS) in cell culture with siRNAs and shRNAs, the latter expressed from lentivirus vectors. Gene expression changes are assessed using QPCR for OAS, Stat1, interferon-inducible transmembrane proteins 1 and 2 and protein kinase R (PKR). PKR activation is an initial trigger of the signaling cascade of the interferon response.

Protein Analyses. A second set of 3 brains/group are harvested for protein analysis. Regions of brains are micro dissected as described above, and after pulverization are resuspended in extraction buffer (50 mM Tris, pH 8.0, 150 mM NaCl, 1% NP-40, 0.5% deoxycholate, 0.1% SDS, 1 mM BetaME, 1× complete protease inhibitor cocktail) for analysis by western blot. HrGFP expression are evaluated and correlated to diminished levels of soluble N171-82Q using anti-GFP and antibodies to the NH2-terminal region of htt (EM48) or the polyglutamine tract (IC2).

Histology. Histology is done on the remaining animals. Mice are perfused with 2% paraformaldehyde in PBS, brains blocked to remove the cerebellum, post-fixed ON, and then cryoprotected in 30% sucrose. Full coronal sections (40 µm) of the entire cerebrum are obtained using a Microtome (American Products Co #860 equipped with a Super Histo Freeze freezing stage). Briefly, every section is collected, and sections 1-6 are placed into 6 successive wells of a 24-well plate. Every 400 microns, two sections each of 10 microns are collected for Nissl and H&E staining. The process is repeated.

EM-48 immuno-staining reveals diffuse nuclear accumulations in N171-82Q mice as early as 4 weeks of age. In 6 mo. old mice inclusions are extensive (Shilling 2001). The increase in cytoplasmic and nuclear EM48 immuno-reactivity, and in EM48 immuno-reactive inclusions over time allow quantitative comparisons between transduced and untransduced cells. Again, control values are obtained from mice injected with shlacZ-expressing vectors, saline injected mice, and wt mice. The contralateral region is used as another control, with care taken to keep in mind the possibility of retrograde and anterograde transport of virus from the injection site.

Quantitation of nuclear inclusions is done using BioQuant™ software in conjunction with a Leitz DM RBE upright microscope equipped with a motorized stage (Applied Scientific Instruments). Briefly, floating sections are stained with anti-NeuN (AMCA secondary) and EM48 antibodies (rhodamine secondary) followed by mounting onto slides. The regions to be analyzed are outlined, and threshold levels for EM48 immunoreactivity set using sections from control injected mice. A minimum of 50 hrGFP-positive and hrGFP negative neurons cells are evaluated per slide (5 slides/mouse), and inclusion intensity measured (arbitrary units). This is done for both striata and cortices. To quantitate cytoplasmic inclusions, the striatum is outlined and total EM48 aggregate density measured. Threshold values are again done using control hemispheres and control injected mice.

Additional wells of sections are stained with anti-GFAP, anti-neurofilament, and the lectin GSA to assay for viral or viral+hairpin induced gliosis, neuritic changes, and microglial activation, respectively. GFAP-stained brain sections from N171-82Q mice show gliosis by 4 months (Yu 1998), although earlier time points have not been reported.

Stereology. In a separate experiment on N171-82Q mice and wt mice, unbiased stereology using BioQuant™ software is done to assess transduction efficiency. Stereology allows for an unbiased assessment of efficiency of transduction (number of cells transduced/input). AAV5 (AAV5hrGFP, AAV5shHD.hrGFP) and FIV (VSVg-.FIVhrGFP, VSVg.FIVshHD.hrGFP) transduction efficiency is compared in the striatum and somatosensory cortex in HD and wildtype mice, with n=5 each. Mice are harvested at 12 and 20 weeks. The cerebrum is sectioned in its entirety and stored at −20° C. until analysis. Briefly, six weeks after gene transfer with VSVg.FIVhrGFP (n=3) or AAV5hrGFP (n=3), every section of an HD mouse cerebrum is mounted and an initial assessment of the required numbers of sections and grid and dissector size done using the coefficient of error (as determined by Martheron's quadratic approximation formula) as a guide.

The 171-82Q HD mouse model has important neuropathological and behavioral characteristics relevant to HD. Onset of disease occurs earlier than HD knock-in or YAC transgenic models, allowing an initial, important assessment of the protective effects of RNAi on the development of neuropathology and dysfunctional behavior, without incurring extensive long term housing costs. Admittedly, disease onset is slower and less aggressive than the R6/2 mice created by Bates and colleagues (Mangiarini 1996), but the R6/2 line is difficult to maintain and disease is so severe that it may be less applicable and less predicative of efficacy in clinical trials.

N171-82Q mice (n=6/group) and age-matched littermates (n=6/group) are be weighed twice a month from 4 wks on, and baseline rotarod tests performed at 5 and 7 weeks of age. Numbers of mice per group are as described in Schilling et al (Shilling 1999) in which statistically significant differences between N171-82Q and wildtype littermates were described. At 7 weeks of age (after testing is complete), AAV (AAVshHDEx2.2, AAVshlacZ, AAVhrGFP, saline) or FIV (FIVshEx2.2, FIVshlacZ, FIVhrGFP, saline) is injected bilaterally into the striatum and cortex. Rotarod tests are repeated at 3-week intervals starting at age 9 weeks, until sacrifice at 6 months. The clasping behavior is assessed monthly starting at 3 months.

Behavioral testing. N171-82Q mice are given four behavioral tests, all of which are standard assays for progressive disease in HD mouse models. The tests allow comparisons of behavioral changes resulting from RNAi to those incurred in HD mouse models given other experimental therapies. For example, HD mice given cystamine or creatine therapy showed delayed impairments in rotarod performance, and in some cases delayed weight loss (Ferrante 2000, Dedeoglu 2002, Dedeogu 2003) In addition to the rotarod, which is used to assay for motor performance and general neurological dysfunction, the activity monitor allows assessment of the documented progressive hypoactivity in N171-82Q mice. The beam analysis is a second test of motor performance that has also been used in HD mice models (Carter 1999). Clasping, a phenotype of generalized neurological dysfunction, is straightforward and takes little time. Clasping phenotypes were corrected in R. Hen's transgenic mice possessing an inducible mutant htt.

Accelerated rotarod. N171-82Q and age-matched littermates are habituated to the rotarod at week 4, and 4 trials per day for 4 days done on week 5 and 7, and every 3 weeks hence using previously described assays (Shilling 1999, Clark 1997) in use in the lab. Briefly, 10 min trials are run on an Economex rotarod (Columbus Instruments) set to accelerate from 4 to 40 rpm over the course of the assay. Latency to fall is recorded and averages/group determined and plotted. Based on prior work (Shilling 1999) 6 mice will give sufficient power to assess significance.

Clasping behavior. Normal mice splay their limbs when suspended, but mice with neurological deficits can exhibit the opposite, with fore and hind limbs crunched into the abdomen (clasping). All mice are suspended and scored for clasping monthly. The clasp must be maintained for at least 30 sec. to be scored positive.

Activity monitor. Most HD models demonstrate hypokinetic behavior, particularly later in the disease process. This can be measured in several ways. One of the simplest methods is to monitor home cage activity with an infrared sensor (AB-system 4.0, Neurosci Co., LTD). Measurements are taken over 3 days with one day prior habituation to the testing cage (standard 12-hour light/dark cycle). Activity monitoring is done at 12, 17, and 20 and 23 weeks of age.

Beam walking. N171Q-82Q and age matched littermates are assayed for motor performance and coordination using a series of successively more difficult beams en route to an enclosed safety platform. The assay is as described by Carter et al (Carter 1999). Briefly, 1 meter-length beams of 28, 17 or 11 mm diameter are placed 50 cm above the bench surface. A support stand and the enclosed goal box flank the ends. Mice are trained on the 11 mm beam at 6 weeks of age over 4 days, with 3 trials per day. If mice can traverse the beam in <20 sec. trials are initiated. A trial is then run on each beam, largest to smallest, with a 60 sec cutoff/beam and one minute rest between beams. A second trial is run and the mean scores of the two trials evaluated.

RNAi cannot replace neurons; it only has the potential to protect non-diseased neurons, or inhibit further progression of disease at a point prior to cell death. N171-82Q mice do not show noticeable cellular loss, and is therefore an excellent model of early HD in humans. The general methodology is the similar to that described above, except that the viruses are injected at 4 months, when N171-82Q mice have measurable behavioral dysfunction and inclusions. Animals are sacrificed at end stage disease or at 8 months, whichever comes first. Histology, RNA and protein in harvested brains are analyzed as described above.

It is important to confirm the biological effects of virally expressed shHDs in a second mouse model, as it is with any therapy. The Detloff knock-in mouse (the CHL2 line, also notated as HdhCAGQ150) is used as a second model of early HD disease phenotypes. These mice have a CAG expansion of approximately 150 units, causing brain pathologies similar to HD including gliosis and neural inclusions in the cortex and striatum. They also show progressive motor dysfunction and other behavioral manifestations including rotarod deficits, clasping, gait abnormalities and hypoactivity.

Heterozygous CHL2 mice express the mutant and wildtype allele at roughly equivalent levels, and shRNAs directed against mouse HD silence both transcripts. shmHDEx2.1 causes reductions in gene expression, but not complete silencing. Disease severity in mouse models is dependent on mutant htt levels and CAG repeat length.

The inventors created shmHDEx2 (shRNA for murine HD) directed against a region in mouse exon 2 that reduces expression of the full-length mouse Hdh transcript in vitro. Transduction of neurons with shmHDEx2-expressing viruses, and its impacts on neuropathological progression, behavioral dysfunction and the appearance of EM48 immuno-reactive inclusions in CHL2 mice is tested. shmHD- or shlacZ-expressing vectors in CHL2 and wildtype brain is tested. In this experiment, virus is injected into the striatum of wt or CHL2 mice (10/group) using the coordinates described above, at 3 months of age. Two months later mice are sacrificed and brains removed and processed for RNA (n=5/group) and protein (n=5).

A second study tests the vectors in the Detloff model. Briefly, 15 mice per group are injected into the striatum and cortex at 3 months of age with AAV (AAVshmHD, AAVshlacZ, AAVhrGFP, saline) or FIV (VSVg.FIV.shmHD, VSVg.FIVshlacZ, VSVg.FIVhrGFP, saline) expressing the transgenes indicated. To assess the impact of RNAi, activity performed. The mice are sacrificed at 16-18 months of age and five brains/group are processed for histology and sections banked in 24-well tissue culture plates. The remaining brains are processed for RNA (n=6) and protein analysis (n=5). Northern blots or western blots are required to analyze wildtype and mutant htt expression because the only distinguishing characteristic is size.

Development of Effective Allele-Specific siRNAs

Mutant htt leads to a toxic gain of function, and inhibiting expression of the mutant allele has a profound impact on disease (Yamamoto 2000). Also, selectively targeting the disease allele would be desirable if non-disease allele silencing is deleterious. At the present time, there is one documented disease linked polymorphism in exon 58 (Lin 2001). Most non-HD individuals have 4 GAGs in Hdh exon 58 while 38% of HD patients have 3 GAGs. As described above, RNAi can be accomplished against the 3-GAG repeat.

Prior work by the inventors showed the importance of using full-length targets for testing putative shRNAs. In some cases, shRNAs would work against truncated, but not full-length targets, or vice-versa. Thus, it is imperative that testable, full-length constructs are made to confirm allele-specific silencing. The V5 and FLAG tags provide epitopes to evaluate silencing at the mRNA and protein levels. This is important as putative shRNAs may behave as miRNAs, leading to inhibition of expression but not message degradation.

Designing the siRNAs. Methods are known for designing siRNAs (Miller 2003, Gonzalez-Alegre 2003, Xia 2002, Kao 2003). Information is also know about the importance of maintaining flexibility at the 5' end of the antisense strand for loading of the appropriate antisense sequence into the RISC complex (Khvorova 2003 Schwarz 2003). DNA sequences are generated by PCR. This method allows the rapid generation of many candidate shRNAs, and it is significantly cheaper than buying shRNAs. Also, the inserts can be cloned readily into our vector shuttle plasmids for generation of virus. The reverse primer is a long oligonucleotide encoding the antisense sequence, the loop, the sense sequence, and a portion of the human U6 promoter. The forward primer is specific to the template in the PCR reaction. PCR products are cloned directly into pTOPO blunt from InVitrogen, plasmids transformed into DH5a, and bacteria plated onto Kanr plates (the PCR template is Ampr). Kanr clones are picked and sequenced. Sequencing is done with an extended 'hot start' to allow effective read-through of the hairpin. Correct clones are transfected into cells along with plasmids expressing the target or control sequence (HttEx58.GAG3V5 and HttEx58.GAG4FLAG, respectively) and silencing evaluated by western blot. Reductions in target mRNA levels are assayed by Q-RTPCR. The control for western loading is neomycin phosphotransferase or hrGFP, which are expressed in the target-containing plasmids and provide excellent internal controls for transfection efficiency. The control for Q-RTPCR is HPRT.

Cell lines expressing targets with the identified polymorphism or control wildtype sequences are created. Target gene expression are under control of an inducible promoter. PC6-3, Tet repressor (TetR+) cells, a PC-12 derivative with a uniform neuronal phenotype (Xia 2002) are used. PC6-3 cells are transfected with plasmids expressing HDEx58.GAG3V5 (contains neo marker) and HDEx58GAG4FLG (contains puro marker), and G418+/puromycin+ positive clones selected and characterized for transcript levels and htt-V5 or htt-Flag protein levels.

FIV vectors expressing the allele specific shRNAs are generated and used to test silencing in the inducible cell lines. FIV vectors infect most epithelial and neuronal cell lines with high efficiency and are therefore useful for this purpose. They also efficiently infect PC6-3 cells. AAV vectors are currently less effective in in vitro screening because of poor transduction efficiency in many cultured cell lines.

Cells are transduced with 1 to 50 infectious units/cell in 24-well dishes, 3 days after induction of mutant gene expression. Cells are harvested 72 h after infection and the effects on HDEx58.GAG3V5 or HDEx58GAG4FLG expression monitored.

EXAMPLE 10

Micro RNAi-Therapy for Polyglutamine Disease

Post-transcriptional gene silencing occurs when double stranded RNA (dsRNA) is introduced or naturally expressed in cells. RNA interference (RNAi) has been described in plants (quelling), nematodes, and *Drosophila*. This process serves at least two roles, one as an innate defense mechanism, and another developmental (Waterhouse 2001 Fire 1999, Lau 2001, Lagos-Quintana 2001, Lee 2001). RNAi may regulate developmental expression of genes via the processing of small, temporally expressed RNAs, also called microRNAs (Knight 2001, Grishok 2001). Harnessing a cell's ability to respond specifically to small dsRNAs for target mRNA degradation has been a major advance, allowing rapid evaluation of gene function (Gonczy 2000, Fire 1998, Kennerdell 1998, Hannon 2002, Shi 2003, Sui 2002).

Most eukaryotes encode a substantial number of small noncoding RNAs termed micro RNAs (miRNAs) (Zeng 2003, Tijsterman 2004, Lee 2004, Pham 2004). mir-30 is a 22-nucleotide human miRNA that can be naturally processed from a longer transcript bearing the proposed miR-30 stem-loop precursor. mir-30 can translationally inhibit an mRNA-bearing artificial target sites. The mir-30 precursor stem can be substituted with a heterologous stem, which can be processed to yield novel miRNAs and can block the expression of endogenous mRNAs.

Huntington's disease (HD) and Spinocerebellar ataxia type I (SCA1) are two of a class of dominant, neurodegenerative diseases caused by a polyglutamine (polyQ) expansion. The mutation confers a toxic gain of function to the protein, with polyQ length predictive of age of onset and disease severity. There is no curative or preventative therapy for HD or SCA1, supporting the investigation of novel strategies. As described above, the inventors showed that gene silencing by RNA interference (RNAi) can be achieved in vitro and in vivo by expressing short hairpin RNAs (shRNAs) specific for mRNAs encoding ataxin-1 or huntingtin. Currently, strong, constitutive polIII promoters (U6 and H1) are used to express shRNAs, which are subsequently processed into functional small interfering RNAs (siRNAs). However, strong, constitutive expression of shRNAs may be inappropriate for diseases that take several decades to manifest. Moreover, high-level expression may be unnecessary for sustained benefit, and in some systems may induce a non-specific interferon response leading to global shut-down of gene expression. The inventors therefore generated polII-expressed microRNAs (miRNAs) as siRNA shuttles as an alternative strategy. Due to their endogenous nature, miRNA backbones may prevent the induction of the interferon response.

Using human mir-30 as a template, miRNA shuttles were designed that upon processing by dicer released siRNAs specific for ataxin-1. Briefly, the constructs were made by cloning a promoter (such as an inducible promoter) and an miRNA shuttle containing an embedded siRNA specific for a target sequence (such as ataxin-1) into a viral vector. By cloning the construct into a viral vector, the construct can be effectively introduced in vivo using the methods described in the Examples above. Constructs containing polII-expressed miRNA shuttles with embedded ataxin-1-specific siRNAs were co-transfected into cells with GFP-tagged ataxin-1, and gene silencing was assessed by fluorescence microscopy and western analysis. Dramatic arid dose-dependent gene silencing relative to non-specific miRNAs carrying control siRNAs was observed. This polII-based expression system exploits the structure of known miRNAs and supports tissue-specific as well as inducible siRNA expression, and thus, serves as a unique and powerful alternative to dominant neurodegenerative disease therapy by RNAi.

Briefly, the constructs were made by cloning a promoter (such as an inducible promoter) and an miRNA shuttle containing an embedded siRNA specific for a target sequence (such as ataxin-1) into a viral vector. By cloning the construct into a viral vector, the construct can be effectively introduced in vivo using the methods described in the Examples above.

EXAMPLE 11

Huntington's Disease (HD)

Subsequent to the experiments described in Example 9 above, the inventors have made additional siRNA molecules specific for regions of the HD gene (FIG. 35A-L). All of these sequences have been tested, and were found to be effective in RNA interference.

shHD1.1=SEQ ID NO: 106
shHD1.2=SEQ ID NO: 107
shHD1.3=SEQ ID NO: 108
shHD1.4=SEQ ID NO: 109 shHD1.5=SEQ ID NO: 110
shHD1.6=SEQ ID NO: 111
shHD1.7=SEQ ID NO: 112
shHD1.8=SEQ ID NO: 113
shHD1.9=SEQ ID NO: 114
shHD2.1=SEQ ID NO: 115
shHD2.2=SEQ ID NO: 145
shHD2.3=SEQ ID NO: 116
shHD2.4=SEQ ID NO: 117
shHD2.5=SEQ ID NO: 118
shHD2.6=SEQ ID NO: 119
shHD3.1=SEQ ID NO: 120
shHD3.2=SEQ ID NO: 121
shHD4.1=SEQ ID NO: 122
shHD8.1=SEQ ID NO: 123
shHD8.2=SEQ ID NO: 124
shHD12.1=SEQ ID NO: 125
shHD17.1=SEQ ID NO: 126
shHD17.2=SEQ ID NO: 127
shHD22.1=SEQ ID NO: 128
shHD28.1=SEQ ID NO: 129
shHD30.1=SEQ ID NO: 130
shHD32.1=SEQ ID NO: 131
shHD34.1=SEQ ID NO: 132
shHD34.2=SEQ ID NO: 133
shHD35.1=SEQ ID NO: 134
shHD37.1=SEQ ID NO: 135
shHD38.1=SEQ ID NO: 136
shHD38.2=SEQ ID NO: 137
shHD40.1=SEQ ID NO: 138
shHD42.1=SEQ ID NO: 139
shHD42.2=SEQ ID NO: 140
shHD58.1=SEQ ID NO: 141
shHD58.2=SEQ ID NO: 146
shHD63.1=SEQ ID NO: 142

The normal human huntingtin gene is SEQ ID NO:143, and the corresponding normal mouse huntington gene is SEQ ID NO:144.

A particular nucleic acid sequence also encompasses variants. A variant of a molecule is a sequence that is substantially similar to the sequence of the native molecule. For nucleotide sequences, variants include those sequences that, because of the degeneracy of the genetic code, encode the identical amino acid sequence of the native protein. The sequences listed above also encompass nucleic acids containing known analogs of natural nucleotides that have similar binding properties as the reference nucleic acid and are metabolized in a manner similar to naturally occurring nucleotides. The present invention encompasses nucleic acid sequences wherein at least 12 of the nucleotides the same as in the sequences provided, but wherein the remaining nucleotides may be replaced with other nucleotides.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

CITATIONS

Adelman et al., DNA, 2, 183 (1983).
Alisky et al., Hum Gen Ther, 11, 2315 (2000b).
Alisky et al., NeuroReport, 11, 2669 (2000a).
Altschul et al., JMB, 215, 403 (1990).
Altschul et al., Nucleic Acids Res. 25, 3389 (1997).
Ambrose et al., Somat Cell Mol Genet. 20, 27-38 (1994)
Anderson et al., Gene Ther., 7(12), 1034-8 (2000).
Andreason and Evans, Biotechniques, 6, 650 (1988).
Augood et al., Neurology, 59, 445-8 (2002).
Augood et al., Ann. Neurol., 46, 761-769 (1999).
Bass, Nature, 411, 428 (2001).
Batzer et al., Nucl. Acids Res., 19, 508 (1991).
Baulcombe, Plant Mol. Biol., 32, 79 (1996).
Bates et al., Curr Opin Neurol 16:465-470, 2003.
Behr et al., Proc. Natl. Acad. Sci. USA, 86, 6982 (1989).
Bernstein et al., Nature, 409, 363 (2001).
Bledsoe et al., NatBiot, 18, 964 (2000).
Brantl, Biochemica and Biophysica Acta, 1575, 15 (2002).
Brash et al., Molec. Cell. Biol., 7, 2031 (1987).
Breakefield et al., Neuron, 31, 9-12 (2001).
Bridge et al., Nat Genet 34:263-264, 2003.
Brooks et al., Proc. Natl. Acad. Sci. U.S.A, 99, 6216 (2002).
Brummelkamp, T. R. et al., *Science* 296:550-553 (2002).
Burright, E. N. et al., Cell, 82, 937-948 (1995)
Capecchi, Cell, 22, 479 (1980).
Caplan et al., Proc. Natl. Acad. Sci. U.S.A, 98, 9742 (2001).
Caplen et al., Hum. Mol. Genet., 11(2), 175-84 (2002).
Carter et al., J Neurosci 19:3248, 1999.
Cemal et al., Hum. Mol. Genet., 11(9), 1075-94 (2002).
Chai et al., Hum. Mol. Genet., 8, 673-682 (1999b).
Chai et al., J. Neurosci., 19, 10338 (1999).
Chan et al., Hum Mol Genet., 9(19), 2811-20 (2000).
Chen, H. K. et al., Cell, 113, 457-68 (2003)
Chiu and Rana, Mol. Cell., 10(3), 549-61 (2002).
Clark, H. B. et al., J. Neurosci., 17(19), 7385-7395 (1997)
Cogoni et al., Antonie Van Leeuwenhoek, 65, 205 (1994).
Corpet et al., Nucl. Acids Res., 16, 10881 (1988).
Crea et al., Proc. Natl. Acad. Sci. U.S.A., 75, 5765 (1978).
Cullen, Nat. Immunol., 3, 597-9 (2002).
Cummings, C. J. et al., Nat. Genet., 19(2), 148-154 (1998)
Davidson et al., Proc. Natl. Acad. Sci. U.S.A, 97, 3428 (2000).
Davidson, B. L. et al., The Lancet Neurol., 3, 145-149 (2004)
Davidson et al., Nat Rev Neurosci 4:353-364, 2003.
Dayhoff et al., Atlas of Protein Sequence and Structure (Natl. Biomed. Res. Found. 1978)
Dedeoglu et al., J Neurochem 85:1359-1367, 2003.
Dedeoglu et al., J Neurosci 22:8942-8950, 2002.
Doheny et al., Neurology, 59, 1244-1246 (2002).
Donze and Picard, Nucleic Acids Res., 30(10) (2002).
During et al., Gene Ther 5:820-827, 1998.
Elbashir et al., EMBO J., 20(23), 6877-88 (2001c).
Elbashir et al., Genes and Development, 15, 188 (2001).
Elbashir et al., Nature, 411, 494 (2001).
Emamian, E. S. et al., Neuron, 38, 375-87 (2003)
Fahn et al., Adv. Neurol., 78, 1-10 (1998).
Feigner et al., Proc. Natl. Acad. Sci., 84, 7413 (1987).
Fernandez-Funez, P. et al., Nature, 408, 101-106 (2000)
Ferrante et al., J Neurosci 20:4389-4397, 2000.
Fire et al., Nature, 391(6669), 806-11 (1998).
Fire A. Trends Genet 15(9):358-363, 1999
Frisella et al., Mol Ther 3(3):351-358, 2001.
Gaspar et al., Am. J. Hum. Genet., 68(2), 523-8 (2001).
Gelfand, PCR Strategies, Academic Press (1995).
Gitlin et al., Nature, 418(6896), 430-4 (2002).
Goeddel et al., Nucleic Acids Res., 8, 4057 (1980).
Gonczy et al., Nature 408:331-336, 2000.
Gonzalez-Alegre et al., Nat Genet 3:219-223, 1993.
Goodchild et al., Mov. Disord., 17(5), 958, Abstract (2002).

Grishok et al., Cell 106:23-34, 2001.
Hamilton and Baulcombe, Science, 286, 950 (1999).
Hammond et al., Nature, 404, 293 (2000).
Hannon G J. Nature 418:244-251, 2002.
Harper et al., Meth Mol Biol. In Press 2004
Hewett et al., Hum. Mol. Gen., 9, 1403-1413 (2000).
Higgins et al., CABIOS, 5, 151 (1989).
Higgins et al., Gene, 73, 237 (1988).
Hilberg et al., Proc. Natl. Acad. Sci. USA, 84, 5232 (1987).
Holland et al., Proc. Natl. Acad. Sci. USA, 84, 8662 (1987).
Hornykiewicz et al., N. Engl. J. Med., 315, 347-353 (1986).
Huang et al., CABIOS, 8, 155 (1992).
Hutton et al., Nature, 393, 702-705 (1998).
Innis and Gelfand, PCR Methods Manual, Academic Press (1999).
Innis et al., PCR Protocols, Academic Press (1995).
Jacque et al., Nature, 418(6896), 435-8 (2002).
Johnston, Nature, 346, 776 (1990).
Kang et al., J Virol 76:9378-9388, 2002.
Karlin and Altschul, Proc. Natl. Acad. Sci. USA, 87, 2264 (1990).
Karlin and Altschul, Proc. Natl. Acad. Sci. USA, 90, 5873 (1993)
Kennerdell and Carthew, Cell, 95, 1017 (1998).
Kao et al., J Biol Chem 2003.
Kawasaki, H., et al., Nucleic Acids Res, 31, 981-7 (2003)
Khvorova, A., et al., Cell, 115, 505 (2003)
Kitabwalla and Ruprecht, N. Engl. J. Med., 347, 1364-1367 (2002).
Klein et al., Ann. Neurol., 52, 675-679 (2002).
Klein et al., Curr. Opin. Neurol., 4, 491-7 (2002).
Klement, I. A. et al., Cell, 95, 41-53 (1998)
Knight et al., Science 293:2269-2271, 2001.
Konakova et al., Arch. Neurol., 58, 921-927 (2001).
Krichevsky and Kosik, Proc. Natl. Acad. Sci. U.S.A., 99(18), 11926-9 (2002).
Kriegler, M. Gene Transfer and Expression, A Laboratory Manual, W.H. Freeman Co, New York, (1990).
Kunath et al., Nat Biotechnol 21:559-561, 2003.
Kunkel et al., Meth. Enzymol., 154, 367 (1987).
Kunkel, Proc. Natl. Acad. Sci. USA, 82, 488 (1985).
Kustedjo et al., J. Biol. Chem., 275, 27933-27939 (2000).
Laccone et al., Hum. Mutat., 13(6), 497-502 (1999).
Lagos-Quintana et al., Science 294:853-858, 2001.
Lai et al., Proc. Natl. Acad. Sci. USA, 86, 10006 (1989).
Larrick, J. W. and Burck, K. L., Gene Therapy. Application of Molecular Biology, Elsevier Science Publishing Co., Inc., New York, p. 71-104 (1991).
Lau et al., Science 294:858-862, 2001.
Lawn et al., Nucleic Acids Res., 9, 6103 (1981).
Lee, N. S., et al., *Nat. Biotechnol.* 19:500-505 (2002).
Lee et al., Science 294:862-864, 2001.
Lee et al., Cell, 117, 69-81 (2004)
Leger et al., J. Cell. Sci., 107, 3403-12 (1994).
Leung et al., Neurogenetics, 3, 133-43 (2001).
Li et al., Nat Genet 25:385-389, 2000.
Lin et al., Hum. Mol. Genet., 10(2), 137-44 (2001).
Loeffler et al., J. Neurochem., 54, 1812 (1990).
Lotery et al., Hum Gene Ther 13:689-696, 2002.
Mangiarini et al., Cell 87(3):493-506, 1996.
Manche et al., Mol. Cell Biol., 12, 5238 (1992).
Margolis and Ross, Trends Mol. Med., 7, 479 (2001).
Martinez et al., Cell, 110(5), 563-74 (2002).
McCaffrey et al., Nature, 418(6893), 38-9 (2002).
McManus and Sharp, Nat. Rev. Genet. 3(10), 737-47 (2002).
Meade et al., J Comp Neurol 449:241-269, 2002.
Meinkoth and Wahl, Anal. Biochem., 138, 267 (1984).
Methods in Molecular Biology, 7, Gene Transfer and Expression Protocols, Ed. E. J. Murray, Humana Press (1991).
Miller, et al., Mol. Cell. Biol., 10, 4239 (1990).
Miller, V. M. et al., PNAS USA, 100, 7195-200 (2003)
Minks et al., J. Biol. Chem., 254, 10180 (1979).
Miyagishi, M. & Taira, K. *Nat. Biotechnol.* 19:497-500 (2002).
Moulder et al., J. Neurosci., 19, 705 (1999).
Murray, E. J., ed. Methods in Molecular Biology, Vol. 7, Humana Press Inc., Clifton, N.J., (1991).
Myers and Miller, CABIOS, 4, 11 (1988).
Nasir et al., Cell, 81, 811-823 (1995).
Needleman and Wunsch, JMB, 48, 443 (1970).
Nykänen et al., Cell, 107, 309 (2001).
Ogura and Wilkinson, Genes Cells, 6, 575-97 (2001).
Ohtsuka et al., JBC, 260, 2605 (1985).
Okabe et al., FEBS Lett., 407, 313 (1997).
Ooboshi et al., Arterioscler. Thromb. Vasc. Biol., 17, 1786 (1997).
Orr et al., Nat. Genet. 4, 221-226 (1993)
Orr et al., Cell 101:1-4, 2000.
Ozelius et al., Genomics, 62, 377-84 (1999).
Ozelius et al., Nature Genetics, 17, 40-48 (1997).
Passini et al., J Virol 77:7034-7040, 2003.
Paul, C. P., et al., *Nat. Biotechnol.* 19:505-508 (2002).
Paulson et al., Ann. Neurol., 41(4), 453-62 (1997).
Pearson and Lipman, Proc. Natl. Acad. Sci. USA, 85, 2444 (1988).
Pearson et al., Meth. Mol. Biol., 24, 307 (1994).
Pham et al., Cell, 117:83-94 (2004)
Pittman et al., J. Neurosci., 13(9), 3669-80 (1993).
Plasterk et al., Cell, 117, 1-4 (2004)
Poorkaj et al., Ann. Neurol., 43, 815-825 (1998).
Quantin, B., et al., Proc. Natl. Acad. Sci. USA, 89, 2581 (1992).
Reynolds, A. et al., Nat. Biotechnol., 22, 326-30 (2004)
Rosenfeld, M. A., et al., Science, 252, 431 (1991).
Rossolini et al., Mol. Cell. Probes, 8, 91 (1994).
Rubinson et al., Nat Genet 33:401-406, 2003.
Sambrook and Russell, Molecular Cloning: A Laboratory Manual, Cold Spring Harbor Laboratory Press Cold Spring Harbor, N.Y. (2001).
Scharfmann et al., Proc. Natl. Acad. Sci. USA, 88, 4626 (1991).
Schilling et al., Hum Mol Genet 8(3):397-407, 1999.
Schilling et al., Neurobiol Dis 8:405-418, 2001.
Schwarz et al., Mol. Cell., 10(3), 537-48 (2002).
Shi Y, Trends Genet 19:9-12, 2003.
Shipley et al., J. Biol. Chem., 268, 12193 (1993).
Skinner, P. J. et al., Nature, 389, 971-234 (1997)
Skorupa et al., Exp Neurol 160:17-27, 1999.
Sledz et al., Nat Cell Biol 5:834-839, 2003.
Smith et al., Adv. Appl. Math., 2, 482 (1981).
Stein et al., J. Virol., 73, 3424 (1999).
Stein et al., Mol Ther 3(6):850-856, 2001.
Stein et al., RNA, 9(2), 187-192 (2003).
Sui et al., PNAS USA 99(8):5515-5520, 2002.
Svoboda et al., Development, 127, 4147 (2000).
Tanemura et al., J. Neurosci., 22(1), 133-41 (2002).
Tang et al., Genes Dev., 17(1), 49-63 (2003).
Ternin, H., "Retrovirus vectors for gene transfer", in Gene Transfer, Kucherlapati R, Ed., pp 149-187, Plenum, (1986).
Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993).
Timmons and Fire, Nature, 395, 854 (1998).
Trottier et al., Nature, 378(6555), 403-6 (1995).
Turner et al., Mol. Biotech., 3, 225 (1995).
Tuschl, Nat. Biotechnol., 20, 446-8 (2002).
Urabe, M., et al., Hum. Gene Ther., 13, 1935-1943 (2002)
Valerio et al., Gene, 84, 419 (1989).
Viera et al., Meth. Enzymol., 153, 3 (1987).
Walker and Gaastra, Techniques in Mol. Biol. (MacMillan Publishing Co. (1983).
Walker et al., Neurology, 58, 120-4 (2002).
Waterhouse et al., Proc. Natl. Acad. Sci. U.S.A, 95, 13959 (1998).
Waterhouse et al., Nature 411:834-842, 2001.
Wianny and Zernicka-Goetz, Nat. Cell Biol., 2, 70 (2000).
Williams, R. W. et al., J. Comp. Neurol., 278, 344-52 (1988)
Xia et al., Nat. Biotechnol., 19, 640 (2001).
Xia et al., Nat. Biotechnol., 20(10), 1006-10 (2002).
Xiao et al., Exp Neurol 144:113-124, 1997.
Yamamoto et al., Cell, 101(1), 57-66 (2000).
Yang et al., Mol. Cell Biol., 21, 7807 (2001).
Yu et al., Proc. Natl. Acad. Sci., 99, 6047-6052 (2002).
Yu et al., J Neurosci 23:2193-2202, 2003.
Zamore et al., Cell, 101, 25 (2000).
Zeng et al., RNA, 9:112-123 (2003)
Zhou et al., J Cell Biol 163:109-118, 2003.
Zoghbi and Orr, Annu. Rev. Neurosci., 23, 217-47 (2000).
Zoghbi et al., Semin Cell Biol., 6, 29-35 (1995)
Zu, T. et al., In Preparation (2004)

What is claimed is:

1. An isolated RNA duplex comprising a first strand of RNA and a second strand of RNA, wherein the first strand comprises at least 15 contiguous nucleotides encoded by SEQ ID NO:97, and wherein the second strand is complementary to at least 12 contiguous nucleotides of the first strand.

2. The RNA duplex of claim 1, wherein the duplex is between 15 and 30 base pairs in length.

3. The RNA duplex of claim 1, wherein the duplex is between 19 and 25 base pairs in length.

4. The RNA duplex of claim 1, wherein the first and/or second strand further comprises an overhang region.

5. The RNA duplex of claim 1, wherein the first and/or second strand further comprises a 3' overhang region, a 5' overhang region, or both 3' and 5' overhang regions.

6. The RNA duplex of claim 4, wherein the overhang region is from 1 to 10 nucleotides in length.

7. The RNA duplex of claim 1, wherein the first strand and the second strand are operably linked by means of an RNA loop strand to form a hairpin structure comprising a duplex structure and a loop structure.

8. The RNA duplex of claim 7, wherein the loop structure contains from 4 to 10 nucleotides.

9. The RNA duplex of claim 7, wherein the loop structure contains 4, 5 or 6 nucleotides.

10. The RNA duplex of claim 7, wherein the loop structure corresponds to SEQ ID NO:61 or SEQ ID NO:64.

11. An expression cassette comprising a nucleic acid encoding at least one strand of the RNA duplex of claim 1.

12. The expression cassette of claim 11, further comprising a promoter.

13. The expression cassette of claim 12, wherein the promoter is a regulatable promoter.

14. The expression cassette of claim 12, wherein the promoter is a constitutive promoter.

15. The expression cassette of claim 12, wherein the promoter is a CMV, RSV, pol II or pol III promoter.

16. The expression cassette of claim 11, wherein the expression cassette further comprises a polyadenylation signal.

17. The expression cassette of claim 16, wherein the polyadenylation signal is a synthetic minimal polyadenylation signal.

18. The expression cassette of claim 11, further comprising a marker gene.

19. A vector comprising the expression cassette of claim 11.

20. A method of suppressing the accumulation of huntingtin or ataxin-1 in a cell comprising introducing into the cell in an amount sufficient to suppress accumulation of huntingtin or ataxin-1 in the cell
  (a) a ribonucleic acid (RNA) duplex, wherein the RNA duplex comprises a first strand of RNA and a second strand of RNA, wherein the first strand comprises at least 15 contiguous nucleotides encoded by SEQ ID NO:97 or SEQ ID NO:100, and wherein the second strand is complementary to at least 12 contiguous nucleotides of the first strand; or
  (b) a vector comprising an expression cassette comprising a nucleic acid encoding a first strand of RNA and a second strand of RNA of an RNA duplex, wherein the first strand comprises at least 15 contiguous nucleotides encoded by SEQ ID NO:97 or SEQ ID NO:100.

21. The method of claim 20, wherein the first strand comprises at least 15 contiguous nucleotides encoded by SEQ ID NO:97.

22. The method of claim 20, wherein the first strand comprises at least 15 contiguous nucleotides encoded by SEQ ID NO:100.

23. The method of claim 20, wherein the duplex is between 15 and 30 base pairs in length.

24. The method of claim 20, wherein the duplex is between 19 and 25 base pairs in length.

25. The method of claim 20, wherein the first and/or second strand further comprises an overhang region.

26. The method of claim 20, wherein the first and/or second strand further comprises a 3' overhang region, a 5' overhang region, or both 3' and 5' overhang regions.

27. The method of claim 25, wherein the overhang region is from 1 to 10 nucleotides in length.

28. The method of claim 20, wherein the first strand and the second strand are operably linked by means of an RNA loop strand to form a hairpin structure comprising a duplex structure and a loop structure.

29. The method of claim 28, wherein the loop structure contains from 4 to 10 nucleotides.

30. The method of claim 28, wherein the loop structure contains 4, 5 or 6 nucleotides.

31. The method of claim 28, wherein the loop structure corresponds to SEQ ID NO:61 or SEQ ID NO:64.

32. The method of claim 20, wherein the expression cassette further comprises a promoter.

33. The method of claim 32, wherein the promoter is a regulatable promoter.

34. The method of claim 32, wherein the promoter is a constitutive promoter.

35. The method of claim 32, wherein the promoter is a CMV, RSV, pol II or pol III promoter.

36. The method of claim 20, the expression cassette further comprises a polyadenylation signal.

37. The method of claim 36, wherein the polyadenylation signal is a synthetic minimal polyadenylation signal.

38. The method of claim 20, wherein the vector further comprises a marker gene.

* * * * *

```
                          SEQUENCE LISTING

<160> NUMBER OF SEQ ID NOS: 146

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaggtaccag atcttagtta ttaatagtaa tcaattacgg                            40

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaatcgatgc atgcctcgag acggttcact aaaccagctc tgc                       43

<210> SEQ ID NO 3
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctagaactag taataaagga tcctttattt tcattggatc cgtgtgttgg tttttttgtgt    60 gcggccgcg                                                             69

<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcgacgcggc cgcacacaaa aaaccaacac acggatccaa tgaaataaag gatcctttta     60
ttactagtt                                                             69
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cacaagctgg agtacaacta c                                              21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtacttgtac tccagctttg tg                                             22

<210> SEQ ID NO 7
<211> LENGTH: 28
<212> TYPE: DNA
<213> ORGANISM: Homo sapiens

<400> SEQUENCE: 7
cagcagcagc aggggga cct atcaggac                                      28

<210> SEQ ID NO 8
<211> LENGTH: 28
<212> TYPE: DNA
<213> ORGANISM: Homo sapiens

<400> SEQUENCE: 8
cagcagcagc agcgggacct atcaggac                                       28

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tatagtgagt cgtatta                                                   17

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatacgact cactatag                                                  18

<210> SEQ ID NO 11
<211> LENGTH: 22
<212> TYPE: DNA
<213> ORGANISM: Homo sapiens

<400> SEQUENCE: 11
```

```
cggcaagctg cgcatgaagt tc                                              22

<210> SEQ ID NO 12
<211> LENGTH: 22
<212> TYPE: DNA
<213> ORGANISM: Homo sapiens

<400> SEQUENCE: 12
atgaacttca tgctcagctt gc                                              22

<210> SEQ ID NO 13
<211> LENGTH: 22
<212> TYPE: DNA
<213> ORGANISM: Homo sapiens

<400> SEQUENCE: 13
atgaacttca gggtcagctt gc                                              22

<210> SEQ ID NO 14
<211> LENGTH: 22
<212> TYPE: DNA
<213> ORGANISM: Homo sapiens

<400> SEQUENCE: 14
cggcaagctg accctgaagt tc                                              22

<210> SEQ ID NO 15
<211> LENGTH: 22
<212> TYPE: DNA
<213> ORGANISM: Homo sapiens

<400> SEQUENCE: 15
cagcagcggg acctatcagg ac                                              22

<210> SEQ ID NO 16
<211> LENGTH: 22
<212> TYPE: DNA
<213> ORGANISM: Homo sapiens

<400> SEQUENCE: 16
ctgtcctgat aggtcccgct gc                                              22

<210> SEQ ID NO 17
<211> LENGTH: 20
<212> TYPE: DNA
<213> ORGANISM: Homo sapiens

<400> SEQUENCE: 17
cagcagcagg gggacctatc                                                 20

<210> SEQ ID NO 18
<211> LENGTH: 20
<212> TYPE: DNA
<213> ORGANISM: Homo sapiens

<400> SEQUENCE: 18
ctgataggtc cccctgctgc                                                 20

<210> SEQ ID NO 19
<211> LENGTH: 22
<212> TYPE: DNA
<213> ORGANISM: Homo sapiens

<400> SEQUENCE: 19
```
cagcagccgg acctatcagg ac					22

<210> SEQ ID NO 20
<211> LENGTH: 22
<212> TYPE: DNA
<213> ORGANISM: Homo sapiens

<400> SEQUENCE: 20
ctgtcctgat aggtccggct gc					22

<210> SEQ ID NO 21
<211> LENGTH: 20
<212> TYPE: DNA
<213> ORGANISM: Homo sapiens

<400> SEQUENCE: 21
cagcagcagc gggacctatc					20

<210> SEQ ID NO 22
<211> LENGTH: 20
<212> TYPE: DNA
<213> ORGANISM: Homo sapiens

<400> SEQUENCE: 22
ctgataggtc ccgctgctgc					20

<210> SEQ ID NO 23
<211> LENGTH: 21
<212> TYPE: DNA
<213> ORGANISM: Homo sapiens

<400> SEQUENCE: 23
ttgaaaaaca gcagcaaaag c					21

<210> SEQ ID NO 24
<211> LENGTH: 21
<212> TYPE: DNA
<213> ORGANISM: Homo sapiens

<400> SEQUENCE: 24
ctgcttttgc tgctgttttt c					21

<210> SEQ ID NO 25
<211> LENGTH: 22
<212> TYPE: DNA
<213> ORGANISM: Homo sapiens

<400> SEQUENCE: 25
cagcagcagc agcagcagca gc					22

<210> SEQ ID NO 26
<211> LENGTH: 22
<212> TYPE: DNA
<213> ORGANISM: Homo sapiens

<400> SEQUENCE: 26
ctgctgctgc tgctgctgct gc					22

<210> SEQ ID NO 27
<211> LENGTH: 22
<212> TYPE: DNA
<213> ORGANISM: Homo sapiens

```
<400> SEQUENCE: 27
tcgaagtgat ggaagatcac gc                                       22

<210> SEQ ID NO 28
<211> LENGTH: 22
<212> TYPE: DNA
<213> ORGANISM: Homo sapiens

<400> SEQUENCE: 28
cagcgtgatc ttccatcact tc                                       22

<210> SEQ ID NO 29
<211> LENGTH: 22
<212> TYPE: DNA
<213> ORGANISM: Homo sapiens

<400> SEQUENCE: 29
cagccgggag tcgggaaggt gc                                       22

<210> SEQ ID NO 30
<211> LENGTH: 22
<212> TYPE: DNA
<213> ORGANISM: Homo sapiens

<400> SEQUENCE: 30
ctgcaccttc ccgactcccg gc                                       22

<210> SEQ ID NO 31
<211> LENGTH: 24
<212> TYPE: DNA
<213> ORGANISM: Homo sapiens

<400> SEQUENCE: 31
acgtcctcgg cggcggcagt gtgc                                     24

<210> SEQ ID NO 32
<211> LENGTH: 24
<212> TYPE: DNA
<213> ORGANISM: Homo sapiens

<400> SEQUENCE: 32
ttgcacactg ccgcctccgc ggac                                     24

<210> SEQ ID NO 33
<211> LENGTH: 21
<212> TYPE: DNA
<213> ORGANISM: Homo sapiens

<400> SEQUENCE: 33
acgtctccat ggcatctcag c                                        21

<210> SEQ ID NO 34
<211> LENGTH: 21
<212> TYPE: DNA
<213> ORGANISM: Homo sapiens

<400> SEQUENCE: 34
ttgctgagat gccatggaga c                                        21

<210> SEQ ID NO 35
<211> LENGTH: 22
<212> TYPE: DNA
<213> ORGANISM: Homo sapiens
```

```
<400> SEQUENCE: 35
gtggccagat ggaagtaaaa tc                                              22

<210> SEQ ID NO 36
<211> LENGTH: 22
<212> TYPE: DNA
<213> ORGANISM: Homo sapiens

<400> SEQUENCE: 36
cagattttac ttccatctgg cc                                              22

<210> SEQ ID NO 37
<211> LENGTH: 22
<212> TYPE: DNA
<213> ORGANISM: Homo sapiens

<400> SEQUENCE: 37
gtggccacat ggaagtaaaa tc                                              22

<210> SEQ ID NO 38
<211> LENGTH: 22
<212> TYPE: DNA
<213> ORGANISM: Homo sapiens

<400> SEQUENCE: 38
cagattttac ttccatgtgg cc                                              22

<210> SEQ ID NO 39
<211> LENGTH: 22
<212> TYPE: DNA
<213> ORGANISM: Homo sapiens

<400> SEQUENCE: 39
gtggccagat gcaagtaaaa tc                                              22

<210> SEQ ID NO 40
<211> LENGTH: 22
<212> TYPE: DNA
<213> ORGANISM: Homo sapiens

<400> SEQUENCE: 40
cagattttac ttgcatctgg cc                                              22

<210> SEQ ID NO 41
<211> LENGTH: 22
<212> TYPE: DNA
<213> ORGANISM: Homo sapiens

<400> SEQUENCE: 41
gtggccaggt ggaagtaaaa tc                                              22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 42
atgaacttca tgctcagctt gc                                              22
```

```
<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 43
cggcaagctg agcatgaagt tc                                             22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 44
cagtggcttc tggcacagca gc                                             22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 45
aagctgctgt gccagaagcc ac                                             22

<210> SEQ ID NO 46
<211> LENGTH: 42
<212> TYPE: DNA
<213> ORGANISM: Homo sapiens

<400> SEQUENCE: 46
gtaagcagag tggctgagga gatgacattt ttccccaaag ag                       42

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 47
cagagtggct gaggagatga c                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 48
gtgtcatctc ctcagccact c                                              21

<210> SEQ ID NO 49
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      DNA oligonucleotide transcribing siRNA

<400> SEQUENCE: 49
cagagtggct gagatgac                                                  18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 50
atgtcatctc agccactc                                                  18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 51
ctgagatgac attttttcccc                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 52
ttggggaaaa atgtcatctc                                                20

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 53
gagtggctga gatgacattt ttc                                            23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 54
gggaaaaatg tcatctcagc cac                                            23

<210> SEQ ID NO 55
<211> LENGTH: 39
<212> TYPE: DNA
<213> ORGANISM: Homo sapiens
```

```
<400> SEQUENCE: 55
gtaagcagag tggctgagat gacatttttc cccaaagag                    39

<210> SEQ ID NO 56
<211> LENGTH: 21
<212> TYPE: RNA
<213> ORGANISM: Homo sapiens

<400> SEQUENCE: 56
aagaaagaac uuucagcuac c                                       21

<210> SEQ ID NO 57
<211> LENGTH: 21
<212> TYPE: RNA
<213> ORGANISM: Homo sapiens

<400> SEQUENCE: 57
gguagcugaa aguucuuucu u                                       21

<210> SEQ ID NO 58
<211> LENGTH: 8
<212> TYPE: RNA
<213> ORGANISM: Homo sapiens

<400> SEQUENCE: 58 gaagcuug                                                      8

<210> SEQ ID NO 59
<211> LENGTH: 56
<212> TYPE: RNA
<213> ORGANISM: Homo sapiens

<400> SEQUENCE: 59
aagaaagaac uuucagcuac cgaagcuugg guagcugaaa guucuuucuu uuuuuu  56

<210> SEQ ID NO 60
<211> LENGTH: 21
<212> TYPE: DNA
<213> ORGANISM: Homo sapiens

<400> SEQUENCE: 60
aagaaagaac tttcagctac c                                       21

<210> SEQ ID NO 61
<211> LENGTH: 8
<212> TYPE: DNA
<213> ORGANISM: Homo sapiens

<400> SEQUENCE: 61 gaagcttg                                                      8

<210> SEQ ID NO 62
<211> LENGTH: 21
<212> TYPE: DNA
<213> ORGANISM: Homo sapiens

<400> SEQUENCE: 62
ggtagctgaa agttctttct t                                       21

<210> SEQ ID NO 63
<211> LENGTH: 19
<212> TYPE: DNA
<213> ORGANISM: Homo sapiens
```

```
<400> SEQUENCE: 63
agaactttca gctaccaag                                              19

<210> SEQ ID NO 64
<211> LENGTH: 10
<212> TYPE: DNA
<213> ORGANISM: Homo sapiens

<400> SEQUENCE: 64
cttcctgtca                                                        10

<210> SEQ ID NO 65
<211> LENGTH: 21
<212> TYPE: DNA
<213> ORGANISM: Homo sapiens

<400> SEQUENCE: 65
cttggtagct gaaagttctt t                                           21

<210> SEQ ID NO 66
<211> LENGTH: 19
<212> TYPE: DNA
<213> ORGANISM: Homo sapiens

<400> SEQUENCE: 66
tgcctcaaca aagttatca                                              19

<210> SEQ ID NO 67
<211> LENGTH: 21
<212> TYPE: DNA
<213> ORGANISM: Homo sapiens

<400> SEQUENCE: 67
tgataacttt gttgaggcat t                                           21

<210> SEQ ID NO 68
<211> LENGTH: 21
<212> TYPE: DNA
<213> ORGANISM: Homo sapiens

<400> SEQUENCE: 68
cagcttgtcc aggtttatga a                                           21

<210> SEQ ID NO 69
<211> LENGTH: 21
<212> TYPE: DNA
<213> ORGANISM: Homo sapiens

<400> SEQUENCE: 69
ttcataaacc tggacaagct g                                           21

<210> SEQ ID NO 70
<211> LENGTH: 21
<212> TYPE: DNA
<213> ORGANISM: Homo sapiens

<400> SEQUENCE: 70
gaccgtgtga atcattgtct a                                           21

<210> SEQ ID NO 71
<211> LENGTH: 21
<212> TYPE: DNA
```

```
<213> ORGANISM: Homo sapiens

<400> SEQUENCE: 71
tagacaatga ttcacacggt c                                              21

<210> SEQ ID NO 72
<211> LENGTH: 21
<212> TYPE: DNA
<213> ORGANISM: Homo sapiens

<400> SEQUENCE: 72
tggcacagtc tgtcagaaat t                                              21

<210> SEQ ID NO 73
<211> LENGTH: 21
<212> TYPE: DNA
<213> ORGANISM: Homo sapiens

<400> SEQUENCE: 73
aatttctgac agactgtgcc a                                              21

<210> SEQ ID NO 74
<211> LENGTH: 21
<212> TYPE: DNA
<213> ORGANISM: Homo sapiens

<400> SEQUENCE: 74
ctggaatgtt ccggagaatc a                                              21

<210> SEQ ID NO 75
<211> LENGTH: 21
<212> TYPE: DNA
<213> ORGANISM: Homo sapiens

<400> SEQUENCE: 75
tgattctccg gaacattcca g                                              21

<210> SEQ ID NO 76
<211> LENGTH: 21
<212> TYPE: DNA
<213> ORGANISM: Homo sapiens

<400> SEQUENCE: 76
ttctcttctg tgattatgtc t                                              21

<210> SEQ ID NO 77
<211> LENGTH: 21
<212> TYPE: DNA
<213> ORGANISM: Homo sapiens

<400> SEQUENCE: 77
agacataatc acagaagaga a                                              21

<210> SEQ ID NO 78
<211> LENGTH: 21
<212> TYPE: DNA
<213> ORGANISM: Homo sapiens

<400> SEQUENCE: 78
gtccaccccc tccatcattt a                                              21

<210> SEQ ID NO 79
<211> LENGTH: 21
```

<212> TYPE: DNA
<213> ORGANISM: Homo sapiens

<400> SEQUENCE: 79
taaatgatgg aggggtgga c                                          21

<210> SEQ ID NO 80
<211> LENGTH: 21
<212> TYPE: DNA
<213> ORGANISM: Homo sapiens

<400> SEQUENCE: 80
aagaaagacc gtgtgaatca t                                          21

<210> SEQ ID NO 81
<211> LENGTH: 21
<212> TYPE: DNA
<213> ORGANISM: Homo sapiens

<400> SEQUENCE: 81
atgattcaca cggtctttct t                                          21

<210> SEQ ID NO 82
<211> LENGTH: 21
<212> TYPE: DNA
<213> ORGANISM: Homo sapiens

<400> SEQUENCE: 82
gggcatcgct atggaactgt t                                          21

<210> SEQ ID NO 83
<211> LENGTH: 21
<212> TYPE: DNA
<213> ORGANISM: Homo sapiens

<400> SEQUENCE: 83
aacagttcca tagcgatgcc c                                          21

<210> SEQ ID NO 84
<211> LENGTH: 21
<212> TYPE: DNA
<213> ORGANISM: Homo sapiens

<400> SEQUENCE: 84
gccgctgcac cgaccaaaga a                                          21

<210> SEQ ID NO 85
<211> LENGTH: 21
<212> TYPE: DNA
<213> ORGANISM: Homo sapiens

<400> SEQUENCE: 85
ttctttggtc ggtgcagcgg c                                          21

<210> SEQ ID NO 86
<211> LENGTH: 21
<212> TYPE: DNA
<213> ORGANISM: Homo sapiens

<400> SEQUENCE: 86
gaccctggaa aagctgatga a                                          21

<210> SEQ ID NO 87

```
<211> LENGTH: 21
<212> TYPE: DNA
<213> ORGANISM: Homo sapiens

<400> SEQUENCE: 87
ttcatcagct tttccagggt c                                               21

<210> SEQ ID NO 88
<211> LENGTH: 21
<212> TYPE: DNA
<213> ORGANISM: Homo sapiens

<400> SEQUENCE: 88
agctttgatg gattctaatc t                                               21

<210> SEQ ID NO 89
<211> LENGTH: 21
<212> TYPE: DNA
<213> ORGANISM: Homo sapiens

<400> SEQUENCE: 89
agattagaat ccatcaaagc t                                               21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 90
aagaggagga ggccgacgcc c                                               21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 91
aagaaagaac tttcagctac c                                               21

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 92
agaactttca gctaccaag                                                  19

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 93
aaagaacttt cagctaccaa g                                               21
```

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 94
tgcctcaaca aagttatca                                              19

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 95
aatgcctcaa caaagttatc a                                           21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 96
aagaaagaac tttcagctac c                                           21

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 97
agaactttca gctaccaag                                              19

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 98
aaagaacttt cagctaccaa g                                           21

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 99
tgcctcaaca aagttatca                                              19

```
<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 100
aatgcctcaa caaagttatc a                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 101
gaggaagagg aggaggccga c                                              21

<210> SEQ ID NO 102
<211> LENGTH: 21
<212> TYPE: DNA
<213> ORGANISM: Homo sapiens

<400> SEQUENCE: 102
ggacacaagg ctgagcagca g                                              21

<210> SEQ ID NO 103
<211> LENGTH: 51
<212> TYPE: DNA
<213> ORGANISM: Homo sapiens

<400> SEQUENCE: 103
cagcagcacc tcagcagggc tgcaggatta gtcaaccacc tcagcagggc t             51

<210> SEQ ID NO 104
<211> LENGTH: 6
<212> TYPE: DNA
<213> ORGANISM: Homo sapiens

<400> SEQUENCE: 104 actagt                                                                6

<210> SEQ ID NO 105
<211> LENGTH: 10
<212> TYPE: DNA
<213> ORGANISM: Homo sapiens

<400> SEQUENCE: 105
cttcctgtca                                                           10

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 106
gccagtaggc tccaagtctt c                                              21
```

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 107
caggaagccg tcatggcaac c                                         21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 108
aaccctggaa aagctgatga a                                         21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 109
aaaagctgat gaaggctttc g                                         21

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 110
aagtcgtttc agcagcaaca gc                                        22

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 111
aacagcagca gcagccaccg c                                         21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 112
tcaaccccct cagccgccgc c                                         21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 113
agaggaaccg ctgcaccgac c                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 114
accgctgcac cgaccaaaga a                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 115
ggaactctca gccaccaaga a                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 116
aagaaagacc gtgtgaatca t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 117
gaccgtgtga atcattgtct a                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 118
gtctaacaat atgtgaaaac a                                              21

<210> SEQ ID NO 119

```
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 119
tggcacagtc tctcagaaat t                                             21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 120
gggcatcgct atggaactgt t                                             21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 121
agtgcctcaa caaagtcatc a                                             21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 122
agctttgatg gattctaatc t                                             21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 123
cagcagcagg tcaaggacac a                                             21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 124
cagcttgtcc aggtttatga a                                             21

<210> SEQ ID NO 125
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 125
cctgccatgg acctgaatga t                                              21

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 126
catcttgaac tacatcgatc at                                             22

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 127
aactacatcg atcatggaga                                                20

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 128
ccaaggacaa gctgatccag t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 129
caaactgcat gatgtcctga a                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 130
ggatacctga aatcctgctt t                                              21

<210> SEQ ID NO 131
<211> LENGTH: 21
<212> TYPE: DNA
```

<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 131
cgtgcagata agaatgctat t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 132
aagtgggcca gttcagggaa t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 133
gttcagggaa tcagaggcaa t                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 134
catcatggcc agtggaagga a                                              21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 135
cagcagtgcc acaaggagaa t                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 136
tgaagccctt ggagtgttaa a                                              21

<210> SEQ ID NO 137
<211> LENGTH: 21
<212> TYPE: DNA
<213> ORGANISM: Artificial Sequence

```
<220> FEATURE:
<223> OTHER INFORMATION: Description of Artificial Sequence: Synthetic
      DNA oligonucleotide transcribing siRNA

<400> SEQUENCE: 137
agcccttgga gtgttaaata c                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 138
ctggaatgtt ccggagaatc a                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 139
gaatgtgcaa tagagaaata g                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 140
ttctcttctg tgattatgtc t                                              21

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 141
gatgaggaag aagaggaaga aagt                                           24

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 142
gtccaccccc tccatcattt a                                              21

<210> SEQ ID NO 143
<211> LENGTH: 9493
<212> TYPE: DNA
<213> ORGANISM: Homo sapiens
```

<400> SEQUENCE: 143

```
gctgccggga cgggtccaag atggacggcc gctcaggttc tgcttttacc tgcggcccag    60
cgccgcgagt cggcccgagg cctccgggga ctgccgtgcc gggcgggaga ccgccatggc   120
gaccctggaa aagctgatga aggccttcga gtccctcaag tccttccagc agcaacagcc   180
gccaccgccg ccgccgccgc cgccgcctcc tcagcttcct cagccgccgc cgcaggcaca   240
gccgctgctg cctcagccgc agccgccccc gccgccgccc cgccgccac ccggcccggc   300
tgtggctgag gagccgctgc accgaccaaa gaaagaactt tcagctacca agaaagaccg   360
tgtgaatcat tgtctgacaa tatgtgaaaa catagtggca cagtctgtca gaaattctcc   420
agaatttcag aaacttctgg gcatcgctat ggaacttttt ctgctgtgca gtgatgacgc   480
agagtcagat gtcaggatgg tggctgacga atgcctcaac aaagttatca agctttgat   540
ggattctaat cttccaaggt tacagctcga gctctataag gaaattaaaa agaatggtgc   600
ccctcggagt ttgcgtgctg ccctgtggag gtttgctgag ctggctcacc tggttcggcc   660
tcagaaatgc aggccttacc tggtgaacct tctgccgtgc ctgactcgaa caagcaagag   720
acccgaagaa tcagtccagg agaccttggc tgcagctgtt cccaaaatta tggcttcttt   780
tggcaattt gcaaatgaca atgaaattaa ggttttgtta aaggccttca tagcgaacct   840
gaagtcaagc tcccccacca ttcggcggac agcggctgga tcagcagtga gcatctgcca   900
gcactcaaga aggacacaat atttctatag ttggctacta aatgtgctct taggcttact   960
cgttcctgtc gaggatgaac actccactct gctgattctt ggcgtgctgc tcaccctgag  1020
gtatttggtg cccttgctgc agcagcaggt caaggacaca agcctgaaag gcagcttcgg  1080
agtgacaagg aaagaaatgg aagtctctcc ttctgcagag cagcttgtcc aggtttatga  1140
actgacgtta catcatacac agcaccaaga ccacaatgtt gtgaccggag ccctggagct  1200
gttgcagcag ctcttcagaa cgcctccacc cgagcttctg caaaccctga ccgcagtcgg  1260
gggcattggg cagctcaccg ctgctaagga ggagtctggt ggccgaagcc gtagtgggag  1320
tattgtggaa cttatagctg agggggttc ctcatgcagc cctgtccttt caagaaaaca  1380
aaaaggcaaa gtgctcttag gagaagaaga agccttggag gatgactctg aatcgagatc  1440
ggatgtcagc agctctgcct taacagcctc agtgaaggat gagatcagtg agagctggc  1500
tgcttcttca gggtttcca ctccaggtc agcaggtcat gacatcatca cagaacagcc  1560
acggtcacag cacacactgc aggcggactc agtggatctg ccagctgtg acttgacaag  1620
ctctgccact gatggggatg aggaggatat cttgagccac agctccagcc aggtcagcgc  1680
cgtcccatct gaccctgcca tggacctgaa tgatgggacc caggcctcgt cgcccatcag  1740
cgacagctcc cagaccacca ccgaagggcc tgattcagct gttacccctt cagacagttc  1800
tgaaattgtg ttagacggta ccgacaacca gtatttgggc ctgcagattg acagcccca  1860
ggatgaagat gaggaagcca caggtattct tcctgatgaa gcctcggagg ccttcaggaa  1920
ctcttccatg gcccttcaac aggcacattt attgaaaaac atgagtcact gcaggcagcc  1980
ttctgacagc agtgttgata aatttgtgtt gagagatgaa gctactgaac cgggtgatca  2040
agaaaacaag ccttgccgca tcaaaggtga cattggacag tccactgatg atgactctgc  2100
acctcttgtc cattgtgtcc gccttttatc tgcttcgttt ttgctaacag ggggaaaaaa  2160
tgtgctggtt ccggacaggg atgtgagggt cagcgtgaag gccctggccc tcagctgtgt  2220
gggagcagct gtgccctcc acccggaatc tttcttcagc aaactctata agttcctct   2280
tgacaccacg gaatacccctg aggaacagta tgtctcagac atcttgaact acatcgatca  2340
```

```
tggagaccca caggttcgag gagccactgc cattctctgt gggaccctca tctgctccat    2400
cctcagcagg tcccgcttcc acgtgggaga ttggatgggc accattagaa ccctcacagg    2460
aaatacattt tctttggcgg attgcattcc tttgctgcgg aaaacactga aggatgagtc    2520
ttctgttact tgcaagttag cttgtacagc tgtgaggaac tgtgtcatga gtctctgcag    2580
cagcagctac agtgagttag gactgcagct gatcatcgat gtgctgactc tgaggaacag    2640
ttcctattgg ctggtgagga cagagcttct ggaaaccctt gcagagattg acttcaggct    2700
ggtgagcttt ttggaggcaa agcagaaaaa cttacacaga ggggctcatc attatacagg    2760
gcttttaaaa ctgcaagaac gagtgctcaa taatgttgtc atccatttgc ttggagatga    2820
agaccccagg gtgcgacatg ttgccgcagc atcactaatt aggcttgtcc caaagctgtt    2880
ttataaatgt gaccaaggac aagctgatcc agtagtggcc gtggcaagag atcaaagcag    2940
tgtttacctg aaacttctca tgcatgagac gcagcctcca tctcatttct ccgtcagcac    3000
aataaccaga atatatagag ctataaacct actaccaagc ataacagacg tcactatgga    3060
aaataacctt tcaagagtta ttgcagcagt ttctcatgaa ctaatcacat caaccaccag    3120
agcactcaca tttggatgct gtgaagcttt gtgtcttctt tccactgcct tcccagtttg    3180
catttggagt ttaggttggc actgtggagt gcctccactg agtgcctcag atgagtctag    3240
gaagagctgt accgttggga tggccacaat gattctgacc ctgctctcgt cagcttggtt    3300
cccattggat ctctcagccc atcaagatgc tttgattttg gccggaaact tgcttgcagc    3360
cagtgctccc aaatctctga aagttcatg ggcctctgaa gaagaagcca acccagcagc    3420
caccaagcaa gaggaggtct ggccagccct gggggaccgg gccctggtgc ccatggtgga    3480
gcagctcttc tctcacctgc tgaaggtgat taacatttgt gcccacgtcc tggatgacgt    3540
ggctcctgga cccgcaataa aggcagcctt gccttctcta caaaccccc cttctctaag    3600 tcccatccga cgaaagggga aggagaaaga accaggagaa caagcatctg taccgttgag    3660
tcccaagaaa ggcagtgagg ccagtgcagc ttctagacaa tctgatacct caggtcctgt    3720
tacaacaagt aaatcctcat cactggggag tttctatcat cttccttcat acctcaaact    3780
gcatgatgtc ctgaaagcta cacacgctaa ctacaaggtc acgctggatc ttcagaacag    3840
cacggaaaag tttggagggt ttctccgctc agccttggat gttctttctc agatactaga    3900
gctggccaca ctgcaggaca ttgggaagtg tgttgaagag atcctaggat acctgaaatc    3960
ctgctttagt cgagaaccaa tgatggcaac tgtttgtgtt caacaattgt tgaagactct    4020 cttggcaca aacttggcct cccagtttga tggcttatct tccaacccca gcaagtcaca    4080
aggccgagca cagcgccttg gctcctccag tgtgaggcca ggcttgtacc actactgctt    4140
catggccccg tacacccact tcacccaggc cctcgctgac gccagcctga gaacatggt    4200 gcaggcggag caggagaacg acacctcggg atggtttgat gtcctccaga aagtgtctac    4260
ccagttgaag acaaacctca cgagtgtcac aaagaaccgt gcagataaga atgctattca    4320
taatcacatt cgtttgtttg aacctcttgt tataaaagct ttaaaacagt acacgactac    4380
aacatgtgtg cagttacaga agcaggtttt agatttgctg gcgcagctgg ttcagttacg    4440
ggttaattac tgtcttctgg attcagatca ggtgtttatt ggctttgtat tgaaacagtt    4500
tgaatacatt gaagtgggcc agttcaggga atcagaggca atcattccaa acatcttttt    4560
cttcttggta ttactatctt atgaacgcta tcattcaaaa cagatcattg gaattcctaa    4620
aatcattcag ctctgtgatg gcatcatggc cagtggaagg aaggctgtga cacatgccat    4680
```

```
accggctctg cagcccatag tccacgacct ctttgtatta agaggaacaa ataaagctga    4740
tgcaggaaaa gagcttgaaa cccaaaaaga ggtggtggtg tcaatgttac tgagactcat    4800
ccagtaccat caggtgttgg agatgttcat tcttgtcctg cagcagtgcc acaaggagaa    4860
tgaagacaag tggaagcgac tgtctcgaca gatagctgac atcatcctcc caatgttagc    4920
caaacagcag atgcacattg actctcatga agcccttgga gtgttaaata cattatttga    4980
gattttggcc ccttcctccc tccgtccggt agacatgctt ttacggagta tgttcgtcac    5040
tccaaacaca atggcgtccg tgagcactgt tcaactgtgg atatcgggaa ttctggccat    5100
tttgagggtt ctgatttccc agtcaactga agatattgtt cttctcgta ttcaggagct     5160 ctccttctct ccgtatttaa tctcctgtac agtaattaat aggttaagag atggggacag    5220
tacttcaacg ctagaagaac acagtgaagg gaaacaaata aagaatttgc agaagaaac     5280 attttcaagg tttctattac aactggttgg tattcttta gaagacattg ttacaaaaca     5340
gctgaaggtg gaaatgagtg agcagcaaca tactttctat tgccaggaac taggcacact    5400
gctaatgtgt ctgatccaca tcttcaagtc tggaatgttc cggagaatca cagcagctgc    5460
cactaggctg ttccgcagtg atggctgtgg cggcagtttc tacaccctgg acagcttgaa    5520
cttgcgggct cgttccatga tcaccaccca cccggccctg gtgctgctct ggtgtcagat    5580
actgctgctt gtcaaccaca ccgactaccg ctggtgggca gaagtgcagc agaccccgaa    5640
aagacacagt ctgtccagca caaagttact tagtccccag atgtctggag aagaggagga    5700
ttctgacttg gcagccaaac ttggaatgtg caatagagaa atagtacgaa gaggggctct    5760
cattctcttc tgtgattatg tctgtcagaa cctccatgac tccgagcact taacgtggct    5820
cattgtaaat cacattcaag atctgatcag ccttcccac gagcctccag tacaggactt     5880
catcagtgcc gttcatcgga actctgctgc cagcggcctg ttcatccagg caattcagtc    5940
tcgttgtgaa aacctttcaa ctccaaccat gctgaagaaa actcttcagt gcttggaggg    6000
gatccatctc agccagtcgg gagctgtgct cacgctgtat gtggacaggc ttctgtgcac    6060
ccctttccgt gtgctggctc gcatggtcga catccttgct tgtcgccggg tagaaatgct    6120
tctggctgca aatttacaga gcagcatggc ccagttgcca atggaagaac tcaacagaat    6180
ccaggaatac cttcagagca gcgggctcgc tcagagacac caaaggctct attccctgct    6240
ggacaggttt cgtctctcca ccatgcaaga ctcacttagt ccctctcctc cagtctcttc    6300
ccacccgctg gacggggatg ggcacgtgtc actggaaaca gtgagtccgg acaaagactg    6360
gtacgttcat cttgtcaaat cccagtgttg gaccaggtca gattctgcac tgctggaagg    6420
tgcagagctg gtgaatcgga ttcctgctga agatatgaat gccttcatga tgaactcgga    6480
gttcaaccta agcctgctag ctccatgctt aagcctaggg atgagtgaaa tttctggtgg    6540
ccagaagagt gcccttttg aagcagcccg tgaggtgact ctggcccgtg tgagcggcac     6600
cgtgcagcag ctccctgctg tccatcatgt cttccagccc gagctgcctg cagagccggc    6660
ggcctactgg agcaagttga atgatctgtt tggggatgcc gcactgtatc agtccctgcc    6720
cactctggcc cgggccctgg cacagtacct ggtggtggtc tccaaactgc ccagtcattt    6780
gcaccttcct cctgagaaag agaaggacat tgtgaaattc gtggtggcaa cccttgaggc    6840
cctgtcctgg catttgatcc atgagcagat cccgctgagt ctggatctcc aggcagggct    6900
ggactgctgc tgcctggccc tgcagctgcc tggcctctgg agcgtggtct cctccacaga    6960
gtttgtgacc cacgccgtgc ccctcatcta ctgtgtgcac ttcatcctgg aggccgttgc    7020
agtgcagcct ggagagcagc ttcttagtcc agaaagaagg acaaataccc caaaagccat    7080
```

```
cagcgaggag gaggaggaag tagatccaaa cacacagaat cctaagtata tcactgcagc    7140
ctgtgagatg gtggcagaaa tggtggagtc tctgcagtcg gtgttggcct tgggtcataa    7200
aaggaatagc ggcgtgccgg cgtttctcac gccattgcta aggaacatca tcatcagcct    7260
ggcccgcctg cccttgtca acagctacac acgtgtgccc ccactggtgt ggaagcttgg    7320
atggtcaccc aaaccgggag gggattttgg cacagcattc cctgagatcc ccgtggagtt    7380
cctccaggaa aaggaagtct ttaaggagtt catctaccgc atcaacacac taggctggac    7440
cagtcgtact cagtttgaag aaacttgggc caccctcctt ggtgtcctgg tgacgcagcc    7500
cctcgtgatg gagcaggagg agagcccacc agaagaagac acagagagga cccagatcaa    7560
cgtcctggcc gtgcaggcca tcacctcact ggtgctcagt gcaatgactg tgcctgtggc    7620
cggcaaccca gctgtaagct gcttggagca gcagccccgg aacaagcctc tgaaagctct    7680
cgacaccagg tttgggagga agctgagcat tatcagaggg attgtggagc aagagattca    7740
agcaatggtt tcaaagagag agaatattgc cacccatcat ttatatcagg catgggatcc    7800
tgtcccttct ctgtctccgg ctactacagg tgccctcatc agccacgaga gctgctgct    7860 acagatcaac cccgagcggg agctggggag catgagctac aaaactcggcc aggtgtccat    7920 acactccgtg tggctgggga acagcatcac accctgagg gaggaggaat gggacgagga    7980
agaggaggag gaggccgacg cccctgcacc ttcgtcacca cccacgtctc cagtcaactc    8040
caggaaacac cgggctggag ttgacatcca ctcctgttcg cagttttgc ttgagttgta    8100 cagccgctgg atcctgccgt ccagctcagc caggaggacc ccggccatcc tgatcagtga    8160
ggtggtcaga tcccttctag tggtctcaga cttgttcacc gagcgcaacc agtttgagct    8220
gatgtatgtg acgctgacag aactgcgaag ggtgcaccct tcagaagacg agatcctcgc    8280
tcagtacctg gtgcctgcca cctgcaaggc agctgccgtc cttgggatgg acaaggccgt    8340
ggcggagcct gtcagccgcc tgctggagag cacgctcagg agcagccacc tgcccagcag    8400
ggttggagcc ctgcacggcg tcctctatgt gctggagtgc gacctgctgg acgacactgc    8460
caagcagctc atcccggtca tcagcgacta tctcctctcc aacctgaaag gatcgcccca    8520
ctgcgtgaac attcacagcc agcagcacgt actggtcatg tgtgccactg cgttttacct    8580
cattgagaac tatcctctgg acgtagggcc ggaattttca gcatcaataa tacagatgtg    8640
tggggtgatg ctgtctggaa gtgaggagtc caccccctcc atcatttacc actgtgccct    8700
cagaggcctg gagcgcctcc tgctctctga gcagctctcc cgcctggatg cagaatcgct    8760
ggtcaagctg agtgtggaca gagtgaacgt gcacagcccg caccgggcca tggcggctct    8820
gggcctgatg ctcacctgca tgtacacagg aaaggagaaa gtcagtccgg gtagaacttc    8880
agaccctaat cctgcagccc ccgacagcga gtcagtgatt gttgctatgg agcgggtatc    8940
tgttcttttt dataggatca ggaaaggctt tccttgtgaa gccagagtgg tggccaggat    9000
cctgccccag tttctagacg acttcttccc accccaggac atcatgaaca aagtcatcgg    9060
agagtttctg tccaaccagc agccatatccc ccagttcatg gccaccgtgg tgtataaggt    9120
gtttcagact ctgcacagca ccgggcagtc gtccatggtc cgggactggg tcatgctgtc    9180
cctctccaac ttcacgcaga gggccccggt cgccatggcc acgtggagcc tctcctgctt    9240
ctttgtcagc gcgtccacca gcccgtgggt cgcggcgatc ctcccacatg tcatcagcag    9300
gatgggcaag ctggagcagg tggacgtgaa ccttttctgc ctggtcgcca cagacttcta    9360
cagacaccag atagaggagg agctcgaccg cagggccttc cagtctgtgc ttgaggtggt    9420
```

| | | |
|---|---|---|
| tgcagcccca ggaagcccat atcaccggct gctgacttgt ttacgaaatg tccacaaggt | 9480 | |
| caccacctgc tga | 9493 | |

<210> SEQ ID NO 144
<211> LENGTH: 9998
<212> TYPE: DNA
<213> ORGANISM: Mus musculus
<220> FEATURE:
<221> NAME/KEY: modified_base
<222> LOCATION: (9800)
<223> OTHER INFORMATION: a, c, t, g, unknown or other

<400> SEQUENCE: 144

| | | |
|---|---|---|
| cccattcatt gccttgctgc taagtggcgc cgcgtagtgc cagtaggctc caagtcttca | 60 | |
| gggtctgtcc catcgggcag gaagccgtca tggcaaccct ggaaaagctg atgaaggctt | 120 | |
| tcgagtcgct caagtcgttt cagcagcaac agcagcagca gccaccgccg cagccgccgc | 180 | |
| caccgccgcc gccgcctccg cctcaacccc ctcagccgcc gcctcagggg cagccgccgc | 240 | |
| cgccaccacc gccgctgcca ggtccggcag aggaaccgcg gcaccgacca aagaaggaac | 300 | |
| tctcagccac caagaaagac cgtgtgaatc attgtctaac aatatgtgaa acattgtgg | 360 | |
| cacagtctct cagaaattct ccagaatttc agaaactctt gggcatcgct atggaactgt | 420 | |
| ttctgctgtg cagtgacgat gcggagtcag atgtcagaat ggtggctgat gagtgcctca | 480 | |
| acaaagtcat caaagctttg atggattcta atcttccaag gctacagtta gaactctata | 540 | |
| aggaaattaa aagaatggt gctcctcgaa gtttgcgtgc tgccctgtgg aggtttgctg | 600 | |
| agctggctca cctggttcga cctcagaagt gcaggcctta cctggtgaat cttcttccat | 660 | |
| gcctgacccg aacaagcaaa agaccggagg aatcagttca ggagaccttg gctgcagctg | 720 | |
| ttcctaaaat tatggcttct tttggcaatt tcgcaaatga caatgaaatt aaggttctgt | 780 | |
| tgaaagcttt catagcaaat ctgaagtcaa gctctcccac cgtgcggcgg acagcagccg | 840 | |
| gctcagccgt gagcatctgc caacattcta ggaggacaca gtacttctac aactggctcc | 900 | |
| ttaatgtcct cctaggtctg ctggttccca tggaagaaga gcactccact ctcctgatcc | 960 | |
| tcggtgtgtt gctcacattg aggtgtctag tgcccttgct ccagcagcag gtcaaggaca | 1020 | |
| caagtctaaa aggcagcttt ggggtgacac ggaaagaaat ggaagtctct ccttctacag | 1080 | |
| agcagcttgt ccaggtttat gaactgactt tgcatcatac tcagcaccaa gaccacaatg | 1140 | |
| tggtgacagg ggcactggag ctcctgcagc agctcttccg taccctcca cctgaactcc | 1200 | |
| tgcaagcact gaccacacca ggagggcttg gcagctcac tctggttcaa gaagaggccc | 1260 | |
| ggggccgagg ccgcagcggg agcatcgtgg agcttttagc tggagggggt tcctcgtgca | 1320 | |
| gccctgtcct ctcaagaaag cagaaaggca aagtgctctt aggagaggaa gaagccttgg | 1380 | |
| aagatgactc ggagtccaga tcagatgtca gcagctcagc ctttgcagcc tctgtgaaga | 1440 | |
| gtgagattgg tggagagctc gctgcttctt caggtgtttc cactcctggt tctgttggtc | 1500 | |
| acgacatcat cactgagcag cctagatccc agcacacact tcaagcagac tctgtggatt | 1560 | |
| tgtccggctg tgacctgacc agtgctgcta ctgatgggga tgaggaggac atcttgagcc | 1620 | |
| acagctccag ccagttcagt gctgtcccat ccgaccctgc catggacctg aatgatggga | 1680 | |
| cccaggcctc ctcacccatc agtgacagtt ctcagaccac cactgaagga cctgattcag | 1740 | |
| ctgtgactcc ttcggacagt tctgaaattg tgttagatgg tgccgatagc cagtatttag | 1800 | |
| gcatgcagat aggacagcca caggaggacg atgaggaggg agctgcaggt gttctttctg | 1860 | |
| gtgaagtctc agatgttttc agaaaactctt ctctggccct tcaacaggca cacttgttgg | 1920 | |

```
aaagaatggg ccatagcagg cagccttccg acagcagtat agataagtat gtaacaagag    1980
atgaggttgc tgaagccagt gatccagaaa gcaagccttg ccgaatcaaa ggtgacatag    2040
gacagcctaa tgatgatgat tctgctcctc tggtacattg tgtccgtctt ttatctgctt    2100
cctttttgtt aactggtgaa aagaaagcac tggttccaga cagagacgtg agagtcagtg    2160
tgaaggccct ggccctcagc tgcattggtg cggctgtggc ccttcatcca gagtcgttct    2220
tcagcagact gtacaaagta cctcttaata ccacggaaag tactgaggaa cagtatgttt    2280
ctgacatctt gaactacatc gatcatggag acccacaggt ccgaggagct actgccattc    2340
tctgtgggac ccttgtctac tccatcctca gtaggtcccg tctccgtgtt ggtgagtggc    2400
tgggcaacat cagaaccctg acaggaaata cattttctct ggtggactgc attcctttac    2460
tgcagaaaac gttgaaggat gaatcttctg ttacttgcaa gttggcttgt acagctgtga    2520
ggcactgtgt cctgagtctt tgcagcagca gctacagtga cttgggatta caactgctta    2580
ttgatatgct gcctctgaag aacagctcct actggctggt gaggaccgaa ctgctggaca    2640
ctctggcaga gattgacttc aggctcgtga gttttttgga ggcaaaagca gaaagtttac    2700
accgaggggc tcatcattat acagggtttc taaaactaca agaacgagta ctcaataatg    2760
tggtcattta tttgcttgga gatgaagacc ccagggttcg acatgttgct gcaacatcat    2820
taacaaggct tgtcccaaag ctgttttaca agtgtgacca aggacaagct gatccagttg    2880
tggctgtagc gagggatcag agcagtgtct acctgaagct cctcatgcat gagacccagc    2940
caccatcaca ctttttctgtc agcaccatca ccagaatcta tagaggctat agcttactgc    3000
caagtataac agatgtcacc atggaaaaca atctctcaag agttgttgcc gcagtttctc    3060
atgaactcat tacgtcaaca acacgggcac tcacatttgg atgctgtgaa gccttgtgtc    3120
ttctctcagc agcctttcca gtttgcactt ggagtttagg atggcactgt ggagtgcccc    3180
cactgagtgc ctctgatgag tccaggaaga gctgcactgt tgggatggcc tccatgattc    3240
tcaccttgct ttcatcagct tggttcccac tggatctctc agcccatcag gatgccttga    3300
ttttggctgg aaacttgcta gcagcgagtg cccccaagtc tctgagaagt tcatggacct    3360
ctgaagaaga agccaactca gcagccacca gacaggagga atctggcct gctctggggg    3420
atcggactct agtgcccttg gtggagcagc ttttctccca cctgctgaag gtgatcaata    3480
tctgtgctca tgtcttggac gatgtgactc ctggaccagc aatcaaggca gccttgcctt    3540
ctctaacaaa ccccccttct ctaagtccta ttcgacggaa agggaaggag aaagaacctg    3600
gagaacaagc ttctactcca atgagtccca agaaagttgg tgaggccagt gcagcctctc    3660
gacaatcaga cacctcagga cctgtcacag caagtaaatc atcctcactg gggagtttct    3720
accatctccc ctcctacctc aaactgcatg atgtcctgaa agccactcac gccaactata    3780
aggtcacctt agatcttcag aacagcactg aaaagtttgg ggggttcctg cgctctgcct    3840
tggacgtcct ttctcagatt ctagagctgg cgacactgca ggacattgga aagtgtgttg    3900
aagaggtcct tggatacctg aaatcctgct ttagtcgaga accaatgatg gcaactgtct    3960
gtgtgcagca gctattgaag actctctttg ggacaaactt agcctcacag tttgatggct    4020
tatcttccaa ccccagcaag tctccagtgcc gagctcagcg ccttggctct tcaagtgtga    4080
ggcccggctt atatcactac tgcttcatgg caccatacac gcacttcaca caggccttgg    4140
ctgacgcaag cctgaggaac atggtgcagg cggagcagga gcgtgatgcc tcggggtggt    4200
ttgatgtact ccagaaagtg tctgcccaat tgaagacgaa cctaacaagc gtcacaaaga    4260
```

```
accgtgcaga taagaatgct attcataatc acattaggtt atttgagcct cttgttataa      4320
aagcattgaa gcagtacacc acgacaacat ctgtacaatt gcagaagcag gttttggatt      4380
tgctggcaca gctggttcag ctacgggtca attactgtct actggattca gaccaggtgt      4440
tcatcgggtt tgtgctgaag cagtttgagt acattgaagt gggccagttc agggaatcag      4500
aggcaattat tccaaatata ttttcttcc tggtattact gtcttatgag cgctaccatt       4560
caaaacagat cattggaatt cctaaaatca tccagctgtg tgatggcatc atggccagtg      4620
gaaggaaggc cgttacacat gctataccctg ctctgcagcc cattgtccat gacctctttg    4680
tgttacgagg aacaaataaa gctgatgcag ggaaagagct tgagacacag aaggaggtgg     4740
tggtctccat gctgttacga ctcatccagt accatcaggt gctggagatg ttcatccttg     4800
tcctgcagca gtgccacaag gagaatgagg acaagtggaa acggctctct cggcaggtcg     4860
cagacatcat cctgcccatg ttggccaagc agcagatgca tattgactct catgaagccc    4920
ttggagtgtt aaataccttg tttgagattt tggctccttc ctccctacgt cctgtggaca     4980
tgcttttgcg gagtatgttc atcactccaa gcacaatggc atctgtaagc actgtgcagc    5040
tgtggatatc tggaatcctc gccattctga gggttctcat ttcccagtca accgaggaca    5100
ttgttctttg tcgtattcag gagctctcct tctctccaca cttgctctcc tgtccagtga    5160
ttaacaggtt aaggggtgga ggcggtaatg taacactagg agaatgcagc gaagggaaac    5220
aaaagagttt gccagaagat acattctcaa ggtttctttt acagctggtt ggtattcttc    5280
tagaagacat cgttacaaaa cagctcaaag tggacatgag tgaacagcag catacgttct    5340
actgccaaga gctaggcaca ctgctcatgt gtctgatcca catattcaaa tctggaatgt    5400
tccggagaat cacagcagct gccactagac tcttcaccag tgatggctgt gaaggcagct    5460
tctatactct agagagcctg aatgcacggg tccgatccat ggtgcccacg cacccagccc    5520
tggtactgct ctggtgtcag atcctacttc tcatcaacca cactgaccac cggtggtggg    5580
cagaggtgca gcagacaccc aagagacaca gtctgtcctg cacgaagtca cttaaccccc    5640
agaagtctgg cgaagaggag gattctggct cggcagctca gctgggaatg tgcaatagag    5700
aaatagtgcg aagaggggcc cttattctct tctgtgatta tgtctgtcag aatctccatg    5760
actcagaaca cttaacatgg ctcattgtga atcacattca agatctgatc agcttgtctc    5820
atgagcctcc agtacaagac tttattagtg ccattcatcg taattctgca gctagtggtc    5880
tttttatcca ggcaattcag tctcgctgtg aaaatctttc aacgccaacc actctgaaga    5940
aaacacttca gtgcttggaa ggcatccatc tcagccagtc tggtgctgtg ctcacactat    6000
atgtggacag gctcctgggc accccttcc gtgcgctggc tcgcatggtc gacaccctgg     6060
cctgtcgccg ggtagaaatg cttttggctg caaatttaca gagcagcatg gcccagttgc    6120
cagaggagga actaaacaga atccaagaac acctccagaa cagtgggctt gcacaaagac    6180
accaaaggct ctattcactg ctggacagat tccgactctc tactgtgcag gactcactta    6240
gccccttgcc cccagtcact tcccacccac tggatgggga tgggcacaca tctctggaaa    6300
cagtgagtcc agacaaagac tggtacctcc agcttgtcag atcccagtgt tggaccagat    6360
cagattctgc actgctggaa ggtgcagagc tggtcaaccg tatccctgct gaagatatga    6420
atgacttcat gatgagctcg gagttcaacc taagcctttt ggctccctgt ttaagccttg    6480
gcatgagcga gattgctaat ggccaaaaga gtccctctct tgaagcagcc cgtggggtga    6540
ttctgaaccg ggtgaccagt gttgttcagc agcttcctgc tgtccatcaa gtcttccagc    6600
ccttcctgcc tatagagccc acggcctact ggaacaagtt gaatgatctg cttggtgata    6660
```

```
ccacatcata ccagtctctg accatacttg cccgtgccct ggcacagtac ctggtggtgc    6720
tctccaaagt gcctgctcat ttgcaccttc ctcctgagaa ggaggggac acggtgaagt     6780
ttgtggtaat gacagttgag gccctgtcat ggcatttgat ccatgagcag atcccactga    6840
gtctggacct ccaagccggg ctagactgct gctgcctggc actacaggtg cctggcctct    6900
gggggggtgct gtcctcccca gagtacgtga ctcatgcctg ctccctcatc cattgtgtgc   6960
gattcatcct ggaagccatt gcagtacaac ctggagacca gcttctcggt cctgaaagca    7020
ggtcacatac tccaagagct gtcagaaagg aggaagtaga ctcagatata caaaacctca    7080
gtcatgtcac ttcggcctgc gagatggtgg cagacatggt ggaatccctg cagtcagtgc    7140
tggccttggg ccacaagagg aacagcaccc tgccttcatt tctcacagct gtgctgaaga    7200
acattgttat cagtctggcc cgactccccc tagttaacag ctatactcgt gtgcctcctc    7260
tggtatggaa actcgggtgg tcacccaagc ctggagggga ttttggcaca gtgtttcctg    7320
agatccctgt agagttcctc caggagaagg agatcctcaa ggagttcatc taccgcatca    7380
acaccctagg gtggaccaat cgtacccagt tcgaagaaac ttgggccacc ctccttggtg    7440
tcctggtgac tcagcccctg gtgatggaac aggaagagag cccaccagag gaagacacag    7500
aaagaaccca gatccatgtc ctggctgtgc aggccatcac ctctctagtg ctcagtgcaa    7560
tgaccgtgcc tgtggctggc aatccagctg taagctgctt ggagcaacag ccccggaaca    7620
agccactgaa ggctctcgat accagatttg aagaaagct gagcatgatc agagggattg     7680
tagaacaaga aatccaagag atggtttccc agagagagaa tactgccact caccattctc    7740
accaggcgtg ggatcctgtc ccttctctgt taccagctac tacaggtgct cttatcagcc    7800
atgacaagct gctgctgcag atcaacccag agcgggagcc aggcaacatg agctacaagc    7860
tgggccaggt gtccatacac tccgtgtggc tgggaaataa catcacaccc ctgagagagg    7920
aggaatggga tgaggaagaa gaggaagaaa gtgatgtccc tgcaccaacg tcaccacctg    7980
tgtctccagt caattccaga aaacaccgtg ccggggttga tattcactcc tgttcgcagt    8040
ttctgcttga attgtacagc cgatggatcc tgccatccag tgcagccaga aggaccccg     8100
tcatcctgat cagtgaagtg gttcgatctc ttcttgtagt gtcagactta ttcaccgaac    8160
gtacccagtt tgaaatgatg tatctgacgc tgacagaact acggagagtg cacccttcag    8220
aagatgagat cctcattcag tacctggtgc ctgccacctg taaggcagct gctgtccttg    8280
gaatggacaa aactgtggca gagccagtca gccgcctact ggagagcaca ctgaggagca    8340
gccacctgcc cagccagatc ggagccctgc acggcatcct ctatgtgttg gagtgtgacc    8400
tcttggatga cactgcaaag cagctcattc cagttgttag tgactatctg ctgtccaacc    8460
tcaaaggaat agcccactgc gtgaacattc acagccagca gcatgtgctg gtaatgtgtg    8520
ccactgcttt ctacctgatg gaaaactacc ctctggatgt gggaccagaa ttttcagcat    8580
ctgtgataca gatgtgtgga gtaatgctgt ctggaagtga ggagtccacc ccctccatca    8640
tttaccactg tgccctccgg ggtctggagc ggctcctgct gtctgagcag ctatctcggc    8700
tagacacaga gtccttggtc aagctaagtg tggacagagt gaatgtacaa agcccacaca    8760
gggccatggc agccctaggc ctgatgctca cctgcatgta cacaggaaag gaaaaagcca    8820
gtccaggcag agcttctgac cccagccctg ctacacctga cagcgagtct gtgattgtag    8880
ctatggagcg agtgtctgtt ctctttgata ggatccgcaa gggatttccc tgtgaagcca    8940
gggttgtggc aaggatcctg cctcagttcc tagatgactt ctttccacct caagatgtca    9000
```

```
tgaacaaagt cattggagag ttcctgtcca atcagcagcc atacccacag ttcatggcca    9060
ctgtagttta caaggttttt cagactctgc acagtgctgg gcagtcatcc atggtccggg    9120
actgggtcat gctgtccctg tccaacttca cacaaagaac tccagttgcc atggccatgt    9180
ggagcctctc ctgcttcctt gttagcgcat ctaccagccc atgggtttct gcgatccttc    9240
cacatgtcat cagcaggatg ggcaaactgg aacaggtgga tgtgaacctt ttctgcctgg    9300
ttgccacaga cttctacaga caccagatag aggaggaatt cgaccgcagg gctttccagt    9360
ctgtgtttga ggtggtggct gcaccaggaa gtccatacca caggctgctt gcttgtttgc    9420
aaaatgttca caaggtcacc acctgctgag tagtgcctgt gggacaaaag gctgaaagaa    9480
ggcagctgct ggggcctgag cctccaggag cctgctccaa gcttctgctg gggctgcctt    9540
ggccgtgcag gcttcacttg tgtcaagtgg acagccaggc aatggcagga gtgctttgca    9600
atgagggcta tgcagggaac atgcactatg ttggggttga gcctgagtcc tgggtcctgg    9660
cctcgctgca gctggtgaca gtgctaggtt gaccaggtgt ttgtcttttt cctagtgttc    9720
ccctggccat agtcgccagg ttgcagctgc cctggtatgt ggatcagaag tcctagctcc    9780
tgccagatgg ttctgagccn gcctgctcca ctgggctgga gagctccctc ccacatttac    9840
ccagtaggca tacctgccac accagtgtct ggacacaaat gaatggtgtg tggggctggg    9900
aactggggct gccaggtgtc cagcaccatt ttcctttctg tgttttcttc tcaggagtta    9960
aaatttaatt atatcagtaa agagattaat tttaatgt                           9998

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 145
aagaaggaac tctcagccac c                                                21

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 146
aagaagagga agaaagtgat gtcc                                             24
```